(12) United States Patent
Doemling

(10) Patent No.: US 9,187,441 B2
(45) Date of Patent: Nov. 17, 2015

(54) P53-MDM2 ANTAGONISTS

(75) Inventor: Alexander Doemling, Solinger (DE)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 177 days.

(21) Appl. No.: 13/821,756

(22) PCT Filed: Sep. 8, 2011

(86) PCT No.: PCT/US2011/001553
§ 371 (c)(1),
(2), (4) Date: Sep. 19, 2013

(87) PCT Pub. No.: WO2012/033525
PCT Pub. Date: Mar. 15, 2012

(65) Prior Publication Data
US 2014/0005386 A1  Jan. 2, 2014

Related U.S. Application Data

(60) Provisional application No. 61/381,038, filed on Sep. 8, 2010.

(51) Int. Cl.
| | |
|---|---|
| *C07D 403/06* | (2006.01) |
| *C07D 401/12* | (2006.01) |
| *C07D 295/155* | (2006.01) |
| *C07D 213/56* | (2006.01) |
| *C07D 209/14* | (2006.01) |
| *C07D 209/20* | (2006.01) |
| *C07D 209/26* | (2006.01) |
| *C07D 209/30* | (2006.01) |
| *C07D 209/42* | (2006.01) |
| *C07C 209/26* | (2006.01) |

(52) U.S. Cl.
CPC .......... *C07D 295/155* (2013.01); *C07C 209/26* (2013.01); *C07D 209/14* (2013.01); *C07D 209/20* (2013.01); *C07D 209/30* (2013.01); *C07D 209/42* (2013.01); *C07D 213/56* (2013.01); *C07D 401/12* (2013.01); *C07D 403/06* (2013.01)

(58) Field of Classification Search
CPC ............. C07D 295/155; C07D 209/20; C07D 209/30; C07D 209/26; C07D 209/14; C07D 209/42; C07D 213/56; C07D 401/12; C07D 403/06
See application file for complete search history.

(56) References Cited

U.S. PATENT DOCUMENTS

| | | | |
|---|---|---|---|
| 5,378,729 A | 1/1995 | Kohn et al. | |
| 5,654,301 A | 8/1997 | Kohn et al. | |
| 7,041,687 B2 | 5/2006 | Binch et al. | |
| 7,504,436 B2 * | 3/2009 | Thormann et al. | ............ 514/575 |
| 2008/0280769 A1 | 11/2008 | Doemling | |

FOREIGN PATENT DOCUMENTS

| | | |
|---|---|---|
| CN | 1224015 | 7/1999 |
| DE | 2259567 A1 | 6/1974 |
| EP | 0 400 440 A1 | 12/1990 |
| WO | WO 2004/099124 A2 | 11/2004 |
| WO | WO 2008/119741 A2 | 10/2008 |

OTHER PUBLICATIONS

Biao et al., "Preparation of diindole heterocyclic compounds as anti-inflammatory and anticancer agents," *Shanghai Inst. of Organic Chemistry, Chinese Acad. of Sciences*, Jul. 28, 1999, 2 pages. Database Accession No. 2000-416843.
Waki et al., Peptide Synthesis Using the Four-Component Condensation (Ugi Reaction), *Journ. of the American Chemical Society*, (1977), pp. 6075-6082, vol. 99, No. 18.
Database Registry [Online]. Chemical Abstracts Service, Columbus, Ohio, Apr. 15, 2010, Chemical Library; Supplier; Aurora Fine Chemicals: XP002717305. [Database Accession No. 1219353-74-8].
Database Registry [Online]. Chemical Abstracts Service, Columbus, Ohio, Jul. 4, 2008, database: asinex ltd.: XP002717309. [Database Accession No. 1032752-53-6].
Database Registry [Online]. Chemical Abstracts Service, Columbus, Ohio, Jul. 3, 2008, database: asinex ltd.: XP002717310. [Database Accession No. 1032574-07-4].
Database Registry [Online]. Chemical Abstracts Service, Columbus, Ohio, Jun. 30, 2008, database: asinex ltd.: XP002717311. [Database Accession No. 1031854-71-3].
Database Registry [Online]. Chemical Abstracts Service, Columbus, Ohio, May 27, 2008, database: asinex ltd.: XP002717312. Database Accession No. 1022944-01-9.

(Continued)

*Primary Examiner* — Rebecca Anderson
(74) *Attorney, Agent, or Firm* — Foley & Lardner LLP

(57) ABSTRACT

Novel p53-Mdm2 antogonists that conform to Formula I or to Formula II:

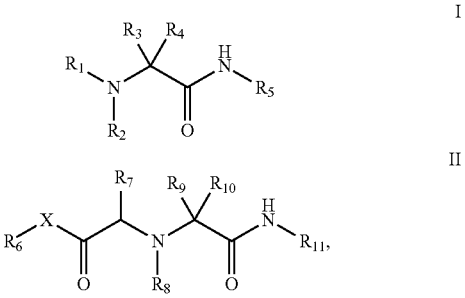

where the prescribed substituent groups are defined, are useful in treating or preventing cancer. In particular, the compounds and their pharmaceutical compositions are useful for treating relapsed/refractory acute myeloid and lymphoid leukemia and refractory chronic lymphocytic leukemia/small cell lymphocytic lymphomas.

20 Claims, 6 Drawing Sheets

(56) References Cited

OTHER PUBLICATIONS

Database Registry [Online]. Chemical Abstracts Service, Columbus, Ohio, Mar. 20, 2008, database: zinc (shoichet laboratory): XP002717313. [Database Accession No. 1009278-67-4]/.
Database Registry [Online]. Chemical Abstracts Service, Columbus, Ohio, Feb. 21, 2008, database: zinc (shoichet laboratory): XP002717314. [Database Accession No. 1004887-90-4].
Astrid Pernet-Poil-Chevrier, et al., "New Chiral Nitrones as Precursors of α,α-disubstituted amino-acids, according to the SRS Principle," *Tetrahedron: Asymmetry* 17, (2006), pp. 1969-1974.
Database Registry [Online]. Chemical Abstracts Service, Columbus, Ohio, Jan. 12, 2009, chemical library; supplier: akos consulting and solutions gmbh: XP002717306. [Database Accession No. 1093186-02-7].
Database Registry [Online]. Chemical Abstracts Service, Columbus, Ohio, Aug. 28, 2008, database: chemdb (University of California Irvine): XP002717309. [Database Accession No. 1039682-80-8].
Database Registry [Online]. Chemical Abstracts Service, Columbus, Ohio, Jul. 7, 2008, database: asinex ltd.: XP002717308. [Database Accession No. 1032864-97-3].
Supplemental European Search Report issued in related European Patent Application No. 11823879, dated Jan. 8, 2014.
CCP4 (Collaborative Computational Project, No. 4), "The CCP4 Suite: Programs for Protein Crystallagraphy", Acta Crystallogr. D. Biol. Crystallogr., 1994, 50, 760-763.
Czarna, A. et al., "Robust Generation of Lead Compounds for Protein-Protein Interactions by Computational and MCR Chemistry: p53/Hdm2 Antagonists", Agnew. Chem. Int. Ed 2010, 49, 5352-5356.
Ding, KE et al., "Structure-Based Design of Potent Non-Peptide MDM2 Inhibitors", Journal of American Chemical Society 2005, vol. 127, pp. 10130-10131. See abstract, figure 1, scheme 1.
D'Silva, L. et al., "Monitoring the Effects of Antagonists on Protein-Protein Interactions with NMR Spectroscopy", J. Am. Chem. Soc. 2005, 127, 13220-13226.
Duncan, Sara J. et al., "Isolation and Structure Elucidation of Chlorofusin. a Novel p53-MDM2 Antagonist from a Fusarium sp.", Journal of American Chemical Society 2001, vol. 123, pp. 554-560. See abstract. figures 1-5, conclusion.
Fry, D.C. et al., "Targeting protein-protein interactions for cancer therapy", J. Mol. Med 2005, 83, 955-963.
Kohn, Harold et al., "Preparation and Anticonvulsant Activity of a Series of Functionalized a-Aromatic and a-Heteroaromatic Amino Acids" Journal of Medicinal Chemistry 1990, vol. 33, pp. 919-926. See abstract, table I-III.
Mori, S. et al., "Improved Sensitivity of HSQC Spectra of Exchanging Protons at Short Interscan Delays Using a New Fast HSQC (FHSQC) Detection Scheme That Avoids Water Saturation", J. Magn. Reson. B 1995, 108, 94-98.
PCT/US2011/001553 International Search Report, mailed Apr. 30, 2012.
Perrakis, A. et al., "Automated protein model building combined with iterative structure refinement", Nature Struct. Biol. 1999, 6: 458-463.
Popowicz, G.M. et al., "Molecular Basis for the Inhibition of p53 by Mdmx", Cell Cycle. 2007, 6, 2386-2392.
Popowicz, G.M. et al., "The Structure-Bawsed Design of Mdm2/Mdmx-p53 Inhibitors Gets Serious", Angew. Chem. Int. Ed. 2011, 50, 2680-2688.
Singh, Jasbir et al., "CRelationship Between Structure and Bioavailability in a Series of Hydroxamate Based Metalloprotease Inhibitors", Bioorganic & Medicinal Chemistry Letters 1995, vol. 5, No. 4, pp. 337-342. See abstract, figures 1-4, tables 2-4.

* cited by examiner

P53-MDM2 ANTAGONISTS

CROSS-REFERENCE TO RELATED PATENT APPLICATIONS

This application is a national phase of international application PCT/US2011/001553, filed Sep. 8, 2011, and published as WO 2012/033525 on Mar. 15, 2012, which claims the benefit of U.S. provisional application No. 61/381,038, filed Sep. 8, 2010. The respective contents of these applications are incorporated herein by reference in their entirety.

BACKGROUND OF THE INVENTION

The protein-protein interaction (PPI) between the transcription factor p53 and its negative regulator Mdm2 is a major target in current cancer drug discovery. Disrupting the interaction between p53 and Mdm2 was shown to restore the wild type p53 activity and drive cancer cells selectively into apoptosis.[1] Many investigations of small molecule p53-Mdm2 antagonists in different cancer cell lines and animal models support their usefulness as potential anticancer agents with a novel mode-of-action. While several classes of small molecule p53-Mdm2 antagonists have been described in the literature, only a few compounds are of sufficient potency and have been structurally characterized. See Czarna, A.; Beck, B.; Srivastava, S.; Popowicz, G. M.; Wolf, S.; Huang, Y.; Bista, M.; Holak, T. A.; Dömling, A. *Angew. Chem. Int. Ed.* 2010, 49, 5352-5356, and Popowicz, G. M.; Dömling, A.; Holak, T. A., *Angew. Chem. Int. Ed* 2011, 50, 2680-2688.

Protein-protein interaction antagonists are described to be challenging targets for small molecule drug discovery due to their often extended and rather flat interfaces. However, the interface between p53 and Mdm2 is accessible to small molecules based on its dimension, concavity and hydrophobicity of the binding site. See Fry, D.; Vassilev, L. *J. Mol. Med.* 2005, 83, 955-963. While p53-Mdm2 antagonists have been discovered by different analytical techniques, including high throughput screening (HTS), computational HTS and structure-based design, the present inventors used of a web-based and structure-based design tool, "ANCHOR.QUERY," which led to the discovery and optimization of new potent p53-Mdm2 antagonists, based on the Ugi multicomponent reaction.

SUMMARY OF THE INVENTION

The present invention relates to novel, small-molecule antagonists of the p53-Mdm2 complex, which antagonists are according to Formulae I and II. Pursuant to one embodiment, Formula I compounds are provided, along with their stereoisomers, tautomers, and pharmaceutically acceptable salts and esters thereof.

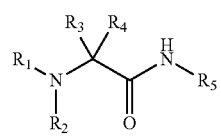

I

In Formula I, substituent $R_1$ and $R_2$ are each independently selected from the group consisting of hydrogen, straight or branched chain $(C_1\text{-}C_6)$alkyl, $(C_3\text{-}C_{14})$aryl, formyl, acetyl, benzyl, $(C_3\text{-}C_{14})$aryl$(C_1\text{-}C_6)$alkylene-, —C(O)— $(C_1\text{-}C_6)$alkyl, $(C_3\text{-}C_{14})$heteroaryl-$(C_1\text{-}C_6)$alkylene-, and $(C_3\text{-}C_{14})$heterocycloalkyl-$(C_1\text{-}C_6)$alkylene-.

Substituent $R_3$ is an optionally substituted indole, such as

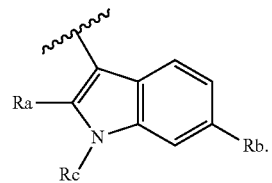

When the indole is substituted $R_a$ is selected from the group consisting of hydrogen, —C(O)R', and —C(O)OR', substituent $R_b$ is hydrogen, Cl, Br, or F and $R_c$ is H or —C(O)OR$^d$.

When $R_c$ is —C(O)OR$^d$, $R^d$ is hydrogen or straight or branched chain $(C_1\text{-}C_6)$alkyl.

Substituent $R_4$ is hydrogen and $R_5$ is selected from the group consisting of straight or branched chain $(C_1\text{-}C_6)$alkyl, $(C_3\text{-}C_{14})$aryl, benzyl, $(C_3\text{-}C_{14})$aryl$(C_1\text{-}C_6)$alkylene-, $(C_3\text{-}C_{14})$cycloalkyl, and $(C_3\text{-}C_{14})$heteroaryl-$(C_1\text{-}C_6)$alkylene-.

For Formula I compounds any alkyl, benzyl, aryl, $(C_3\text{-}C_{14})$aryl$(C_1\text{-}C_6)$alkylene-, heteroaryl, cycloalkyl, $(C_3\text{-}C_{14})$heteroaryl-$(C_1\text{-}C_6)$alkylene-, or heterocycloalkyl is optionally substituted with one or more members selected from the group consisting of —OH, —Cl, —F, —Br, —I, -oxy$(C_3\text{-}C_{14})$aryl, $(C_1\text{-}C_6)$alkyl, $(C_3\text{-}C_{14})$aryl, $(C_3\text{-}C_{14})$heteroaryl, $(C_3\text{-}C_{14})$aryl$(C_1\text{-}C_6)$alkylene-, $(C_3\text{-}C_{14})$heterocycloalkyl-$(C_1\text{-}C_6)$alkylene-, —C(O)R', —C(O)OR', and oxo.

Substituent R' is selected from the group consisting of hydrogen, straight or branched chain $(C_1\text{-}C_6)$alkyl, —NH—(OH), —NH—$(C_1\text{-}C_6)$alkylene-$(C_3\text{-}C_{14})$heteroaryl, —$(C_3\text{-}C_{14})$heterocycloalkylene-N(R")(R'''), —NH—$(C_1\text{-}C_6)$alkylene-OR$^e$, —NH—$(C_1\text{-}C_6)$alkylene-N(R")(R''') and —$(C_1\text{-}C_6)$alkylene-OH, while R" and R''' are each independently selected from the group consisting of hydrogen, straight or branched chain $(C_1\text{-}C_6)$alkyl, and —$(C_1\text{-}C_6)$alkylene-OH, —$(C_1\text{-}C_6)$alkylene-N(R$^f$)(R$^g$).

Alternatively, R" and R''' together with the nitrogen atom to which they are bonded form a an aryl ring, a saturated or unsaturated $(C_3\text{-}C_{14})$ cyclic structure that optionally has 1-3 heteroatoms selected from —N, —S, or —O; and Substituents R$^e$, R$^f$, and R$^g$, are each independently hydrogen or straight or branched chain $(C_1\text{-}C_6)$alkyl.

For certain Formula I compounds substituent R$^b$ is chlorine, R$^a$ is hydrogen, —C(O)R', or —C(O)OR' and R$^c$ is hydrogen. In one embodiment, R$^a$ is —C(O)OR' and R' is either a hydrogen or an ethyl.

In another embodiment, the present invention provides Formula I compounds in which R$^a$ is —C(O)R' and R' is —NH—$(C_1\text{-}C_6)$alkylene-$(C_3\text{-}C_{14})$heteroaryl, such as a

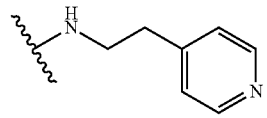 [SMILES: *NCCc1ccncc1]

group. Alternatively, R' is a —$(C_3\text{-}C_{14})$heterocycloalkylene-N(R")(R''') moiety, for example, substituent R' is a

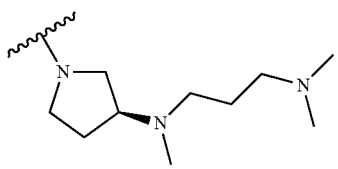 [SMILES: *N1CC[C@H](N(C)CCCN(C)C)C1]

group.

Also provided compounds, pursuant to another embodiment of the invention, are compounds that conform to Formula II, as well as stereoisomers, tautomers, and pharmaceutically acceptable salts and esters thereof.

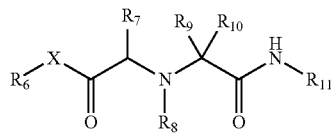

In Formula II, substituent X is —(O)—, or —NH—.

Substituent $R_6$ is selected from the group consisting of hydrogen, straight or branched chain ($C_1$-$C_6$)alkyl, —NH—(OH), and —OH and $R_7$ is hydrogen or straight or branched chain —($C_1$-$C_6$)alkyl.

Substituents $R_8$ and $R_{10}$ are hydrogens, and substituent $R_9$ in Formula II is an optionally substituted indole depicted structurally as

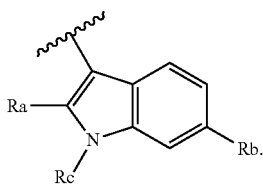

When the indole is substituted, $R_a$ is selected from the group consisting of hydrogen, —C(O)R', and —C(O)OR', $R_b$ is hydrogen, Cl, Br, or F and $R_c$ is H or —C(O)OR$^d$.

In one embodiment $R^d$ is hydrogen. Alternatively, $R^d$ is a straight or branched chain ($C_1$-$C_6$)alkyl.

Substituent $R_{11}$ in Formula II is selected from the group consisting of straight or branched chain ($C_1$-$C_6$)alkyl, ($C_3$-$C_{14}$)aryl, benzyl, ($C_3$-$C_{14}$)aryl($C_1$-$C_6$)alkylene-, ($C_3$-$C_{14}$)cycloalkyl, and ($C_3$-$C_{14}$)heteroaryl-($C_1$-$C_6$)alkylene-.

Any alkyl, benzyl, aryl, ($C_3$-$C_{14}$)aryl($C_1$-$C_6$)alkylene-, heteroaryl, cycloalkyl, or heterocycloalkyl in Formula II is optionally substituted with one or more members selected from the group consisting of —OH, —Cl, —F, —Br, —I, -oxy($C_3$-$C_{14}$)aryl, ($C_1$-$C_6$)alkyl, ($C_3$-$C_{14}$)aryl, ($C_3$-$C_{14}$)heteroaryl, ($C_3$-$C_{14}$)aryl($C_1$-$C_6$)alkylene-, ($C_3$-$C_{14}$)heterocycloalkyl-($C_1$-$C_6$)alkylene-, —C(O)R', —C(O)OR', and oxo.

When substituent groups —C(O)R', or —C(O)OR' are present, R' is selected from the group consisting of hydrogen, straight or branched chain ($C_1$-$C_6$)alkyl, —NH—(OH), —NH—($C_1$-$C_6$)alkylene-($C_3$-$C_{14}$)heteroaryl, and —($C_1$-$C_6$)alkylene-OH.

According to an embodiment of the invention, a Formula II compound is provided where substituent $R_{11}$ is benzyl, variable X is —(O) and $R_6$ is hydrogen or —($C_1$-$C_6$)alkyl.

According to an embodiment for Formula II compounds, substituent $R_{11}$ is benzyl, X is —NH— and $R_6$ is —($C_1$-$C_6$) alkyl or a group selected from

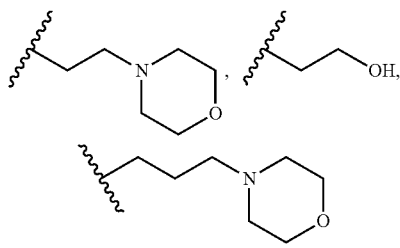

and NH(OH).

DETAILED DESCRIPTION OF THE PREFERRED EMBODIMENTS

Figure 1:
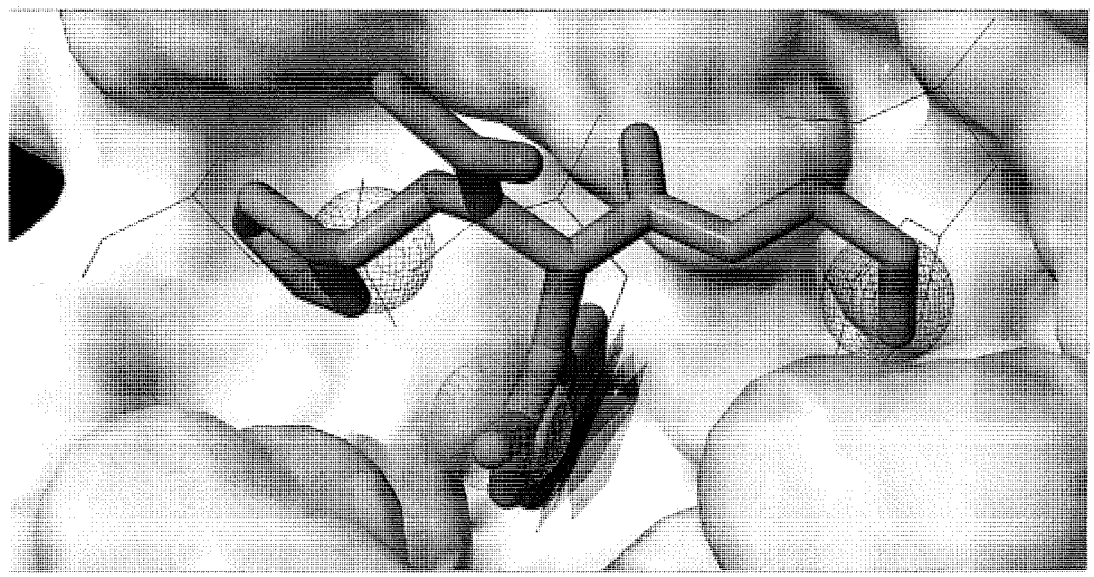
FIG. 1 illustrates a screenshot of pharmacophore-based virtual screening platform ANCHOR.QUERY, related to discovery of MCR-derived Mdm2 antagonists. The Mdm2 receptor is shown in surface representation (PDB ID: 1YCR). The hot spot p53 derived amino acids Phe19 and Leu26 are shown as lines and green spheres and the Trp23 indole anchor as yellow disk. The virtual Ugi-4-component reaction (U-4CR) product is depicted as grey sticks.

The compounds of the invention are antagonist of p53-Mdm2 interactions. Thus, inventive compounds that conform to Formula I and their pharmaceutical compositions are useful in treating or preventing cancer. In particular, they are useful for the treatment of patients with relapsed/refractory acute myeloid and lymphoid leukemia and refractory chronic lymphocytic leukemia/small cell lymphocytic lymphomas.

DEFINITIONS

Unless indicated otherwise, the terms and phrases used in this description have the following meanings:

"Alkyl" refers to straight, branched chain, or cyclic hydrocarbyl groups including from 1 to about 20 carbon atoms. For instance, an alkyl can have from 1 to 10 carbon atoms or 1 to 6 carbon atoms. Exemplary alkyl includes straight chain alkyl groups such as methyl, ethyl, propyl, butyl, pentyl, hexyl, heptyl, octyl, nonyl, decyl, undecyl, dodecyl, and the like, and also includes branched chain isomers of straight chain alkyl groups, for example without limitation, —CH($CH_3$)$_2$, —CH($CH_3$)($CH_2CH_3$), —CH($CH_2CH_3$)$_2$, —C($CH_3$)$_3$, —C($CH_2CH_3$)$_3$, —CH$_2$CH($CH_3$)$_2$, —CH$_2$CH($CH_3$)

(CH$_2$CH$_3$), —CH$_2$CH(CH$_2$CH$_3$)$_2$, —CH$_2$C(CH$_3$)$_3$—CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_3$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, and the like. Thus, alkyl groups include primary alkyl groups, secondary alkyl groups, and tertiary alkyl groups.

The phrase "substituted alkyl" refers to alkyl substituted at one or more positions, for example, 1, 2, 3, 4, 5, or even 6 positions, which substituents are attached at any available atom to produce a stable compound, with substitution as described herein. "Optionally substituted alkyl" refers to alkyl or substituted alkyl.

Each of the terms "halogen," "halide," and "halo" refers to —F, —Cl, —Br, or —I.

The terms "alkylene" and "substituted alkylene" refer to divalent alkyl and divalent substituted alkyl, respectively. Examples of alkylene include without limitation, ethylene (—CH$_2$—CH$_2$—). "Optionally substituted alkylene" refers to alkylene or substituted alkylene.

"Alkene" refers to straight, branched chain, or cyclic hydrocarbyl groups including from 2 to about 20 carbon atoms having 1-3, 1-2, or at least one carbon to carbon double bond. "Substituted alkene" refers to alkene substituted at 1 or more, e.g., 1, 2, 3, 4, 5, or even 6 positions, which substituents are attached at any available atom to produce a stable compound, with substitution as described herein. "Optionally substituted alkene" refers to alkene or substituted alkene.

The term "alkenylene" refers to divalent alkene. Examples of alkenylene include without limitation, ethenylene (—CH═CH—) and all stereoisomeric and conformational isomeric forms thereof. "Substituted alkenylene" refers to divalent substituted alkene. "Optionally substituted alkenylene" refers to alkenylene or substituted alkenylene.

"Alkyne or "alkynyl" refers to a straight or branched chain unsaturated hydrocarbon having the indicated number of carbon atoms and at least one triple bond. An alkynyl group can be unsubstituted or optionally substituted with one or more substituents as described herein below.

The term "alkynylene" refers to divalent alkyne. Examples of alkynylene include without limitation, ethynylene, propynylene. "Substituted alkynylene" refers to divalent substituted alkyne.

The term "alkoxy" refers to an —O-alkyl group having the indicated number of carbon atoms. For example, a (C$_1$-C$_6$) alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "aryl," alone or in combination refers to an aromatic monocyclic or bicyclic ring system having three to fourteen carbon atoms, such as phenyl or naphthyl. "Aryl" also includes aromatic ring systems that are optionally fused with a cycloalkyl ring, as herein defined.

A "substituted aryl" is an aryl that is independently substituted with one or more substituents attached at any available atom to produce a stable compound, wherein the substituents are as described herein. "Optionally substituted aryl" refers to aryl or substituted aryl.

"Arylene" denotes divalent aryl, and "substituted arylene" refers to divalent substituted aryl. "Optionally substituted arylene" refers to arylene or substituted arylene.

The term "heteroatom" refers to N, O, and S. Inventive compounds that contain N or S atoms can be optionally oxidized to the corresponding N-oxide, sulfoxide, or sulfone compounds.

"Heteroaryl," alone or in combination with any other moiety described herein, refers to a monocyclic aromatic ring structure containing 5 or 6 ring atoms, or a bicyclic aromatic group having 8 to 10 atoms, containing one or more, such as 1-4, 1-3, or 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or heteroatom is the point of attachment of the heteroaryl ring structure such that a stable compound is produced. Examples of heteroaryl groups include, but are not limited to, pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl.

A "substituted heteroaryl" is a heteroaryl that is independently substituted, unless indicated otherwise, with one or more, e.g., 1, 2, 3, 4 or 5, also 1, 2, or 3 substituents, also 1 substituent, attached at any available atom to produce a stable compound, wherein the substituents are as described herein. "Optionally substituted heteroaryl" refers to heteroaryl or substituted heteroaryl.

"Heteroarylene" refers to divalent heteroaryl, and "substituted heteroarylene" refers to divalent substituted heteroaryl. "Optionally substituted heteroarylene" refers to heteroarylene or substituted heteroarylene.

"Heterocycloalkyl" means a saturated or unsaturated non-aromatic monocyclic, bicyclic, tricyclic or polycyclic ring system that has from 5 to 14 atoms in which from 1 to 3 carbon atoms in the ring are replaced by heteroatoms of O, S or N. A heterocycloalkyl is optionally fused with benzo or heteroaryl of 5-6 ring members, and includes oxidized S or N, such as sulfinyl, sulfonyl and N-oxide of a tertiary ring nitrogen. The point of attachment of the heterocycloalkyl ring is at a carbon or heteroatom such that a stable ring is retained. Examples of heterocycloalkyl groups include without limitation morpholino, tetrahydrofuranyl, dihydropyridinyl, piperidinyl, pyrrolidinyl, piperazinyl, dihydrobenzofuryl, and dihydroindolyl.

"Optionally substituted heterocycloalkyl" denotes heterocycloalkyl that is substituted with 1 to 3 substituents, e.g., 1, 2 or 3 substituents, attached at any available atom to produce a stable compound, wherein the substituents are as described herein.

The term "cycloalkyl" refer to monocyclic, bicyclic, tricyclic, or polycyclic, 3- to 14-membered ring systems, which are either saturated, unsaturated or aromatic. The heterocycle may be attached via any atom. Cycloalkyl also contemplates fused rings wherein the cycloalkyl is fused to an aryl or hetroaryl ring as defined above. Representative examples of cycloalkyl include, but are not limited to cyclopropyl, cycloisopropyl, cyclobutyl, cyclopentyl, cyclohexyl, cyclopropene, cyclobutene, cyclopentene, cyclohexene, phenyl, naphthyl, anthracyl, benzofuranyl, and benzothiophenyl. A cycloalkyl group can be unsubstituted or optionally substituted with one or more substituents as described herein below.

The term "cycloalkylene" refers to divalent cycloalkylene. The term "optionally substituted cycloalkylene" refers to cycloalkylene that is substituted with 1 to 3 substituents, e.g., 1, 2 or 3 substituents, attached at any available atom to produce a stable compound, wherein the substituents are as described herein.

The term "nitrile or cyano" can be used interchangeably and refer to a —CN group which is bound to a carbon atom of a heteroaryl ring, aryl ring and a heterocycloalkyl ring.

The term "oxo" refers to a =O atom attached to a saturated or unsaturated ($C_3$-$C_8$) cyclic or a ($C_1$-$C_8$) acyclic moiety. The =O atom can be attached to a carbon, sulfur, and nitrogen atom that is part of the cyclic or acyclic moiety.

The term "amine or amino" refers to an —$NR^fR^g$ group wherein $R^f$ and $R^g$ each independently refer to a hydrogen, ($C_1$-$C_8$)alkyl, aryl, heteroaryl, heterocycloalkyl, ($C_1$-$C_8$)haloalkyl, and ($C_1$-$C_6$)hydroxyalkyl group.

The term "amide" refers to a —NR'R"C(O)— group wherein R' and R" each independently refer to a hydrogen, ($C_1$-$C_8$)alkyl, ($C_1$-$C_8$)alkylene-($C_3$-$C_6$)aryl, ($C_1$-$C_8$)alkylene-($C_3$-$C_6$)heteroaryl, or ($C_3$-$C_6$)aryl.

The term "carboxamido" refers to a —C(O)NR'R" group wherein R' and R" each independently refer to a hydrogen, ($C_1$-$C_8$)alkyl, ($C_1$-$C_8$)alkylene-($C_3$-$C_6$)aryl, ($C_1$-$C_8$)alkylene-($C_3$-$C_6$)heteroaryl, or ($C_3$-$C_6$)aryl.

The term "hydroxyalkyl," refers to an alkyl group having the indicated number of carbon atoms wherein one or more of the alkyl group's hydrogen atoms is replaced with an —OH group. Examples of hydroxyalkyl groups include, but are not limited to, —$CH_2OH$, —$CH_2CH_2OH$, —$CH_2CH_2CH_2OH$, —$CH_2CH_2CH_2CH_2OH$, —$CH_2CH_2CH_2CH_2CH_2OH$, —$CH_2CH_2CH_2CH_2CH_2CH_2OH$, and branched versions thereof.

The term "aminoalkyl," refers to an ($C_1$-$C_6$)alkyl group wherein one or more hydrogen atoms in the $C_1$-$C_6$ alkyl group is replaced with a —$NR^fR^g$ group, where $R^f$ and $R^g$ can be the same or different, for example, $R^f$ and $R^g$ each independently refer to a hydrogen, ($C_1$-$C_8$)alkyl, aryl, heteroaryl, heterocycloalkyl, ($C_1$-$C_8$)haloalkyl, and ($C_1$-$C_6$)hydroxyalkyl group. Examples of aminoalkyl groups include, but are not limited to, aminomethyl, aminoethyl, 4-aminobutyl and 3-aminobutylyl.

A "hydroxyl" or "hydroxy" refers to an —OH group.

The term "($C_3$-$C_{14}$)heteroaryl-($C_1$-$C_6$)alkylene" refers to a divalent alkylene wherein one or more hydrogen atoms in the $C_1$-$C_6$ alkylene group is replaced a ($C_3$-$C_{14}$)heteroaryl group. Examples of ($C_3$-$C_{14}$)heteroaryl-($C_1$-$C_6$)alkylene groups include without limitation 1-pyridylbutylene, quinolinyl-2-butylene and 1-pyridyl-2-methylpropylene.

The term "($C_3$-$C_{14}$)heterocycloalkyl-($C_1$-$C_6$)alkylene" refers to a divalent alkylene wherein one or more hydrogen atoms in the $C_1$-$C_6$ alkylene group is replaced by a ($C_3$-$C_{14}$)heterocycloalkyl group. Examples of ($C_3$-$C_{14}$)heterocycloalkyl-($C_1$-$C_6$)alkylene groups include without limitation 1-morpholinopropylene, azetidinyl-2-butylene and 1-tetrahydrofuranyl-2-methylpropylene.

The term "($C_3$-$C_{14}$)aryl-($C_1$-$C_6$)alkylene" refers to a divalent alkylene wherein one or more hydrogen atoms in the $C_1$-$C_6$ alkylene group is replaced a ($C_3$-$C_{14}$)aryl group. Examples of ($C_3$-$C_{14}$)aryl-($C_1$-$C_6$)alkylene groups include without limitation benzyl.

An "acetyl" group refers to —$C(O)CH_3$.

A "formyl" refers to —C(O)H.

The compound of the invention can exist in various isomeric forms, including configurational, geometric, and conformational isomers. Compounds of the present invention may also exist in one or more tautomeric forms, including both single tautomers and mixtures of tautomers. For instance, the inventive compounds can undergo keto to enol tautomerism, amide to imide tautomerism, lactam to lactim tautomerism and amine to imine tautomerism. The term "isomer" is intended to encompass all isomeric forms of a compound of this invention, including tautomeric forms of the compound.

The compounds of the present invention may also exist in open-chain or cyclized forms. In some cases one or more of the cyclized forms may result in loss of water. The specific composition of the open-chain and cyclized forms may be dependent on how the compound is isolated, stored or administered. For example the compound may exist primarily in an open-chained form under acidic conditions but cyclize under neutral conditions. All forms are included in the invention.

Some compounds described here can have asymmetric centers and therefore exist in different enantiomeric and diastereomeric forms. A compound of the invention can be in the form of an optical isomer or a diastereomer. Accordingly, the invention encompasses compounds of the invention and their uses as described herein in the form of their optical isomers, diastereoisomers and mixtures thereof, including a racemic mixture. Optical isomers of the compounds of the invention can be obtained by known techniques such as asymmetric synthesis, chiral chromatography, or via chemical separation of stereoisomers through the employment of optically active resolving agents.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

A "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts, such as the acetate, amsonate (4,4-diaminostilbene-2, 2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

A "patient" includes an animal, such as a human, cow, horse, sheep, lamb, pig, chicken, turkey, quail, cat, dog, mouse, rat, rabbit or guinea pig. The animal can be a mammal such as a non-primate and a primate (e.g., monkey and human). In one embodiment, a patient is a human, such as a human infant, child, adolescent or adult.

The terms "anchor" or "anchor residue" are defined as an amino acid side chain which is deeply buried within the protein-protein interaction interface.

Novel p53/Mdm2 Antagonists

Analysis of protein-protein interactions at the p53-Mdm2 interfaces informed the present inventor's conception of two new classes of small-molecule antagonists conforming to Formula I and Formula II, respectively.

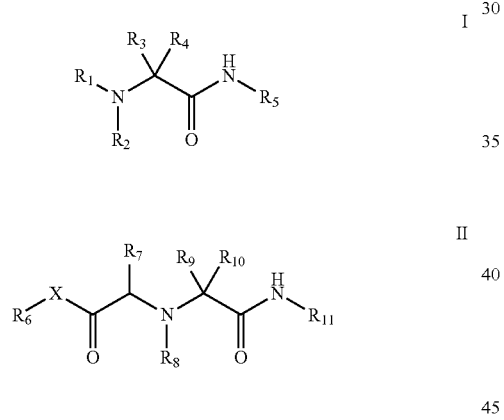

Based in part on the observation that the indole side chain of Trp23 is buried within Mdm2's pocket, a series of Formulae I and II compounds was prepared, which compounds possessed an optionally substituted indole ring. These compounds were tested for their ability to antagonize the p53-Mdm2 interaction.

The inventive compounds according to Formula I were synthesized using the Ugi four-component reaction (U-4CR). As shown in Scheme 1, an appropriately substituted 3-formylindole was used as a synthon for the ANCHOR group. A preliminary investigation of the Ugi reaction, using 3-formylindole (1), benzyl isocyanide, a primary amine (e.g., isobutylamine or benzylamine) and acetic acid, gave the desired condensation products 7a-b after stirring at room temperature for 2 days. The corresponding Boc-deprotected products 8a-b were obtained by the subsequent deprotection of 7a-b using a 10% solution of TFA in dichloromethane at room temperature, overnight.

Scheme 1. Ugi four-component reaction of 3-formylindoles

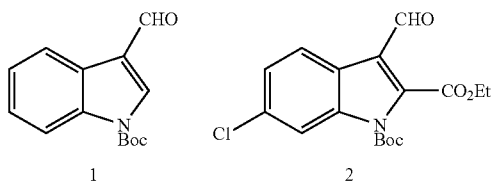

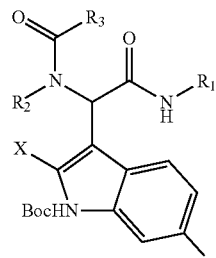

Method A:

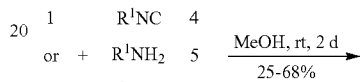

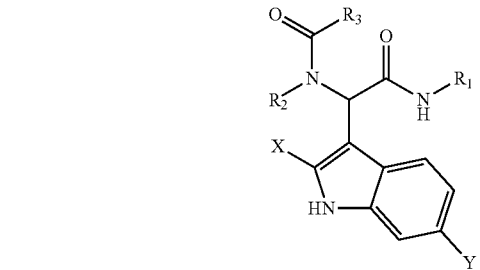

7a-b (X = H, Y = H)
7c-g (X = CO$_2$Et, Y = Cl)

8a-b (X = H, Y = H)
8c-g (X = CO$_2$Et, Y = Cl)

Method B:

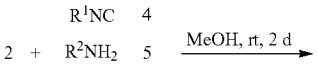

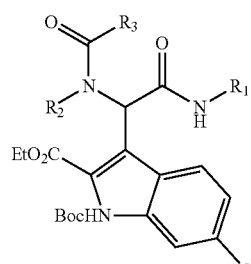

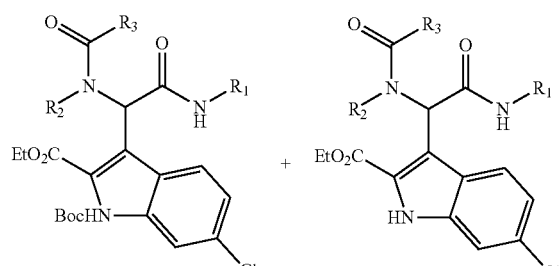

7h-i 8h-i

Method C:

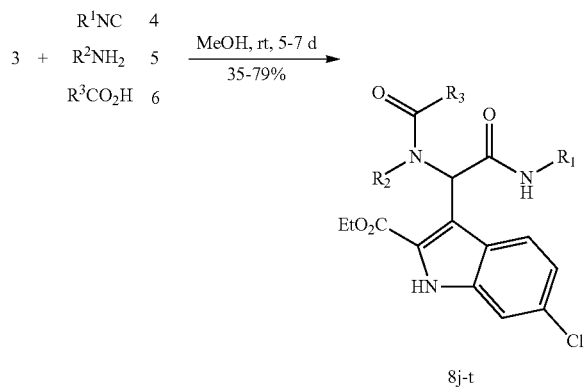

8j-t

The Ugi condensation protocol was varied to account for differences in reactivity of the different starting materials. See Scheme 1, methods A-C For instance, compounds 8c-g were synthesized using 3-formylindole 2 as the starting material and Method B as illustrated in Scheme 1. However, Boc-deprotected products 8h-i were formed when formic acid or butyric acid was used as the staring carboxylic acid (Method B, Scheme 1).

When the un-protected indole aldehyde 3 is used as the starting material, however, the reaction proceeds slowly. The final products were obtained after 5 days of stirring at room temperature with yields comparable to those obtained using Boc-protected 3-formylindole 2 the (Method C, Scheme 1).

Base catalyzed hydrolysis of indole derivatives 8 having an esterified carboxylic acid group at position-2 of the indole produced the corresponding free carboxylic acid analogs 9 (Method D, Scheme 2).

Scheme 2. Synthesis of indole-2-carboxylic acid derivatives 9

Method D:

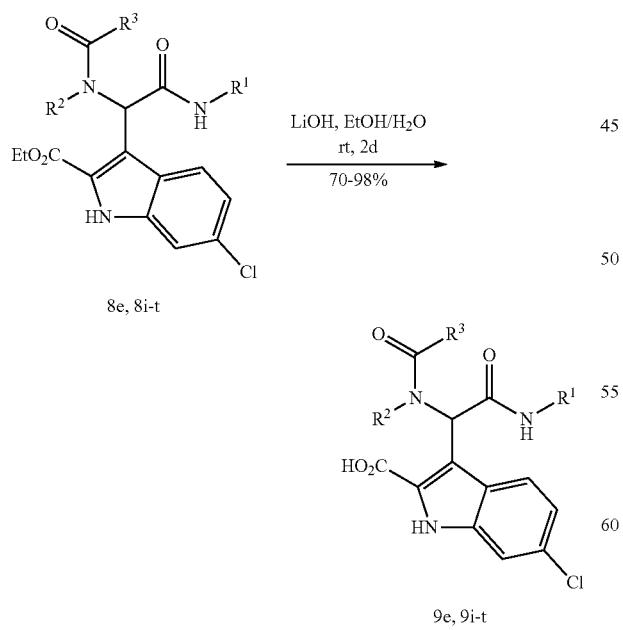

To evaluate the role of hydrogen bonding in binding, the present inventor used an inorganic acid to remove the —C(O) $R^3$ group of compounds synthesized using method (A)-(C) illustrated in Scheme 1 above. Thus, de-acylation using an inorganic acid, such as hydrochloric acid in dioxane, gave the corresponding secondary amines as illustrated for two exemplary compounds in Scheme 3. To enhance the solubility of Formula I compounds solubilizing substituents were introduced a C-2 of the indole ring.

Thus, compound 13 was synthesized as illustrated in Scheme 4 by coupling a primary amine to the carboxyl group at C-2 of the indole in compound 8e in the presence of 1,5,7-triazabicyclo[4,4,0]dec-5-ene (TBD) to give the corresponding amide. The transformation of the C-2 carboxyl group to an amide, however, lead to a decrease in the binding affinity by 2- to 3-fold.

Scheme 3:

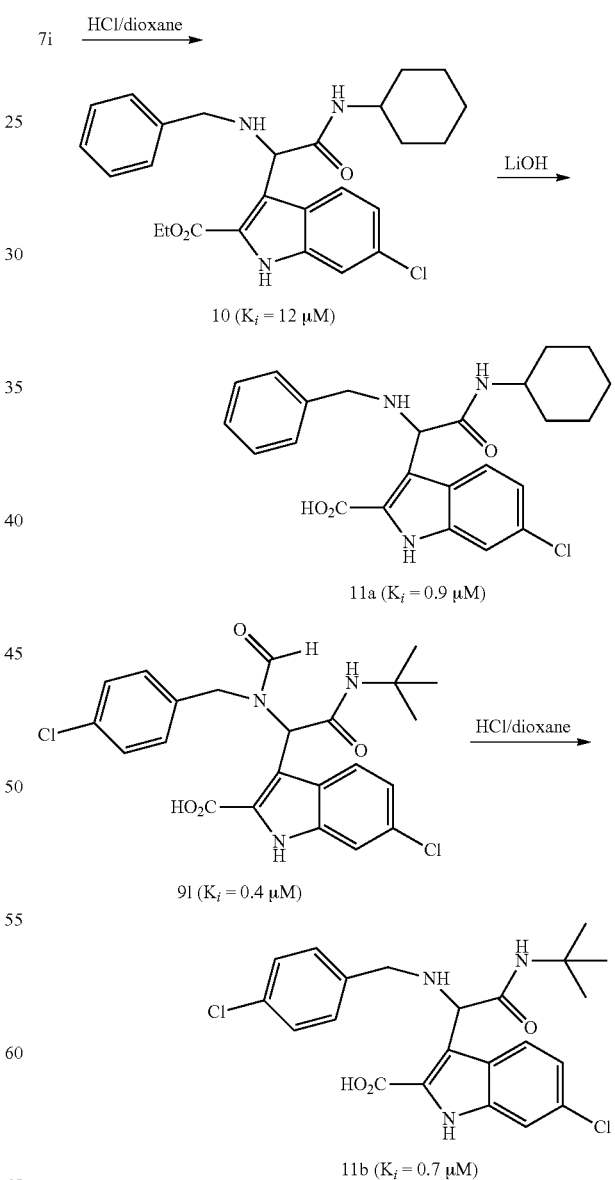

Scheme 4:

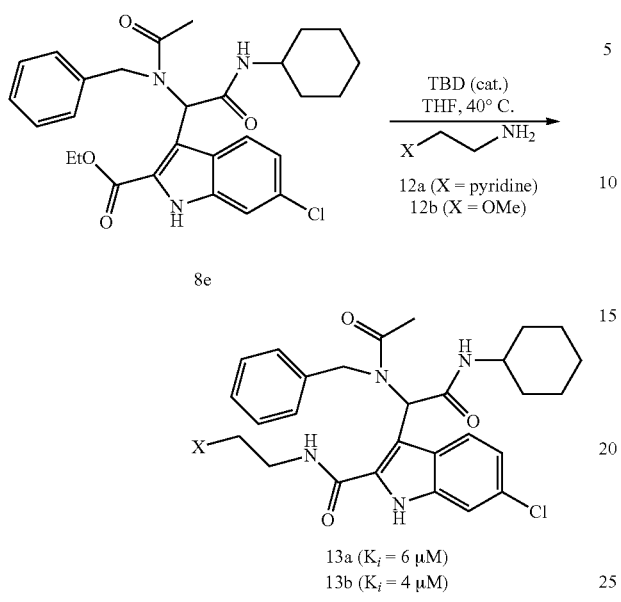

13a ($K_i$ = 6 μM)
13b ($K_i$ = 4 μM)

Binding Affinity of Formula I Compounds

Fluorescence polarization (FP) assay was employed to measure the binding affinities of small molecules with Mdm2. The Nutlin-3a a known antagonist of p53-Mdm2 interaction and having a Ki=0.04 μM for Mdm2 was as a control in the FP assays. Table 1 illustrates the value of inhibition constants ($K_i$'s) for various Formula I compounds.

The results from FP studies indicate that binding is enhanced by introduction of a hydrophobic residue at $R^2$ (See compound 8, Table 1). Enhanced binding is thought to be due to increased hydrophobic interactions between the substituent at $R^2$ in compound 8 which occupies the Leu26 pocket of Mdm2. Compound 8l was found as the most potent one in this series, which indicates the optimal combination of the fragments.

TABLE 1

SAR study of a Representative Formula I compound (8)

| ID | $R^1$ | $R^2$ | $R^3$ | Ki (μM)[1] |
|---|---|---|---|---|
| 8c | benzyl | isobutyl | Me | 4 |
| 8d | benzyl | benzyl | Me | 6 |
| 8e | cyclohexyl | benzyl | Me | 2 |
| 8f | cyclohexyl | 4-chlorobenzyl | Me | 22 |
| 8g | cyclohexyl | 3,4-dichlorobenzyl | Me | 9 |
| 8h | cyclohexyl | benzyl | $^n$Pr | 25 |
| 8i | cyclohexyl | benzyl | H | 14 |
| 8j | cyclohexyl | 4-chlorobenzyl | H | 50 |
| 8k | cyclohexyl | 4-fluorobenzyl | H | 30 |
| 8l | tert-butyl | 4-chlorobenzyl | H | 1.8 |

TABLE 1-continued

SAR study of a Representative Formula I compound (8)

| ID | R¹ | R² | R³ | Ki (μM)[1] |
|---|---|---|---|---|
| 8m | tert-butyl | 3,4-dichlorobenzyl | H | 4 |
| 8n | tert-butyl | 2,4-dichlorobenzyl | H | 10 |
| 8o | tert-butyl | (6-chloropyridin-3-yl)methyl | H | 2.7 |
| 8p | tert-butyl | (R)-1-(4-chlorophenyl)ethyl | H | n.i. |
| 8q | tert-butyl | (S)-1-(4-chlorophenyl)ethyl | H | 8 |
| 8r | tert-butyl | 4-hydroxybenzyl | H | 11 |
| 8s | tert-butyl | 4-phenylbenzyl | H | n.i. |
| 8t | tert-butyl | 4-phenoxybenzyl | H | n.i. |

[1]Inhibition constant (Ki) was measured by FP assay (SI).
The abbreviation n.i. stands for "no interaction".

Formula I compounds, such as analogs of compound 8 are, bind tightly to Mdm2 as illustrated by their low micromolar $K_i$ values. To illuminate the role of a free carboxylic acid residue at C-2 of indole, certain analogs of compound 8 were hydrolyzed, using aqueous basic conditions (Scheme 2). The binding constants ($K_i$ values) for Formula I compounds having a free carboxylic acid residue at C-2 of indole were determined by FP assay and are illustrated in Table 2.

TABLE 2

SAR study of a Representative Formula I Compound (9)

| ID | R¹ | R² | R³ | Ki (μM)[1] |
|---|---|---|---|---|
| 9e | cyclohexyl | benzyl | Me | 1.6 |
| 9i | cyclohexyl | benzyl | H | 1.6 |
| 9j | cyclohexyl | 4-chlorobenzyl | Me | 2.3 |
| 9k | cyclohexyl | 4-fluorobenzyl | H | n.d. |
| 9l | tert-butyl | 4-chlorobenzyl | H | 0.4 |
| 9m | tert-butyl | 3,4-dichlorobenzyl | H | 0.6 |
| 9n | tert-butyl | 2,4-dichlorobenzyl | H | 0.5 |

TABLE 2-continued

SAR study of a Representative Formula I Compound (9)

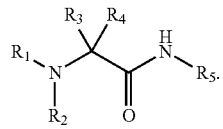

| ID | R[1] | R[2] | R[3] | Ki (μM)[1] |
|---|---|---|---|---|
| 9o | tert-butyl | (6-chloropyridin-3-yl)methyl | H | 4 |
| 9p | tert-butyl | 1-(4-chlorophenyl)ethyl | H | 10.5 |
| 9q | tert-butyl | 1-(4-chlorophenyl)ethyl (stereo) | H | 0.9 |
| 9r | tert-butyl | 4-hydroxybenzyl | H | 11 |
| 9s | tert-butyl | 4-phenylbenzyl | H | 2.5 |
| 9t | tert-butyl | 4-phenoxybenzyl | H | 1.8 |

[1]Inhibition constant (Ki) was measured by FP assay (SI).
The abbreviation n.d. stands for "not determined".

As the data in Table 2 illustrate, hydrolysis of the ester improved binding interactions with Mdm2 as indicated by the lower $K_i$ values for analogs of compound 9. Compound 9l showed greatest potency with a $K_i$ value in the sub-micromolar range. Preparative supercritical fluid chromatography (SFC) was employed to separate the two enantiomers of compound 9l. The enantiomer (+) 9l ($K_i$=300 nM) proved more potent than enantiomer (−) 9l ($K_i$=700 nM). Compound 9l also showed good water solubility (1.3 mg/ml), indicating that Formula I compounds possess drug-like properties and, hence, are candidate therapeutics for treatment of diseases such as cancer.

As noted, the present invention provides compounds in accordance with Formula I

I

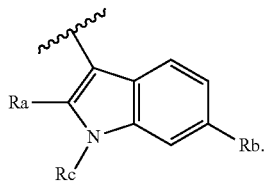

In this context, $R_1$ and $R_2$ of a Formula I compound are each independently selected from the group consisting of hydrogen, straight or branched chain ($C_1$-$C_6$)alkyl, ($C_3$-$C_{14}$)aryl, formyl, acetyl, benzyl, ($C_3$-$C_{14}$)aryl($C_1$-$C_6$)alkylene-, —C(O)— ($C_1$-$C_6$)alkyl, ($C_3$-$C_{14}$)heteroaryl-($C_1$-$C_6$)alkylene-, and ($C_3$-$C_{14}$)heterocycloalkyl-($C_1$-$C_6$)alkylene-.

Substituent $R_3$ is a substituted indole, such as

[indole structure with Ra, Rb, Rc substituents]

In one embodiment the indole each of $R_a$, $R_b$ and $R_c$ are hydrogens. In some embodiments substituent group $R_a$ is selected from the group consisting of hydrogen, —C(O)R', and —C(O)OR', substituent group $R_b$ is hydrogen, Cl, Br, or F and $R_c$ is H or —C(O)OR$^d$.

Substituent $R^d$ is hydrogen or straight or branched chain ($C_1$-$C_6$)alkyl.

Substituent $R_5$ is selected from the group consisting of straight or branched chain ($C_1$-$C_6$)alkyl, ($C_3$-$C_{14}$)aryl, benzyl, ($C_3$-$C_{14}$)aryl($C_1$-$C_6$)alkylene-, ($C_3$-$C_{14}$)cycloalkyl, and ($C_3$-$C_{14}$)heteroaryl-($C_1$-$C_6$)alkylene-.

For Formula I compounds, any alkyl, benzyl, aryl, ($C_3$-$C_{14}$)aryl($C_1$-$C_6$)alkylene-, heteroaryl, cycloalkyl, ($C_3$-$C_{14}$) heteroaryl-($C_1$-$C_6$)alkylene-, or heterocycloalkyl is optionally substituted with one or more members selected from the group consisting of —OH, —Cl, —F, —Br, —I, -oxy($C_3$-$C_{14}$)aryl, ($C_1$-$C_6$)alkyl, ($C_3$-$C_{14}$)aryl, ($C_3$-$C_{14}$)heteroaryl, ($C_3$-$C_4$)aryl($C_1$-$C_6$)alkylene-, ($C_3$-$C_{14}$)heterocycloalkyl-($C_1$-$C_6$)alkylene-, —C(O)R', —C(O)OR', and oxo.

For Formula I compounds having a —C(O)R', or —C(O) OR' substituent groups, R' is selected from the group consisting of hydrogen, straight or branched chain ($C_1$-$C_6$)alkyl, —NH—(OH), —NH—($C_1$-$C_6$)alkylene-($C_3$-$C_{14}$)heteroaryl, —($C_3$-$C_{14}$)heterocycloalkylene-N(R")(R'''), —NH—($C_1$-$C_6$)alkylene-OR$^e$, —NH—($C_1$-$C_6$)alkylene-N (R')(R''') and —($C_1$-$C_6$)alkylene-OH.

Substituent R" and R''' are each independently selected from the group consisting of hydrogen, straight or branched chain ($C_1$-$C_6$)alkyl, and —($C_1$-$C_6$)alkylene-OH, —($C_1$-$C_6$) alkylene-N(R$^f$)(R$^g$), or R' and R''' together with the nitrogen atom to which they are bonded form a an aryl ring, a saturated or unsaturated ($C_3$-$C_{14}$) cyclic structure that optionally has 1-3 heteroatoms selected from —N, —S, or —O, while R$^e$, R$^f$, and R$^g$, are each independently hydrogen or straight or branched chain ($C_1$-$C_6$)alkyl.

The category of Formula I compounds includes without limitation the compounds identified in Table 3 below. While some of these exemplary compounds are depicted with stereochemistry, it should be understood that the invention encompasses all possible stereoisomers of the compounds, such as diastereomers.

TABLE 3
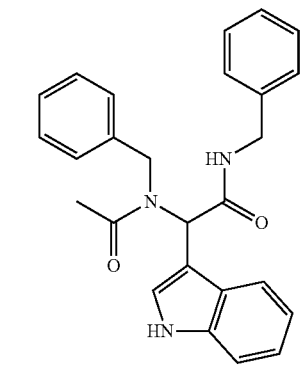 [SMILES: CC(=O)N(Cc1ccccc1)C(C(=O)NCc1ccccc1)c1c[nH]c2ccccc12]
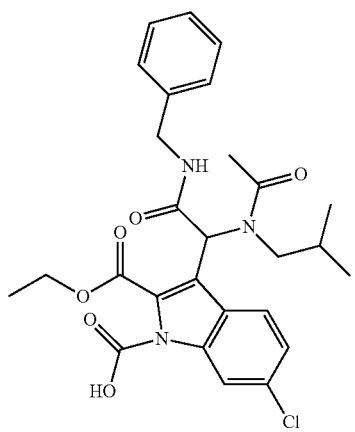 [SMILES: CCOC(=O)c1c(C(C(=O)NCc2ccccc2)N(CC(C)C)C(C)=O)c2ccc(Cl)cc2n1C(=O)O]
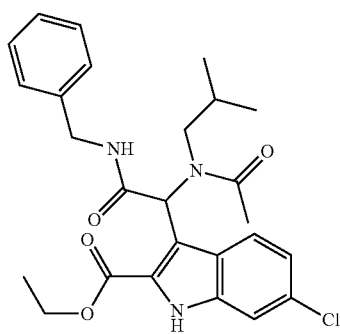 [SMILES: CCOC(=O)c1[nH]c2cc(Cl)ccc2c1C(C(=O)NCc1ccccc1)N(CC(C)C)C(C)=O]
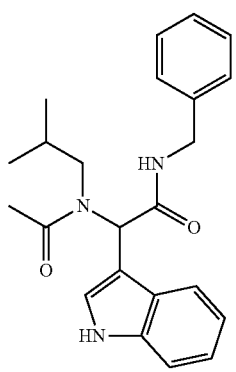 [SMILES: CC(=O)N(CC(C)C)C(C(=O)NCc1ccccc1)c1c[nH]c2ccccc12]
TABLE 3-continued
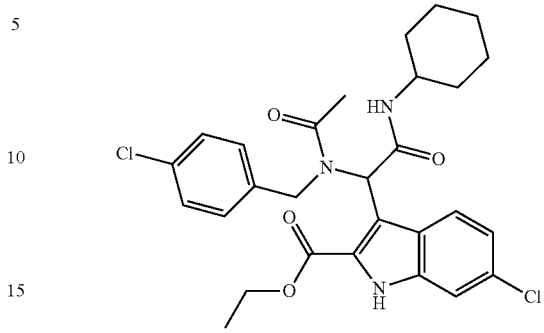
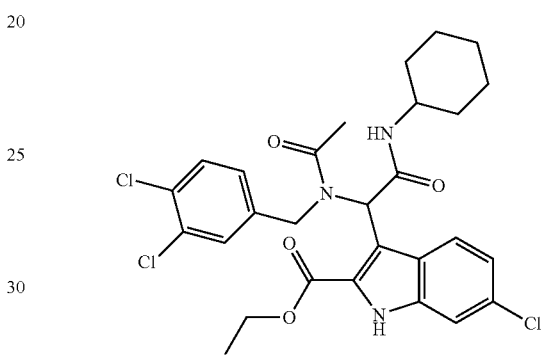
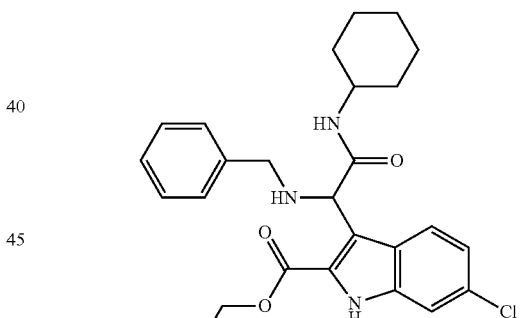
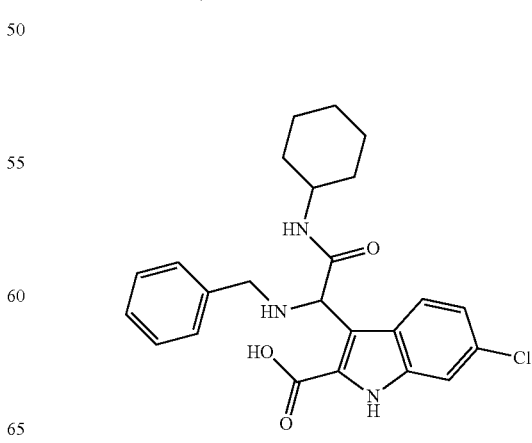

TABLE 3-continued
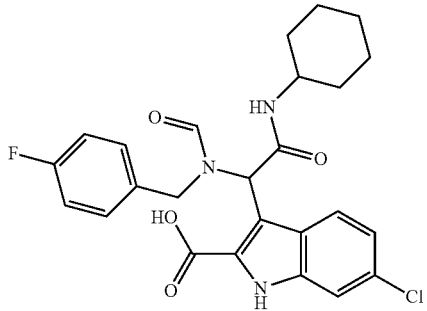 [SMILES: O=CN(Cc1ccc(F)cc1)C(C(=O)NC1CCCCC1)c1c(C(=O)O)[nH]c2cc(Cl)ccc12]
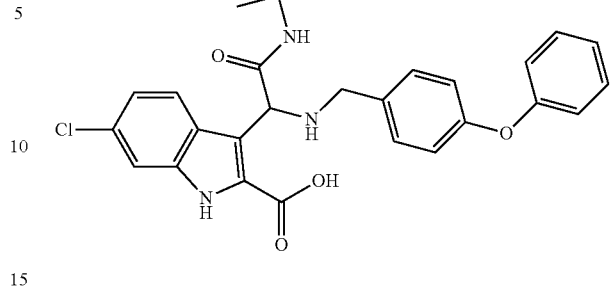
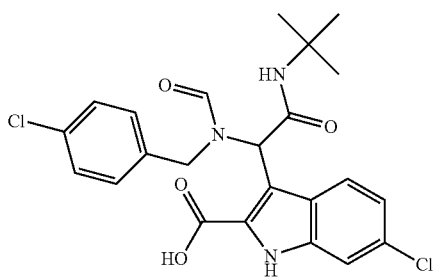 [SMILES: CC(C)(C)NC(=O)C(c1c(C(=O)O)[nH]c2cc(Cl)ccc12)N(C=O)Cc1ccc(Cl)cc1]
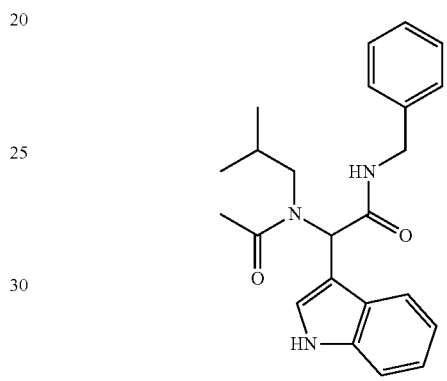
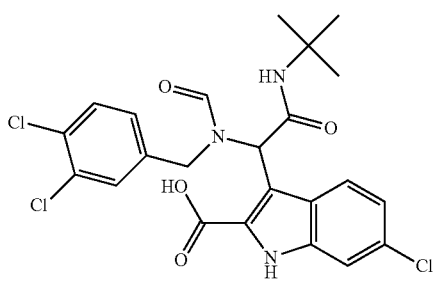 [SMILES: CC(C)(C)NC(=O)C(c1c(C(=O)O)[nH]c2cc(Cl)ccc12)N(C=O)Cc1ccc(Cl)c(Cl)c1]
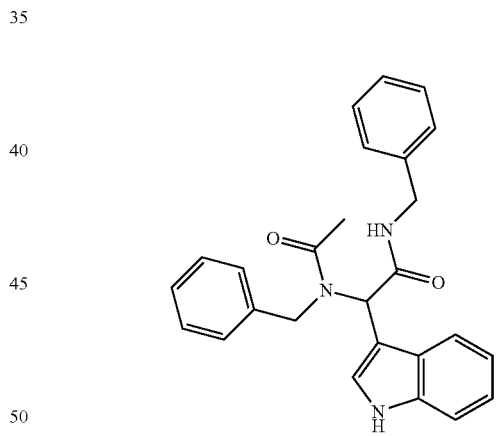
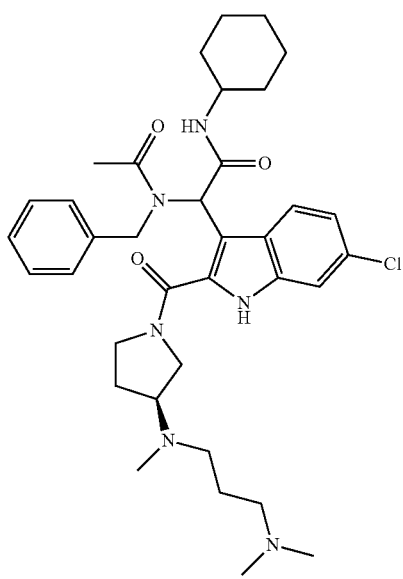 [SMILES: CC(=O)N(Cc1ccccc1)C(C(=O)NC1CCCCC1)c1c(C(=O)N2CC[C@H](N(C)CCCN(C)C)C2)[nH]c2cc(Cl)ccc12]
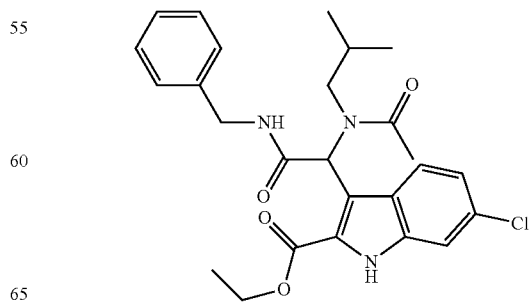

TABLE 3-continued
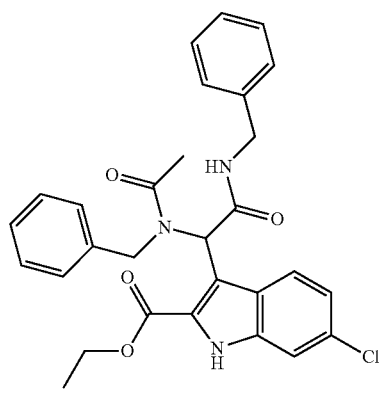 [SMILES: CCOC(=O)c1[nH]c2cc(Cl)ccc2c1C(C(=O)NCc1ccccc1)N(Cc1ccccc1)C(C)=O]
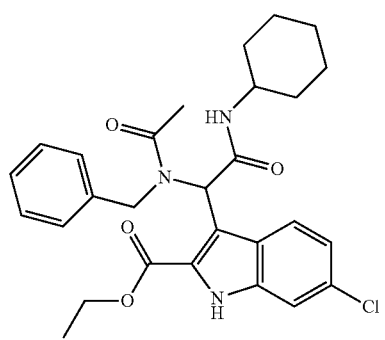 [SMILES: CCOC(=O)c1[nH]c2cc(Cl)ccc2c1C(C(=O)NC1CCCCC1)N(Cc1ccccc1)C(C)=O]
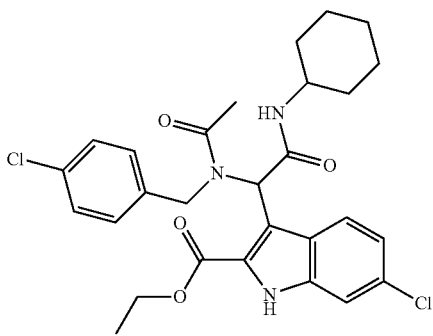 [SMILES: CCOC(=O)c1[nH]c2cc(Cl)ccc2c1C(C(=O)NC1CCCCC1)N(Cc1ccc(Cl)cc1)C(C)=O]
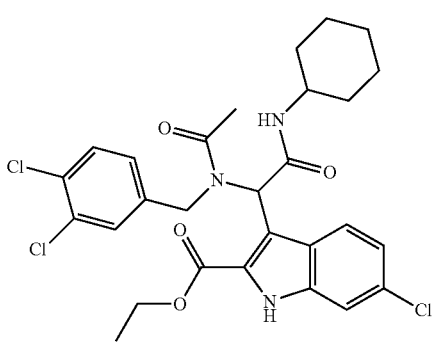 [SMILES: CCOC(=O)c1[nH]c2cc(Cl)ccc2c1C(C(=O)NC1CCCCC1)N(Cc1ccc(Cl)c(Cl)c1)C(C)=O]
TABLE 3-continued
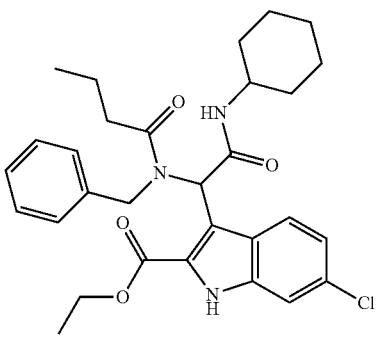 [SMILES: CCCC(=O)N(Cc1ccccc1)C(C(=O)NC1CCCCC1)c1c(C(=O)OCC)[nH]c2cc(Cl)ccc12]
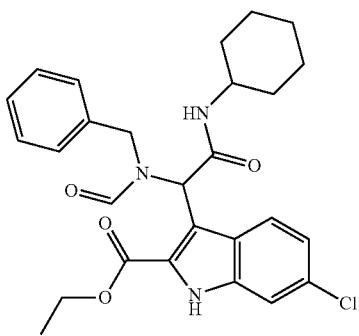 [SMILES: CCOC(=O)c1[nH]c2cc(Cl)ccc2c1C(C(=O)NC1CCCCC1)N(C=O)Cc1ccccc1]
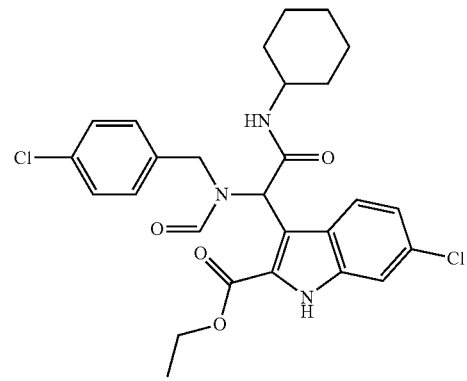 [SMILES: CCOC(=O)c1[nH]c2cc(Cl)ccc2c1C(C(=O)NC1CCCCC1)N(C=O)Cc1ccc(Cl)cc1]
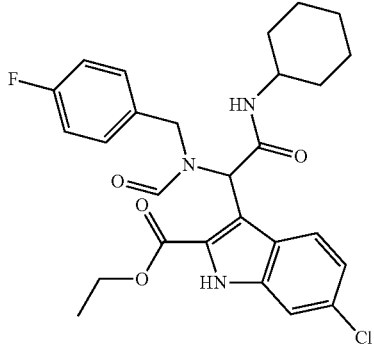 [SMILES: CCOC(=O)c1[nH]c2cc(Cl)ccc2c1C(C(=O)NC1CCCCC1)N(C=O)Cc1ccc(F)cc1]

TABLE 3-continued
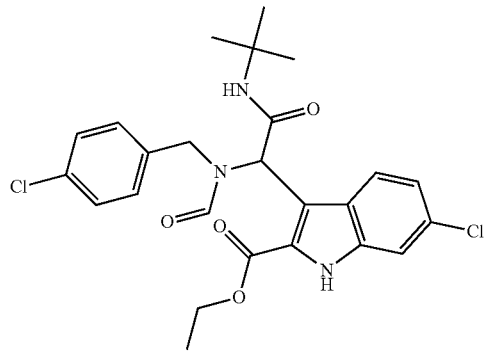 [SMILES: CCOC(=O)c1[nH]c2cc(Cl)ccc2c1C(C(=O)NC(C)(C)C)N(C=O)Cc1ccc(Cl)cc1]
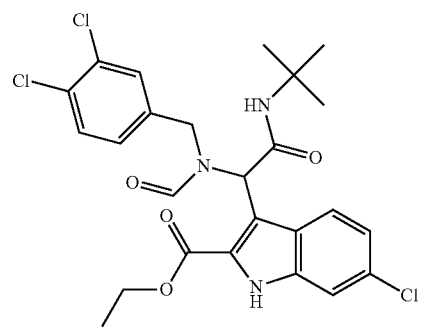 [SMILES: CCOC(=O)c1[nH]c2cc(Cl)ccc2c1C(C(=O)NC(C)(C)C)N(C=O)Cc1ccc(Cl)c(Cl)c1]
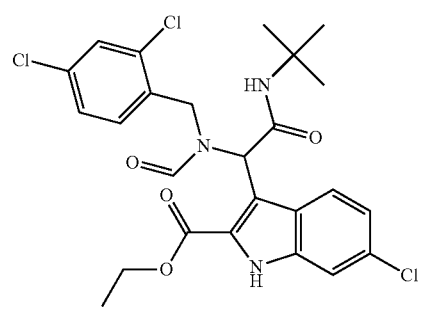 [SMILES: CCOC(=O)c1[nH]c2cc(Cl)ccc2c1C(C(=O)NC(C)(C)C)N(C=O)Cc1ccc(Cl)cc1Cl]
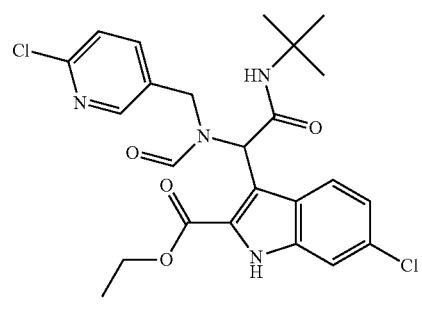 [SMILES: CCOC(=O)c1[nH]c2cc(Cl)ccc2c1C(C(=O)NC(C)(C)C)N(C=O)Cc1ccc(Cl)nc1]
TABLE 3-continued
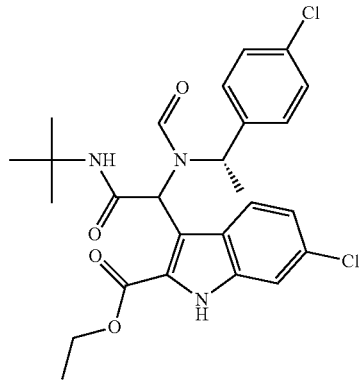 [SMILES: CCOC(=O)c1[nH]c2cc(Cl)ccc2c1C(C(=O)NC(C)(C)C)N(C=O)[C@@H](C)c1ccc(Cl)cc1]
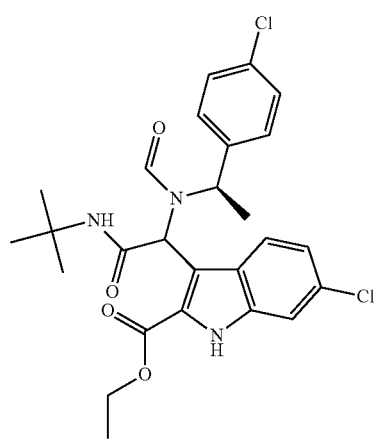 [SMILES: CCOC(=O)c1[nH]c2cc(Cl)ccc2c1C(C(=O)NC(C)(C)C)N(C=O)[C@H](C)c1ccc(Cl)cc1]
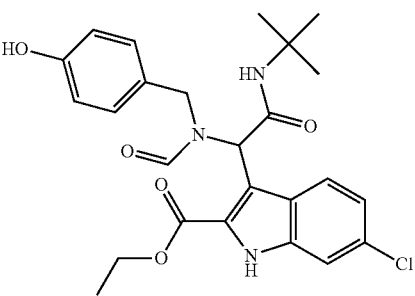 [SMILES: CCOC(=O)c1[nH]c2cc(Cl)ccc2c1C(C(=O)NC(C)(C)C)N(C=O)Cc1ccc(O)cc1]
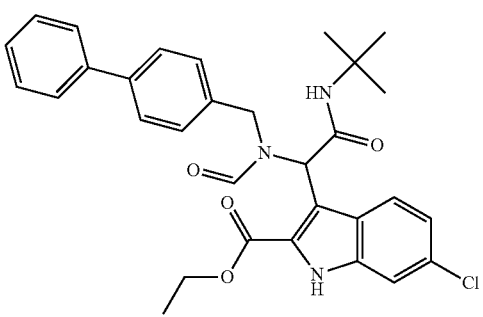 [SMILES: CCOC(=O)c1[nH]c2cc(Cl)ccc2c1C(C(=O)NC(C)(C)C)N(C=O)Cc1ccc(-c2ccccc2)cc1]

TABLE 3-continued
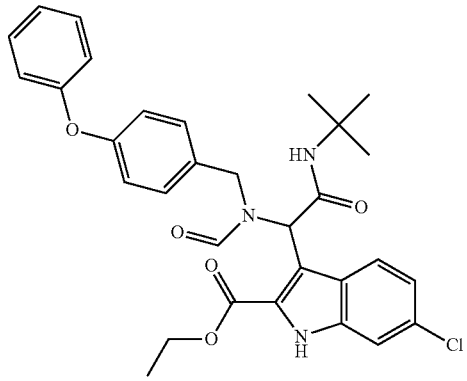 [SMILES: CCOC(=O)c1[nH]c2cc(Cl)ccc2c1C(C(=O)NC(C)(C)C)N(C=O)Cc1ccc(Oc2ccccc2)cc1]
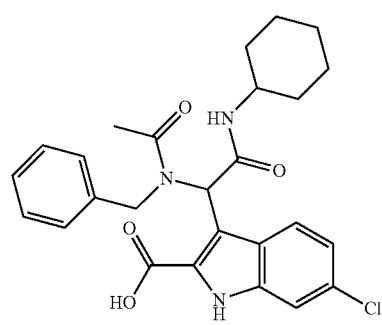 [SMILES: CC(=O)N(Cc1ccccc1)C(C(=O)NC1CCCCC1)c1c(C(=O)O)[nH]c2cc(Cl)ccc12]
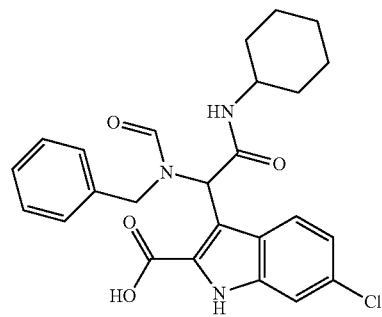 [SMILES: O=CN(Cc1ccccc1)C(C(=O)NC1CCCCC1)c1c(C(=O)O)[nH]c2cc(Cl)ccc12]
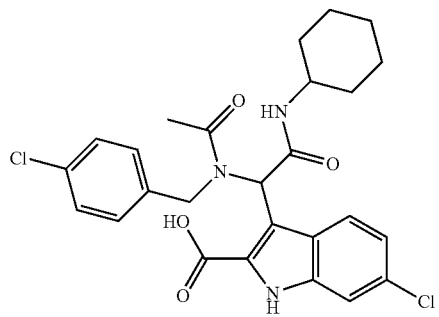 [SMILES: CC(=O)N(Cc1ccc(Cl)cc1)C(C(=O)NC1CCCCC1)c1c(C(=O)O)[nH]c2cc(Cl)ccc12]
TABLE 3-continued
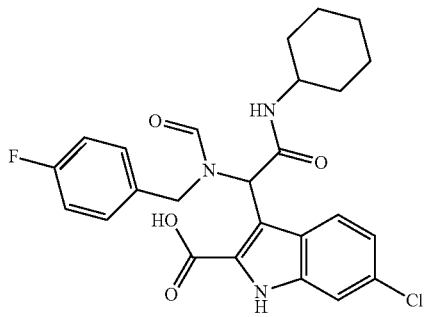 [SMILES: O=CN(Cc1ccc(F)cc1)C(C(=O)NC1CCCCC1)c1c(C(=O)O)[nH]c2cc(Cl)ccc12]
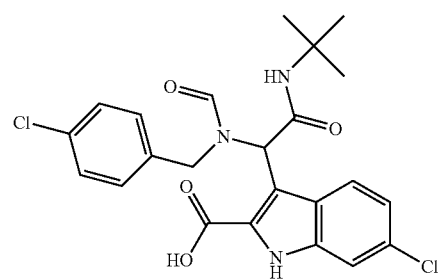 [SMILES: CC(C)(C)NC(=O)C(c1c(C(=O)O)[nH]c2cc(Cl)ccc12)N(C=O)Cc1ccc(Cl)cc1]
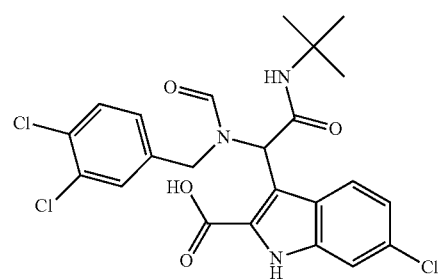 [SMILES: CC(C)(C)NC(=O)C(c1c(C(=O)O)[nH]c2cc(Cl)ccc12)N(C=O)Cc1ccc(Cl)c(Cl)c1]
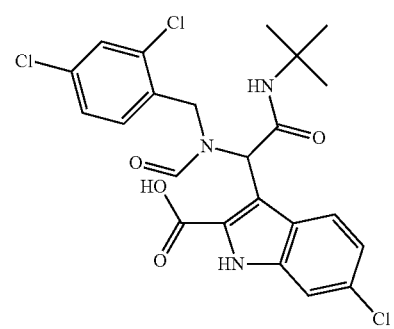 [SMILES: CC(C)(C)NC(=O)C(c1c(C(=O)O)[nH]c2cc(Cl)ccc12)N(C=O)Cc1ccc(Cl)cc1Cl]
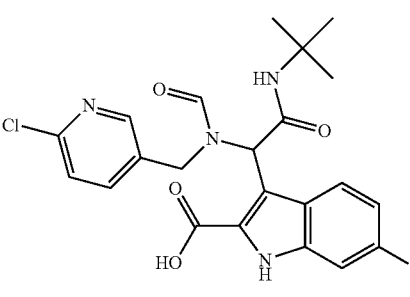

TABLE 3-continued
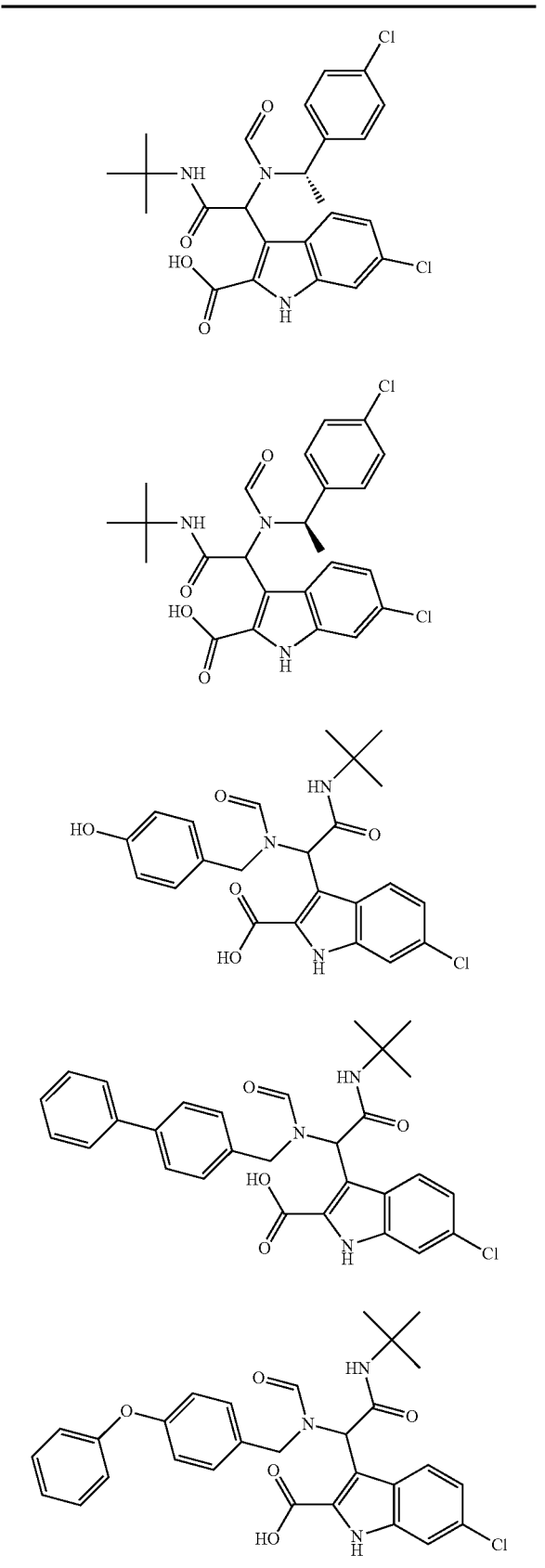
TABLE 3-continued
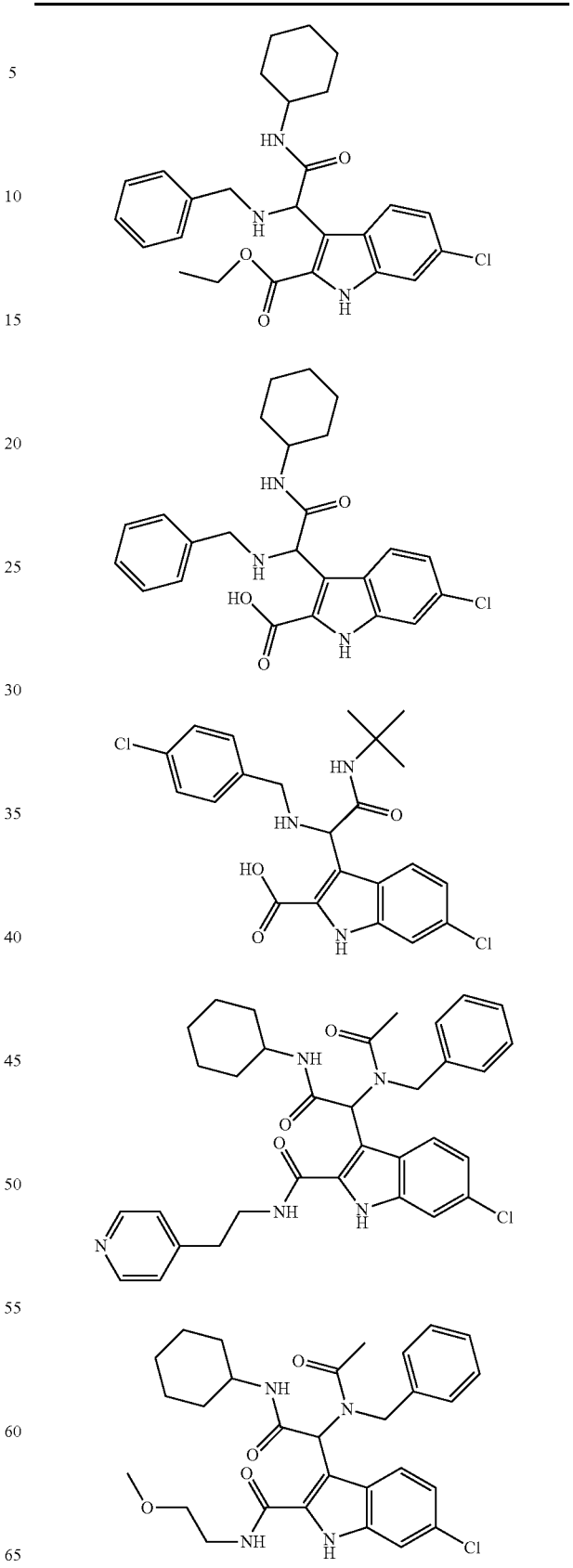

TABLE 3-continued

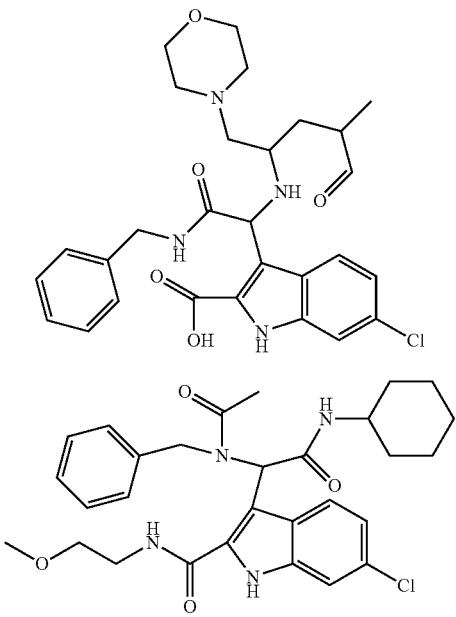

Fluorinated Analogs of Formula I

The introduction of fluorine has been especially valuable in the process of drug discovery. For example, fluorine has been used to increase the binding affinity of small molecules to its target, alter $pK_B$ and logD, improve target selectivity, improve oral absorption and prevent metabolism. Moreover, synthetic protocols for the regioselective introduction of fluorine are well established in the literature.

To enhance binding of Formula I compounds, the present inventor performed a systematic fluorine scan (F-scan) for p53-Mdm2 antagonists conforming to Formula I. In particular, the inventor studied the contributions to binding interactions when one or more hydrogen atoms of the 2-aminobenzyl group residing at C-3 of indole were replaced by fluorine atoms.

Structure-activity studies by the present inventor based on a crystal structure of a Formula I p53-Mdm2 antagonist 3-(2-(tert-butylamino)-1-(N-4-chorobenzyl)formamido)-2-oxo-ethyl)-6-chloro-1H-indole-2-carboxylic acid (A), showed that substitutent groups on compound (A) that correspond to side chain residues of to Trp23, Phe19 and Leu26 of p53 occupied similar positions within the Mdm2 binding pocket.

Figure 2:
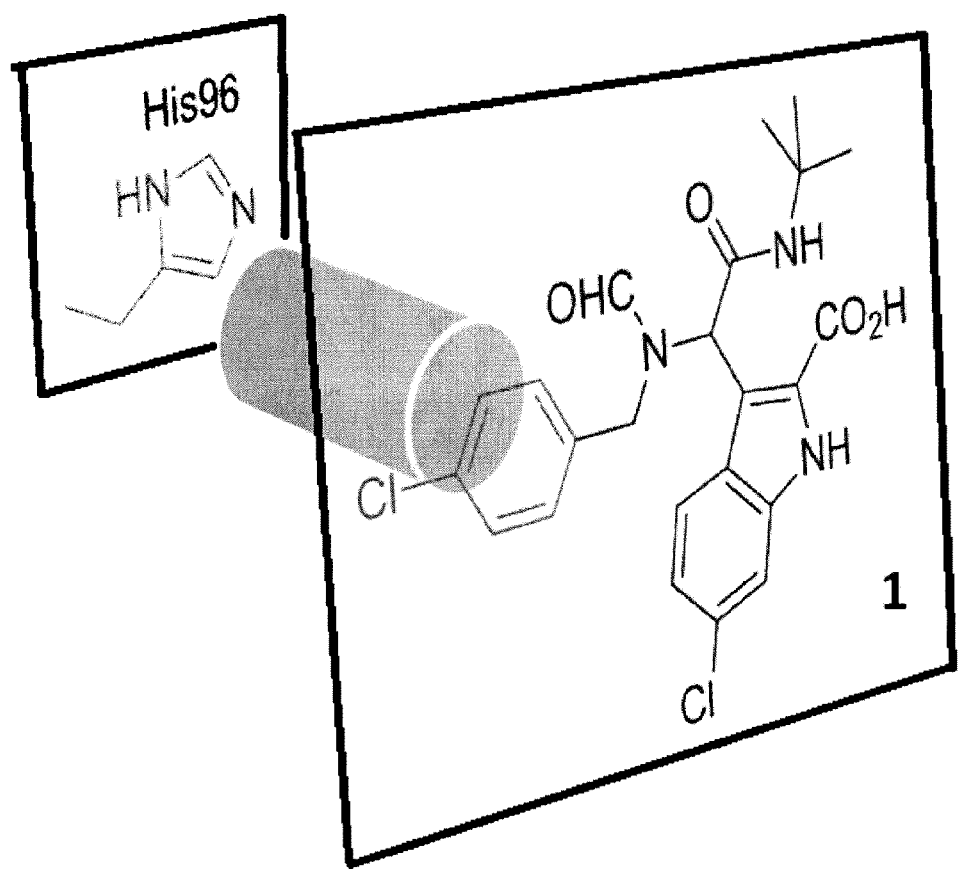
FIG. 2 illustrates a co-crystal structure of p53-Mdm2 antagonist (A) complexed to Mdm2. A parallel alignment between the benzyl group of the compound (A) and the imidazole ring of His96 (Mdm2), indicate that the benzyl ring is suitable for optimizing π-π interactions.
Figure 3A:
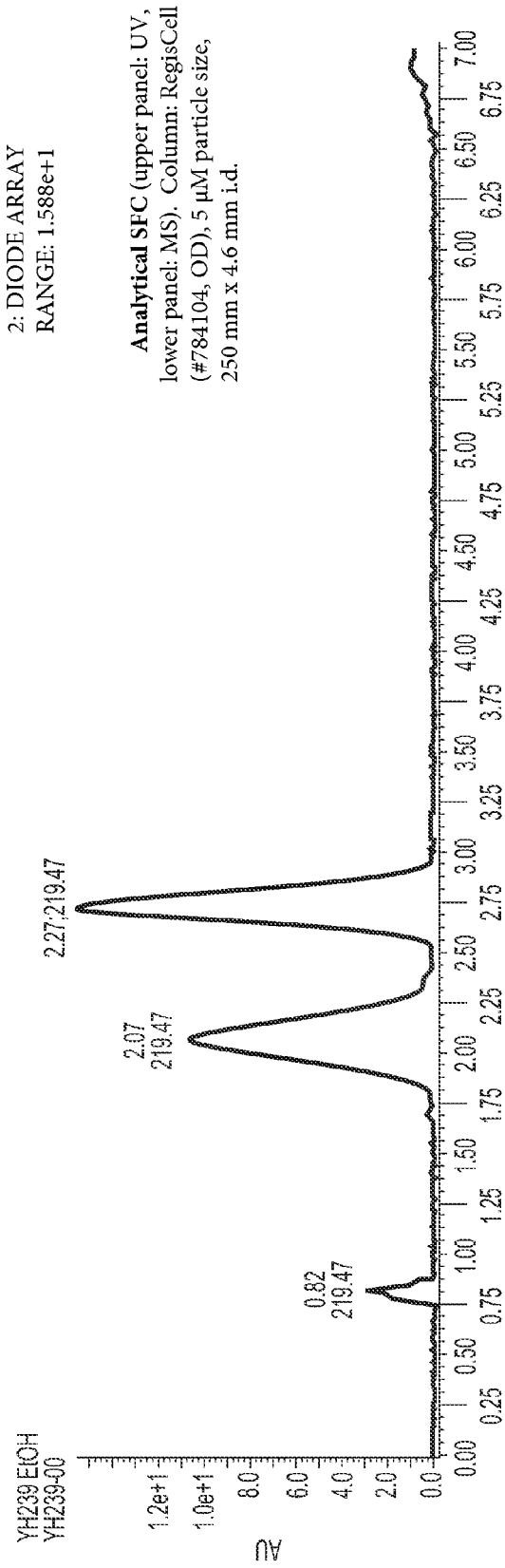
FIG. 3 illustrates a representative chromatographic trace for resolving the enantiomers of a Formula I compound (8l) using (A) analytical supercritical fluid chiral chromatography (upper panel: UV, lower panel: MS); column: RegisCell (#784104, OD), 5 μM particle size, 250 mm×4.6 mm i.d.; flow rate: 4 mL/min.; modifier: isocratic elution with 20% ethanol; injection volume: 5 μL, and (B) preparative supercritical fluid chiral chromatography (upper panel: UV 220 nm, lower panel: UV); column: RegisCell (#784106, OD), 5 μM particle size, 250 mm×21.1 mm i.d.; flow rate: 100 g/min; modifier: isocratic elution with 20% ethanol; injection volume: 500 μL.
Figure 3A:
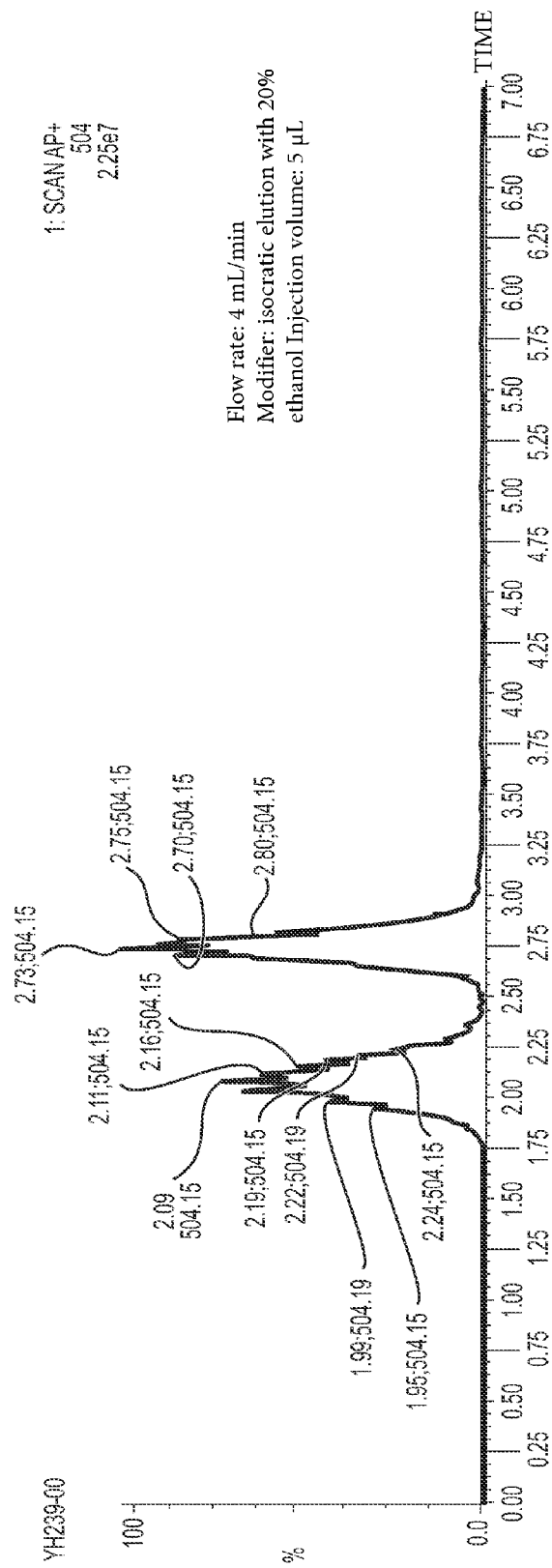
Figure 3B:
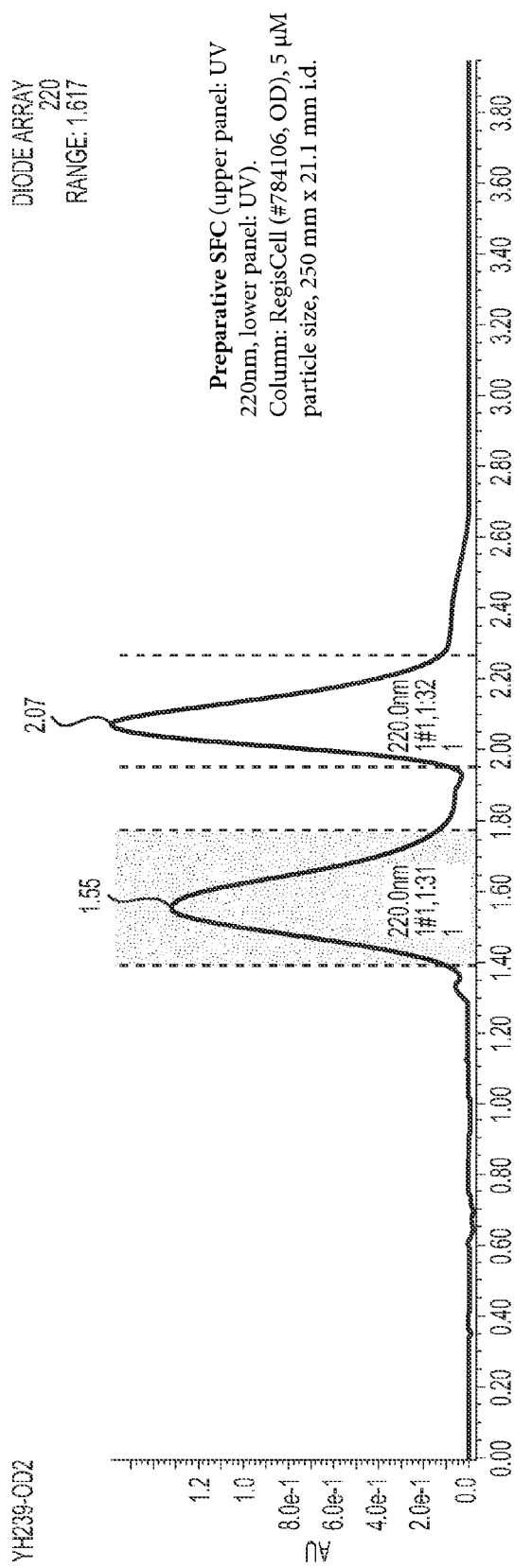
Figure 3B:
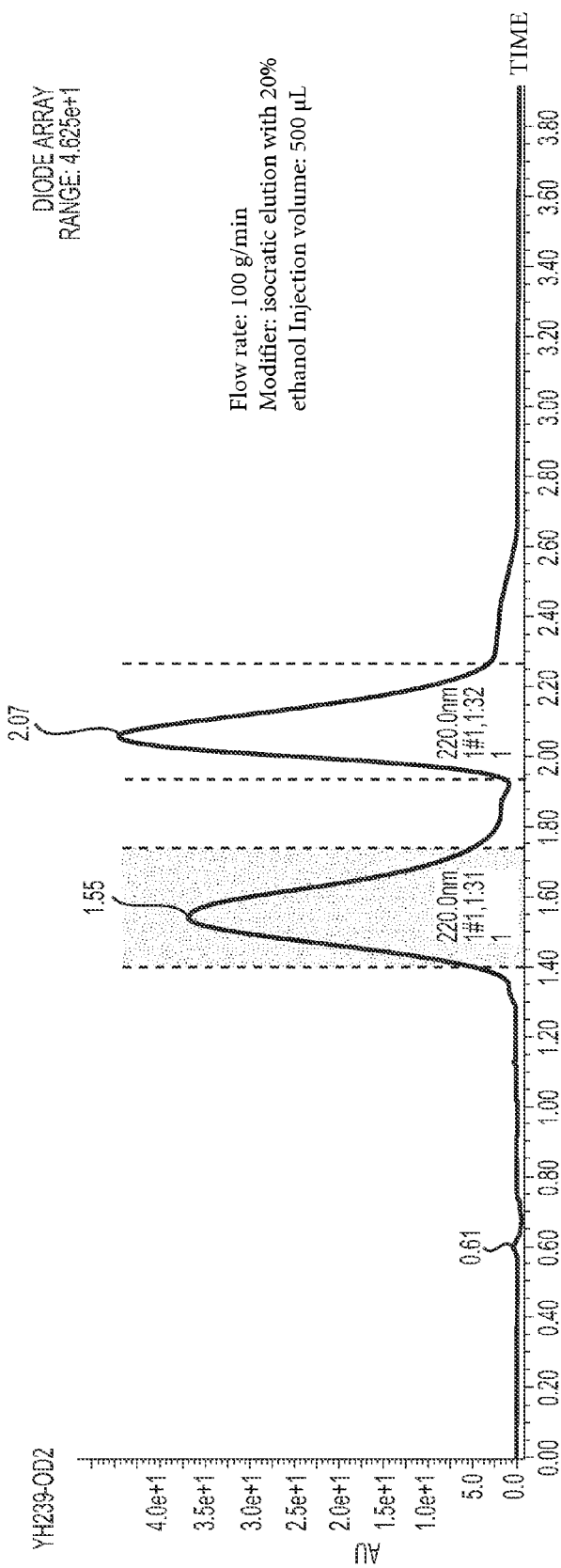

The crystal structure of (A)-complexed to Mdm2 further revealed that the benzyl substituent of (A) was involved in stacking interaction with the imidazole ring of His96 of Mdm2 (FIG. 2). Without ascribing to a particular theory, the present inventor believes that substitution of the hydrogen atoms of the benzyl ring with one or more fluorine atoms should enhance π-stacking interactions between the imidazole ring of His96 and the benzyl group of compound (A). Thus, all 19 fluoro-isomers of compound (A) were synthesized.

Fluorescent polarization (FP) studies indicate that Formula I compounds having a free carboxylic acid group at C-2 of indole (compounds 7B-7T), exhibit enhanced binding potency compared with the corresponding parent ethyl ester compounds (6B-6T). Interestingly, the $K_i$ values of compounds 7B-7T varied by a factor of 44, with $K_i$ values between 5.7 μM and 130 nM. The most potent analog is compound 7m ($K_i$=130 nM, molecular weight: 495 Da.).

Additionally, compound 7m exhibits a higher binding efficiency index (BEI=13.9) than the known p53-Mdm2 antagonist Nutlin-3a, which indicates that tcompound 7m would exhibit better efficacy than nutlin-3a (BEI=12.3). In the context of the present invention the term "BEI" refers to the ratio $pK_i/MW$ (KDa).

Moreover, compound 7m exhibits superior aqueous solubility (0.85 mg/mL) than Nutlin (0.1 mg/mL), and its calculated lipophilicity is lower (cLogP=3.69), than that of nutlin-3a (cLogP=5.17).

Table 4 illustrates the inhibition constants ($K_i$ values) for fluorinated compounds 6B-6T and $K_i$ values for the corresponding 2-indole carboxylic acids (compounds 7B-7T). As shown by the data in Table 4 many Formula I compounds bound tightly to Mdm2 with $K_i$ values in the nanomolar range.

TABLE 4

| No. | X | $K_i (6)^a$ | $K_i (7)^a$ | cLogP $(7)^b$ |
|---|---|---|---|---|
| A | H | 1.5 | 1.8 | 3.26 |
| B | 4-F | 2.2 | 0.45 | 3.40 |
| C | 3-F | 1.3 | 0.81 | |
| D | 2-F | 3 | 1.7 | |
| E | 3,4-F | 0.5 | 0.25 | 3.54 |
| F | 2,4-F | 6 | 2.3 | |
| G | 2,3-F | 3 | 0.2 | |
| H | 2,5-F | 10 | 2.5 | |
| I | 3,5-F | 2.4 | 0.3 | |
| J | 2,6-F | 4.5 | 5.7 | |
| K | 2,3,4-F | 2.1 | 0.15 | 3.69 |
| L | 2,4,5-F | 5 | 2.3 | |
| M | 3,4,5-F | 0.4 | 0.13 | |
| N | 2,3,6-F | 4.3 | 3.2 | |
| O | 2,4,6-F | 6.8 | 3.2 | |
| P | 2,3,5-F | 2.5 | 0.17 | |
| Q | 2,3,5,6-F | 6.7 | 3 | 3.83 |
| R | 2,3,4,6-F | 5.8 | 3 | |
| S | 2,3,4,5-F | 7 | 0.7 | |
| T | 2,3,4,5,6-F | 5.8 | 1.8 | 3.97 |

Exemplary fluorinated Formula I compounds include without limitation compounds mentioned in Table 5 below.

TABLE 5

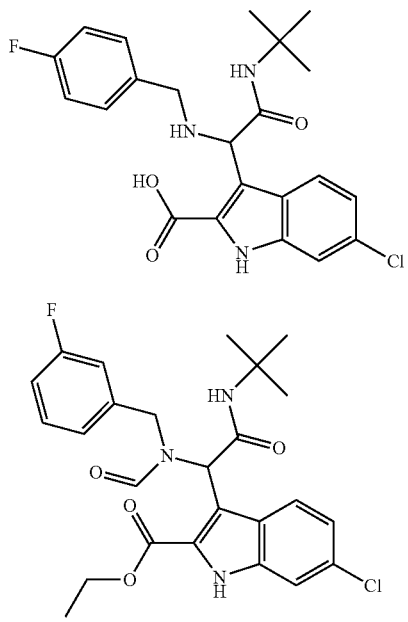

TABLE 5-continued
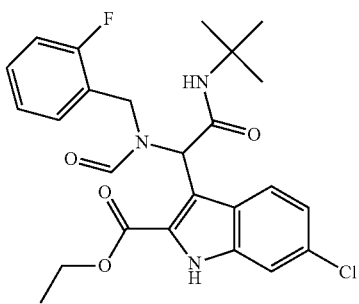 [SMILES: CCOC(=O)c1[nH]c2cc(Cl)ccc2c1C(C(=O)NC(C)(C)C)N(C=O)Cc1ccccc1F]
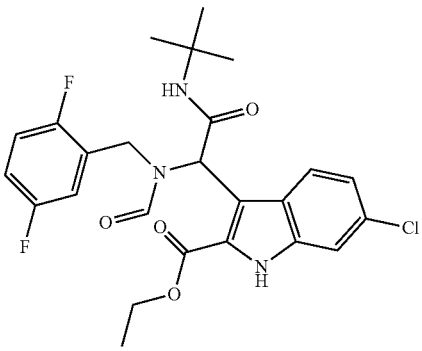
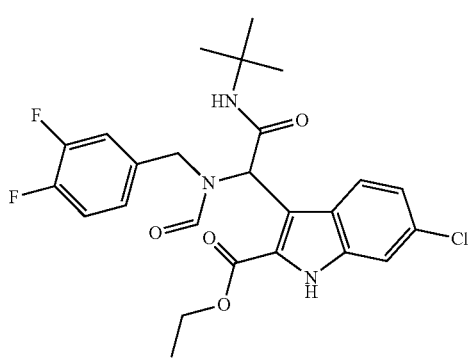 [SMILES: CCOC(=O)c1[nH]c2cc(Cl)ccc2c1C(C(=O)NC(C)(C)C)N(C=O)Cc1ccc(F)c(F)c1]
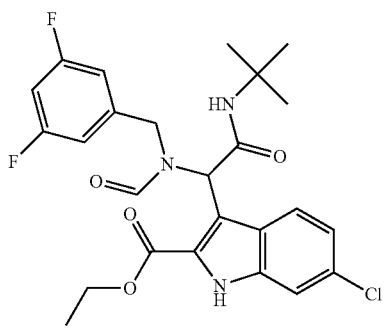
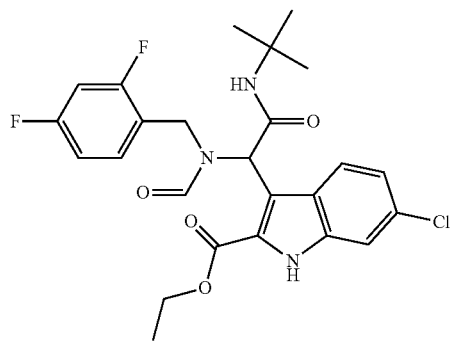 [SMILES: CCOC(=O)c1[nH]c2cc(Cl)ccc2c1C(C(=O)NC(C)(C)C)N(C=O)Cc1ccc(F)cc1F]
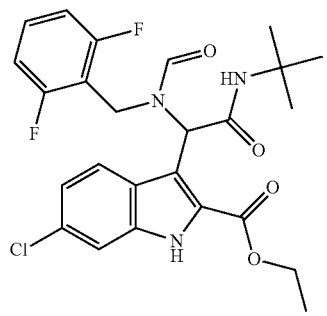
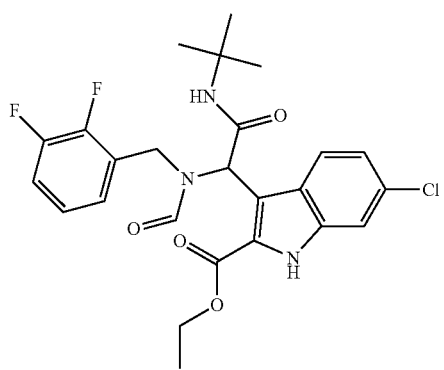 [SMILES: CCOC(=O)c1[nH]c2cc(Cl)ccc2c1C(C(=O)NC(C)(C)C)N(C=O)Cc1cccc(F)c1F]
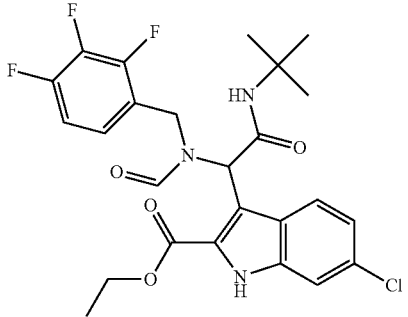 [SMILES: CCOC(=O)c1[nH]c2cc(Cl)ccc2c1C(C(=O)NC(C)(C)C)N(C=O)Cc1ccc(F)c(F)c1F]

TABLE 5-continued
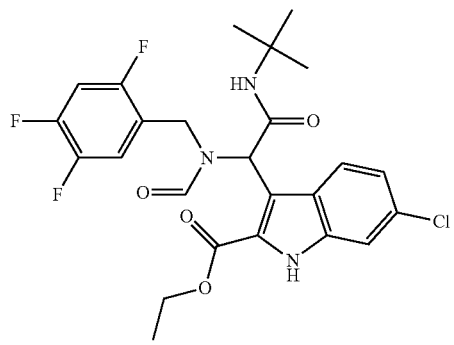 [SMILES: CCOC(=O)c1[nH]c2cc(Cl)ccc2c1C(C(=O)NC(C)(C)C)N(C=O)Cc1cc(F)c(F)cc1F]
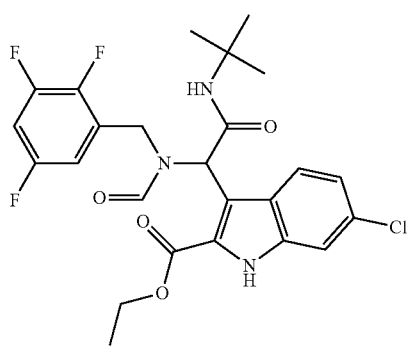
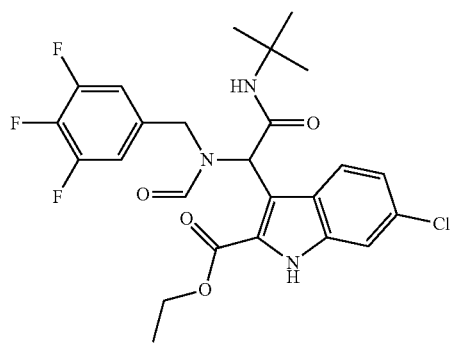 [SMILES: CCOC(=O)c1[nH]c2cc(Cl)ccc2c1C(C(=O)NC(C)(C)C)N(C=O)Cc1cc(F)c(F)c(F)c1]
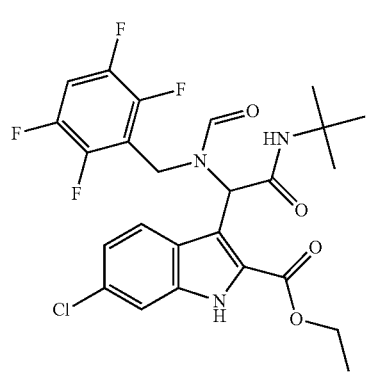
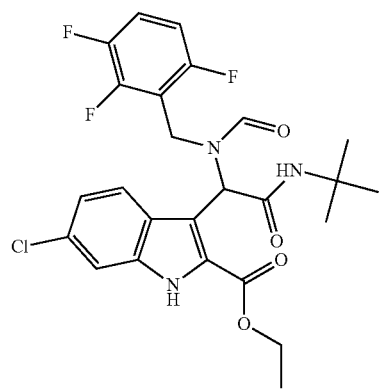 [SMILES: CCOC(=O)c1[nH]c2cc(Cl)ccc2c1C(C(=O)NC(C)(C)C)N(C=O)Cc1c(F)ccc(F)c1F]
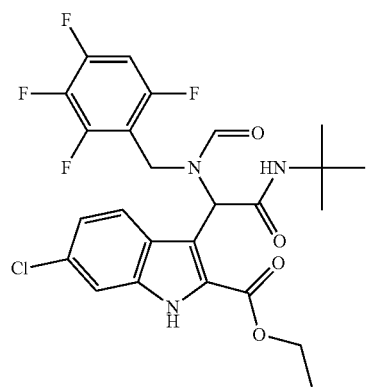
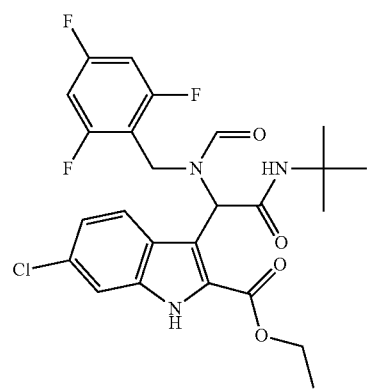 [SMILES: CCOC(=O)c1[nH]c2cc(Cl)ccc2c1C(C(=O)NC(C)(C)C)N(C=O)Cc1c(F)cc(F)cc1F]
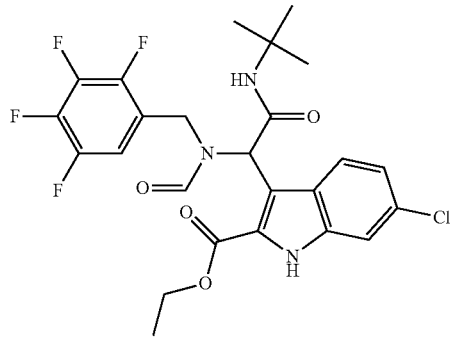 [SMILES: CCOC(=O)c1[nH]c2cc(Cl)ccc2c1C(C(=O)NC(C)(C)C)N(C=O)Cc1cc(F)c(F)c(F)c1F]

TABLE 5-continued

TABLE 5-continued
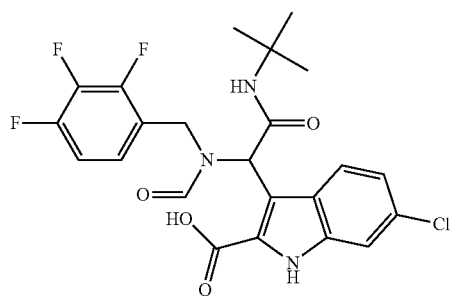 [SMILES: CC(C)(C)NC(=O)C(c1c(C(=O)O)[nH]c2cc(Cl)ccc12)N(C=O)Cc1ccc(F)c(F)c1F]
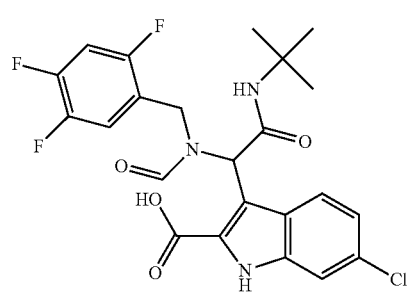 [SMILES: CC(C)(C)NC(=O)C(c1c(C(=O)O)[nH]c2cc(Cl)ccc12)N(C=O)Cc1cc(F)c(F)cc1F]
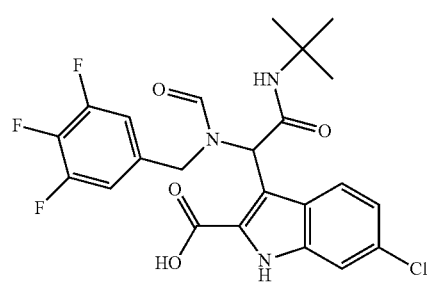 [SMILES: CC(C)(C)NC(=O)C(c1c(C(=O)O)[nH]c2cc(Cl)ccc12)N(C=O)Cc1cc(F)c(F)c(F)c1]
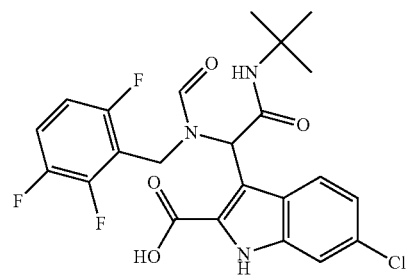 [SMILES: CC(C)(C)NC(=O)C(c1c(C(=O)O)[nH]c2cc(Cl)ccc12)N(C=O)Cc1c(F)ccc(F)c1F]
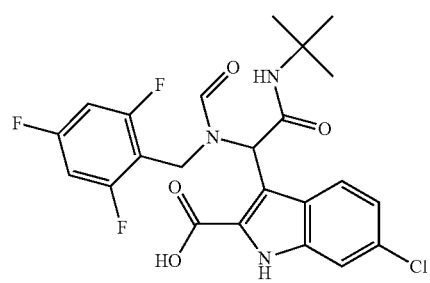 [SMILES: CC(C)(C)NC(=O)C(c1c(C(=O)O)[nH]c2cc(Cl)ccc12)N(C=O)Cc1c(F)cc(F)cc1F]
TABLE 5-continued
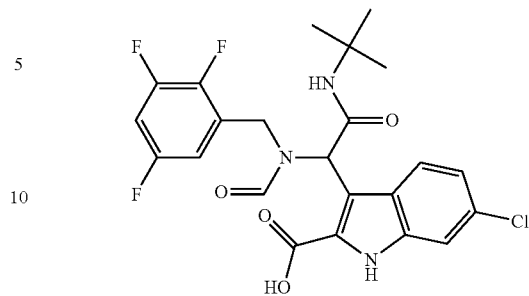
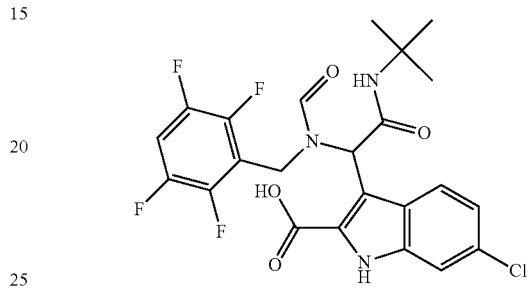
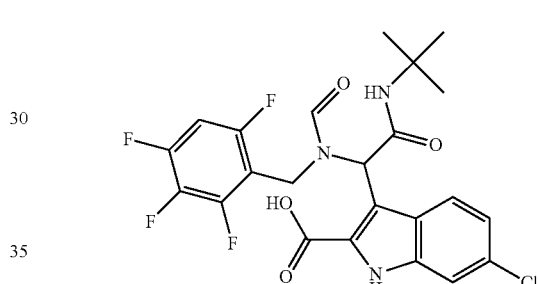
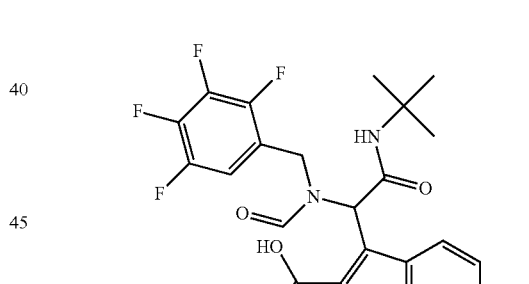
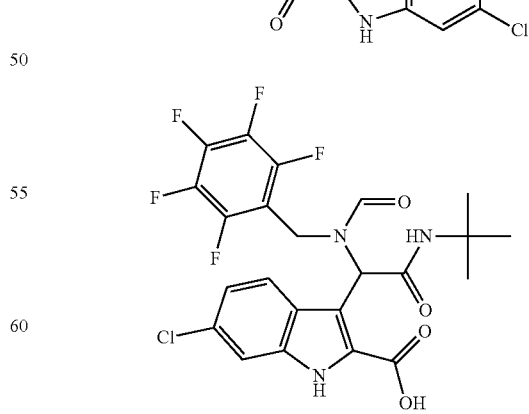
The present invention also provides compounds that conform to Formula II:

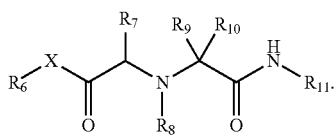

For compounds that conform to Formula II, X is —(O)—, or —NH—.

Substituent $R_6$ is selected from the group consisting of hydrogen, straight or branched chain $(C_1-C_6)$alkyl, —NH—(OH), and —OH, while $R_7$ is hydrogen or straight or branched chain —$(C_1-C_6)$alkyl.

Substituent groups $R_8$ and $R_{10}$ are both hydrogen, while $R_9$ is indole or a substituted indole group.

For certain Formula II compounds $R_9$ is a substituted indole, such as

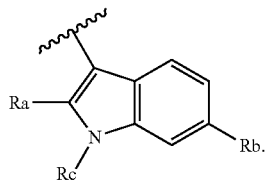

For compounds containing a substituted indole as $R_9$, substituent $R_a$ is selected from the group consisting of hydrogen, —C(O)R', and —C(O)OR', substituent $R_b$ is hydrogen, Cl, Br, or F and substituent $R_c$ is H or —C(O)OR$^d$. When $R_c$ is C(O)OR$^d$, substituent R$^d$ is hydrogen or straight or branched chain $(C_1-C_6)$alkyl.

$R_{11}$ is selected from the group consisting of straight or branched chain $(C_1-C_6)$alkyl, $(C_3-C_{14})$aryl, benzyl, $(C_3-C_{14})$aryl$(C_1-C_6)$alkylene-, $(C_3-C_{14})$cycloalkyl, and $(C_3-C_{14})$heteroaryl-$(C_1-C_6)$alkylene-;

For Formula II compounds, any alkyl, benzyl, aryl, $(C_3-C_{14})$aryl$(C_1-C_6)$alkylene-, heteroaryl, cycloalkyl, or heterocycloalkyl is optionally substituted with one or more members selected from the group consisting of —OH, —Cl, —F, —Br, —I, -oxy$(C_3-C_{14})$aryl, $(C_1-C_6)$alkyl, $(C_3-C_{14})$aryl, $(C_3-C_{14})$heteroaryl, $(C_3-C_{14})$aryl$(C_1-C_6)$alkylene-, $(C_3-C_{14})$heterocycloalkyl-$(C_1-C_6)$alkylene-, —C(O)R', —C(O)OR', and oxo.

When substituent groups —C(O)R', or —C(O)OR' are present in a Formula II compound, substituent R' is selected from the group consisting of hydrogen, straight or branched chain $(C_1-C_6)$alkyl, —NH—(OH), —NH—$(C_1-C_6)$alkylene-$(C_3-C_{14})$heteroaryl, and —$(C_1-C_6)$alkylene-OH.

The category of Formula II compounds includes without limitation compounds identified in Table 6 below.

TABLE 6

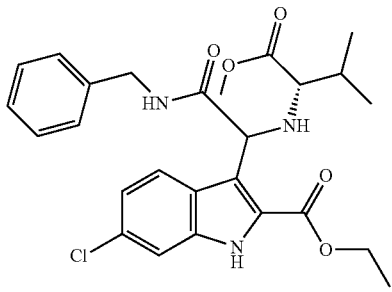 [SMILES: CCOC(=O)c1[nH]c2cc(Cl)ccc2c1C(N[C@H](C(=O)OC)C(C)C)C(=O)NCc1ccccc1]

TABLE 6-continued

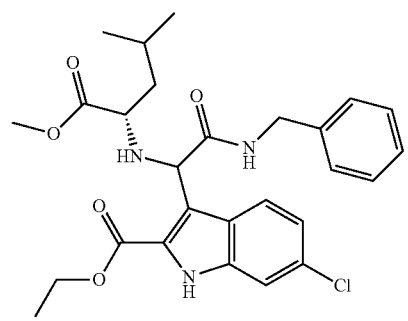 [SMILES: CCOC(=O)c1[nH]c2cc(Cl)ccc2c1C(N[C@@H](CC(C)C)C(=O)OC)C(=O)NCc1ccccc1]

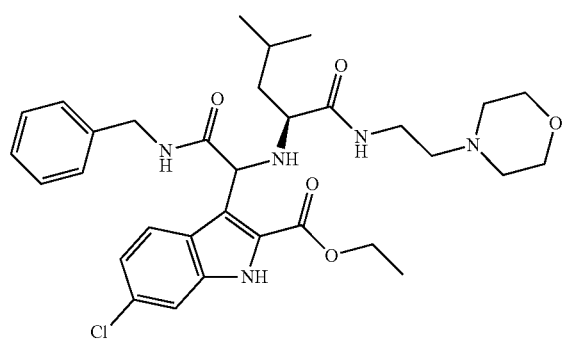 [SMILES: CCOC(=O)c1[nH]c2cc(Cl)ccc2c1C(N[C@@H](CC(C)C)C(=O)NCCN1CCOCC1)C(=O)NCc1ccccc1]

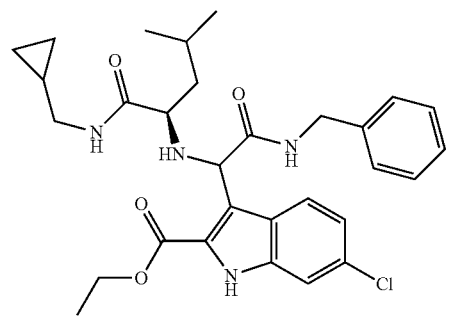 [SMILES: CCOC(=O)c1[nH]c2cc(Cl)ccc2c1C(N[C@H](CC(C)C)C(=O)NCC1CC1)C(=O)NCc1ccccc1]

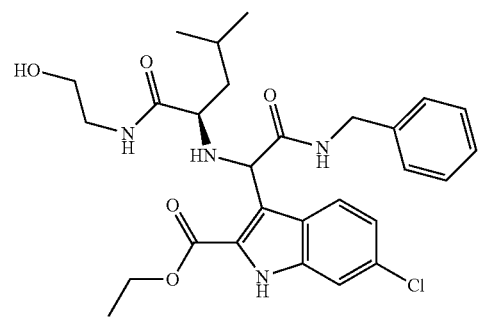 [SMILES: CCOC(=O)c1[nH]c2cc(Cl)ccc2c1C(N[C@H](CC(C)C)C(=O)NCCO)C(=O)NCc1ccccc1]

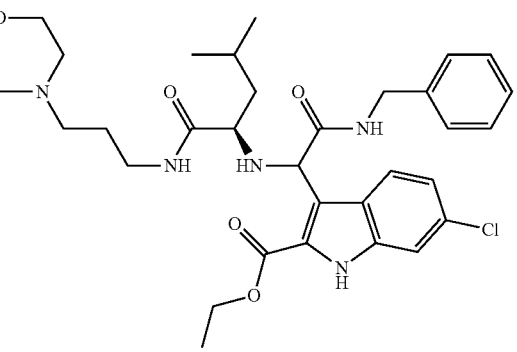

TABLE 6-continued

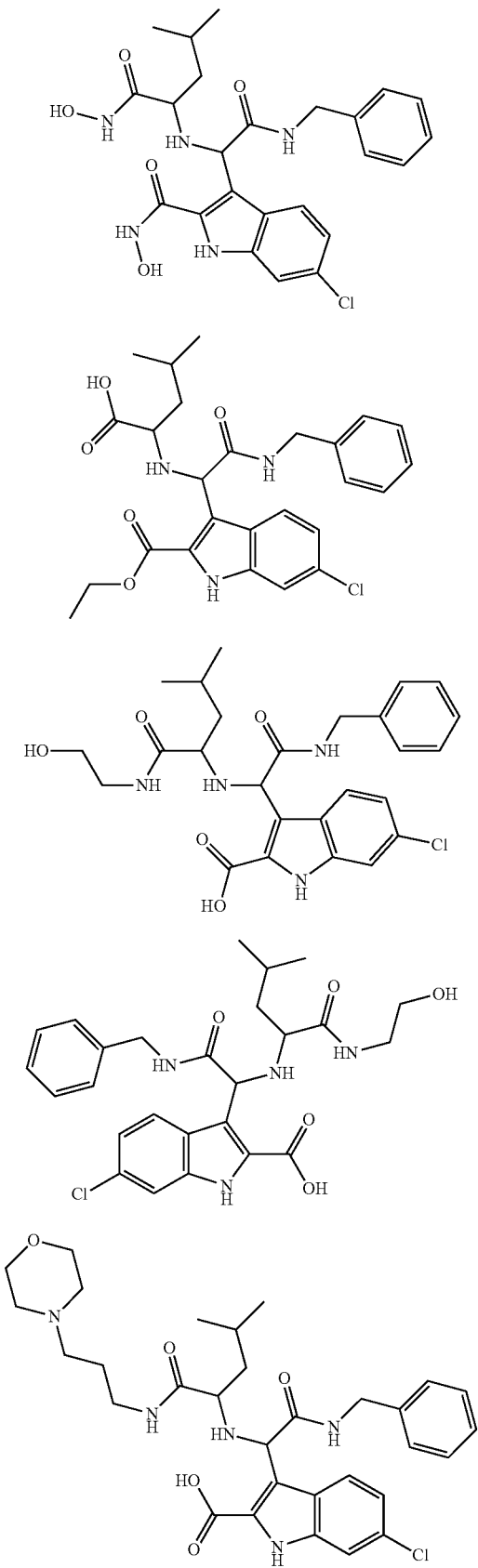

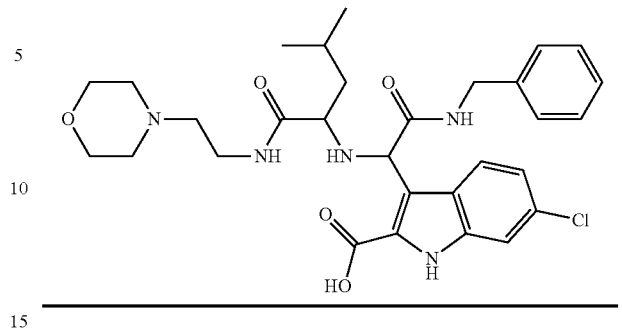

As previously noted, the invention includes all possible stereoisomers of the compounds, nothwithstanding the fact that some exemplary compounds in Table 6 are depicted with stereochemistry.

Synthesis of Formula I Compounds

General Procedure for Ugi Reaction/De-Protection

Scheme 1—Method A

The mixture of Boc-protected indole-3-aldehyde (0.2 mmol), amine (0.2 mmol), isocyanide (0.2 mmol), acid (0.2 mmol) in 0.5 mL of methanol was stirred at RT for 2 days. The product was purified by chromatography on silica gel. The Boc-protected compound was treated with DCM and TFA, and the Ugi product was purified by chromatography on silica gel.

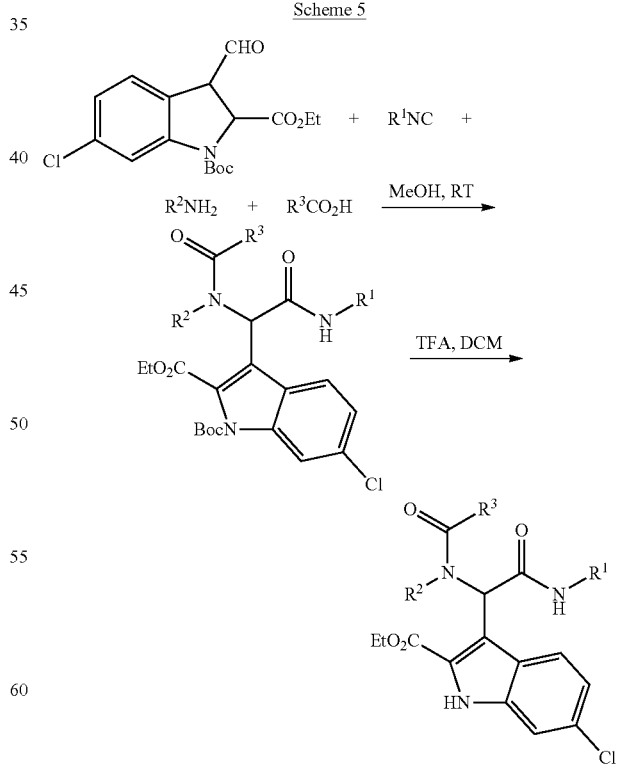

General Procedure for Hydrolysis:

The Ugi compound was treated with KOH (or LiOH) in EtOH/water (1:1), then the reaction mixture was acidified with 1M HCl (pH~6). The mixture was extracted with DCM (10 mL×3). The combined organic layer was dried over sodium sulfate, and evaporated.

Scheme 6

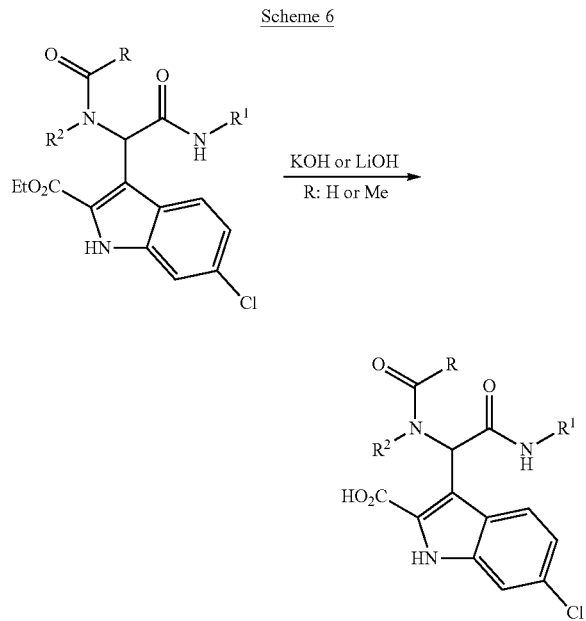

General Procedure for Removal of —N(R²)Acyl Group:

The acid derivative was treated with 0.4 mL of dioxane (4M HCl), 0.1 mL of water and stirred overnight under 60° C. The product was obtained after evaporation.

Scheme 7

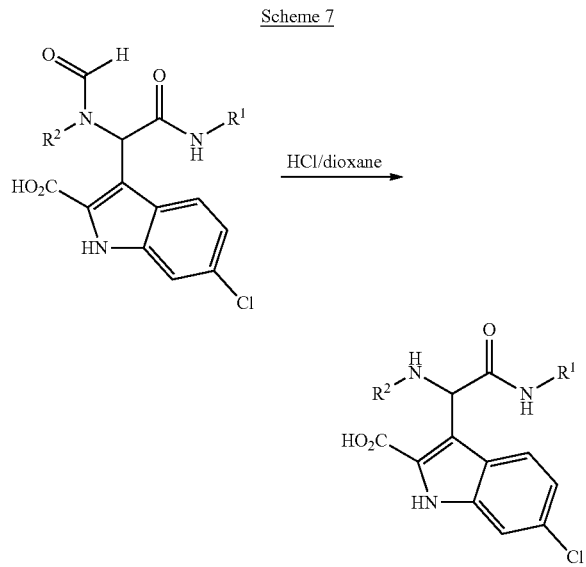

General Procedure for Coupling at C-2 of Indole:

The mixture of acid derivative and amine in the presence of a peptide coupling reagent such at carbonyl diimidazole, HOBt or HATU was stirred at 40° C. overnight. The product was purified by chromatography on silica gel.

Scheme 8

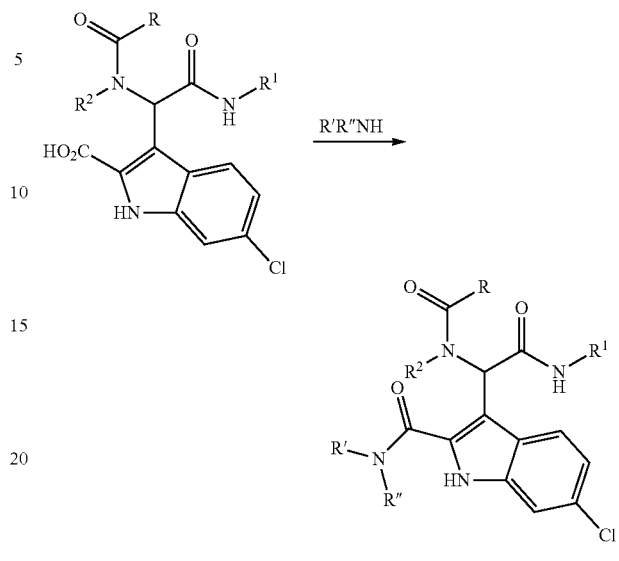

Protocol for Fluorescence Polarization (FP) Assay:

Fluorescent polarization experiments were performed as follows. Briefly, the fluorescence polarization experiments were read on an Ultra Evolution 384-well plate reader (Tecan) with the 485 nm excitation and 535 nm emission filters. The fluorescence intensities parallel (Intparallel) and perpendicular (Intperpedicular) to the plane of excitation were measured in parallel perpendicular black 384-well NBS assay plates (Corning) at room temperature (~20° C.). The background fluorescence intensities of blank samples containing the references buffer were subtracted and steady-state fluorescence polarization was calculated using the equation: $P=(Int_{parallel}-GInt_{perpendicular})/(Int_{parallel}+GInt_{perpendicular})$, and the correction factor G (G=0.998 determined empirically) was introduced to eliminate differences in the transmission of vertically and horizontally polarized light. All fluorescence polarization values were expressed in millipolarization units (mP). The binding affinities of the fluorescent p53-derived peptide of Hu et al. (the P4 peptide)[1] towards Mdm2 was determined in the buffer which contained 50 mM NaCl, 10 mM Tris pH 8.0, 1 mM EDTA, 10% DMSO. Competition binding assays were performed using the 10 nM fluorescent P4 peptide and 100 nM Mdm2. Binding constant and inhibition curves were fitted using the SigmaPlot (SPSS Science Software).

NMR Methods:

All NMR spectra were acquired at 298 K on a Bruker DRX 600 MHz spectrometer equipped with a cryoprobe. Typically, NMR samples contained 0.1-0.2 mM protein in 50 mM KH2PO4 and 50 mM Na2HPO4, pH 7.4, containing 150 mM NaCl and 5 mM β-Mercaptoethanol. Water suppression was carried out using the WATERGATE sequence. NMR data were processed using the Bruker program Xwin-NMR version 3.5. NMR ligand binding experiments were carried out in an analogous way to those previously described. See D'Silva L., et. al., *J. Am. Chem. Soc.* 2005, 127, 13220-13226 and Popowicz G. M., et. al., *Cell Cycle.* 2007, 6, 2386-2392. The maximum concentration of DMSO at the end of titration experiments was less than 1%. The pH was maintained constant during the entire titration. The 1H-15N-HSQC spectra were recorded using fast HSQC pulse sequence as described by Mori et. al., *J. Magn. Reson. B* 1995, 108, 94-98.

Crystallization and Structure Determination

Purified MDM2 was concentrated up to 5 mg/ml. To the protein is added a 3-fold excess of an inhibitor of choice, followed by further concentration of the protein-inhibitor complex to achieve the final protein concentration of about 15 mg/ml. The crystallization was carried out at both 4° C. and 20° C. exploring several crystallization conditions and using the sitting drop vapor diffusion method.

Briefly, each 2 μl drop consisted of a 1:1 (vol/vol) mixture of protein in a suitable buffer.

The well consists of a solution consisting of 150 mM KBr and 30% polyethylene glycol (PEG 2000 MME). The crystals were soaked in cryo-solutions containing mother liquor supplemented with 20% MPD or glycerol and were flash frozen in liquid nitrogen. X-ray data sets were collected on the SLS beamline PXII at the Paul Scherrer Institut, Villigen, Switzerland.

Although, crystals diffracted up to 2.1 Å they showed high mosaicity and anisotropic diffraction. The data sets were integrated, scaled and merged by XDS and XSCALE programs. The structures were determined by molecular replacement (Starting model PDB ID 1YCR) using the Molrep program from the CCP4 suite. See CCP4 (Collaborative Computational Project, Number 4) *Acta Crystallogr. D. Biol. Crystallogr.*, 1994, 50, 760-763. Model building and refinement were carried out by several cycles of the manual model building in program Mifit and refinement using REFMAC5. Water molecules were added using Arp/Warp as disclosed by Perrakis, A., R. Morris, et al. *Nature Struct. Biol.* 1999, 6: 458-463. The limited quality of diffraction data does not allow refinement to progress below $R/R_{free}$ 22.3/30.8 but the ligands were clearly visible in the electron density map. The structures of both complexes found in an asymmetric unit are nearly identical regardless of crystal contacts.

COMPOUNDS

Tert-butyl 3-(1-(N-benzylacetamido)-2-(benzylamino)-2-oxoethylindole-1-carboxylate (YH146)

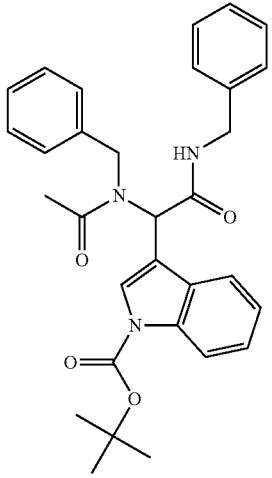 [SMILES: CC(=O)N(Cc1ccccc1)C(C(=O)NCc1ccccc1)c1cn(C(=O)OC(C)(C)C)c2ccccc12]

The final product was obtained as an off-white solid (70 mg, yield: 68%). HPLC/MS: $t_R$=11.80 min; m/z=512.0 [M+H]$^+$. HRMS: $C_{31}H_{33}N_3O_4$, [M+Na]$^+$; 534.2369 (calcd.), 534.2367 (found).

N-benzyl-2-(N-benzylacetamido)-2-(1H-indol-3-yl)acetamide (YH149)

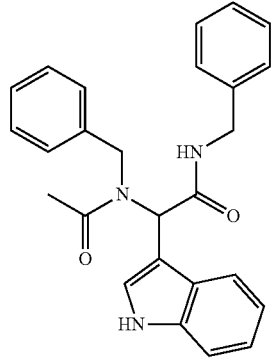 [SMILES: CC(=O)N(Cc1ccccc1)C(C(=O)NCc1ccccc1)c1c[nH]c2ccccc12]

The final product was obtained as an off-white solids (26 mg, yield: 46%). HPLC/MS: $t_R$=10.35 min; m/z=412.2 [M+H]$^+$. HRMS: $C_{26}H_{25}N_3O_2$, [M+Na]$^+$; 434.1844 (calcd.), 434.1812 (found).
$^1$H NMR (600 MHz, CDCl$_3$): 2.05 (s, 3H), 4.38-4.53 (m, 2H), 4.63-4.67 (m, 2H), 6.53 (s, 1H), 6.60 (m, 1H), 6.90 (m, 2H), 7.04-7.06 (m, 3H), 7.13 (m, 1H), 7.21 (m, 1H), 7.24-7.32 (m, 5H), 7.52 (m, 1H), 7.57 (m, 1H), 8.49 (s, 1H).
$^{13}$C NMR (150 MHz, CDCl$_3$): 22.6, 43.6, 50.1, 54.4, 109.2, 111.5, 118.6, 120.3, 122.6, 126.0, 126.1, 126.7, 127.1, 127.4, 127.7, 128.3, 128.6, 135.8, 137.7, 138.0, 170.2, 172.8.

1-tert-butyl 2-ethyl 3-(2-(benzylamino)-1-(N-isobutylacetamido)-2-oxoethyl)-6-chloro-1H-indole-1,2-dicarboxylate (YH147)

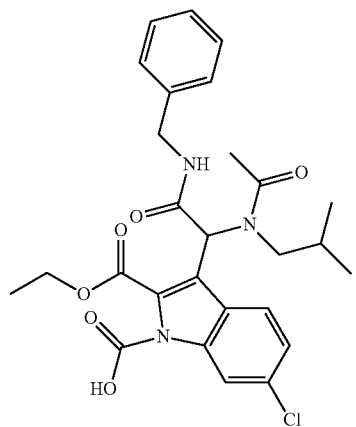 [SMILES: CCOC(=O)c1c(C(C(=O)NCc2ccccc2)N(CC(C)C)C(C)=O)c2ccc(Cl)cc2n1C(=O)O]

The final product was obtained as a yellow solid (32 mg, yield: 27%). HPLC/MS: $t_R$=12.38 min; m/z=583.9 [M+H]$^+$. HRMS: $C_{31}H_{38}N_3O_6Cl$, [M+Na]$^+$; 606.2347 (calcd.), 606.2401 (found).
$^1$H NMR (600 MHz, CDCl$_3$): 0.58 (d, 3H, J=6.0 Hz), 0.75 (d, 3H, J=6.6 Hz), 1.37 (t, 3H, J=72 Hz), 1.46 (m, 1H), 1.65 (s, 9H), 2.22 (s, 3H), 3.24 (d, 2H, J=7.2 Hz), 4.35-4.49 (m, 4H), 6.08 (s, 1H), 6.30 (s, 1H), 7.18-7.26 (m, 6H), 7.74 (m, 1H), 8.14 (m, 1H).

$^{13}$C NMR (150 MHz, CDCl$_3$): 13.9, 14.0, 19.90, 19.91, 22.1, 27.9, 28.5, 43.9, 54.6, 54.7, 62.5, 86.1, 115.3, 117.3, 122.7, 124.5, 125.7, 127.4, 127.9, 128.6, 131.4, 132.8, 136.2, 137.7, 148.4, 161.9, 168.5, 172.2.

Ethyl 3-(2-(benzylamino)-1-(N-isobutylacetamido)-2-oxoethyl)-6-chloro-1H-indole-2-carboxylate (YH145)

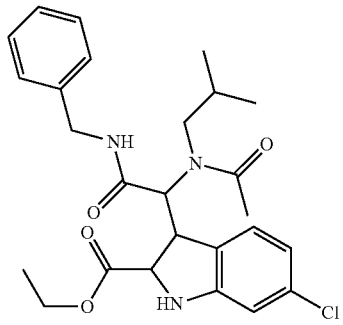 [SMILES: CCOC(=O)C1Nc2cc(Cl)ccc2C1C(C(=O)NCc1ccccc1)N(CC(C)C)C(C)=O]

The final product was obtained as a yellowish solid (17 mg, yield: 64%). HPLC/MS: $t_R$=11.01 min; m/z=484.0 [M+H]$^+$. HRMS: C$_{26}$H$_{30}$ClN$_3$O$_4$, [M+Na]$^+$; 506.1823 (calcd.), 506.1801 (found).

$^1$H NMR (600 MHz, CDCl$_3$, major rotamer): 0.54 (d, 3H, J=6.0 Hz), 0.69 (d, 3H, J=6.0 Hz), 1.36 (t, 3H, J=7.2 Hz), 1.86 (m, 1H), 2.23 (s, 3H), 3.16 (d, 2H, J=7.2 Hz), 4.29-4.51 (m, 4H), 6.10 (s, 1H), 6.87 (s, 1H), 7.06 (m, 1H), 7.18-7.35 (m, 6H), 7.79 (m, 1H), 9.64 (s, 1H).

$^{13}$C NMR (150 MHz, CDCl$_3$, major rotamer): 14.3, 19.8, 20.0, 22.2, 28.6, 42.2, 43.9, 54.8, 55.3, 61.8, 111.9, 115.6, 122.4, 123.5, 125.4, 126.9, 127.0, 127.7, 127.8, 127.9, 128.0, 128.6, 128.8, 131.8, 136.1, 137.6, 137.9, 161.1, 161.2, 169.9, 171.9.

Tert-butyl 3-(2-(benzylamino)-1-(N-isobutylacetamido)-2-oxoethyl)-1H-indole-1-carboxylate (YH155)

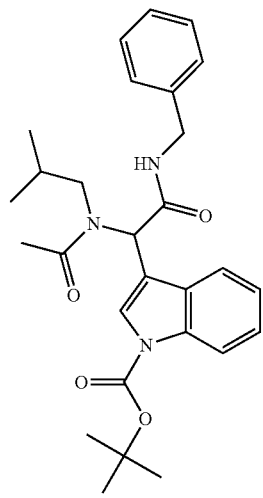 [SMILES: CC(=O)N(CC(C)C)C(C(=O)NCc1ccccc1)c1cn(C(=O)OC(C)(C)C)c2ccccc12]

The final product was obtained an off-white solids (44 mg, yield: 46%). HPLC/MS: $t_R$=12.04 min; m/z=478.1 [M+H]$^+$. HRMS: C$_{28}$H$_{35}$N$_3$O$_4$, [M+Na]$^+$; 500.2525 (calcd.), 500.2558 (found).

$^1$H NMR (600 MHz, CDCl$_3$): 0.72 (d, 1H, J=6.6 Hz), 0.76 (d, 1H, J=6.6 Hz), 1.68 (s, 9H), 1.86 (m, 1H), 2.22 (s, 3H), 3.02-3.13 (m, 2H), 4.41-4.54 (m, 2H), 6.20 (s, 1H), 7.13 (s, 1H), 7.22-7.37 (m, 8H), 8.14 (s, 1H), 8.20 (m, 1H).

$^{13}$C NMR (150 MHz, CDCl$_3$): 19.7, 20.1, 22.4, 27.8, 28.2, 43.5, 54.5, 54.9, 84.1, 113.5, 115.5, 118.4, 123.0, 124.9, 127.2, 127.3, 127.7, 128.6, 129.7, 135.1, 138.1, 149.5, 169.8, 172.5.

N-benzyl-2-(1H-indol-3-yl)-2-(N-isobutylacetamido)acetamide (YH159)

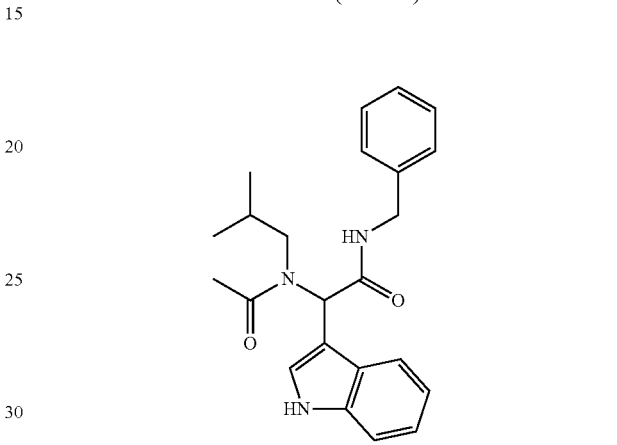

The final product was obtained an off-white solids (19 mg, yield: 55%). HPLC/MS: $t_R$=10.30 min; m/z=378.2 [M+H]$^+$. HRMS: C$_{23}$H$_{27}$N$_3$O$_2$, [M+Na]$^+$; 400.2001 (calcd), 400.1994 (found).

$^1$H NMR (600 MHz, CDCl$_3$): 0.71 (d, 1H, J=6.6 Hz), 0.77 (d, 1H, J=6.6 Hz), 1.84 (m, 1H), 2.21 (s, 3H), 3.07-3.09 (m, 2H), 4.35-4.54 (m, 2H), 6.06 (s, 1H), 6.91 (s, 1H), 7.14-7.28 (m, H), 7.41 (d, 1H, J=7.8 Hz), 7.48 (d, 1H, J=7.8 Hz), 7.74 (s, 1H), 8.79 (s, 1H).

$^{13}$C NMR (150 MHz, CDCl$_3$): 19.7, 20.1, 22.4, 27.8, 43.5, 55.5, 55.6, 109.8, 111.6, 118.1, 120.2, 122.5, 126.1, 127.2, 127.6, 128.6, 135.6, 138.2, 170.6, 172.1.

1-tert-butyl 2-ethyl 6-chloro-3-(1-(N-(4-chlorobenzyl)acetamido)-2-(cyclohexylamino)-2-oxoethyl)-1H-indole-1,2-dicarboxylate (YH173)

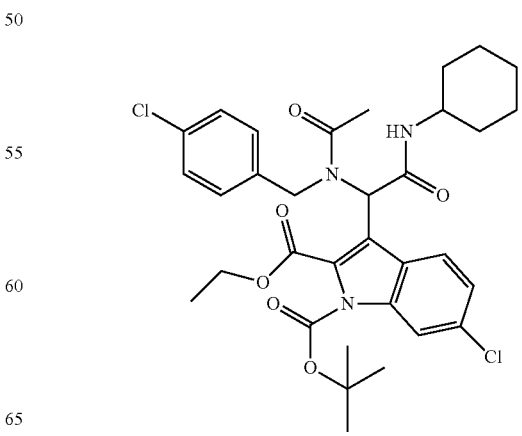

The final product was obtained a yellow solid (53 mg, yield: 41%). HPLC/MS: $t_R$=13.20 min; m/z=643.9 [M+H]$^+$. HRMS: $C_{33}H_{39}Cl_2N_3O_6$, 643.22159 (calcd.), 643.221049 (found).

Ethyl 6-chloro-3-(1-(N-(4-chlorobenzyl)acetamido)-2-(cyclohexylamino)-2-oxoethyl)-1H-indole-2-carboxylate (YH176)

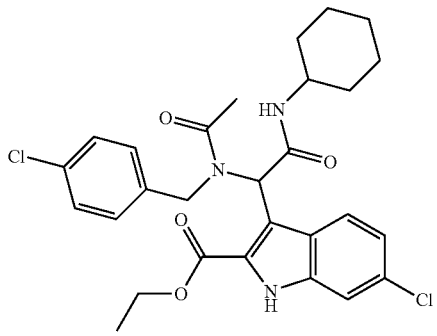 [SMILES: CCOC(=O)c1[nH]c2cc(Cl)ccc2c1C(C(=O)NC1CCCCC1)N(Cc1ccc(Cl)cc1)C(C)=O]

The final product was obtained a off-white solids (32 mg, yield: 71%). HPLC/MS: $t_R$=11.64 min; m/z=543.9 [M+H]$^+$. HRMS: $C_{28}H_{31}Cl_2N_3O_4$, 543.16916 (calcd.), 543.168429 (found).

$^1$H NMR (600 MHz, MeOD, a mixture of rotamers): 0.93-1.36 (m, 6H), 1.38 (t, 3H, J=7.2 Hz), 1.42 (t, 3H, J=7.2 Hz), 1.59-1.89 (m, 8H), 2.22 (s, 2H), 2.37 (s, 3H), 3.79 (m, 2H), 4.34-4.40 (m, 4H), 4.81 (m, 1H), 5.25 (m, 1H), 6.28 (m, 2H), 6.55 (m, 2H), 6.82 (d, 2H, J=7.8 Hz), 6.94 (d, 2H, J=7.8 Hz), 7.12 (m, 1H), 7.16 (m, 1H), 7.35 (s, 1H), 7.40 (s, 1H), 7.74 (m, 2H), 7.91 (d, 1H, J=-7.8 Hz), 8.16 (d, J=7.2 Hz).

$^{13}$C NMR (150 MHz, MeOD, a mixture of rotamers): 13.35, 13.39, 20.6, 20.8, 24.7, 24.75, 24.79, 24.9, 25.08, 25.13, 32.1, 32.2, 32.3, 32.4, 32.5, 49.0, 49.1, 49.7, 54.2, 56.8, 60.7, 60.8, 111.9, 112.1, 113.4, 113.7, 121.2, 121.3, 121.4, 121.5, 124.5, 125.3, 126.2, 126.8, 127.0, 127.4, 127.5, 128.0, 130.5, 130.7, 131.3, 131.8, 136.3, 136.4, 136.5, 137.5, 160.4, 160.7.

1-tert-butyl 2-ethyl 6-chloro-3-(2-(cyclohexylamino)-1-(N-(3,4-dichlorobenzyl)acetamido)-2-oxoethyl)-1H-indole-1,2-dicarboxylate (YH174)

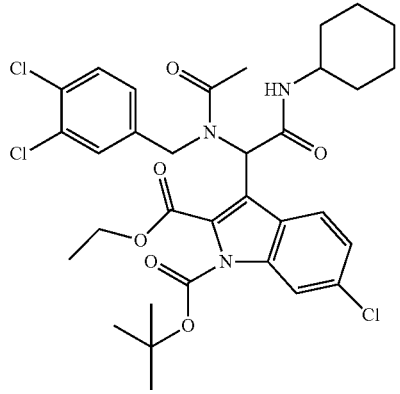 [SMILES: CCOC(=O)c1c(C(C(=O)NC2CCCCC2)N(Cc2ccc(Cl)c(Cl)c2)C(C)=O)c2ccc(Cl)cc2n1C(=O)OC(C)(C)C]

The final product was obtained a yellow solids (34 mg, yield: 25%). HPLC/MS: $t_R$=12.89 min; m/z=677.9 [M+H]$^+$. HRMS: $C_{33}H_{38}Cl_3N_3O_6$, 677.18262 (calcd.), 677.181174 (found).

Ethyl 6-chloro-3-(2-(cyclohexylamino)-1-(N-(3,4-dichlorobenzyl)acetamido)-2-oxoethyl)-1H-indole-2-carboxylate (YH177)

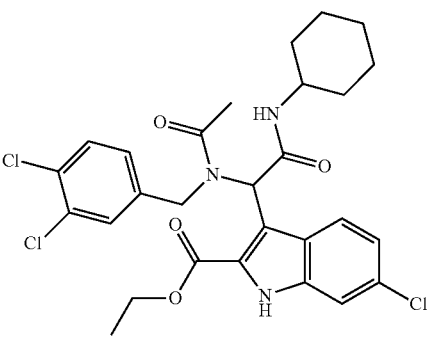 [SMILES: CCOC(=O)c1[nH]c2cc(Cl)ccc2c1C(C(=O)NC1CCCCC1)N(Cc1ccc(Cl)c(Cl)c1)C(C)=O]

The final product was obtained an off-white solids (10 mg, yield: 35%). HPLC/MS: $t_R$=11.93 min; m/z=577.9 [M+H]$^+$. HRMS: $C_{28}H_{30}Cl_3N_3O_4$, 577.13019 (calcd.), 577.129139 (found).

$^1$H NMR (600 MHz, DMSO, a mixture of rotamers): 0.85-1.25 (m, 14H), 1.33-1.38 (m, 5H), 1.50-1.75 (m, 14H), 2.00 (s, 2H), 2.20 (s, 2H), 3.16 (s, 3H), 3.57-3.74 (m, 6H), 4.27-4.36 (m, 4H), 4.77 (m, 1H), 5.07 (m, 1H), 6.29 (m, 2H), 6.44 (m, 1H), 6.63-6.84 (m, 2H), 7.11-7.39 (m, 6H), 7.68-8.13 (m, 5H).

$^{13}$C NMR (150 MHz, DMSO, a mixture of rotamers): 14.6, 14.8, 22.0, 22.3, 24.8, 24.9, 25.0, 25.5, 25.6, 32.65, 32.76, 32.81, 47.0, 48.4, 48.5, 49.1, 49.4, 53.9, 56.5, 61.30, 61.33, 112.5, 112.7, 114.5, 114.7, 121.5, 121.9, 122.1, 122.4, 124.9, 125.8, 126.2, 127.3, 127.7, 128.5, 129.0, 129.6, 129.8, 130.1, 130.2, 130.8, 136.6, 140.5, 140.9, 160.4, 169.0, 171.2.

Ethyl 3-(1-(benzylamino)-2-(cyclohexylamino)-2-oxoethyl)-6-chloro-1H-indole-2-carboxylate (YH194)

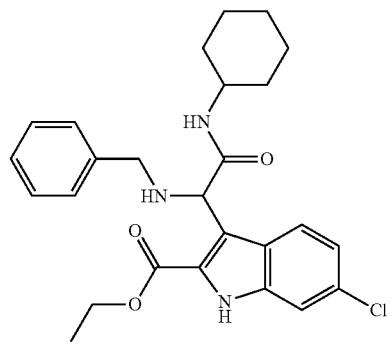 [SMILES: CCOC(=O)c1[nH]c2cc(Cl)ccc2c1C(NCc1ccccc1)C(=O)NC1CCCCC1]

The final product was obtained a yellowish solid (34 mg, yield: 58%). HRMS: $C_{26}H_{30}ClN_3O_3Na$, 490.1873 (calcd.), 490.1864 (found).

H NMR (600 MHz, CDCl$_3$, a mixture of rotamers): 0.82-1.06 (m, 6H), 1.26-1.37 (m, 10H), 1.59-1.92 (m, 10H), 3.64-

3.83 (m, 6H), 4.30-4.70 (m, 7H), 5.61-5.74 (m, 2H), 6.20 (s, 1H), 6.60 (m, 2H), 6.78 (s, 1H), 6.97-7.27 (m, 12H), 7.50 (m, 1H), 7.78 (m, 1H), 8.44 (s, 1H), 8.53 (s, 1H).

$^{13}$C NMR (150 MHz, CDCl$_3$, a mixture of rotamers): 14.3, 14.4, 24.76, 24.80, 24.9, 25.3, 25.4, 32.6, 32.7, 32.8, 32.9, 42.9, 46.4, 48.88, 48.92, 50.1, 52.3, 57.3, 61.6, 61.65, 61.68, 71.1, 72.3, 111.9, 112.3, 113.5, 115.1, 122.2, 122.3, 122.4, 122.7, 124.8, 125.6, 126.0, 126.3, 127.2, 127.3, 127.8, 127.9, 128.2, 128.4, 128.5, 131.6, 131.8, 131.9, 136.0, 137.3, 137.4, 160.6, 160.7, 163.7, 164.8, 167.9, 168.1.

3-(1-(benzylamino)-2-(cyclohexylamino)-2-oxoethyl)-6-chloro-1H-indole-2-carboxylic acid (YH230)

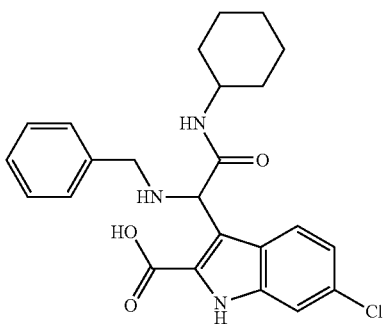 [SMILES: O=C(O)c1[nH]c2cc(Cl)ccc2c1C(NCc1ccccc1)C(=O)NC1CCCCC1]

The final product was obtained a yellow solid (21 mg, 74%). HPLC/MS: $t_R$=12.10 min; m/z=468.2 [M+H]$^+$. HRMS: C$_{24}$H$_{27}$N$_3$O$_3$Cl, 440.1741 (calcd.), 440.1721 (found).

$^1$H NMR (600 MHz, DMSO, a mixture of rotamers): 0.85-1.63 (m, 16H), 3.57 (m, 2H), 4.17 (ABd, 1H, J=16.2 Hz), 4.22 (ABd, J=15.6 Hz), 4.67 (ABd, 1H, J=16.8 Hz), 4.88 (ABd, 1H, J=15.6 Hz), 6.10 (s, 1H), 6.51 (m, 1H), 6.60 (s, 1H), 6.78 (m, 2H), 6.91-7.28 (m, 7H), 7.66-7.91 (m, 4H), 8.27 (s, 1H), 8.34 (s, 1H), 11.56 (s, 1H), 11.88 (s, 1H), 13.15 (br.s, 1H), 13.53 (br.s, 1H).

$^{13}$C NMR (150 MHz, DMSO, a mixture of rotamers): 25.0, 25.1, 25.5, 32.5, 32.6, 47.0, 48.5, 56.2, 112.4, 121.3, 122.4, 125.2, 125.8, 126.7, 126.8, 127.1, 127.7, 127.9, 129.0, 129.3, 136.4, 138.0, 164.2, 168.8.

6-chloro-3-(2-(cyclohexylamino)-1-(N-(4-fluorobenzyl)formamido)-2-oxoethyl)-1H-indole-2-carboxylic acid (YH280)

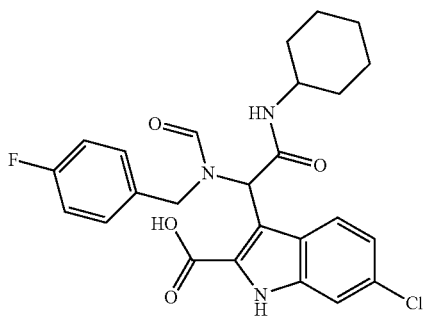 [SMILES: O=CN(Cc1ccc(F)cc1)C(C(=O)NC1CCCCC1)c1c(C(=O)O)[nH]c2cc(Cl)ccc12]

The final product was obtained a yellow solid (45 mg, 92%). HPLC/MS: $t_R$=10.96 min; m/z=486.3 [M+H]$^+$. HRMS: C$_{25}$H$_{25}$N$_3$O$_4$ClFNa, 508.1415 (calcd.), 508.1419 (found).

$^1$H NMR (600 MHz, MeOD, a mixture of rotamers): 0.92-1.12 (m, 8H), 1.29-1.36 (m, 4H), 1.58-1.90 (m, 8H), 2.13-2.37 (m, 2H), 3.67-3.77 (m, 2H), 4.27-4.32 (m, 2H), 4.69 (ABd, 1H, J=16.2 Hz), 5.10 (ABd, H, J=15.0 Hz), 6.33 (s, 1H), 6.50-6.85 (m, 6H) 7.11-7.14 (m, 2H), 7.39-7.42 (m, 2H), 7.69-7.95 (m, 4H), 8.40 (s, 1H), 8.47 (s, 1H).

$^{13}$C NMR (150 MHz, MeOD, a mixture of rotamers): 21.4, 24.3, 24.7, 24.8, 24.9, 25.1, 25.2, 28.9, 32.1, 32.2, 46.0, 49.0, 49.1, 49.3, 52.0, 52.2, 56.5, 111.8, 111.9, 112.4, 113.7, 113.8, 113.9, 114.0, 121.1, 121.2, 121.4, 121.5, 124.8, 125.6, 127.0, 127.1, 128.1, 128.7, 128.8, 130.3, 130.4, 132.9, 133.5, 133.6, 136.3, 160.8, 160.9, 162.4, 162.5, 162.6, 164.8, 165.3, 169.5, 169.6.

3-(2-(tert-butylamino)-1-(N-(4-chlorobenzyl)formamido)-2-oxoethyl)-6-chloro-1H-indole-2-carboxylic acid (YH270)

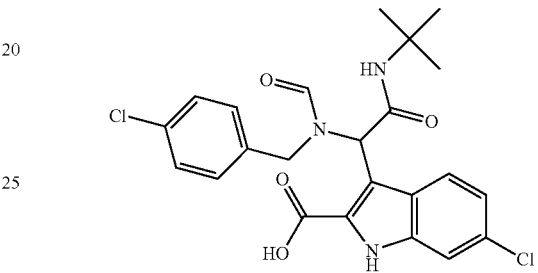

The final product was obtained a yellow solid (58 mg, 94%). HPLC/MS: $t_R$=10.82 min; m/z=476.1 [M+H]$^+$. HRMS: C$_{23}$H$_{23}$Cl$_2$N$_3$O$_4$Na, 498.0963 (calcd.), 498.0947 (found).

$^1$H NMR (600 MHz, MeOD, a mixture of rotamers): 1.25 (s, 9H), 1.31 (s, 5H), 4.29 (m, 2H), 4.70 (ABd, 1H, J=16.2 Hz), 5.13 (ABd, 1H, J=15.0 Hz), 5.52 (s, 1H), 6.25 (s, 1H), 6.47 (m, 1H), 6.77-7.14 (m, 8H), 7.39 (s, 1H), 7.42 (s, 1H), 7.60 (s, 1H), 7.80 (m, 1H), 7.84 (m, 1H), 8.37 (s, 1H), 8.47 (s, 1H).

$^{13}$C NMR (150 MHz, MeOD, a mixture of rotamers): 27.4, 27.5, 46.1, 51.2, 56.9, 111.8, 111.9, 120.9, 121.1, 121.7, 121.9, 124.7, 126.8, 127.2, 127.4, 128.6, 130.3, 130.5, 132.1, 132.2, 135.8, 136.3, 136.5, 165.3, 169.7.

3-(2-(tert-butylamino)-1-(N-(3,4-dichlorobenzyl)formamido)-2-oxoethyl)-6-chloro-1H-indole-2-carboxylic acid (YH289)

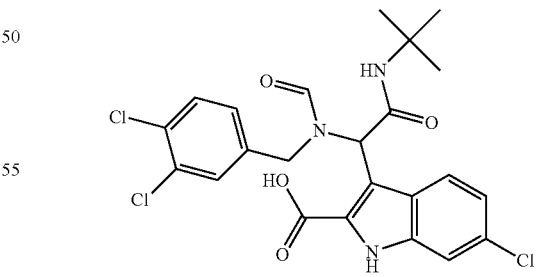

The final product was obtained as a yellow solid (70 mg, 98%). HPLC/MS: $t_R$=11.28 min; m/z=510.2 [M+H]$^+$.

$^1$H NMR (600 MHz, MeOD, a mixture of rotamers): 1.27 (s, 9H), 1.31 (s, 4H), 4.22 (ABd, 1H, J=15.6 Hz), 4.29 (ABd, 1H, J=16.8 Hz), 4.70 (ABd, 1H=16.2 Hz), 5.15 (ABd, 1H, J=16.2 Hz), 5.51 (s, 1H), 6.32 (s, 1H), 6.45 (m, 1H), 6.70-7.15 (m, 6H), 7.40-7.84 (m, 4H), 8.42 (s, 1H), 8.48 (s, 1H).

¹³C NMR (150 MHz, MeOD, a mixture of rotamers): 27.4, 27.5, 45.6, 49.1, 51.3, 52.5, 53.5, 56.8, 111.9, 112.0, 112.3, 113.7, 121.1, 121.2, 121.5, 121.7, 124.7, 125.0, 125.4, 126.6, 127.3, 128.3, 128.8, 129.1, 129.2, 129.9, 130.3, 130.4, 130.9, 131.0, 136.1, 136.2, 137.9, 138.5, 162.1, 162.6, 164.7, 165.3, 169.8.

3-(1-(N-benzylacetamido)-2-(cyclohexylamino)-2-oxoethyl)-6-chloro-N-(2-methoxyethyl)-1H-indole-2-carboxamide (YH220)

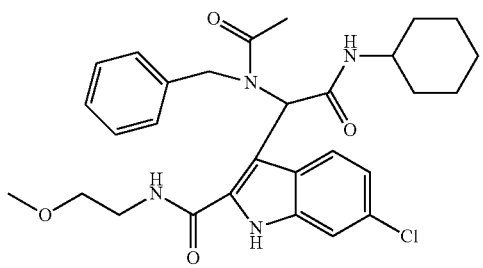 [SMILES: COCCNC(=O)c1[nH]c2cc(Cl)ccc2c1C(C(=O)NC1CCCCC1)N(Cc1ccccc1)C(C)=O]

The final product was obtained as a yellowish solid (14 mg, yield: 26%). HPLC/MS: $t_R$=15.45 min; m/z=539.4 [M+H]$^+$. HRMS: $C_{29}H_{35}N_4O_4Cl$, 538.234684 (calcd.), 538.234872 (found).
¹H NMR (600 MHz, CDCl₃): 0.85-1.33 (m, 7H), 1.56-1.92 (m, 7H), 2.18 (s, 3H), 3.36-3.83 (m, 8H), 4.68 (ABd, 1H, J=18.0 Hz), 4.92 (ABd, 1H, J=17.4 Hz), 6.65 (m, 2H), 6.84 (s, 1H), 6.97 (m, 3H), 7.06 (m, 1H), 7.59 (m, 1H), 7.94 (s, 1H), 10.03 (s, 1H).
¹³C NMR (150 MHz, CDCl₃): 22.2, 24.8, 24.9, 25.3, 32.7, 32.9, 39.5, 40.0, 49.2, 51.2, 53.8, 58.7, 58.8, 58.9, 70.5, 70.6, 108.4, 112.1, 112.2, 120.8, 121.5, 121.6, 122.0, 125.3, 126.8, 127.6, 127.9, 128.1, 128.8, 130.5, 131.6, 135.4, 137.3, 159.8, 161.0, 168.2, 173.8.

2-(N-benzylacetamido)-2-(6-chloro-2-((S)-3-((3-(dimethylamino)propyl)(methyl)amino) pyrrolidine-1-carbonyl)-1H-indol-3-yl)-N-cyclohexylacetamide (YH260)

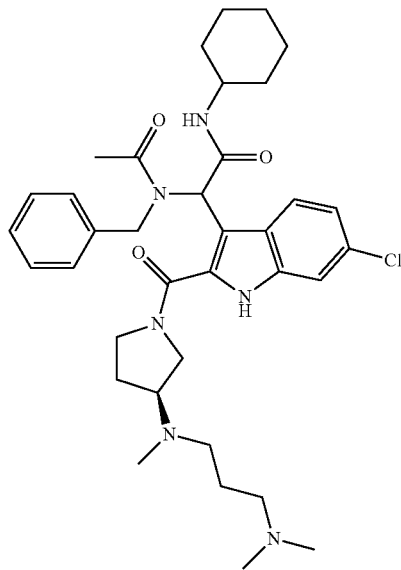 [SMILES: CC(=O)N(Cc1ccccc1)C(C(=O)NC1CCCCC1)c1c(C(=O)N2CC[C@H](N(C)CCCN(C)C)C2)[nH]c2cc(Cl)ccc12]

The final product was obtained a yellowish solid (8 mg, 41% yield). HPLC/MS: $t_R$=10.03 min; m/z=649.6 [M+H]$^+$. HRMS: $C_{36}H_{50}N_6O_3Cl$, 649.3633 (calcd.), 649.3599 (found).
¹H NMR (600 MHz, CDCl₃, a mixture of diastereomers): 0.87-1.32 (m, 10H), 1.52-1.88 (m, 12H), 2.13 (s, 2H), 2.31-2.38 (m, 8H), 2.61-2.81 (m, 2H), 2.97 (s, 3H), 3.74-3.83 (m, 2H), 4.75 (m, 2H), 5.17 (m, 1H), 5.82 (m, 1H), 6.04 (m, 1H), 6.53 (m, 2H), 6.82-7.12 (m, 7H), 7.62 (m, 1H), 7.89 (m, 1H), 13.76 (s, 1H), 13.97 (s, 1H).
¹³C NMR (150 MHz, CDCl₃, a mixture of diastereomers): 22.4, 22.9, 24.6, 24.7, 25.4, 29.6, 31.3, 32.7, 43.8, 45.8, 47.3, 48.2, 50.0, 53.0, 55.4, 111.1, 112.0, 121.1, 122.6, 125.4, 125.7, 126.1, 126.9, 127.4, 128.0, 129.1, 131.9, 135.7, 138.9, 172.4.

3-(2-(tert-butylamino)-2-oxo-1-(4-phenoxybenzylamino)ethyl)-6-chloro-1H-indole-2-carboxylic acid (YH287)

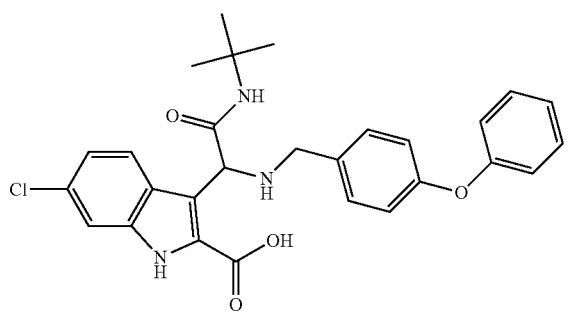 [SMILES: CC(C)(C)NC(=O)C(NCc1ccc(Oc2ccccc2)cc1)c1c(C(=O)O)[nH]c2cc(Cl)ccc12]

The final product was obtained a yellow solid (40 mg, yield: 94%). HPLC/MS: $t_R$=11.03 min; m/z=506.4 [M+H]$^+$. HRMS: $C_{28}H_{29}ClN_3O_4$, 506.1847 (calcd.), 506.1888 (found).
¹H NMR (600 MHz, MeOD, a mixture of rotamers): 1.28 (s, 9H), 1.84 (s, 3H), 4.28-4.34 (m, 2H), 5.89 (s, 1H), 6.59-6.81 (m, 3H), 7.01-7.20 (m, 8H), 7.36-7.55 (m, 6H), 7.84 (m, 1H).
¹³C NMR (150 MHz, MeOD, a mixture of rotamers): 27.4, 42.5, 51.5, 71.1, 72.2, 106.0, 110.5, 112.1, 117.8, 118.1, 118.2, 118.8, 119.2, 121.4, 121.9, 123.4, 123.8, 124.9, 126.4, 128.2, 129.2, 129.6, 129.8, 131.0, 132.1, 136.5, 156.3, 156.5, 157.4, 158.8, 165.4.

Tert-butyl 3-(2-(benzylamino)-1-(N-isobutylacetamido)-2-oxoethyl)-1H-indole-1-carboxylate (7a)

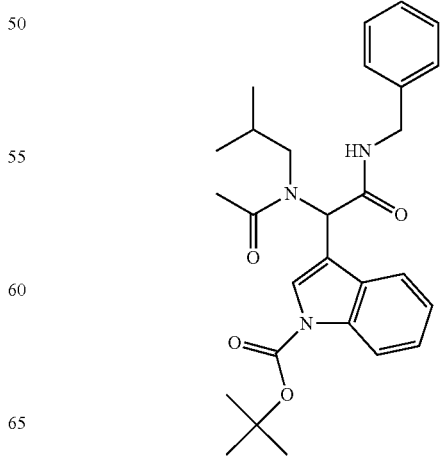

The final product is an off-white solids (44 mg, yield: 46%). HPLC/MS: $t_R$=12.04 min; m/z=478.1 [M+H]$^+$ HRMS: $C_{28}H_{35}N_3O_4$, [M+Na]$^+$; 500.2525 (calcd.), 500.2558 (found). $^1$H NMR (600 MHz, CDCl$_3$): 0.72 (d, 1H, J=6.6 Hz), 0.76 (d, 1H, J=6.6 Hz), 1.68 (s, 9H), 1.86 (m, 1H), 2.22 (s, 3H), 3.02-3.13 (m, 2H), 4.41-4.54 (m, 2H), 6.20 (s, 1H), 7.13 (s, 1H), 7.22-7.37 (m, 8H), 8.14 (s, 1H), 8.20 (m, 1H). $^{13}$C NMR (150 MHz, CDCl$_3$): 19.7, 20.1, 22.4, 27.8, 28.2, 43.5, 54.5, 54.9, 84.1, 113.5, 115.5, 118.4, 123.0, 124.9, 127.2, 127.3, 127.7, 128.6, 129.7, 135.1, 138.1, 149.5, 169.8, 172.5.

N-benzyl-2-(1H-indol-3-yl)-2-(N-isobutylacetamido)acetamide (8a)

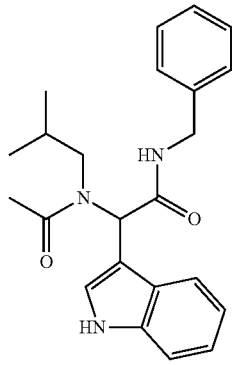 [SMILES: CC(=O)N(CC(C)C)C(C(=O)NCc1ccccc1)c1c[nH]c2ccccc12]

The final product is an off-white solids (19 mg, yield: 55%). HPLC/MS: $t_R$=10.30 min; m/z=378.2 [M+H]HRMS: $C_{23}H_{27}N_3O_2$, [M+Na]$^+$; 400.2001 (calcd.), 400.1994 (found). $^1$H NMR (600 MHz, CDCl$_3$): 0.71 (d, 1H, J=6.6 Hz), 0.77 (d, 1H, J=6.6 Hz), 1.84 (m, 1H), 2.21 (s, 3H), 3.07-3.09 (m, 2H), 4.35-4.54 (m, 2H), 6.06 (s, 1H), 6.91 (s, 1H), 7.14-7.28 (m, H), 7.41 (d, 1H, J=7.8 Hz), 7.48 (d, 1H, J=7.8 Hz), 7.74 (s, 1H), 8.79 (s, 1H). $^{13}$C NMR (150 MHz, CDCl$_3$): 19.7, 20.1, 22.4, 27.8, 43.5, 55.5, 55.6, 109.8, 111.6, 118.1, 120.2, 122.5, 126.1, 127.2, 127.6, 128.6, 135.6, 138.2, 170.6, 172.1.

N-benzyl-2-(N-benzylacetamido)-2-(1H-indol-3-yl)acetamide (8b)

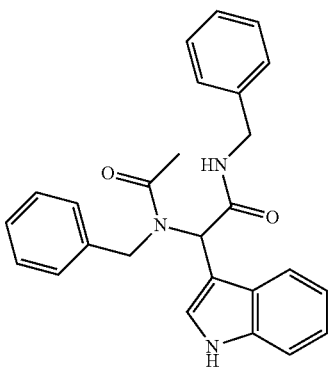 [SMILES: CC(=O)N(Cc1ccccc1)C(C(=O)NCc1ccccc1)c1c[nH]c2ccccc12]

The final product is an off-white solids (26 mg, yield: 46%). HPLC/MS: $t_R$=10.35 min; m/z=412.2 [M+H]HRMS: $C_{26}H_{25}N_3O_2$, [M+Na]$^+$; 434.1844 (calcd.), 434.1812 (found). $^1$H NMR (600 MHz, CDCl$_3$): 2.05 (s, 3H), 4.38-4.53 (m, 2H), 4.63-4.67 (m, 2H), 6.53 (s, 1H), 6.60 (m, 1H), 6.90 (m, 2H), 7.04-7.06 (m, 3H), 7.13 (m, 1H), 7.21 (m, 1H), 7.24-7.32 (m, 5H), 7.52 (m, 1H), 7.57 (m, 1H), 8.49 (s, 1H). $^{13}$C NMR (150 MHz, CDCl$_3$): 22.6, 43.6, 50.1, 54.4, 109.2, 111.5, 118.6, 120.3, 122.6, 126.0, 126.1, 126.7, 127.1, 127.4, 127.7, 128.3, 128.6, 135.8, 137.7, 138.0, 170.2, 172.8

1-tert-butyl 2-ethyl 3-(2-(benzylamino)-1-(N-isobutylacetamido)-2-oxoethyl)-6-chloro-1H-indole-1,2-dicarboxylate (7c)

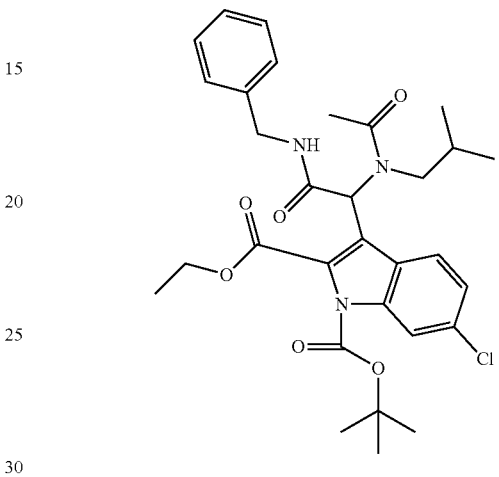

The final product is a yellow solid (32 mg, yield: 27%). HPLC/MS: $t_R$=12.38 min; m/z=583.9 [M+H]$^+$ HRMS: $C_{31}H_{38}N_3O_6Cl$, [M+Na]$^+$; 606.2347 (calcd.), 606.2401 (found). $^1$H NMR (600 MHz, CDCl$_3$): 0.58 (d, 3H, J=6.0 Hz), 0.75 (d, 3H, J=6.6 Hz), 1.37 (t, 3H, J=7.2 Hz), 1.46 (m, 1H), 1.65 (s, 9H), 2.22 (s, 3H), 3.24 (d, 2H, J=7.2 Hz), 4.35-4.49 (m, 4H), 6.08 (s, 1H), 6.30 (s, 1H), 7.18-7.26 (m, 6H), 7.74 (m, 1H), 8.14 (m, 1H). $^{13}$C NMR (150 MHz, CDCl$_3$): 13.9, 14.0, 19.90, 19.91, 22.1, 27.9, 28.5, 43.9, 54.6, 54.7, 62.5, 86.1, 115.3, 117.3, 122.7, 124.5, 125.7, 127.4, 127.9, 128.6, 131.4, 132.8, 136.2, 137.7, 148.4, 161.9, 168.5, 172.2.

Ethyl 3-(2-(benzylamino)-1-(N-isobutylacetamido)-2-oxoethyl)-6-chloro-1H-indole-2-carboxylate (8c)

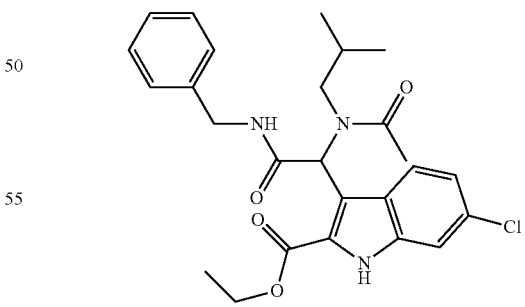

The final product is a yellowish solid (17 mg, yield: 64%). HPLC/MS: $t_R$=11.01 min; m/z=484.0 [M+H]$^+$ HRMS: $C_{26}H_{30}ClN_3O_4$, [M+Na]$^+$; 506.1823 (calcd.), 506.1801 (found). $^1$H NMR (600 MHz, MeOD, a mixture of rotamers): 0.17 (d, 2H, J=6.6 Hz), 0.39 (d, 3H, J=6.0 Hz), 0.52 (d, 2H, J=6.6 Hz), 0.65 (d, 3H, J=6.6 Hz), 1.39 (t, 3H, J=7.2 Hz), 1.43 (t, 2H, J=7.2 Hz), 2.24 (s, 3H), 2.29 (s, 2H), 2.84 (m, 1H), 3.24-3.33 (m, 4H), 3.69 (m, 1H), 4.36-4.42 (m, 7H), 6.65 (s, 1H), 6.94-6.98 (m, 3H), 7.14-7.23 (m, 8H), 7.30-7.41 (m, 3H), 7.51 (m, 2H), 7.58 (m, 1H). $^{13}$C NMR (150 MHz, MeOD, a mixture of rotamers): 13.3, 13.4, 18.6, 18.8, 20.9, 27.7, 28.4, 41.3, 42.9, 43.2, 51.7, 54.2, 55.0, 57.3, 61.0, 111.9, 112.0, 114.2, 115.0, 121.3, 121.4, 121.6, 122.1, 124.7, 126.3, 126.6, 126.9, 127.0, 127.2, 127.7, 127.9, 128.0, 128.2, 130.7, 130.8, 136.4, 136.6, 138.2, 138.3, 160.9, 161.3, 162.2, 171.0, 171.4, 173.0, 173.3.

1-tert-butyl 2-ethyl 3-(1-(N-benzylacetamido)-2-(benzylamino)-2-oxoethyl)-6-chloro-1H-indole-1,2-dicarboxylate (7d)

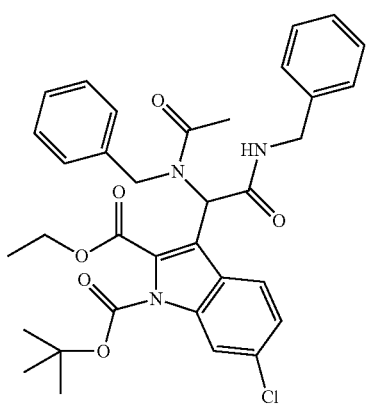 [SMILES: CCOC(=O)c1c(C(C(=O)NCc2ccccc2)N(Cc2ccccc2)C(C)=O)c2ccc(Cl)cc2n1C(=O)OC(C)(C)C]

The final product is a yellow solid (49 mg, yield: 40%). HPLC/MS: $t_R$=12.13 min; m/z=618.0 [M+H]$^+$ HRMS: $C_{34}H_{36}N_3O_6Cl$, [M+Na]$^+$; 640.2190 (calcd.), 640.2181 (found). $^1$H NMR (600 MHz, CDCl$_3$): 1.37 (t, 3H, J=7.2 Hz), 1.59 (s, 9H), 2.12 (s, 3H), 4.35-4.54 (m, 4H), 4.76-4.84 (m, 2H), 6.20 (s, 1H), 6.67 (s, 1H), 6.81 (m, 2H), 6.98-7.00 (m, 3H), 7.17-7.37 (m, 6H), 7.64 (m, 1H), 7.94 (s, 1H). $^{13}$C NMR (150 MHz, CDCl$_3$): 13.9, 22.1, 27.8, 44.0, 50.4, 53.4, 62.4, 85.7, 115.1, 116.9, 121.9, 124.4, 125.5, 126.0, 126.6, 127.5, 127.88, 127.92, 128.6, 131.1, 132.7, 136.0, 137.0, 137.5, 137.5, 148.1, 161.7, 168.4, 172.5.

Ethyl 3-(1-(N-benzylacetamido)-2-(benzylamino)-2-oxoethyl)-6-chloro-1H-indole-2-carboxylate (8d)

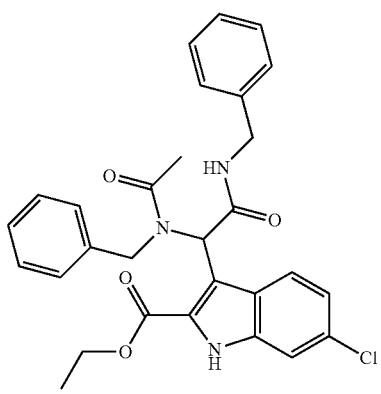 [SMILES: CCOC(=O)c1[nH]c2cc(Cl)ccc2c1C(C(=O)NCc1ccccc1)N(Cc1ccccc1)C(C)=O]

The final product is an off-white solids (18 mg, yield: 44%). HPLC/MS: $t_R$=10.97 min; m/z=518.0 [M+H]HRMS: $C_{29}H_{28}N_3O_4Cl$, [M+Na]$^+$; 540.1666 (calcd.), 540.1695 (found). $^1$H NMR (600 MHz, MeOD, a mixture of rotamers): 1.37 (t, 2H, J=7.2 Hz), 1.41 (t, 3H, J=7.2 Hz), 2.23 (s, 3H), 2.39 (s, 2H), 4.33-4.45 (m, 7H), 4.85 (m, 1H), 6.28 (m, 1H), 6.60 (m, 1H), 6.66 (s, 1H), 6.81 (m, 1H), 6.89 (m, 1H), 6.95-6.99 (m, 4H), 7.12 (s, 1H), 7.19-7.25 (m, 5H), 7.31 (m, 1H), 7.44 (m, 1H), 7.57 (m, 1H). $^{13}$C NMR (150 MHz, MeOD, a mixture of rotamers): 13.3, 13.4, 20.8, 42.9, 43.2, 50.2, 54.4, 60.6, 60.8, 111.7, 111.8, 113.1, 113.5, 121.2, 121.3, 121.6, 124.5, 125.2, 125.5, 125.6, 126.2, 126.6, 126.8, 127.0, 127.3, 127.4, 127.8, 127.9, 128.0, 128.1, 130.38, 130.40, 136.4, 137.5, 138.1, 138.3, 160.5, 160.8.

1-tert-butyl 2-ethyl 3-(1-(N-benzylacetamido)-2-(cyclohexylamino)-2-oxoethyl)-6-chloro-1H-indole-1,2-dicarboxylate (7e)

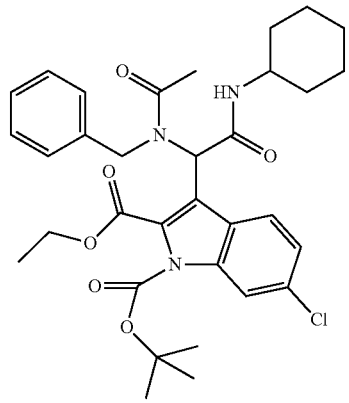 [SMILES: CCOC(=O)c1c(C(C(=O)NC2CCCCC2)N(Cc2ccccc2)C(C)=O)c2ccc(Cl)cc2n1C(=O)OC(C)(C)C]

The final product is a yellowish solid (44 mg, yield: 36%). HPLC/MS: $t_R$=12.91 min; m/z=610.1 [M+H]HRMS: $C_{33}H_{40}N_3O_6Cl$, [M+Na]$^+$; 632.2503 (calcd.), 632.2499 (found). $^1$H NMR (600 MHz, CDCl$_3$): 0.94-1.35 (m, 6H), 1.39 (t, 3H, J=7.2 Hz), 1.60 (s, 9H), 1.66-2.09 (m, 4H), 2.17 (s, 3H), 3.78 (m, 1H), 4.39 (m, 2H), 4.72-4.82 (m, 2H), 5.54 (m, 1H), 6.55 (s, 1H), 6.83 (m, 2H), 7.01 (m, 3H), 7.22-7.28 (m, 1H), 7.72 (m, 1H), 7.96 (s, 1H). $^{13}$C NMR (150 MHz, CDCl$_3$): 13.9, 22.1, 24.8, 24.9, 25.4, 27.8, 32.7, 32.9, 49.0, 50.5, 53.3, 62.4, 85.7, 115.1, 117.1, 122.0, 124.3, 125.5, 126.5, 127.9, 131.2, 132.6, 136.1, 137.1, 148.2, 161.7, 167.3, 172.2.

Ethyl 3-(1-(N-benzylacetamido)-2-(cyclohexylamino)-2-oxoethyl)-6-chloro-1H-indole-2-carboxylate (8e)

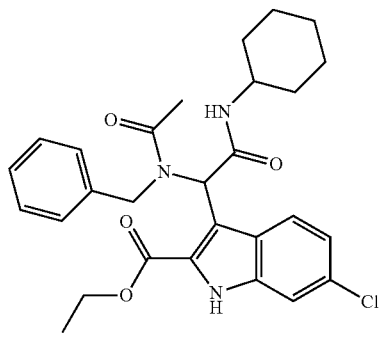 [SMILES: CCOC(=O)c1[nH]c2cc(Cl)ccc2c1C(C(=O)NC1CCCCC1)N(Cc1ccccc1)C(C)=O]

The final product is an off-white solids (16 mg, yield: 44%). HPLC/MS: $t_R$=11.26 min; m/z=509.9 [M+H]$^+$ HRMS: $C_{28}H_{32}N_3O_4Cl$, [M+Na]$^+$; 532.1979 (calcd.), 532.1959

(found). ¹H NMR (600 MHz, MeOD, a mixture of rotamers): 0.98-1.40 (m, 6H), 1.40 (m, 3H), 1.44 (m, 3H), 1.63-1.91 (m, 10H), 2.21 (s, 3H), 2.38 (s, 2H), 3.75-3.85 (m, 3H), 4.34-4.42 (m, 4H), 4.83 (m, 2H), 5.31 (m, 1H), 6.32 (m, 1H), 6.57-7.15 (m, 10H), 7.34 (m, 1H), 7.75 (m, 2H), 7.89 (m, 1H), 8.12 (m, 1H). ¹³C NMR (150 MHz, MeOD, a mixture of rotamers): 12.12, 12.17, 19.4, 19.6, 23.49, 23.54, 23.6, 23.7, 23.86, 23.92, 30.9, 30.98, 31.01, 31.2, 47.6, 47.7, 49.0, 53.0, 55.6, 59.4, 59.5, 110.6, 110.7, 112.1, 112.4, 119.9, 129.97, 120.02, 120.3, 123.3, 123.4, 124.1, 124.2, 124.4, 124.9, 125.6, 126.2, 126.4, 126.9, 129.2, 129.3, 135.1, 136.4, 137.3, 159.2, 159.6.

Ethyl 6-chloro-3-(1-(N-(4-chlorobenzyl)acetamido)-2-(cyclohexylamino)-2-oxoethyl)-1H-indole-2-carboxylate (8f)

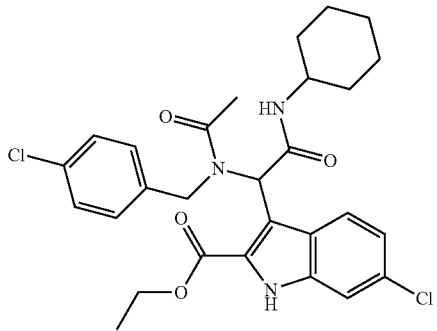 [SMILES: CCOC(=O)c1[nH]c2cc(Cl)ccc2c1C(C(=O)NC1CCCCC1)N(Cc1ccc(Cl)cc1)C(C)=O]

The final product is a off-white solids (32 mg, yield: 71%). HPLC/MS: $t_R$=11.64 min; m/z=543.9 [M+H]⁺ HRMS: $C_{28}H_{31}Cl_2N_3O_4$, 543.16916 (calcd.), 543.168429 (found). ¹H NMR (600 MHz, MeOD, a mixture of rotamers): 0.93-1.36 (m, 6H), 1.38 (t, 3H, J=7.2 Hz), 1.42 (t, 3H, J=7.2 Hz), 1.59-1.89 (m, 8H), 2.22 (s, 2H), 2.37 (s, 3H), 3.79 (m, 2H), 4.34-4.40 (m, 4H), 4.81 (m, 1H), 5.25 (m, 1H), 6.28 (m, 2H), 6.55 (m, 2H), 6.82 (d, 2H, J=7.8 Hz), 6.94 (d, 2H, J=7.8 Hz), 7.12 (m, 1H), 7.16 (m, 1H), 7.35 (s, 1H), 7.40 (s, 1H), 7.74 (m, 2H), 7.91 (d, 1H, J=7.8 Hz), 8.16 (d, 1H, J=7.2 Hz). ¹³C NMR (150 MHz, MeOD, a mixture of rotamers): 13.35, 13.39, 20.6, 20.8, 24.7, 24.75, 24.79, 24.9, 25.08, 25.13, 32.1, 32.2, 32.3, 32.4, 32.5, 49.0, 49.1, 49.7, 54.2, 56.8, 60.7, 60.8, 111.9, 112.1, 113.4, 113.7, 121.2, 121.3, 121.4, 121.5, 124.5, 125.3, 126.2, 126.8, 127.0, 127.4, 127.5, 128.0, 130.5, 130.7, 131.3, 131.8, 136.3, 136.4, 136.5, 137.5, 160.4, 160.7.

Ethyl 6-chloro-3-(2-(cyclohexylamino)-1-(N-(3,4-dichlorobenzyl)acetamido)-2-oxoethyl)-1H-indole-2-carboxylate (8g)

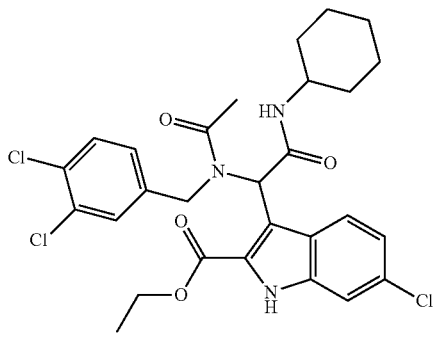 [SMILES: CCOC(=O)c1[nH]c2cc(Cl)ccc2c1C(C(=O)NC1CCCCC1)N(Cc1ccc(Cl)c(Cl)c1)C(C)=O]

The final product is an off-white solids (10 mg, yield: 35%). HPLC/MS: $t_R$=11.93 min; m/z=577.9 [M+H]⁺ HRMS: $C_{28}H_{30}Cl_3N_3O_4$, 577.13019 (calcd.), 577.129139 (found). ¹H NMR (600 MHz, DMSO, a mixture of rotamers): 0.85-1.25 (m, 14H), 1.33-1.38 (m, 5H), 1.50-1.75 (m, 14H), 2.00 (s, 2H), 2.20 (s, 2H), 3.16 (s, 3H), 3.57-3.74 (m, 6H), 4.27-4.36 (m, 4H), 4.77 (m, 1H), 5.07 (m, 1H), 6.29 (m, 2H), 6.44 (m, 1H), 6.63-6.84 (m, 2H), 7.11-7.39 (m, 6H), 7.68-8.13 (m, 5H). ¹³C NMR (150 MHz, DMSO, a mixture of rotamers): 14.6, 14.8, 22.0, 22.3, 24.8, 24.9, 25.0, 25.5, 25.6, 32.65, 32.76, 32.81, 47.0, 48.4, 48.5, 49.1, 49.4, 53.9, 56.5, 61.30, 61.33, 112.5, 112.7, 114.5, 114.7, 121.5, 121.9, 122.1, 122.4, 124.9, 125.8, 126.2, 127.3, 127.7, 128.5, 129.0, 129.6, 129.8, 130.1, 130.2, 130.8, 136.6, 140.5, 140.9, 160.4, 169.0, 171.2.

Scheme 1—Method B:

The mixture of aldehyde (2, 0.2 mmol), isocyanide (4, 0.2 mmol), amine (5, 0.2 mmol), acid (6, 0.2 mmol) in 0.5 mL of methanol was stirred at RT for 2 days. The products (7 and 8) were purified by chromatography on silica gel (petroleum ether/ethyl acetate, 3:1).

1-tert-butyl 2-ethyl 3-(1-(N-benzylbutyramido)-2-(cyclohexylamino)-2-oxoethyl)-6-chloro-1H-indole-1,2-dicarboxylate (7h)

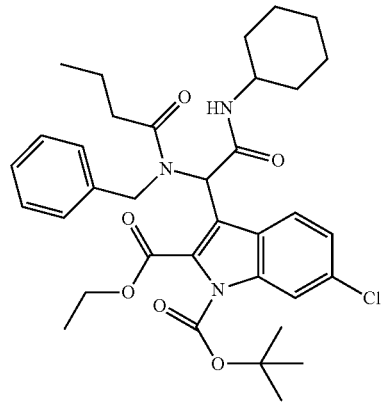 [SMILES: CCCC(=O)N(Cc1ccccc1)C(C(=O)NC1CCCCC1)c1c(C(=O)OCC)n(C(=O)OC(C)(C)C)c2cc(Cl)ccc12]

The final product is a yellow solid (58 mg, yield: 46%). HPLC/MS: $t_R$=13.53 min; m/z=638.0 [M+H]⁺ HRMS: $C_{35}H_{44}ClN_3O_6$, 637.29186 (calcd.), 637.290037 (found). ¹H NMR (600 MHz, CDCl₃): 0.90-1.38 (m, 14H), 1.59 (s, 9H), 1.67-2.46 (m, 8H), 3.78 (m, 1H), 4.37 (m, 2H), 4.71-4.84 (ABd, 2H, J=18.0 Hz), 5.63 (m, 1H), 6.60 (s, 1H), 6.79 (m, 2H), 6.98 (m, 3H), 7.20-7.22 (m, 1H), 7.71 (m, 1H), 7.93 (s, 1H). ¹³C NMR (150 MHz, CDCl₃): 13.9, 14.0, 18.9, 24.78, 24.84, 25.4, 27.8, 32.7, 32.9, 35.5, 49.0, 49.6, 53.2, 62.3, 85.5, 115.0, 117.3, 122.0, 124.2, 125.5, 126.1, 126.4, 127.8, 131.1, 132.6, 136.1, 137.3, 148.2, 161.7, 167.5, 174.6.

Ethyl 3-(1-(N-benzylbutyramido)-2-(cyclohexylamino)-2-oxoethyl)-6-chloro-1H-indole-2-carboxylate (8h)

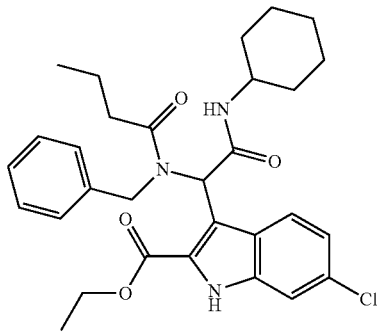 [SMILES: CCCC(=O)N(Cc1ccccc1)C(C(=O)NC1CCCCC1)c1c(C(=O)OCC)[nH]c2cc(Cl)ccc12]

The final product is a yellow solid (37 mg, yield: 34%). HPLC/MS: $t_R$=11.93 min; m/z=538.1 [M+H]$^+$ HRMS: $C_{30}H_{36}ClN_3O_4$, 537.23943 (calcd.), 537.239259 (found). $^1$H NMR (600 MHz, CDCl$_3$, major rotamer): 0.92-1.06 (m, 8H), 1.28-1.39 (m, 6H), 1.57-1.93 (m, 10H), 2.27-2.45 (m, 2H), 3.85 (m, 1H), 4.30-4.31 (m, 2H), 4.47 (ABd, 1H, J=18.0 Hz), 4.78 (ABd, 1H, J=18.0 Hz), 5.56 (m, 1H), 6.53 (m, 1H), 6.64 (m, 2H), 6.97-7.24 (m, 7H), 7.84 (m, 1H), 9.32 (m, 1H). $^{13}$C NMR (150 MHz, CDCl$_3$, major rotamer): 13.9, 14.3, 18.9, 24.8, 24.9, 25.4, 32.90, 32.94, 35.6, 48.8, 49.6, 54.2, 61.6, 111.9, 114.5, 122.3, 122.8, 125.0, 125.7, 126.5, 126.6, 127.3, 127.7, 127.8, 131.5, 135.9, 138.1, 160.9, 169.0, 174.2.

1-tert-butyl 2-ethyl 3-(1-(N-benzylformamido)-2-(cyclohexylamino)-2-oxoethyl)-6-chloro-1H-indole-1,2-dicarboxylate (7i)

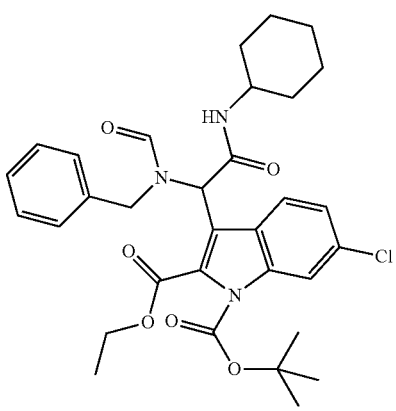 [SMILES: CCOC(=O)c1c(C(C(=O)NC2CCCCC2)N(C=O)Cc2ccccc2)c2ccc(Cl)cc2n1C(=O)OC(C)(C)C]

The final product is an yellow solid (75 mg, yield: 63%). HPLC/MS: $t_R$=12.89 min; m/z=595.9 [M+H]$^+$ HRMS: $C_{32}H_{38}ClN_3O_6Na$, 618.2347 (calcd.), 618.2329 (found). $^1$H NMR (600 MHz, CDCl$_3$, a mixture of rotamers): 0.85-1.06 (m, 6H), 1.27-1.39 (m, 7H), 1.59-1.65 (m, 20H), 1.76-1.92 (m, 3H), 3.75 (m, 2H), 4.24-4.66 (m, 6H), 5.40 (s, 1H), 5.72-5.91 (m, 2H), 6.33 (s, 1H), 6.77-7.05 (m, 6H), 7.16-7.20 (m, 4H), 7.48-7.62 (m, 2H), 7.93 (s, 1H), 8.01 (s, 1H), 8.35 (s, 1H), 8.44 (s, 1H). $^{13}$C NMR (150 MHz, CDCl$_3$, a mixture of rotamers): 13.9, 14.0, 24.65, 24.73, 24.80, 24.84, 25.3, 25.4, 27.8, 27.9, 32.4, 32.6, 32.7, 32.9, 46.3, 49.0, 49.1, 49.8, 51.0, 56.4, 62.3, 85.7, 86.0, 115.0, 115.3, 116.4, 117.7, 121.8, 122.1, 124.2, 124.6, 125.1, 125.9, 126.6, 127.1, 127.4, 127.8, 128.0, 128.4, 130.4, 131.0, 132.7, 133.1, 136.0, 136.3, 136.4, 136.5, 148.1, 148.3, 161.6, 161.7, 163.7, 163.8, 166.2, 166.4.

Ethyl 3-(1-(N-benzylformamido)-2-(cyclohexylamino)-2-oxoethyl)-6-chloro-1H-indole-2-carboxylate (8i)

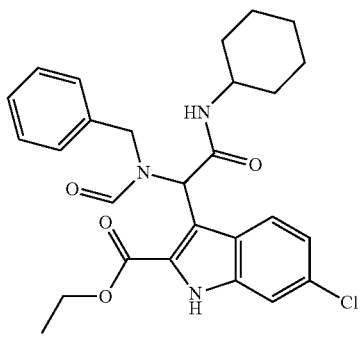 [SMILES: CCOC(=O)c1[nH]c2cc(Cl)ccc2c1C(C(=O)NC1CCCCC1)N(C=O)Cc1ccccc1]

The final product is an yellowish solid (27 mg, yield: 27%). HPLC/MS: $t_R$=16.99 min; m/z=496.3 [M+H]$^+$ HRMS: $C_{27}H_{30}ClN_3O_4Na$, 518.1823 (calcd.), 518.1794 (found). $^1$H NMR (600 MHz, CDCl$_3$, a mixture of rotamers): 0.89-1.31 (m, 12H), 1.33-1.38 (m, 6H), 1.59-1.94 (m, 12H), 3.82 (m, 2H), 4.30-4.72 (m, 8H), 5.59-5.72 (m, 2H), 6.20 (s, 1H), 6.59 (m, 2H), 6.77 (s, 1H), 6.97-7.26 (m, 14H), 7.52 (m, 1H), 7.79 (m, 1H), 8.44 (s, 1H), 8.52 (s, 1H), 9.26 (s, 1H), 9.58 (s, 1H). $^{13}$C NMR (150 MHz, CDCl$_3$, a mixture of rotamers): 14.3, 14.4, 24.75, 24.79, 24.9, 25.3, 25.4, 32.6, 32.7, 32.8, 32.9, 33.0, 46.4, 48.9, 50.1, 52.2, 57.3, 61.6, 61.7, 111.9, 112.3, 113.5, 115.2, 122.3, 122.4, 122.5, 122.7, 124.9, 125.6, 125.9, 126.3, 127.1, 127.26, 127.28, 127.69, 127.72, 127.79, 127.84, 128.3, 128.8, 131.7, 131.8, 135.9, 136.0, 137.3, 137.4, 160.4, 160.6, 160.7, 161.1, 163.7, 164.7, 167.9, 168.1.

Scheme 1—Method C:

The mixture of aldehyde (3, 0.2 mmol), isocyanide (4, 0.2 mmol), amine (5, 0.2 mmol), acid (6, 0.2 mmol) in 0.5 mL of methanol was stirred at RT for 5-7 days. The product (8) was purified by chromatography on silica gel (petroleum ether/ethyl acetate, 1:1).

Ethyl 6-chloro-3-(1-(N-(4-chlorobenzyl)formamido)-2-(cyclohexylamino)-2-oxoethyl)-1H-indole-2-carboxylate (8j)

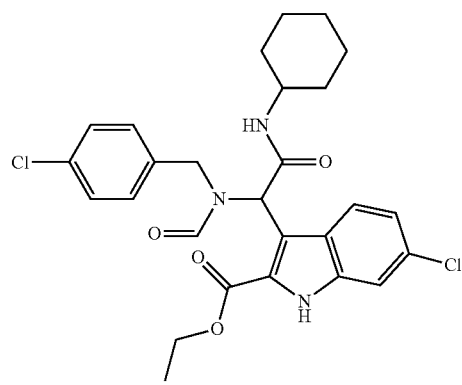 [SMILES: CCOC(=O)c1[nH]c2cc(Cl)ccc2c1C(C(=O)NC1CCCCC1)N(C=O)Cc1ccc(Cl)cc1]

The final product is a yellow solid (55 mg, yield: 52%). HPLC/MS: $t_R$=17.00 min; m/z=530.1 [M+H]$^+$ HRMS: $C_{27}H_{29}N_3O_4Cl_2Na$, 552.1433 (calcd.), 552.1401 (found). $^1$H NMR (600 MHz, CDCl$_3$, a mixture of rotamers): 0.86-1.07 (m, 6H), 1.31-1.39 (m, 9H), 1.58-1.87 (m, 10H), 3.65-3.84 (m, 3H), 4.25 (ABd, 1H, J=15.0 Hz), 4.30-4.35 (m, 4H), 4.59 (ABd, 1H, J=16.8 Hz), 4.85 (ABd, 1H, J=15.6 Hz), 5.57 (m, 1H), 5.65 (m, 1H), 6.18 (s, 1H), 6.51 (m, 1H), 6.76 (s, 1H), 6.79-7.28 (m, 9H), 7.56 (m, 1H), 7.79 (m, 1H), 8.41 (s, 1H), 8.48 (s, 1H), 9.34 (s, 1H), 9.58 (s, 1H). $^{13}$C NMR (150 MHz, CDCl$_3$, a mixture of rotamers): 14.3, 24.7, 24.8, 25.3, 25.4, 32.7, 32.8, 45.9, 49.0, 49.5, 52.1, 56.9, 61.7, 112.0, 112.4, 113.4, 114.9, 122.1, 122.5, 122.6, 124.7, 125.5, 126.4, 127.17, 127.23, 127.3, 127.8, 128.1, 128.2, 128.8, 129.1, 131.8, 131.9, 132.8, 135.86, 135.89, 136.0, 160.5, 160.6, 163.6, 164.6, 167.8, 168.0.

Ethyl 6-chloro-3-(2-(cyclohexylamino)-1-(N-(4-fluorobenzyl)formamido)-2-oxoethyl)-1H-indole-2-carboxylate (8k)

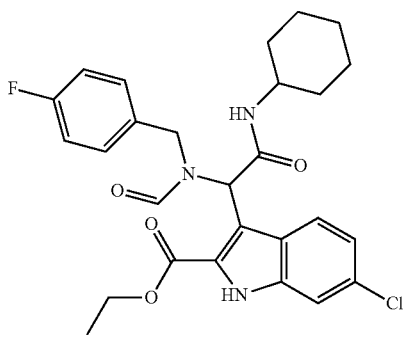 [SMILES: CCOC(=O)c1[nH]c2cc(Cl)ccc2c1C(C(=O)NC1CCCCC1)N(C=O)Cc1ccc(F)cc1]

The final product is a yellow solid (56 mg, yield: 55%). HPLC/MS: $t_R$=16.73 min; m/z=514.3 [M+H]$^+$ HRMS: $C_{27}H_{29}N_3O_4ClFNa$, 536.1728 (calcd.), 536.1700 (found). $^1$H NMR (600 MHz, CDCl$_3$, a mixture of rotamers): 0.88-1.19 (m, 8H), 1.32-1.41 (m, 10H), 1.59-1.96 (m, 14H), 3.85 (m, 3H), 4.27 (ABd, 1H, J=15.0 Hz), 4.34-4.38 (m, 4H), 4.60 (ABd, 1H, J=16.2 Hz), 4.88 (ABd, 1H, J=15.6 Hz), 5.48 (m, 1H), 5.58 (m, 1H), 6.17 (s, 1H), 6.55-6.86 (m, 8H), 7.17 (m, 2H), 7.32 (m, 1H), 7.59 (m, 1H), 7.83 (m, 1H), 8.42 (s, 1H), 8.50 (s, 1H), 9.06 (s, 1H), 9.24 (s, 1H). $^{13}$C NMR (150 MHz, CDCl$_3$, a mixture of rotamers): 14.38, 14.40, 24.7, 24.8, 24.9, 25.3, 25.39, 25.41, 32.7, 32.8, 32.9, 33.0, 33.1, 45.7, 49.0, 49.5, 52.0, 56.8, 61.7, 61.8, 111.8, 112.1, 113.6, 114.5, 114.6, 114.7, 114.9, 115.3, 122.3, 122.6, 122.7, 122.8, 124.8, 125.6, 126.3, 127.1, 127.4, 127.5, 129.09, 129.14, 131.9, 132.1, 133.2, 135.7, 135.8, 160.3, 160.5, 163.5, 164.5, 167.7, 167.8.

Ethyl 3-(2-(tert-butylamino)-1-(N-(4-chlorobenzyl)formamido)-2-oxoethyl)-6-chloro-1H-indole-2-carboxylate (8l)

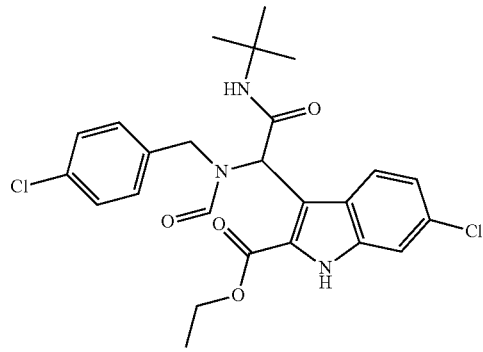 [SMILES: CCOC(=O)c1[nH]c2cc(Cl)ccc2c1C(C(=O)NC(C)(C)C)N(C=O)Cc1ccc(Cl)cc1]

The final product is a yellow solid (70 mg, yield: 70%). HPLC/MS: $t_R$=16.83 min; m/z=504.4 [M+H]HRMS: $C_{25}H_{27}N_3O_4Cl_2Na$, 526.1276 (calcd.), 526.1237 (found). $^1$H NMR (600 MHz, CDCl$_3$, a mixture of rotamers): 1.25 (s, 9H), 1.30 (s, 7H), 1.35-1.39 (m, 10H), 4.22 (ABd, 1H, J=15.0 Hz), 4.29-4.45 (m, 4H), 4.58 (ABd, 1H, J=16.2 Hz), 4.94 (ABd, 1H, J=15.6 Hz), 5.54 (s, 1H), 6.11 (s, 1H), 6.45 (m, 1H), 6.71 (s, 1H), 6.82-7.28 (m, 9H), 7.32 (s, 1H), 7.65 (m, 1H), 7.87 (m, 1H), 8.41 (s, 1H), 8.47 (s, 1H), 9.53 (s, 1H), 9.79 (s, 1H). $^{13}$C NMR (150 MHz, CDCl$_3$, a mixture of rotamers): 14.36, 14.39, 28.4, 28.6, 28.9, 30.8, 46.1, 49.5, 51.9, 52.1, 52.5, 57.1, 61.7, 112.0, 112.3, 115.2, 122.3, 122.5, 122.6, 122.7, 124.7, 126.3, 127.1, 127.2, 127.7, 128.1, 128.6, 128.8, 128.9, 129.1, 129.7, 131.7, 131.9, 132.7, 132.8, 135.9, 136.0, 160.56, 160.64, 163.5, 164.6, 168.0, 168.1.

Ethyl 3-(2-(tert-butylamino)-1-(N-(3,4-dichlorobenzyl)formamido)-2-oxoethyl)-6-chloro-1H-indole-2-carboxylate (8m)

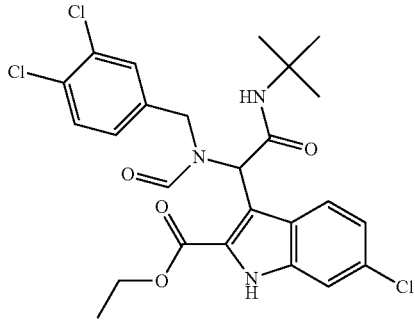 [SMILES: CCOC(=O)c1[nH]c2cc(Cl)ccc2c1C(C(=O)NC(C)(C)C)N(C=O)Cc1ccc(Cl)c(Cl)c1]

The final product is a yellow solid (77 mg, yield: 72%). HPLC/MS: $t_R$=11.93 min; m/z=538.2 [M+H]HRMS: $C_{25}H_{26}Cl_3N_3O_4Na$, 560.0887 (calcd.), 560.0878 (found). $^1$H NMR (600 MHz, CDCl$_3$, a mixture of rotamers): 1.30 (s, 9H), 1.31 (s, 6H), 1.37-1.41 (m, 6H), 4.13 (ABd, 1H, J=15.6 Hz), 4.30-4.36 (m, 4H), 4.59 (m, 1H), 5.03 (ABd, 1H, J=15.6 Hz), 5.60 (m, 1H), 6.16 (s, 1H), 6.30-6.76 (m, 4H), 6.94-7.19 (m, 4H), 7.35 (m, 1H), 7.68 (m, 1H), 7.86 (m, 1H), 8.42 (s, 1H), 8.46 (s, 1H), 9.66 (m, 1H), 9.89 (m, 1H). $^{13}$C NMR (150 MHz, CDCl$_3$, a mixture of rotamers): 14.4, 28.5, 28.6, 45.5, 49.2, 52.0, 52.2, 56.9, 61.8, 61.9, 112.2, 112.4, 113.1, 114.8, 122.0, 122.4, 113.1, 114.8, 122.0, 122.4, 122.7, 122.8, 124.6, 124.9, 125.4, 126.4, 126.6, 127.2, 127.5, 128.9, 129.4, 129.6, 130.5, 130.6, 131.6, 131.9, 132.0, 136.0, 137.7, 138.0, 160.5, 160.6, 163.5, 164.6, 168.1.

Ethyl 3-(2-(tert-butylamino)-1-(N-(2,4-dichlorobenzyl)formamido)-2-oxoethyl)-6-chloro-1H-indole-2-carboxylate (8n)

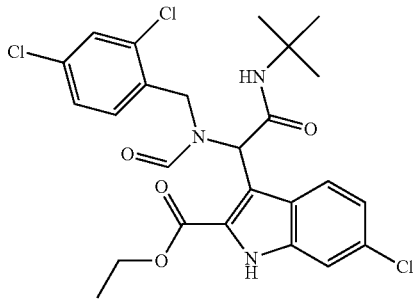 [SMILES: CCOC(=O)c1[nH]c2cc(Cl)ccc2c1C(C(=O)NC(C)(C)C)N(C=O)Cc1ccc(Cl)cc1Cl]

The final product is a yellow solid (92 mg, yield: 86%). HPLC/MS: $t_R$=11.58 min; m/z=537.8 [M+H]$^+$ HRMS: C$_{25}$H$_{26}$N$_3$O$_4$Cl$_3$Na, 560.0887 (calcd.), 560.0880 (found). $^1$H NMR (400 MHz, CDCl$_3$, a mixture of rotamers): 1.26 (s, 9H), 1.29 (s, 5H), 1.35-1.39 (m, 6H), 4.30-4.39 (m, 3H), 4.48-4.61 (m, 3H), 4.96 (ABd, 1H, J=16.4 Hz), 5.59 (s, 1H), 6.18 (s, 1H), 6.73 (s, 1H), 6.82-6.89 (m, 2H), 6.95-7.12 (m, 5H), 7.31 (m, 2H), 7.64 (m, 1H), 7.81 (m, 1H), 8.33 (s, 1H), 8.48 (s, 1H), 9.84 (s, 1H), 10.13 (s, 1H). $^{13}$C NMR (100 MHz, CDCl$_3$, a mixture of rotamers): 14.3, 28.5, 28.6, 28.9, 30.9, 39.5, 44.5, 47.5, 51.9, 52.1, 52.9, 57.3, 61.7, 61.8, 112.0, 112.3, 113.4, 115.0, 122.2, 122.5, 122.7, 122.9, 124.4, 125.3, 126.2, 126.4, 126.6, 127.0, 127.4, 128.7, 128.8, 129.1, 129.3, 129.7, 130.7, 131.8, 132.0, 132.8, 133.1, 133.4, 133.8, 134.1, 136.0, 160.8, 161.4, 164.1, 164.5, 167.8.

Ethyl 3-(2-(tert-butylamino)-1-(N-((6-chloropyridin-3-yl)methyl)formamido)-2-oxoethyl)-6-chloro-1H-indole-2-carboxylate (8o)

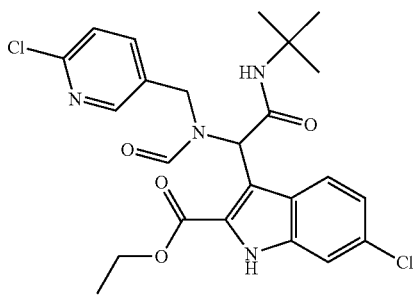 [SMILES: CCOC(=O)c1[nH]c2cc(Cl)ccc2c1C(C(=O)NC(C)(C)C)N(C=O)Cc1ccc(Cl)nc1]

The final product is a yellow solid (48 mg, 48%). HRMS: C$_{24}$H$_{27}$Cl$_2$N$_4$O$_4$, 505.1409 (calcd.), 505.1459 (found). $^1$H NMR (600 MHz, CDCl$_3$, a mixture of rotamers): 1.28 (s, 9H), 1.30 (s, 4H), 1.33-1.36 (m, 6H), 4.22 (ABd, 1H, J=15.0 Hz), 4.27-4.33 (m, 3H), 4.40 (ABd, 1H, J=16.8 Hz), 4.62 (ABd, 1H, J=15.6 Hz), 5.04 (ABd, 1H, J=15.6 Hz), 6.15 (s, 1H), 6.70 (s, 1H), 6.91 (s, 1H), 7.01 (m, 1H), 7.15 (m, 1H), 7.30 (m, 1H), 7.36 (s, 1H), 7.40 (s, 1H), 7.55 (s, 1H), 7.70 (m, 1H), 7.86 (m, 1H), 8.03 (s, 1H), 8.29 (m, 1H), 8.43 (s, 1H), 8.46 (s, 1H). $^{13}$C NMR (150 MHz, CDCl$_3$, a mixture of rotamers): 14.3, 28.5, 28.6, 28.9, 30.9, 43.9, 47.1, 50.5, 51.5, 52.0, 52.2, 56.8, 60.5, 61.7, 112.4, 112.6, 113.0, 114.8, 122.0, 122.3, 122.7, 122.8, 123.1, 123.4, 124.4, 125.2, 126.3, 127.1, 132.1, 132.3, 132.4, 136.1, 136.3, 138.5, 147.1, 148.0, 149.7, 160.6, 160.8, 163.1, 163.3, 164.6, 168.1.

Ethyl 3-(2-(tert-butylamino)-1-(N—((S)-1-(4-chlorophenyl)ethyl)formamido)-2-oxoethyl)-6-chloro-1H-indole-2-carboxylate (8p)

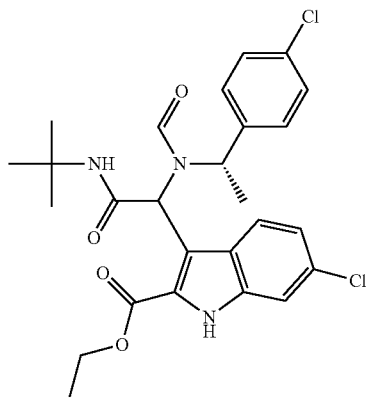 [SMILES: CCOC(=O)c1[nH]c2cc(Cl)ccc2c1C(C(=O)NC(C)(C)C)N(C=O)[C@@H](C)c1ccc(Cl)cc1]

The final product is a yellow solid (55 mg, yield: 53%). HPLC/MS: $t_R$=11.88, 12.12 min; m/z=518.3 [M+H]HRMS: C$_{26}$H$_{29}$Cl$_2$N$_3$O$_4$Na, 540.1433 (calcd.), 540.1450 (found). $^1$H NMR (600 MHz, CDCl$_3$, a 5:3 mixture of diastereomers): 1.09 (m, 6H), 1.24-1.47 (m, 28H), 1.74-1.78 (m, 4H), 4.19-4.69 (m, 6H), 5.56-5.67 (m, 2H), 6.46 (m, 2H), 6.70-6.92 (m, 4H), 6.95-7.19 (m, 8H), 7.29-7.37 (m, 6H), 7.45-7.94 (m, 6H), 8.59 (s, 1H), 8.69 (s, 1H). $^{13}$C NMR (150 MHz, CDCl$_3$, a mixture of diastereomers): 14.3, 14.4, 17.3, 17.7, 21.7, 23.4, 28.3, 28.5, 28.6, 28.9, 30.9, 51.4, 51.7, 51.9, 52.0, 53.5, 54.1, 54.6, 55.7, 55.8, 61.6, 61.7, 61.9, 112.1, 112.3, 113.6, 122.6, 122.7, 124.9, 125.1, 125.4, 125.6, 126.1, 127.1, 127.3, 127.9, 128.4, 128.7, 128.8, 129.0, 130.4, 131.8, 131.9, 132.4, 133.6, 133.8, 135.9, 136.2, 138.1, 139.8, 141.6, 160.5, 160.9, 161.1, 162.0, 163.2, 164.8, 167.9, 168.4.

Ethyl 3-(2-(tert-butylamino)-1-(N—((R)-1-(4-chlorophenyl)ethyl)formamido)-2-oxoethyl)-6-chloro-1H-indole-2-carboxylate (8q)

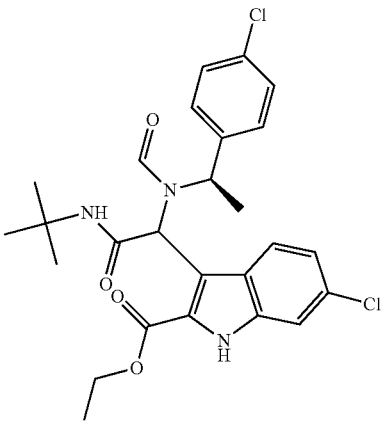 [SMILES: CCOC(=O)c1[nH]c2cc(Cl)ccc2c1C(C(=O)NC(C)(C)C)N(C=O)[C@H](C)c1ccc(Cl)cc1]

The final product is a yellow solid (75 mg, yield: 73%). HPLC/MS: $t_R$=11.88, 12.12 min; m/z=518.3 [M+H]HRMS: $C_{26}H_{29}Cl_2N_3O_4Na$, 540.1433 (calcd.), 540.1473 (found). $^1H$ NMR (600 MHz, CDCl$_3$, a 5:4 mixture of diastereomers): 1.08 (m, 9H), 1.23-1.48 (m, 30H), 1.74-1.77 (m, 4H), 4.25-4.59 (m, 8H), 5.07 (m, 1H), 5.58-5.68 (m, 3H), 5.99 (s, 1H), 6.46 (m, 2H), 6.70-6.91 (m, 4H), 6.95-7.18 (m, 6H), 7.30-7.38 (m, 6H), 7.45-7.93 (m, 6H), 8.59 (s, 1H), 8.68 (s, 1H). $^{13}C$ NMR (150 MHz, CDCl$_3$, a mixture of diastereomers): 14.3, 14.4, 17.3, 17.6, 21.7, 23.4, 28.3, 28.5, 28.6, 51.4, 51.7, 51.9, 52.0, 53.5, 54.1, 54.6, 55.7, 55.8, 61.6, 61.8, 112.2, 112.4, 113.5, 122.4, 122.5, 122.6, 124.8, 125.1, 125.4, 125.6, 126.1, 127.3, 127.6, 127.8, 128.4, 128.6, 128.8, 129.0, 130.4, 131.7, 131.8, 132.4, 133.6, 133.8, 136.0, 136.2, 138.1, 139.8, 141.6, 160.5, 160.9, 161.1, 162.1, 163.2, 164.8, 167.9, 168.4.

Ethyl 3-(2-(tert-butylamino)-1-(N-(4-hydroxybenzyl)formamido)-2-oxoethyl)-6-chloro-1H-indole-2-carboxylate (8r)

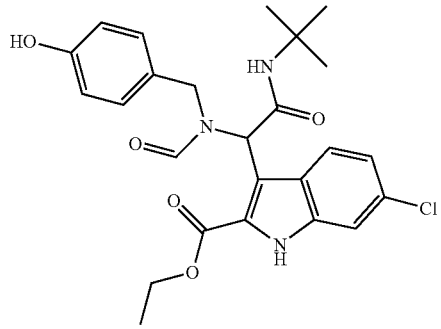 [SMILES: CCOC(=O)c1[nH]c2cc(Cl)ccc2c1C(C(=O)NC(C)(C)C)N(C=O)Cc1ccc(O)cc1]

The final product is a yellow solid (34 mg, yield: 35%). HPLC/MS: $t_R$=10.53 min; m/z=486.3 [M+H]+HRMS: $C_{25}H_{28}ClN_3O_5Na$, 508.1615 (calcd.), 508.1633 (found). $^1H$ NMR (600 MHz, CDCl$_3$, a mixture of rotamers): 1.26 (s, 9H), 1.33-1.41 (m, 24H), 4.11-4.29 (m, 6H), 4.58 (ABd, 1H, J=16.2 Hz), 4.85 (ABd, 1H, J=14.4 Hz), 5.72 (m, 2H), 6.15 (s, 1H), 6.23-7.17 (m, 12H), 7.34-8.27 (m, 6H), 8.44 (s, 1H), 8.47 (s, 1H). $^{13}C$ NMR (150 MHz, CDCl$_3$, a mixture of rotamers): 14.3, 28.4, 28.6, 28.9, 29.7, 30.9, 46.3, 50.0, 50.6, 51.6, 52.1, 52.2, 57.5, 61.6, 61.7, 112.3, 112.4, 112.9, 114.8, 114.9, 115.2, 115.7, 122.3, 122.5, 124.8, 125.5, 126.5, 127.0, 127.5, 128.3, 128.4, 129.0, 129.2, 131.4, 131.8, 136.2, 136.4, 155.7, 155.8, 160.8, 160.9, 163.2, 164.3, 164.9, 168.5, 168.9.

Ethyl 3-(1-(N-(biphenyl-4-ylmethyl)formamido)-2-(tert-butylamino)-2-oxoethyl)-6-chloro-1H-indole-2-carboxylate (8s)

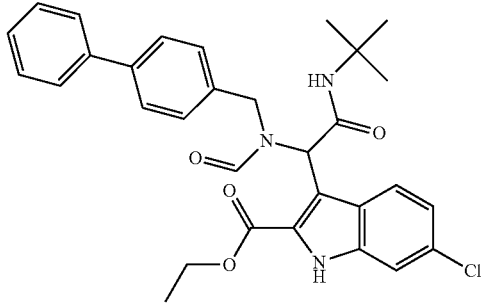 [SMILES: CCOC(=O)c1[nH]c2cc(Cl)ccc2c1C(C(=O)NC(C)(C)C)N(C=O)Cc1ccc(-c2ccccc2)cc1]

The final product is a yellow oil (86 mg, yield: 79%). HPLC/MS: $t_R$=12.12 min; m/z=546.3 [M+H]$^+$ HRMS: $C_{31}H_{32}N_3O_4ClNa$, 568.1979 (calcd.), 568.1971 (found). $^1H$ NMR (600 MHz, CDCl$_3$, a mixture of rotamers): 1.20 (s, 9H), 1.29 (s, 7H), 1.31-1.36 (m, 12H), 4.23-4.59 (m, 8H), 4.87 (ABd, 1H, J=15.0 Hz), 5.65 (m, 2H), 6.16 (s, 1H), 6.59 (m, 2H), 6.73 (s, 1H), 7.08-7.17 (m, 6H), 7.26-7.43 (m, 14H), 7.48-7.56 (m, 4H), 7.62 (m, 1H), 7.85 (m, 1H), 8.43 (m, 1H), 8.52 (s, 1H). $^{13}C$ NMR (150 MHz, CDCl$_3$, a mixture of rotamers): 14.34, 14.37, 28.4, 28.6, 28.9, 30.8, 41.8, 46.5, 49.9, 50.5, 51.9, 52.0, 52.8, 57.6, 61.6, 112.1, 112.4, 112.5, 113.4, 115.4, 122.3, 122.4, 122.8, 124.8, 125.6, 126.3, 126.4, 126.9, 127.0, 127.1, 127.4, 127.5, 128.2, 128.4, 128.8, 131.5, 131.7, 136.1, 136.2, 136.5, 139.9, 140.7, 160.8, 160.9, 161.4, 163.7, 164.8, 168.3.

Ethyl 3-(2-(tert-butylamino)-2-oxo-1-(N-(4-phenoxybenzyl)formamido)ethyl)-6-chloro-1H-indole-2-carboxylate (8t)

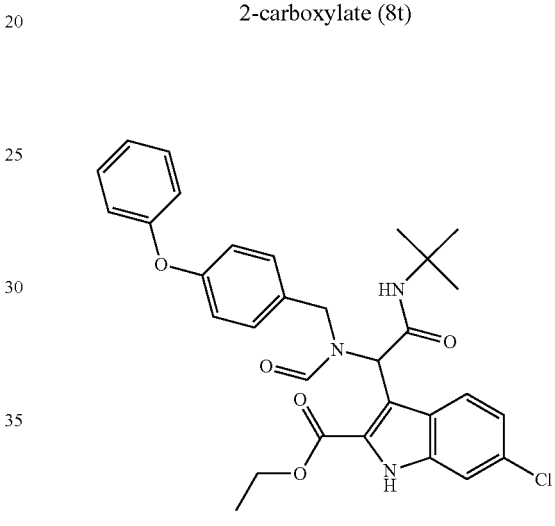

The final product is a yellow solid (80 mg, yield: 71%). HPLC/MS: $t_R$=12.11 min; m/z=562.2 [M+H]$^+$ HRMS: $C_{31}H_{32}ClN_3O_5Na$, 584.1928 (calcd.), 584.1909 (found). $^1H$ NMR (600 MHz, CDCl$_3$, a mixture of rotamers): 1.29 (s, 9H), 1.33 (s, 9H), 1.37-1.41 (m, 6H), 4.30-4.38 (m, 6H), 4.61 (ABd, 1H, J=16.2 Hz), 4.88 (ABd, 1H, J=15.0 Hz), 5.57 (s, 1H), 5.64 (s, 1H), 6.18 (s, 1H), 6.50 (d, 2H, J=8.4 Hz), 6.61 (d, 2H, J=8.4 Hz), 6.74-6.96 (m, 9H), 7.09-7.36 (m, 10H), 7.63 (d, 1H, J=8.4 Hz), 7.88 (d, 2H, J=9.0 Hz), 8.47 (s, 1H), 8.52 (s, 1H), 9.39 (s, 1H), 9.69 (s, 1H). $^{13}C$ NMR (150 MHz, CDCl$_3$, a mixture of rotamers): 14.39, 14.44, 28.5, 28.6, 46.1, 49.6, 52.0, 52.1, 52.5, 57.4, 61.7, 61.8, 111.9, 112.3, 113.6, 115.6, 118.4, 118.6, 118.7, 118.9, 119.0, 122.3, 122.4, 122.5, 122.8, 123.2, 123.3, 124.8, 125.6, 126.2, 127.2, 129.2, 129.4, 129.8, 131.7, 131.9, 132.3, 132.4, 135.9, 156.0, 157.1, 157.2, 160.68, 160.72, 163.6, 164.6, 168.19, 168.24.

Scheme 2—Method D:

The ester compound 8 was treated with LiOH in EtOH/water (1:1), and stirred at RT for 2 days. Then the reaction mixture was acidified with 1M HCl to attain a pH~6. The reaction mixture was extracted with DCM (10 mL×3). The combined organic layer was dried over sodium sulfate, and evaporated.

3-(1-(N-benzylacetamido)-2-(cyclohexylamino)-2-oxoethyl)-6-chloro-1H-indole-2-carboxylic acid (9e)

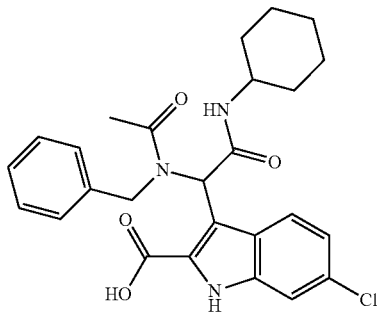 [SMILES: CC(=O)N(Cc1ccccc1)C(C(=O)NC1CCCCC1)c1c(C(=O)O)[nH]c2cc(Cl)ccc12]

The final product is a white solid (39 mg, 81%). HPLC/MS: $t_R$=11.17 min; m/z=482.3 [M+H]HRMS: $C_{26}H_{28}ClN_3O_4Na$, 504.1666 (calcd.), 504.1681 (found). $^1$H NMR (600 MHz, MeOD, a mixture of rotamers): 0.91-1.36 (m, 14H), 1.54-1.86 (m, 10H), 2.04 (s, 3H), 2.40 (s, 3H), 3.71-3.79 (m, 2H), 4.14 (ABd, 1H, J=15.6 Hz), 4.68 (m, 2H), 5.13 (ABd, 1H, J=16.2 Hz), 6.54 (m, 2H), 6.95 (m, 4H), 6.99-7.29 (m, 8H), 7.61 (m, 1H), 7.70 (m, 1H). $^{13}$C NMR (150 MHz, MeOD, a mixture of rotamers): 20.8, 21.1, 24.6, 24.7, 24.8, 25.1, 25.2, 32.1, 32.17, 32.23, 32.3, 48.7, 48.9, 50.0, 57.3, 109.2, 111.47, 111.54, 120.07, 120.13, 120.7, 121.3, 125.0, 125.2, 125.3, 125.4, 126.0, 126.8, 127.7, 128.4, 128.6, 135.18, 135.24, 138.1, 138.3, 171.1, 171.3, 173.2.

3-(1-(N-benzylformamido)-2-(cyclohexylamino)-2-oxoethyl)-6-chloro-1H-indole-2-carboxylic acid (9i)

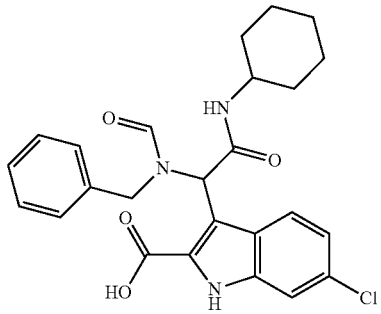 [SMILES: O=CN(Cc1ccccc1)C(C(=O)NC1CCCCC1)c1c(C(=O)O)[nH]c2cc(Cl)ccc12]

The final product is a yellow solid (18 mg, 91%). HPLC/MS: $t_R$=16.91 min; m/z=468.3 [M+H]$^+$ HRMS: $C_{25}H_{27}N_3O_4Cl$, 468.1690 (calcd.), 468.1690 (found). $^1$H NMR (600 MHz, MeOD, a mixture of rotamers): 0.88-1.30 (m, 9H), 1.56-1.84 (m, 9H), 3.63 (m, 2H), 4.26 (m, 2H), 4.68 (ABd, 1H, J=16.2 Hz), 5.09 (ABd, 1H, J=15.0 Hz), 6.27 (s, 1H), 6.48 (m, 1H), 6.78-7.08 (m, 9H), 7.32 (s, 1H), 7.34 (s, 1H), 7.64 (m, 1H), 7.66 (m, 1H), 8.36 (s, 1H), 8.42 (s, 1H). $^{13}$C NMR (150 MHz, MeOD, a mixture of rotamers): 24.7, 24.8, 25.08, 25.14, 32.0, 32.2, 46.7, 48.9, 49.9, 52.2, 56.5, 111.7, 111.9, 113.9, 120.9, 121.1, 121.4, 121.5, 124.7, 125.2, 126.4, 126.5, 126.9, 127.2, 127.3, 130.2, 130.4, 136.27, 136.29, 136.8, 137.5, 164.8, 165.2, 169.48, 169.53.

6-chloro-3-(1-(N-(4-chlorobenzyl)acetamido)-2-(cyclohexylamino)-2-oxoethyl)-1H-indole-2-carboxylic acid (9j)

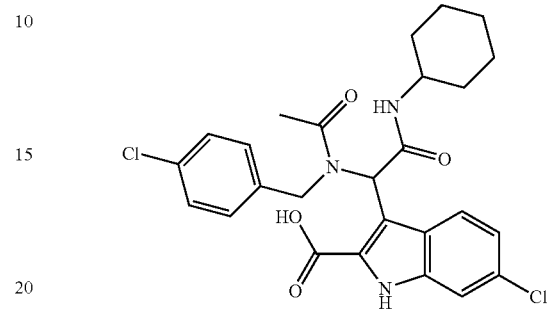

The final product is a yellow solid (16 mg, 70%). HPLC/MS: $t_R$=11.55 min; m/z=516.3 [M+H]$^+$ HRMS: $C_{26}H_{27}Cl_2N_3O_4$, 515.137862 (calcd.), 515.137663 (found). $^1$H NMR (600 MHz, Acetone, a mixture of rotamers): 0.88-1.34 (m, 8H), 1.55-1.95 (m, 8H), 2.29 (s, 3H), 3.32 (s, 2H), 3.73-3.86 (m, 2H), 3.94 (ABd, 1H, J=15.6 Hz), 4.36 (m, 1H), 4.58 (ABd, 1H, J=18.0 Hz), 4.80 (ABd, 1H, J=18.0 Hz), 5.25 (ABd, 1H, J=15.6 Hz), 6.44 (m, 2H), 6.53 (s, 1H), 6.83 (m, 2H), 6.99-7.55 (m, 6H), 7.84 (m, 1H), 7.94 (m, 1H), 10.92 (s, 1H), 11.02 (s, 1H). $^{13}$C NMR (150 MHz, Acetone, a mixture of rotamers): 14.5, 21.1, 21.8, 24.8, 25.3, 32.5, 32.7, 41.9, 47.0, 48.7, 56.6, 64.7, 111.9, 112.2, 120.7, 121.4, 122.2, 123.5, 126.9, 127.4, 127.6, 128.3, 129.2, 130.2, 130.6, 136.3, 138.7, 169.0, 171.0.

6-chloro-3-(2-(cyclohexylamino)-1-(N-(4-fluorobenzyl)formamido)-2-oxoethyl)-1H-indole-2-carboxylic acid (9k)

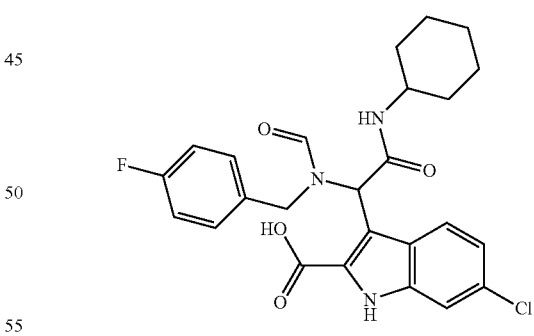

The final product is an yellow solid (45 mg, 92%). HPLC/MS: $t_R$=10.96 min; m/z=486.3 [M+H]$^+$ HRMS: $C_{25}H_{25}N_3O_4ClFNa$, 508.1415 (calcd.), 508.1419 (found). $^1$H NMR (600 MHz, MeOD, a mixture of rotamers): 0.92-1.12 (m, 8H), 1.29-1.36 (m, 4H), 1.58-1.90 (m, 8H), 2.13-2.37 (m, 2H), 3.67-3.77 (m, 2H), 4.27-4.32 (m, 2H), 4.69 (ABd, 1H, J=16.2 Hz), 5.10 (ABd, 1H, J=15.0 Hz), 6.33 (s, 1H), 6.50-6.85 (m, 6H), 7.11-7.14 (m, 2H), 7.39-7.42 (m, 2H), 7.69-7.95 (m, 4H), 8.40 (s, 1H), 8.47 (s, 1H). $^{13}$C NMR (150 MHz, MeOD, a mixture of rotamers): 21.4, 24.3, 24.7, 24.8, 24.9, 25.1, 25.2, 28.9, 32.1, 32.2, 46.0, 49.0, 49.1, 49.3, 52.0, 52.2, 56.5, 111.8, 111.9, 112.4, 113.7, 113.8, 113.9, 114.0, 121.1, 121.2, 121.4, 121.5, 124.8, 125.6, 127.0, 127.1, 128.1, 128.7, 128.8, 130.3, 130.4, 132.9, 133.5, 133.6, 136.3, 160.8, 160.9, 162.4, 162.5, 162.6, 164.8, 165.3, 169.5, 169.6.

3-(2-(tert-butylamino)-1-(N-(4-chlorobenzyl)formamido)-2-oxoethyl)-6-chloro-1H-indole-2-carboxylic acid (9l)

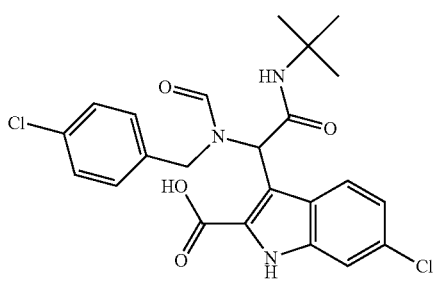 [SMILES: CC(C)(C)NC(=O)C(c1c(C(=O)O)[nH]c2cc(Cl)ccc12)N(C=O)Cc1ccc(Cl)cc1]

The final product is an yellow solid (58 mg, 94%). HPLC/MS: $t_R$=10.82 min; m/z=476.1 [M+H]$^+$ HRMS: $C_{23}H_{23}Cl_2N_3O_4Na$, 498.0963 (calcd.), 498.0947 (found). $^1$H NMR (600 MHz, MeOD, a mixture of rotamers): 1.25 (s, 9H), 1.31 (s, 5H), 4.29 (m, 2H), 4.70 (ABd, 1H, J=16.2 Hz), 5.13 (ABd, 1H, J=15.0 Hz), 6.25 (s, 1H), 6.47 (m, 1H), 6.77 (s, 1H), 6.81-7.14 (m, 8H), 7.39 (s, 1H), 7.42 (s, 1H), 7.60 (s, 1H), 7.80 (m, 1H), 7.84 (m, 1H), 8.37 (s, 1H), 8.47 (s, 1H). $^{13}$C NMR (150 MHz, MeOD, a mixture of rotamers): 27.4, 27.5, 46.1, 48.4, 51.2, 52.7, 56.9, 111.8, 111.9, 120.9, 121.1, 121.7, 121.9, 124.7, 126.8, 127.2, 127.4, 128.6, 130.3, 130.5, 132.1, 132.2, 135.8, 136.3, 136.5, 165.3, 169.7.

3-(2-(tert-butylamino)-1-(N-(3,4-dichlorobenzyl)formamido)-2-oxoethyl)-6-chloro-1H-indole-2-carboxylic acid (9m)

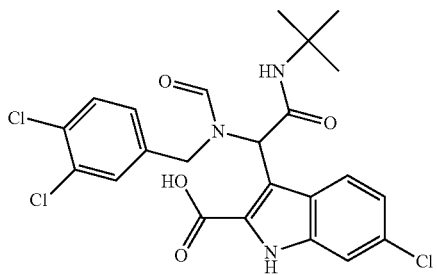 [SMILES: CC(C)(C)NC(=O)C(c1c(C(=O)O)[nH]c2cc(Cl)ccc12)N(C=O)Cc1ccc(Cl)c(Cl)c1]

The final product is a yellow solid (70 mg, 98%). HPLC/MS: $t_R$=11.28 min; m/z=510.2 [M+H]HRMS: $C_{23}H_{23}Cl_3N_3O_4$, 510.0754 (calcd.), 510.0783 (found). $^1$H NMR (600 MHz, MeOD, a mixture of rotamers): 1.27 (s, 9H), 1.31 (s, 4H), 4.22 (ABd, 1H, J=15.6 Hz), 4.29 (ABd, 1H, J=16.8 Hz), 4.70 (ABd, 1H, J=16.2 Hz), 5.15 (ABd, 1H, J=16.2 Hz), 5.51 (s, 1H), 6.32 (s, 1H), 6.45 (m, 1H), 6.70-7.15 (m, 6H), 7.40-7.84 (m, 4H), 8.42 (s, 1H), 8.48 (s, 1H). $^{13}$C NMR (150 MHz, MeOD, a mixture of rotamers): 27.4, 27.5, 45.6, 49.1, 51.3, 52.5, 53.5, 56.8, 111.9, 112.0, 112.3, 113.7, 121.1, 121.2, 121.5, 121.7, 124.7, 125.0, 125.4, 126.6, 127.3, 128.3, 128.8, 129.1, 129.2, 129.9, 130.3, 130.4, 130.9, 131.0, 136.1, 136.2, 137.9, 138.5, 162.1, 162.6, 164.7, 165.3, 169.8.

3-(2-(tert-butylamino)-1-(N-(2,4-dichlorobenzyl)formamido)-2-oxoethyl)-6-chloro 1H-indole-2-carboxylic acid (9n)

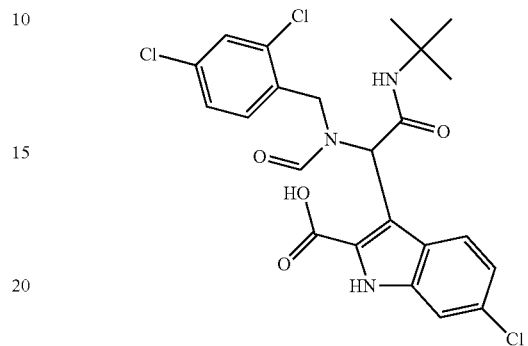

The final product is a yellowish solid (74 mg, 85%). HPLC/MS: $t_R$=11.34 min; m/z=509.9 [M+H]$^+$ HRMS: $C_{23}H_{22}Cl_3N_3O_4Na$, 532.0574 (calcd.), 532.0572 (found). $^1$H NMR (600 MHz, MeOD, a mixture of rotamers): 1.27 (s, 9H), 1.31 (s, 5H), 4.64-4.74 (m, 2H), 4.97-4.99 (m, 2H), 6.38 (s, 1H), 6.82 (s, 1H), 6.99-7.07 (m, 5H), 7.15 (s, 1H), 7.35 (m, 1H), 7.38 (s, 1H), 7.63 (s, 1H), 7.71 (s, 1H), 7.75-7.77 (m, 1H), 7.80 (m, 1H), 8.43 (s, 1H), 8.44 (s, 1H). $^{13}$C NMR (150 MHz, MeOD, a mixture of rotamers): 27.4, 27.5, 44.1, 47.0, 51.3, 52.0, 52.9, 57.0, 111.7, 111.8, 112.1, 113.6, 121.0, 121.2, 121.7, 122.1, 124.5, 125.3, 126.0, 126.1, 127.9, 128.0, 128.7, 129.4, 130.4, 130.5, 132.1, 132.6, 132.8, 134.0, 136.1, 136.3, 165.3, 169.6.

3-(2-(tert-butylamino)-1-(N-((6-chloropyridin-3-yl)methyl)formamido)-2-oxoethyl)-6-chloro-1H-indole-2-carboxylic acid (9o)

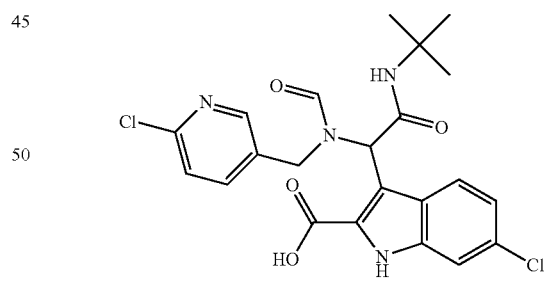

The final product is a yellow solid (28 mg, yield: 74%). HPLC/MS: $t_R$=11.63 min; m/z=476.5 [M+H]$^+$ HRMS: $C_{22}H_{22}Cl_2N_4O_4Na$, 499.0916 (calcd.), 499.0942 (found). $^1$H NMR (600 MHz, MeOD, a mixture of rotamers): 1.16 (s, 9H), 1.19 (s, 4H), 4.21 (ABd, 1H, J=15.6 Hz), 4.27 (ABd, 1H, J=16.8 Hz), 4.62 (ABd, 1H, J=16.8 Hz), 5.02 (ABd, 1H, J=15.6 Hz), 6.16 (s, 1H), 6.61 (s, 1H), 6.92 (m, 1H), 6.97-7.04 (m, 2H), 7.16 (m, 2H), 7.29 (s, 1H), 7.32 (s, 1H), 7.51 (s, 1H), 7.56 (s, 1H), 7.68-7.72 (m, 2H), 8.27 (s, 1H), 8.41 (s, 1H). $^{13}$C NMR (150 MHz, MeOD, a mixture of rotamers): 28.8, 28.9, 45.0, 52.7, 54.0, 58.3, 113.4, 113.5, 115.3, 122.7, 122.8, 123.0, 123.3, 124.4, 124.6, 125.9, 132.0, 132.1, 134.2, 134.6, 137.6, 138.3, 139.9, 147.6, 149.1, 150.5, 166.8, 171.0.

3-(2-(tert-butylamino)-1-(N—((S)-1-(4-chlorophenyl)ethyl)formamido)-2-oxoethyl)-6-chloro-1H-indole-2-carboxylic acid (9p)

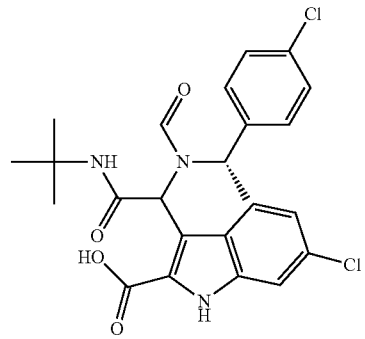 [SMILES: C[C@@H](c1ccc(Cl)cc1)N(C=O)C(C(=O)NC(C)(C)C)c1c(C(=O)O)[nH]c2cc(Cl)ccc12]

The final product is a yellow solid (46 mg, 92%). HPLC/MS: $t_R$=9.30 min; m/z=490.0 [M+H]$^+$ HRMS: $C_{24}H_{25}Cl_2N_3O_4Na$, 512.1120 (calcd.), 512.1072 (found). $^1$H NMR (400 MHz, MeOD, a 3:2 mixture of diastereomers): 1.02 (s, 9H), 1.29 (s, 7H), 1.65 (d, 3H, J=7.2 Hz), 1.75 (d, 2H, J=7.2 Hz), 5.14 (q, 1H, J=6.8 Hz), 5.75 (q, 1H, J=6.8 Hz), 6.25 (s, 1H), 6.70 (s, 1H), 6.81 (m, 1H), 6.98-7.06 (m, 5H), 7.14-7.20 (m, 2H), 7.34-7.53 (m, 7H), 7.72-7.86 (m, 2H), 8.40 (s, 1H), 8.45 (s, 1H). $^{13}$C NMR (100 MHz, MeOD, a mixture of diastereomers): 16.2, 17.6, 21.3, 27.3, 27.4, 27.5, 50.2, 50.5, 50.7, 50.8, 52.8, 54.3, 54.7, 56.3, 108.2, 109.8, 110.8, 111.5, 111.6, 120.1, 120.3, 121.4, 121.6, 125.3, 126.8, 127.5, 127.7, 128.1, 128.7, 130.8, 131.8, 133.3, 134.3, 135.3, 137.3, 140.9, 141.8, 163.5, 165.6, 165.7, 168.1, 169.2, 170.5.

3-(2-(tert-butylamino)-1-(N—((R)-1-(4-chlorophenyl)ethyl)formamido)-2-oxoethyl)-6-chloro-1H-indole-2-carboxylic acid (9q)

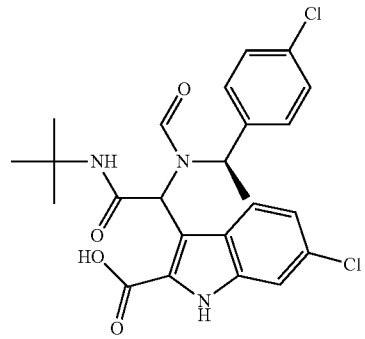 [SMILES: C[C@H](c1ccc(Cl)cc1)N(C=O)C(C(=O)NC(C)(C)C)c1c(C(=O)O)[nH]c2cc(Cl)ccc12]

The final product is a yellow solid (68 mg, 98%). HPLC/MS: $t_R$=11.28 min; m/z=490.2 [M+H]$^+$ HRMS: $C_{24}H_{26}Cl_2N_3O_4$, 490.1300 (calcd.), 490.1290 (found). $^1$H NMR (400 MHz, MeOD, a 3:2 mixture of diastereomers): 1.02 (s, 9H), 1.27 (s, 6H), 1.64 (d, 3H, J=6.8 Hz), 1.76 (m, 2H), 5.12 (m, 1H), 5.75 (q, 1H, J=6.8 Hz), 6.26 (s, 1H), 6.69 (s, 1H), 6.75 (m, 1H), 6.95-7.18 (m, 5H), 7.34-7.52 (m, 6H), 7.72-7.83 (m, 2H), 8.42 (m, 1H), 8.45 (s, 1H). $^{13}$C NMR (100 MHz, MeOD, a mixture of diastereomers): 16.2, 17.6, 21.6, 27.3, 27.4, 27.5, 29.4, 50.8, 50.9, 54.7, 56.4, 110.9, 111.5, 111.6, 120.4, 121.4, 125.4, 126.6, 127.5, 127.6, 128.1, 128.8, 129.3, 130.8, 132.0, 133.3, 134.2, 135.3, 137.3, 140.8, 141.7, 165.6, 169.2, 170.4.

3-(2-(tert-butylamino)-1-(N-(4-hydroxybenzyl)formamido)-2-oxoethyl)-6-chloro-1H-indole-2-carboxylic acid (9r)

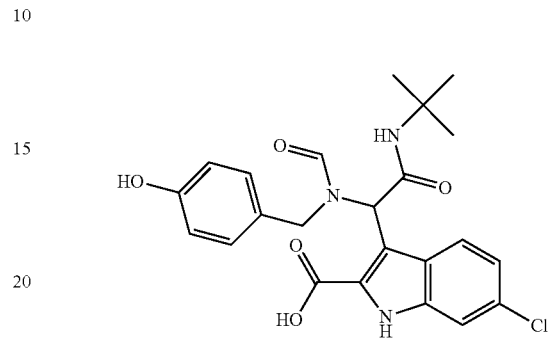

The final product is a yellow solid (24 mg, 91%). HPLC/MS: $t_R$=10.65 min; m/z=458.2 [M+H]$^+$ HRMS: $C_{23}H_{24}ClN_3O_5Na$, 480.1302 (calcd.), 480.1336 (found). $^1$H NMR (600 MHz, MeOD, a mixture of rotamers): 1.21 (s, 9H), 1.31 (s, 7H), 4.21-4.28 (m, 2H), 4.59 (ABd, 1H, J=16.2 Hz), 5.06 (ABd, 1H, J=14.4 Hz), 6.17 (s, 1H), 6.34-6.39 (m, 2H), 6.54 (m, 2H), 6.75 (s, 1H), 6.83 (m, 2H), 7.09-7.13 (m, 2H), 7.41-7.50 (m, 3H), 7.79 (m, 1H), 7.84 (m, 1H), 8.31 (s, 1H), 8.41 (s, 1H). $^{13}$C NMR (150 MHz, MeOD, a mixture of rotamers): 27.4, 27.5, 46.6, 49.6, 51.0, 51.2, 52.0, 52.9, 56.8, 111.8, 111.9, 112.8, 114.1, 114.3, 114.6, 120.8, 121.1, 121.9, 122.1, 124.8, 125.6, 126.7, 127.4, 127.5, 128.2, 129.1, 130.2, 130.5, 136.4, 156.0, 156.2, 162.3, 164.6, 165.2, 169.5.

3-(1-(N-(biphenyl-4-ylmethyl)formamido)-2-(tert-butylamino)-2-oxoethyl)-6-chloro-1H-indole-2-carboxylic acid (9s)

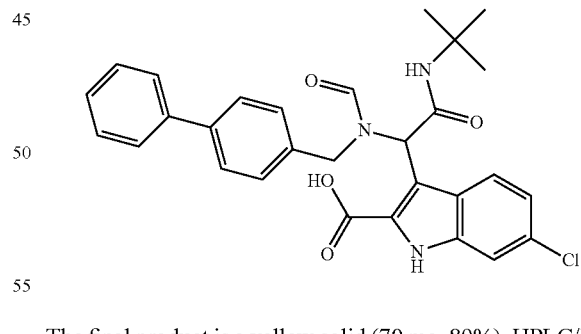

The final product is a yellow solid (70 mg, 89%). HPLC/MS: $t_R$=11.50 min; m/z=518.1 [M+H]$^+$ HRMS: $C_{29}H_{29}ClN_3O_4$, 518.1847 (calcd.), 518.1844 (found). $^1$H NMR (600 MHz, MeOD, a mixture of rotamers): 1.21 (s, 9H), 1.31 (s, 5H), 4.33-4.37 (m, 2H), 4.74 (ABd, 1H, J=16.2 Hz), 5.22 (ABd, 1H, J=15.0 Hz), 6.30 (s, 1H), 6.55 (m, 1H), 6.81 (s, 1H), 6.98-7.16 (m, 5H), 7.29-7.56 (m, 14H), 7.81 (m, 1H), 7.87 (m, 1H), 8.41 (s, 1H), 8.49 (s, 1H). $^{13}$C NMR (150 MHz, MeOD, a mixture of rotamers): 27.4, 27.6, 46.7, 49.9, 51.1, 51.2, 51.3, 52.0, 52.9, 56.9, 111.7, 111.9, 112.5, 114.1, 120.9, 121.1, 121.8, 122.0, 124.8, 125.6, 125.8, 126.0, 126.5, 126.8, 127.9, 128.3, 128.4, 130.3, 130.4, 135.8, 136.3, 136.6, 139.6, 139.7, 140.7, 164.7, 165.3, 169.6, 169.9.

3-(2-(tert-butylamino)-2-oxo-1-(N-(4-phenoxybenzyl)formamido)ethyl)-6-chloro-1H-indole-2-carboxylic acid (9t)

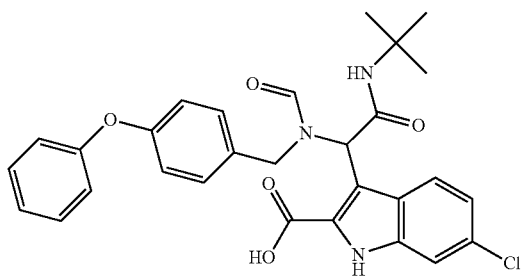 [SMILES: CC(C)(C)NC(=O)C(c1c(C(=O)O)[nH]c2cc(Cl)ccc12)N(C=O)Cc1ccc(Oc2ccccc2)cc1]

The final product is a yellow solid (68 mg, 92%). HPLC/MS: $t_R$=11.53 min; m/z=534.3 [M+H]$^+$ HRMS: $C_{29}H_{28}ClN_3O_5Na$, 556.1615 (calcd.), 556.1614 (found). $^1$H NMR (600 MHz, MeOD, a mixture of rotamers): 1.26 (s, 9H), 1.32 (s, 6H), 4.28-4.32 (m, 2H), 4.70 (ABd, 1H, J=16.2 Hz), 5.17 (ABd, 1H, J=15.6 Hz), 6.30 (s, 1H), 6.44-6.90 (m, 10H), 7.09-7.44 (m, 8H), 7.59-7.87 (m, 4H), 8.39 (s, 1H), 8.48 (s, 1H). $^{13}$C NMR (150 MHz, MeOD, a mixture of rotamers): 27.45, 27.51, 46.2, 51.20, 51.25, 56.8, 111.8, 111.9, 112.5, 114.0, 117.7, 117.8, 118.1, 118.2, 120.9, 121.0, 121.8, 122.0, 122.7, 122.8, 124.8, 125.6, 126.7, 128.6, 129.4, 129.5, 130.2, 130.3, 131.9, 132.6, 136.2, 136.3, 155.9, 156.0, 157.3, 157.4, 164.6, 165.3, 169.8, 170.0.

Synthesis of ethyl 3-(1-(benzylamino)-2-(cyclohexylamino)-2-oxoethyl)-6-chloro-1H-indole-2-carboxylate (10)

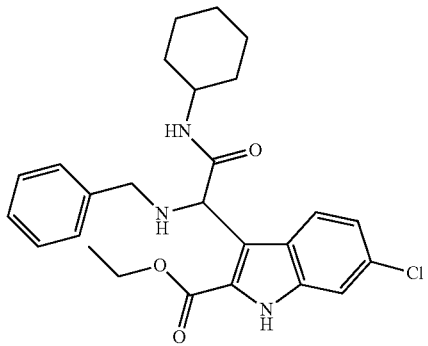 [SMILES: CCOC(=O)c1[nH]c2cc(Cl)ccc2c1C(NCc1ccccc1)C(=O)NC1CCCCC1]

Compound 7i was treated with 0.4 mL of dioxane (2M HCl), 0.1 mL of water stirring overnight under RT. After quenching with 0.5 mL of triethyl amine, the product was purified by chromatography on silica gel (petroleum ether/ethyl acetate, 1:2) as yellowish solids (34 mg, yield: 58%). HRMS: $C_{26}H_{30}ClN_3O_3Na$, 490.1873 (calcd.), 490.1864 (found). $^1$H NMR (600 MHz, CDCl$_3$, a mixture of rotamers): 0.82-1.06 (m, 6H), 1.26-1.37 (m, 10H), 1.59-1.92 (m, 10H), 3.64-3.83 (m, 6H), 4.30-4.70 (m, 7H), 5.61-5.74 (m, 2H), 6.20 (s, 1H), 6.60 (m, 2H), 6.78 (s, 1H), 6.97-7.27 (m, 12H), 7.50 (m, 1H), 7.78 (m, 1H), 8.44 (s, 1H), 8.53 (s, 1H). $^{13}$C NMR (150 MHz, CDCl$_3$, a mixture of rotamers): 14.3, 14.4, 24.76, 24.80, 24.9, 25.3, 25.4, 32.6, 32.7, 32.8, 32.9, 42.9, 46.4, 48.88, 48.92, 50.1, 52.3, 57.3, 61.6, 61.65, 61.68, 71.1, 72.3, 111.9, 112.3, 113.5, 115.1, 122.2, 122.3, 122.4, 122.7, 124.8, 125.6, 126.0, 126.3, 127.2, 127.3, 127.8, 127.9, 128.2, 128.4, 128.5, 131.6, 131.8, 131.9, 136.0, 137.3, 137.4, 160.6, 160.7, 163.7, 164.8, 167.9, 168.1.

Synthesis of 3-(1-(benzylamino)-2-(cyclohexylamino)-2-oxoethyl)-6-chloro-1H-indole-2-carboxylic acid (11a)

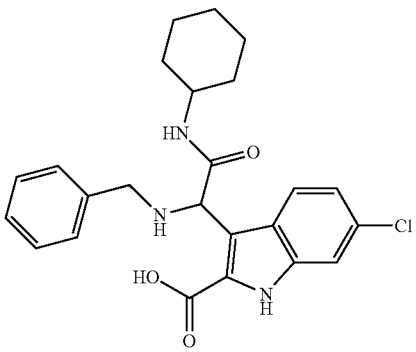 [SMILES: O=C(O)c1[nH]c2cc(Cl)ccc2c1C(NCc1ccccc1)C(=O)NC1CCCCC1]

The mixture of 10 (28 mg), EtOH (0.5 mL), water (0.5 mL), KOH (10 mg) was reflux for 5 h. After cooling, the reaction mixture was acidified with 1M HCl (pH~6). Then the mixture was extracted with DCM (10 mL×3). The combined organic layer was dried over sodium sulfate. After evaporation of the solvent, 21 mg of yellow solids (74%) was obtained. HPLC/MS: $t_R$=12.10 min; m/z=440.4 [M+H]$^+$ HRMS: $C_{24}H_{27}N_3O_3Cl$, 440.1741 (calcd.), 440.1721 (found). $^1$H NMR (600 MHz, DMSO, a mixture of rotamers): 0.85-1.63 (m, 16H), 3.57 (m, 2H), 4.17 (ABd, 1H, J=16.2 Hz), 4.22 (ABd, 1H, J=15.6 Hz), 4.67 (ABd, 1H, J=16.8 Hz), 4.88 (ABd, 1H, J=15.6 Hz), 6.10 (s, 1H), 6.51 (m, 1H), 6.60 (s, 1H), 6.78 (m, 2H), 6.91-7.28 (m, 7H), 7.66-7.91 (m, 4H), 8.27 (s, 1H), 8.34 (s, 1H), 11.56 (s, 1H), 11.88 (s, 1H), 13.15 (br.s, 1H), 13.53 (br.s, 1H). $^{13}$C NMR (150 MHz, DMSO, a mixture of rotamers): 25.0, 25.1, 25.5, 32.5, 32.6, 47.0, 48.5, 56.2, 112.4, 121.3, 122.4, 125.2, 125.8, 126.7, 126.8, 127.1, 127.7, 127.9, 129.0, 129.3, 136.4, 138.0, 164.2, 168.8.

Synthesis of 3-(2-(tert-butylamino)-1-(4-chlorobenzylamino)-2-oxoethyl)-6-chloro-1H-indole-2-carboxylic acid (11b)

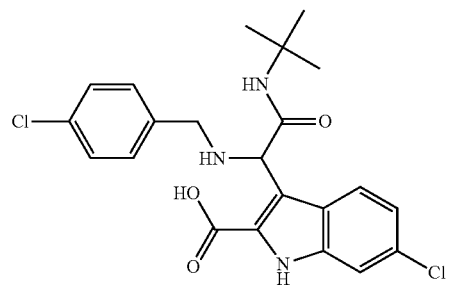 [SMILES: CC(C)(C)NC(=O)C(NCc1ccc(Cl)cc1)c1c(C(=O)O)[nH]c2cc(Cl)ccc12]

Compound 9l (24 mg, 0.05 mmol) was treated with 0.4 mL of dioxane (2M HCl), 0.1 mL of water stirring overnight under 60° C. After evaporation, the product was obtained as yellow solids (20 mg, yield: 89%). HPLC/MS: $t_R$=10.42 min; m/z=448.3 [M+H]$^+$ HRMS: $C_{22}H_{22}Cl_2N_3O_3$, [M−H]$^-$; 446.1038 (calcd.), 446.1050 (found). $^1$H NMR (600 MHz, MeOD, a mixture of rotamers): 1.25 (s, 9H), 1.31 (s, 6H), 4.27-4.33 (m, 2H), 4.70 (ABd, 1H, J=16.2 Hz), 5.13 (ABd, 1H, J=15.6 Hz), 5.88 (s, 1H), 6.24 (s, 1H), 6.47 (m, 1H), 6.76-7.27 (m, 8H), 7.39-7.60 (m, 6H), 7.79-7.85 (m, 2H), 8.38 (s, 1H), 8.47 (s, 1H), 11.35 (s, 1H), 11.60 (s, 1H). $^{13}$C NMR (150 MHz, MeOD, a mixture of rotamers): 27.3, 27.4, 46.5, 50.9, 51.0, 57.1, 111.6, 120.4, 121.3, 125.0, 126.8, 127.3, 127.5, 127.9, 128.6, 128.9, 129.0, 129.6, 131.0, 132.1, 135.3, 135.5, 170.1.

Synthesis of 3-(1-(N-benzylacetamido)-2-(cyclohexylamino)-2-oxoethyl)-6-chloro-N-(2-(pyridin-4-yl)ethyl)-1H-indole-2-carboxamide (13a)

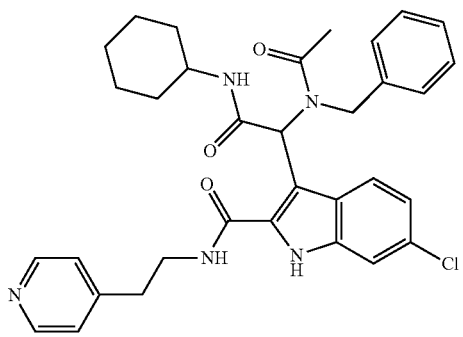 [SMILES: CC(=O)N(Cc1ccccc1)C(C(=O)NC1CCCCC1)c1c(C(=O)NCCc2ccncc2)[nH]c2cc(Cl)ccc12]

The mixture of 8e (50.9 mg, 0.1 mmol), THF (1 mL), 4-(2-aminoethyl)pyridine (0.2 mmol, 23.7 uL), TBD (0.02 mmol, 3 mg) was stirring under 40° C. overnight. The product was purified by chromatography on silica gel (methanol/ethyl acetate, 1:5) as yellow solids (25 mg, yield: 43%). HPLC/MS: $t_R$=9.24 min; m/z=586.0 [M+H]$^+$ HRMS: C$_{33}$H$_{36}$ClN$_5$O$_3$Na, 608.2404 (calcd.), 608.2427 (found). $^1$H NMR (600 MHz, CDCl$_3$): 0.85-1.34 (m, 6H), 1.57-1.92 (m, 7H), 2.03 (s, 3H), 3.04 (m, 2H), 3.74-3.90 (m, 3H), 4.75-4.90 (m, 2H), 5.80 (s, 1H), 6.52 (m, 2H), 6.86 (s, 1H), 6.95-7.02 (m, 4H), 7.20 (m, 2H), 7.32 (s, 1H), 7.49 (m, 1H), 8.42 (m, 2H), 8.57 (s, 1H), 10.11 (br.s, 1H). $^{13}$C NMR (150 MHz, CDCl$_3$): 22.2, 24.7, 24.8, 24.9, 25.3; 29.7, 32.7, 33.0, 34.4, 40.4, 49.3, 51.5, 53.5, 108.3, 112.1, 121.5, 122.1, 124.2, 125.1, 125.2, 126.9, 128.2, 130.6, 131.3, 135.3, 136.9, 148.1, 149.7, 150.3, 160.8, 167.9, 174.3.

Synthesis of 3-(1-(N-benzylacetamido)-2-(cyclohexylamino)-2-oxoethyl)-6-chloro-N-(2-methoxyethyl)-1H-indole-2-carboxamide (13b)

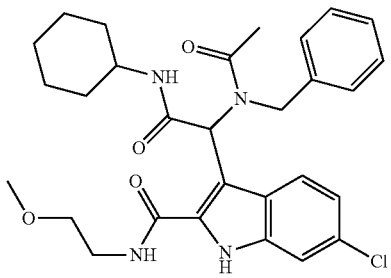 [SMILES: COCCNC(=O)c1[nH]c2cc(Cl)ccc2c1C(C(=O)NC1CCCCC1)N(Cc1ccccc1)C(C)=O]

The mixture of 8e (50.9 mg, 0.1 mmol), THF (1 mL), 2-methoxyethylamine (0.2 mmol, 17.5 uL), TBD (0.02 mmol, 3 mg) was stirring under 40° C. overnight. The product was purified by chromatography on silica gel (ethyl acetate) as yellowish solids (14 mg, yield: 26%). HPLC/MS: $t_R$=15.45 min; m/z=539.4 [M+H]$^+$ HRMS: C$_{29}$H$_{35}$N$_4$O$_4$Cl, 538.234684 (calcd.), 538.234872 (found). $^1$H NMR (600 MHz, CDCl$_3$): 0.85-1.33 (m, 7H), 1.56-1.92 (m, 7H), 2.18 (s, 3H), 3.36-3.83 (m, 8H), 4.68 (ABd, 1H, J=18.0 Hz), 4.92 (ABd, 1H, J=17.4 Hz), 6.65 (m, 2H), 6.84 (s, 1H), 6.97 (m, 3H), 7.06 (m, 1H), 7.59 (m, 1H), 7.94 (s, 1H), 10.03 (s, 1H). $^{13}$C NMR (150 MHz, CDCl$_3$): 22.2, 24.8, 24.9, 25.3, 32.7, 32.9, 39.5, 40.0, 49.2, 51.2, 53.8, 58.7, 58.8, 58.9, 70.5, 70.6, 108.4, 112.1, 112.2, 120.8, 121.5, 121.6, 122.0, 125.3, 126.8, 127.6, 127.9, 128.1, 128.8, 130.5, 131.6, 135.4, 137.3, 159.8, 161.0, 168.2, 173.8.

3-(2-(benzylamino)-1-((4-methyl-1-morpholino-1-oxopentan-2-yl)amino)-2-oxoethyl)-6-chloro-1H-indole-2-carboxylic acid (KK276)

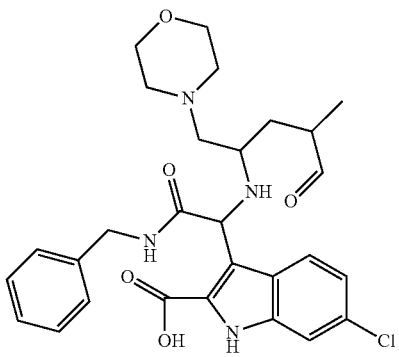 [SMILES: CC(C=O)CC(CN1CCOCC1)NC(C(=O)NCc1ccccc1)c1c(C(=O)O)[nH]c2cc(Cl)ccc12]

The final product has a Molecular Wt of 540.21 g/mol and was obtained in an overall yield of 95%. HPLC-MS r_t:16.30, m/z [M–H]$^+$:541.3, [M–H]$^+$:539.5.

(B) Synthesis of Fluorinated Formula I Compounds

The Ugi-4CR reaction was used to synthesize various mono-, di-, tri-, tetra- and penta-fluorinated analogs of Formula I compounds. See Scheme 9.

Scheme 9

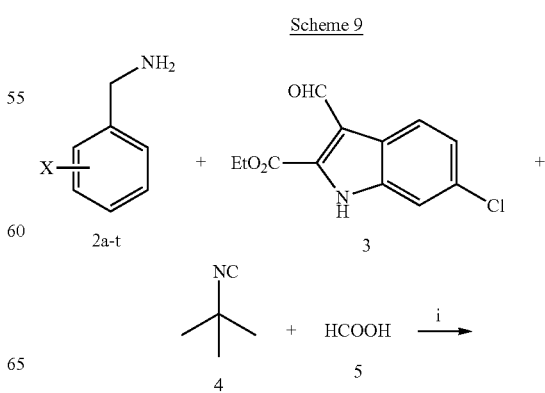

81

-continued

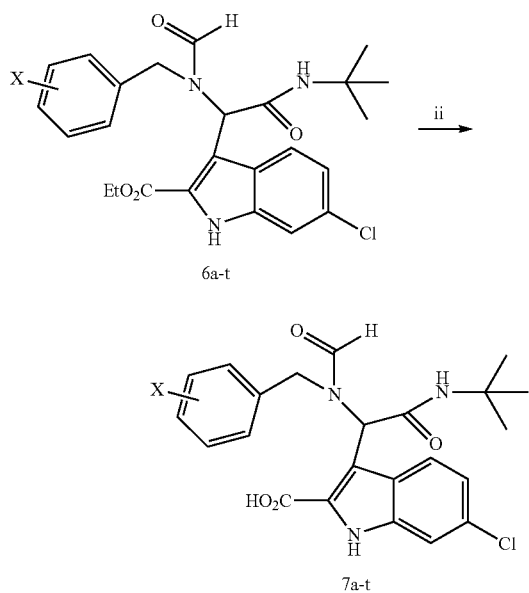

6a-t

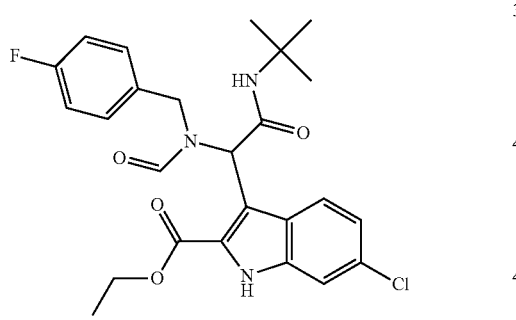

7a-t

Ethyl 3-(2-(tert-butylamino)-1-(N-(4-fluorobenzyl)
formamido)-2-oxoethyl)-6-chloro-1H-indole-2-car-
boxylate (6B)

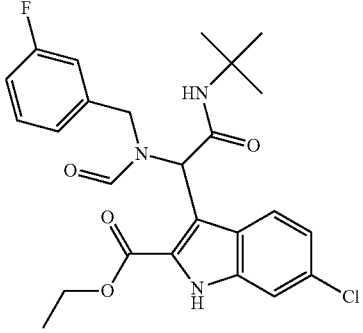 [SMILES: CCOC(=O)c1[nH]c2cc(Cl)ccc2c1C(C(=O)NC(C)(C)C)N(C=O)Cc1cccc(F)c1]

The final compound was obtained as a yellowish solid (75 mg, yield: 77%). HPLC/MS: $t_R$=11.37 min; m/z=488.2 [M+H]$^+$ HRMS: $C_{25}H_{27}ClFN_3O_4Na$, 510.1572 (calcd.), 510.1576 (found). $^1$H NMR (400 MHz, CDCl$_3$, a mixture of rotamers): 1.25 (s, 9H), 1.29 (s, 6H), 1.34-1.38 (m, 6H), 4.23-4.33 (m, 5H), 4.57 (ABd, 1H, J=16.0 Hz), 4.91 (ABd, 1H, J=15.2 Hz), 5.60 (m, 2H), 6.12 (s, 1H), 6.50 (m, 1H), 6.61 (m, 1H), 6.73-6.77 (m, 3H), 6.88-6.91 (m, 2H), 7.11-7.16 (m, 2H), 7.31 (m, 2H), 7.65 (d, 1H, J=8.8 Hz), 7.86 (d, 1H, J=8.8 Hz), 8.41 (s, 1H), 8.46 (s, 1H). $^{13}$C NMR (100 MHz, CDCl$_3$, a mixture of rotamers): 14.31, 14.34, 28.4, 28.6, 28.9, 30.8, 46.0, 49.4, 51.9, 52.0, 52.6, 57.2, 61.6, 122.1, 122.4, 113.4, 114.4, 114.6, 114.7, 114.9, 115.1, 122.2, 122.3, 122.5, 122.7, 124.7, 125.5, 126.3, 127.3, 127.4, 127.5, 129.3, 131.6, 131.8, 133.1, 133.2, 133.3, 136.1, 136.2, 160.6, 160.7, 163.6, 164.6, 168.1, 168.2.

82

Ethyl 3-(2-(tert-butylamino)-1-(N-(3-fluorobenzyl)
formamido)-2-oxoethyl)-6-chloro-1H-indole-2-car-
boxylate (6C)

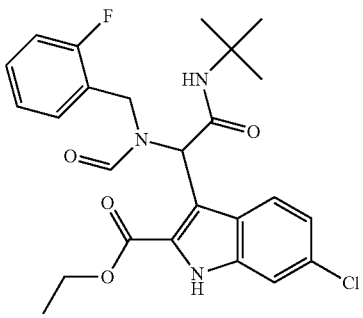 [SMILES: CCOC(=O)c1[nH]c2cc(Cl)ccc2c1C(C(=O)NC(C)(C)C)N(C=O)Cc1ccccc1F]

The final compound was obtained as a yellowish solid (79 mg, yield: 81%). HRMS: $C_{25}H_{27}ClFN_3O_4Na$, 510.1572 (calcd.), 510.1600 (found). $^1$H NMR (600 MHz, CDCl$_3$, a mixture of rotamers): 1.26 (s, 9H), 1.30 (s, 6H), 1.36-1.38 (m, 6H), 4.26-4.35 (m, 5H), 4.60 (ABd, 1H, J=16.8 Hz), 4.93 (ABd, 1H, J=15.6 Hz), 5.65 (m, 2H), 6.16 (s, 1H), 6.21-6.28 (m, 2H), 6.62 (m, 2H), 6.65-6.78 (m, 3H), 6.86 (m, 1H), 6.99-7.03 (m, 2H), 7.13-7.16 (m, 2H), 7.32 (m, 2H), 7.65 (d, 1H, J=9.0 Hz), 7.86 (d, 1H, J=8.4 Hz), 8.42 (s, 1H), 8.48 (s, 1H), 9.86 (s, 1H), 10.15 (s, 1H). $^{13}$C NMR (150 MHz, CDCl$_3$, a mixture of rotamers): 14.3, 14.4, 28.4, 28.6, 28.9, 30.9, 46.2, 49.6, 50.5, 50.7, 51.4, 51.9, 52.1, 52.5, 57.2, 61.7, 112.1, 112.4, 112.5, 112.6, 112.9, 113.8, 113.9, 114.2, 114.3, 114.9, 121.3, 122.1, 122.4, 122.5, 123.0, 123.2, 124.7, 125.5, 126.4, 127.4, 129.2, 129.3, 129.5, 131.6, 131.8, 136.1, 139.9, 140.3, 160.8, 160.9, 161.5, 161.7, 163.2, 163.3, 163.6, 164.7, 168.2.

Ethyl 3-(2-(tert-butylamino)-1-(N-(2-fluorobenzyl)
formamido)-2-oxoethyl)-6-chloro-H-indole-2-car-
boxylate (6D)

The final compound was obtained as a yellowish solid (82 mg, yield: 84%). HRMS: $C_{25}H_{27}ClFN_3O_4Na$, 510.1572 (calcd.), 510.1604 (found). $^1$H NMR (600 MHz, CDCl$_3$, a mixture of rotamers): 1.24 (s, 9H), 1.31 (s, 7H), 1.34-1.37 (m, 6H), 4.28-4.34 (m, 4H), 4.44 (ABd, 1H, J=16.2 Hz), 4.54 (ABd, 1H, J=15.6 Hz), 4.60 (ABd, 1H, J=16.2 Hz), 5.02 (ABd, 1H, J=15.0 Hz), 5.67 (m, 2H), 6.15 (s, 1H), 6.38 (m, 1H), 6.67 (s, 1H), 6.69 (m, 1H), 6.76 (m, 1H), 6.87 (m, 1H), 6.96 (m, 1H), 7.07-7.14 (m, 4H), 7.23 (m, 2H), 7.61 (d, 1H, J=8.4 Hz), 7.80 (d, 1H, J=9.0 Hz), 8.45 (s, 1H), 8.47 (s, 1H). $^{13}$C NMR (150 MHz, CDCl$_3$, a mixture of rotamers): 14.2, 14.3, 28.4, 28.6, 28.9, 30.9, 40.9, 41.0, 45.0, 45.1, 51.9, 52.0, 52.9, 53.5, 57.6, 61.6, 61.7, 112.0, 112.3, 113.3, 114.9, 115.0, 115.4, 115.5, 122.2, 122.4, 122.9, 123.5, 123.7, 123.8, 124.1, 124.2, 124.4, 124.5, 125.5, 126.0, 127.2, 128.9, 129.0, 129.1, 129.2, 130.4, 131.6, 131.7, 136.1, 159.7, 159.8, 160.9, 161.4, 163.2, 164.1, 164.7, 168.0, 168.2.

Ethyl 3-(2-(tert-butylamino)-1-(N-(3,4-difluorobenzyl)formamido)-2-oxoethyl)-6-chloro-1H-indole-2-carboxylate (6E)

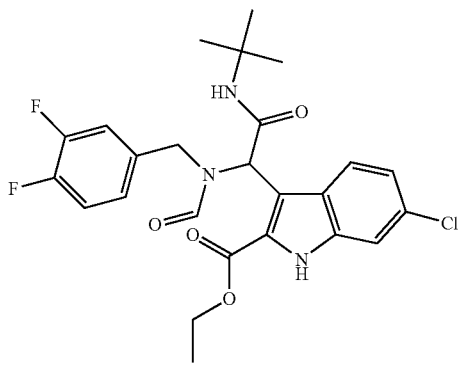 [SMILES: CCOC(=O)c1[nH]c2cc(Cl)ccc2c1C(C(=O)NC(C)(C)C)N(C=O)Cc1ccc(F)c(F)c1]

The final compound was obtained as a yellowish solid (79 mg, yield: 78%). HPLC/MS: $t_R$=11.48 min; m/z=506.0 [M+H]$^+$ HRMS: $C_{25}H_{26}N_3O_4F_2ClNa$, 528.1478 (calcd.), 528.1483 (found). $^1$H NMR (600 MHz, CDCl$_3$, a mixture of rotamers): 1.28 (s, 9H), 1.30 (s, 6H), 1.37-1.39 (m, 6H), 4.17 (ABd, 1H, J=15.6 Hz), 4.30-4.36 (m, 4H), 4.58 (ABd, 1H, J=16.2 Hz), 4.98 (ABd, 1H, J=15.6 Hz), 5.62 (m, 2H), 6.15 (m, 2H), 6.39 (m, 1H), 6.47 (m, 1H), 6.65-6.78 (m, 4H), 7.15-7.17 (m, 2H), 7.35 (m, 2H), 7.68 (d, 1H, J=9.0 Hz), 7.86 (d, 1H, J=9.0 Hz), 8.41 (s, 1H), 8.45 (s, 1H). $^{13}$C NMR (150 MHz, CDCl$_3$, a mixture of rotamers): 14.3, 14.4, 28.5, 28.6, 28.9, 30.8, 45.8, 49.2, 52.0, 52.2, 52.4, 57.0, 61.7, 61.8, 112.1, 112.4, 113.1, 114.5, 114.6, 114.8, 116.1, 116.2, 116.3, 116.4, 116.5, 121.6, 122.1, 122.4, 122.5, 122.7, 123.2, 124.6, 125.4, 126.3, 127.2, 131.8, 131.9, 134.4, 134.5, 134.8, 136.0, 148.2, 148.3, 148.8, 148.9, 150.4, 150.5, 160.6, 160.7, 163.5, 164.6, 168.1.

Ethyl 3-(2-(tert-butylamino)-1-(N-(2,4-difluorobenzyl)formamido)-2-oxoethyl)-6-chloro-1H-indole-2-carboxylate (6F)

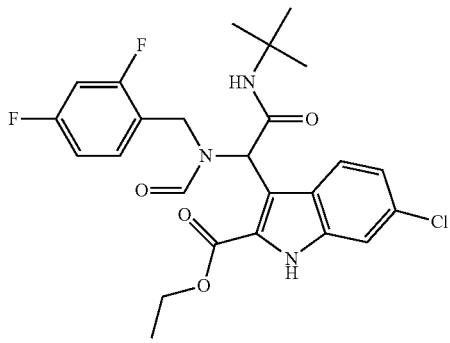 [SMILES: CCOC(=O)c1[nH]c2cc(Cl)ccc2c1C(C(=O)NC(C)(C)C)N(C=O)Cc1ccc(F)cc1F]

The final compound was obtained as a yellowish solid (68 mg, yield: 67%). HRMS: $C_{25}H_{26}ClF_2N_3O_4Na$, 528.1478 (calcd.), 528.1456 (found). $^1$H NMR (600 MHz, CDCl$_3$, a mixture of rotamers): 1.26 (s, 9H), 1.32 (s, 6H), 1.36-1.42 (m, 6H), 4.36-4.50 (m, 7H), 4.60 (ABd, 1H, J=16.2 Hz), 4.98 (ABd, 1H, J=16.2 Hz), 5.55 (m, 2H), 6.13 (s, 1H), 6.36 (m, 1H), 6.43 (m, 1H), 6.50 (m, 1H), 6.59 (m, 1H), 6.66-6.69 (m, 2H), 6.82-6.86 (m, 2H), 7.11-7.19 (m, 3H), 7.33-7.36 (m, 2H), 7.66 (d, 1H, J=9.0 Hz), 7.85 (d, 1H, J=9.0 Hz), 8.24 (s, 1H), 8.44 (m, 2H). $^{13}$C NMR (150 MHz, CDCl$_3$, a mixture of rotamers): 14.3, 14.4, 28.5, 28.6, 28.9, 30.9, 35.6, 40.3, 44.5, 51.9, 52.1, 52.7, 57.3, 61.7, 61.8, 103.1, 103.8, 103.9, 110.3, 110.5, 111.1, 111.5, 111.9, 122.1, 113.3, 115.4, 122.4, 122.7, 122.9, 124.5, 125.5, 126.0, 127.2, 131.2, 131.8, 132.0, 136.0, 160.7, 160.8, 161.2, 163.0, 163.9, 164.5, 167.8, 168.1.

Ethyl 3-(2-(tert-butylamino)-1-(N-(2,3-difluorobenzyl)formamido)-2-oxoethyl)-6-chloro-1H-indole-2-carboxylate (6G)

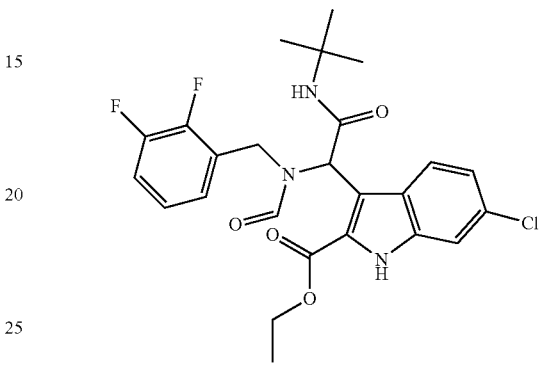

The final compound was obtained as a yellowish solid (66 mg, yield: 65%). HRMS: $C_{25}H_{26}ClF_2N_3O_4Na$, 528.1478 (calcd.), 528.1489 (found). $^1$H NMR (600 MHz, CDCl$_3$, a mixture of rotamers): 1.27 (s, 9H), 1.32 (s, 6H), 1.35-1.40 (m, 6H), 4.34-4.39 (m, 4H), 4.50-4.57 (m, 2H), 4.65 (ABd, 1H, J=16.2 Hz), 5.03 (ABd, 1H, J=15.6 Hz), 5.57 (s, 1H), 5.62 (s, 1H), 6.15 (m, 2H), 6.63 (m, 1H), 6.67 (s, 1H), 6.86 (m, 2H), 6.95 (m, 2H), 7.11-7.16 (m, 2H), 7.31-7.33 (m, 2H), 7.66 (d, 1H, J=8.4 Hz), 7.85 (d, 1H, J=9.0 Hz), 8.45 (m, 2H). $^{13}$C NMR (150 MHz, CDCl$_3$, a mixture of rotamers): 14.2, 14.3, 28.4, 28.6, 40.6, 44.7, 52.0, 52.1, 52.7, 57.4, 61.7, 61.9, 111.9, 112.1, 113.2, 115.3, 115.9, 116.0, 116.1, 116.2, 122.3, 122.5, 122.7, 122.8, 123.2, 123.3, 123.8, 124.5, 124.9, 125.5, 126.0, 126.4, 126.9, 127.0, 127.2, 131.9, 132.1, 135.9, 147.6, 149.3, 150.9, 160.8, 163.9, 164.5, 167.7, 168.0.

Ethyl 3-(2-(tert-butylamino)-1-(N-(2,5-difluorobenzyl)formamido)-2-oxoethyl)-6-chloro-1H-indole-2-carboxylate (6H)

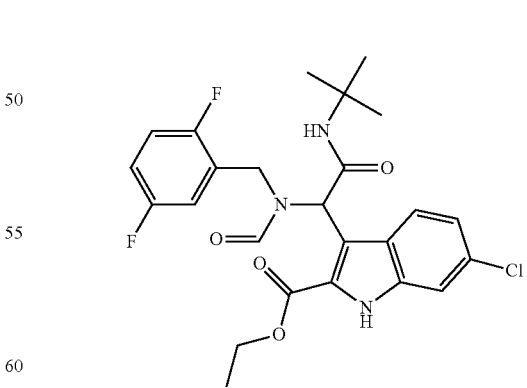

The final compound was obtained as a yellowish solid (46 mg, yield: 46%). HPLC/MS: $t_R$=10.62 min; m/z=406.3 [M+H]$^+$ HRMS: $C_{25}H_{26}ClF_2N_3O_4Na$, 528.1478 (calcd.), 528.1469 (found). $^1$H NMR (400 MHz, CD$_2$Cl$_2$, a mixture of rotamers): 1.30 (s, 9H), 1.32 (s, 5H), 1.41-1.47 (m, 4H), 4.38-4.59 (m, 6H), 4.62 (ABd, 1H, J=16.8 Hz), 4.95 (ABd, 1H, J=16.0 Hz), 5.48 (s, 1H), 6.19 (s, 1H), 6.28 (m, 1H), 6.66 (s, 1H), 6.69-6.79 (m, 4H), 7.00-7.12 (m, 4H), 7.17-7.21 (m, 2H), 7.39 (m, 2H), 7.73 (d, 1H, J=8.8 Hz), 7.88 (d, 1H, J=8.8 Hz), 8.29 (m, 2H), 8.41 (s, 1H), 8.48 (s, 1H), 9.03 (s, 1H), 9.19 (s, 1H). $^{13}$C NMR (100 MHz, CD$_2$Cl$_2$, a mixture of rotamers): 14.0, 14.1, 28.2, 28.3, 35.6, 40.2, 40.3, 44.2, 51.2, 51.9, 52.5, 57.0, 61.8, 61.9, 111.6, 111.8, 113.4, 114.5, 114.7, 115.3, 115.4, 115.5, 115.8, 115.9, 116.0, 116.2, 116.3, 116.5, 122.4, 122.5, 122.6, 123.0, 124.7, 125.6, 126.4, 127.3, 131.7, 131.9, 135.7, 160.6, 160.9, 163.6, 164.2, 167.7.

Ethyl 3-(2-(tert-butylamino)-1-(N-(3,5-difluorobenzyl)formamido)-2-oxoethyl)-6-chloro-1H-indole-2-carboxylate (6I)

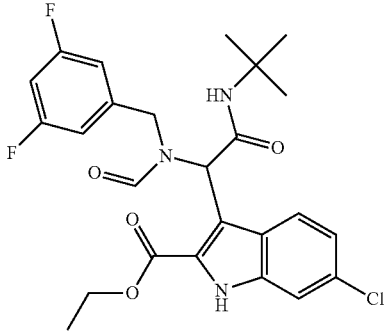 [SMILES: CCOC(=O)c1[nH]c2cc(Cl)ccc2c1C(C(=O)NC(C)(C)C)N(C=O)Cc1cc(F)cc(F)c1]

The final compound was obtained as a yellowish solid (75 mg, yield: 74%). HRMS: C$_{25}$H$_{26}$ClF$_2$N$_3$O$_4$Na, 528.1478 (calcd.), 528.1453 (found). $^1$H NMR (600 MHz, CDCl$_3$, a mixture of rotamers): 1.31 (s, 9H), 1.33 (s, 6H), 1.41-1.44 (m, 6H), 4.21 (ABd, 1H, J=15.6 Hz), 4.34-4.50 (m, 6H), 5.02 (ABd, 1H, J=16.2 Hz), 5.49 (m, 2H), 6.06 (m, 2H), 6.17 (s, 1H), 6.33 (m, 2H), 6.50 (m, 2H), 6.74 (s, 1H), 6.83 (m, 1H), 7.19-7.21 (m, 2H), 7.36-7.37 (m, 2H), 7.70 (d, 1H, J=9.0 Hz), 7.90 (d, 1H, J=8.4 Hz), 8.42 (s, 1H), 8.49 (s, 1H). $^{13}$C NMR (150 MHz, CDCl$_3$, a mixture of rotamers): 14.4, 28.5, 28.6, 28.9, 30.9, 41.3, 46.0, 49.4, 50.9, 52.0, 52.2, 52.3, 56.9, 61.9, 62.0, 102.1, 102.3, 108.3, 108.5, 109.8, 110.0, 111.9, 112.2, 113.1, 115.1, 122.2, 122.5, 122.8, 122.9, 124.7, 125.5, 126.4, 127.3, 132.1, 132.3, 135.8, 141.5, 160.5, 161.2, 163.4, 167.9, 168.0.

Ethyl 3-(2-(tert-butylamino)-1-(N-(2,6-difluorobenzyl)formamido)-2-oxoethyl)-6-chloro-1H-indole-2-carboxylate (6J)

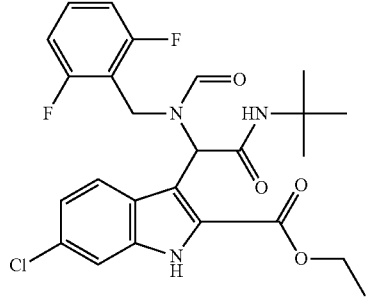 [SMILES: CCOC(=O)c1[nH]c2cc(Cl)ccc2c1C(C(=O)NC(C)(C)C)N(C=O)Cc1c(F)cccc1F]

The final compound was obtained as a yellowish solid (75 mg, yield: 74%). HRMS: C$_{25}$H$_{26}$ClF$_2$N$_3$O$_4$Na, 528.1478 (calcd.), 528.1467 (found). $^1$H NMR (600 MHz, CDCl$_3$, a mixture of rotamers): 1.21 (s, 9H), 1.33 (s, 9H), 1.36 (m, 6H), 4.25-4.31 (m, 4H), 4.49-4.57 (m, 2H), 4.68 (ABd, 1H, J=15.0 Hz), 5.13 (ABd, 1H, J=15.0 Hz), 5.65 (s, 1H), 5.81 (s, 1H), 6.02 (s, 1H), 6.55-6.58 (m, 3H), 6.80 (m, 2H), 6.89 (m, 1H), 7.05 (m, 3H), 7.20 (m, 1H), 7.63 (d, 1H, J=9.0 Hz), 7.70 (d, 1H, J=9.0 Hz), 8.29 (s, 1H), 8.44 (s, 1H). $^{13}$C NMR (150 MHz, CDCl$_3$, a mixture of rotamers): 14.2, 14.3, 28.4, 28.6, 35.4, 39.0, 51.9, 53.7, 57.2, 61.5, 61.7, 111.0, 111.1, 111.2, 111.3, 111.6, 111.9, 112.3, 112.8, 113.0, 115.1, 122.0, 122.2, 122.4, 122.8, 124.7, 125.6, 125.9, 127.2, 129.6, 131.4, 131.6, 136.1, 136.2, 160.9, 161.0, 164.0, 164.1, 167.8, 168.2.

Ethyl 3-(2-(tert-butylamino)-2-oxo-1-(N-(2,3,4-trifluorobenzyl)formamido)ethyl)-6-chloro-1H-indole-2-carboxylate (6K)

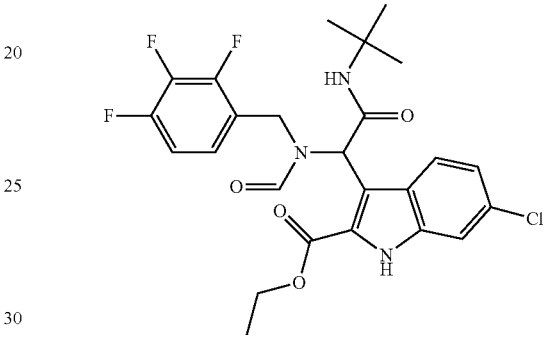

The final compound was obtained as a yellowish solid (40 mg, yield: 38%). HRMS: C$_{25}$H$_{25}$ClF$_3$N$_3$O$_4$Na, 546.1383 (calcd.), 546.1398 (found). $^1$H NMR (600 MHz, CDCl$_3$, a mixture of rotamers): 1.28 (s, 9H), 1.33 (s, 6H), 1.40-1.46 (m, 6H), 4.44-4.54 (m, 6H), 4.65 (ABd, 1H, J=16.2 Hz), 5.00 (ABd, 1H, J=15.6 Hz), 5.46 (s, 1H), 6.13-6.16 (m, 2H), 6.51 (m, 1H), 6.66 (s, 1H), 6.75-6.79 (m, 1H), 6.94-6.99 (m, 2H), 7.11-7.19 (m, 2H), 7.38 (s, 1H), 7.69 (d, 1H, J=8.4 Hz), 7.88 (d, 1H, J=9.0 Hz), 8.06 (s, 1H), 8.29 (m, 2H), 8.44 (s, 1H), 9.35 (br.s, 1H), 9.44 (br.s, 1H). $^{13}$C NMR (150 MHz, CDCl$_3$, a mixture of rotamers): 14.3, 14.4, 28.5, 28.6, 28.9, 30.9, 35.6, 40.3, 44.4, 52.0, 52.2, 52.5, 57.2, 61.8, 62.0, 111.0, 111.2, 111.6, 111.7, 111.8, 112.0, 112.2, 112.3, 113.3, 115.5, 122.4, 122.7, 122.9, 123.0, 123.7, 124.5, 125.4, 125.9, 127.1, 132.1, 132.4, 135.8, 160.6, 160.7, 161.1, 162.9, 163.7, 164.4, 167.5, 167.8.

Ethyl 3-(2-(tert-butylamino)-2-oxo-1-(N-(2,4,5-trifluorobenzyl)formamido)ethyl)-6-chloro-1H-indole-2-carboxylate (6L)

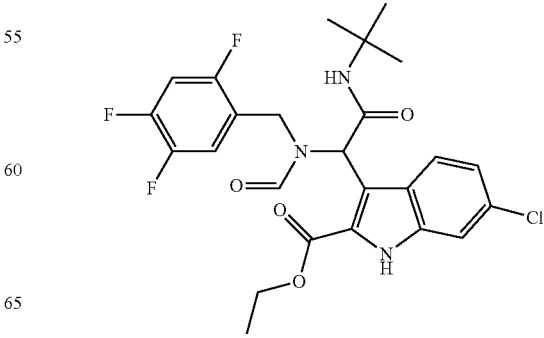

The final compound was obtained as a yellowish solid (42 mg, yield: 40%). HRMS: $C_{25}H_{25}ClF_3N_3O_4Na$, 546.1383 (calcd.), 546.1370 (found). $^1H$ NMR (600 MHz, CDCl$_3$, a mixture of rotamers): 1.29 (s, 9H), 1.31 (s, 5H), 3.36-4.47 (m, 6H), 4.58 (ABd, 1H, J=16.2 Hz), 4.92 (ABd, 1H, J=15.6 Hz), 5.58 (m, 2H), 6.18 (s, 1H), 6.27 (m, 1H), 6.56-6.64 (m, 2H), 6.70 (s, 1H), 6.88-6.94 (m, 2H), 7.12-7.23 (m, 3H), 7.35 (s, 1H), 7.38 (s, 1H), 7.67 (d, 1H, J=8.4 Hz), 7.85 (d, 1H, J=9.0 Hz), 8.27 (m, 1H), 8.41 (s, 1H), 8.44 (s, 1H). $^{13}C$ NMR (150 MHz, CDCl$_3$, a mixture of rotamers): 14.2, 14.3, 28.5, 28.6, 28.9, 30.8, 35.3, 40.1, 44.0, 52.0, 52.2, 52.5, 57.1, 61.8, 61.9, 104.5, 104.6, 104.8, 105.5, 105.6, 112.1, 112.2, 113.1, 115.0, 122.2, 122.6, 122.7, 124.4, 125.3, 126.1, 127.2, 132.1, 136.0, 160.8, 161.5, 163.3, 163.8, 164.6, 167.8, 168.0.

Ethyl 3-(2-(tert-butylamino)-2-oxo-1-(N-(3,4,5-trifluorobenzyl)formamido)ethyl)-6-chloro-1H-indole-2-carboxylate (6M)

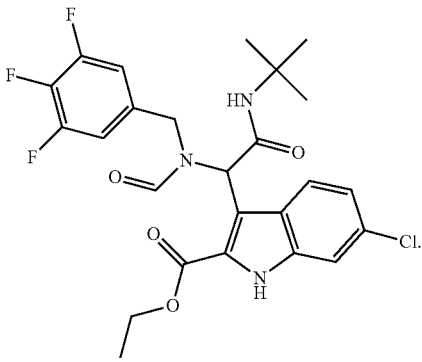 [SMILES: CCOC(=O)c1[nH]c2cc(Cl)ccc2c1C(C(=O)NC(C)(C)C)N(C=O)Cc1cc(F)c(F)c(F)c1]

The final compound was obtained as a yellowish solid (80 mg, yield: 76%). HRMS: $C_{25}H_{25}ClF_3N_3O_4Na$, 546.1383 (calcd.), 546.1384 (found). $^1H$ NMR (600 MHz, CDCl$_3$, a mixture of rotamers): 1.32 (s, 14H), 1.41-1.44 (m, 5H), 4.14 (ABd, 1H, J=15.6 Hz), 4.33 (ABd, 1H, J=16.8 Hz), 4.39-4.43 (m, 3H), 4.58 (ABd, 1H, J=16.2 Hz), 5.01 (ABd, 1H, J=15.6 Hz), 6.17 (m, 2H), 6.39-6.42 (m, 2H), 6.75 (s, 1H), 7.19-7.21 (m, 2H), 7.38-7.40 (m, 2H), 7.71 (d, 1H, J=8.4 Hz), 7.89 (d, 1H, J=8.4 Hz), 8.40 (s, 1H), 8.46 (s, 1H). $^{13}C$ NMR (150 MHz, CDCl$_3$, a mixture of rotamers): 14.3, 28.5, 28.6, 45.7, 49.1, 52.1, 52.2, 56.8, 61.9, 62.0, 109.5, 109.6, 109.7, 109.9, 110.9, 111.0, 111.1, 112.0, 112.3, 113.2, 115.0, 122.1, 122.4, 122.8, 123.0, 124.6, 125.4, 126.3, 127.2, 132.1, 132.3, 135.9, 160.5, 163.4, 164.4, 167.9.

Ethyl 3-(2-(tert-butylamino)-2-oxo-1-(N-(2,3,6-trifluorobenzyl)formamido)ethyl)-6-chloro-1H-indole-2-carboxylate (6N)

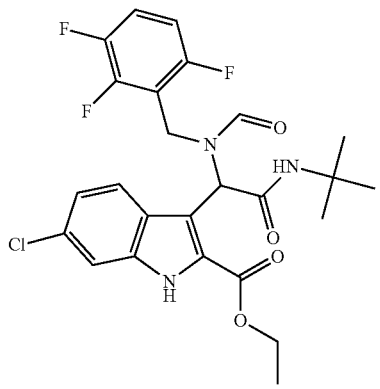 [SMILES: CCOC(=O)c1[nH]c2cc(Cl)ccc2c1C(C(=O)NC(C)(C)C)N(C=O)Cc1c(F)ccc(F)c1F]

The final compound was obtained as a yellowish solid (72 mg, yield: 69%). HRMS: $C_{25}H_{25}ClF_3N_3O_4Na$, 546.1383 (calcd.), 546.1387 (found). $^1H$ NMR (600 MHz, CDCl$_3$, a mixture of rotamers): 1.24 (s, 9H), 1.33 (s, 7H), 1.37-1.40 (m, 6H), 4.31-4.37 (m, 4H), 4.61 (m, 2H), 4.70 (ABd, 1H, J=15.0 Hz), 5.11 (ABd, 1H, J=15.0 Hz), 5.56 (s, 1H), 5.63 (s, 1H), 6.05 (s, 1H), 6.48 (m, 1H), 6.57 (s, 1H), 6.72 (m, 1H), 6.83-6.88 (m, 2H), 6.98-7.02 (m, 1H), 7.09-7.10 (m, 2H), 7.34 (m, 2H), 7.67 (d, 1H, J=8.4 Hz), 7.76 (d, 1H, J=9.0 Hz), 8.29 (s, 1H), 8.47 (s, 1H). $^{13}C$ NMR (150 MHz, CDCl$_3$, a mixture of rotamers): 14.1, 14.3, 28.4, 28.6, 28.9, 30.9, 35.5, 39.4, 50.7, 51.9, 52.0, 53.3, 57.0, 61.7, 61.9, 111.8, 112.1, 112.7, 115.1, 122.3, 122.4, 122.7, 122.8, 124.7, 125.5, 126.0, 127.2, 131.8, 131.9, 136.0, 136.1, 160.7, 160.8, 160.9, 161.0, 163.1, 163.8, 163.9, 167.6, 168.0.

Ethyl 3-(2-(tert-butylamino)-2-oxo-1-(N-(2,4,6-trifluorobenzyl)formamido)ethyl)-6-chloro-1H-indole-2-carboxylate (6O)

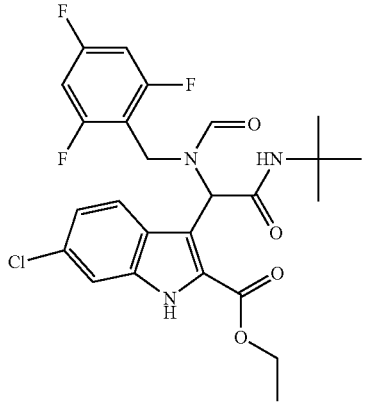 [SMILES: CCOC(=O)c1[nH]c2cc(Cl)ccc2c1C(C(=O)NC(C)(C)C)N(C=O)Cc1c(F)cc(F)cc1F]

The final compound was obtained as a yellowish solid (64 mg, yield: 61%). HRMS: $C_{25}H_{25}ClF_3N_3O_4K$, 562.1123 (calcd.), 562.1135 (found). $^1H$ NMR (600 MHz, CDCl$_3$, a mixture of rotamers): 1.24 (s, 9H), 1.34 (s, 9H), 1.36-1.43 (m, 6H), 4.34-4.39 (m, 4H), 4.53-4.55 (m, 2H), 4.64 (ABd, 1H, J=14.4 Hz), 5.08 (ABd, 1H, J=14.4 Hz), 5.48 (s, 1H), 5.59 (s, 1H), 6.00 (s, 1H), 6.33-6.36 (m, 2H), 6.56-6.60 (m, 3H), 7.10-7.12 (m, 2H), 7.34 (m, 2H), 7.68 (d, 1H, J=8.4 Hz), 7.78 (d, 1H, J=9.0 Hz), 8.28 (s, 1H), 8.45 (s, 1H), 9.46 (s, 1H), 9.68 (s, 1H). $^{13}C$ NMR (150 MHz, CDCl$_3$, a mixture of rotamers): 14.2, 14.4, 28.5, 28.6, 35.0, 38.8, 52.0, 53.4, 56.9, 61.7, 61.9, 99.9, 100.0, 100.1, 111.7, 112.1, 113.1, 115.4, 122.3, 122.5, 122.8, 123.0, 124.7, 125.6, 125.8, 127.1, 131.9, 132.1, 135.9, 160.7, 160.9, 163.8, 167.6, 168.0.

Ethyl 3-(2-(tert-butylamino)-2-oxo-1-(N-(2,3,5-trifluorobenzyl)formamido)ethyl)-6-chloro-1H-indole-2-carboxylate (6P)

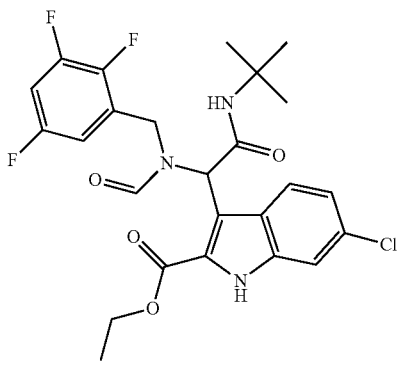 [SMILES: CCOC(=O)c1[nH]c2cc(Cl)ccc2c1C(C(=O)NC(C)(C)C)N(C=O)Cc1cc(F)cc(F)c1F]

The final compound was obtained as a yellowish solid (50 mg, yield: 48%). HRMS: $C_{25}H_{25}ClF_3N_3O_4Na$, 546.1383 (calcd.), 546.1355 (found). $^1$H NMR (600 MHz, CDCl$_3$, a mixture of rotamers): 1.30 (s, 9H), 1.33 (s, 5H), 4.43-4.57 (m, 6H), 4.66 (ABd, 1H, J=16.8 Hz), 5.01 (ABd, 1H, J=16.2 Hz), 5.46 (m, 2H), 5.99 (m, 1H), 6.19 (s, 1H), 6.22 (m, 1H), 6.59-6.66 (m, 3H), 6.70 (s, 1H), 6.87-6.91 (m, 2H), 7.15-7.20 (m, 2H), 7.36-7.38 (m, 2H), 7.70 (d, 1H, J=9.0 Hz), 7.88 (d, 1H, J=9.0 Hz), 8.06 (s, 1H), 8.30 (m, 1H), 8.43 (s, 1H), 8.48 (s, 1H). $^{13}$C NMR (150 MHz, CDCl$_3$, a mixture of rotamers): 14.3, 14.4, 28.5, 28.6, 28.9, 30.9, 35.6, 40.3, 44.3, 52.0, 52.2, 52.4, 57.1, 61.9, 62.1, 104.7, 104.8, 104.9, 105.0, 110.5, 110.7, 111.1, 111.3, 111.9, 112.0, 113.0, 115.2, 122.3, 122.6, 122.8, 123.0, 124.4, 125.4, 126.1, 127.2, 132.2, 132.4, 135.7, 135.8, 160.6, 160.7, 161.2, 162.9, 163.7, 164.4, 167.6, 167.8.

Ethyl 3-(2-(tert-butylamino)-2-oxo-1-(N-(2,3,5,6-tetrafluorobenzyl)formamido)ethyl)-6-chloro-1H-indole-2-carboxylate (6Q)

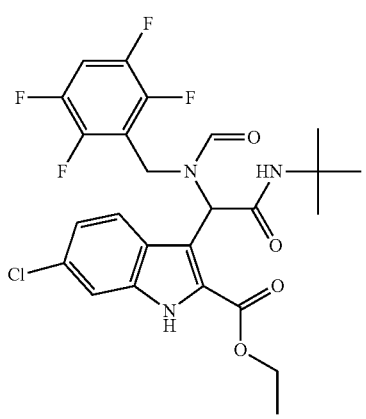 [SMILES: CCOC(=O)c1[nH]c2cc(Cl)ccc2c1C(C(=O)NC(C)(C)C)N(C=O)Cc1c(F)c(F)cc(F)c1F]

The final compound was obtained as a yellowish solid (79 mg, yield: 73%). HPLC/MS: $t_R$=11.03 min; m/z=541.9 [M+H]$^+$ HRMS: $C_{25}H_{24}ClF_4N_3O_4Na$, 564.1289 (calcd.), 564.1276 (found). $^1$H NMR (400 MHz, CDCl$_3$, a mixture of rotamers): 1.24 (s, 9H), 1.30 (s, 5H), 1.32-1.38 (m, 6H), 4.24-4.35 (m, 3H), 4.58-4.63 (m, 2H), 4.74 (ABd, 1H, J=15.2 Hz), 5.07 (ABd, 1H, J=15.2 Hz), 5.70 (s, 1H), 5.72 (s, 1H), 6.08 (s, 1H), 6.58 (s, 1H), 6.75 (m, 1H), 6.88 (m, 1H), 7.00 (m, 1H), 7.06-7.09 (m, 2H), 7.35 (m, 2H), 7.65 (d, 1H, J=8.8 Hz), 7.72 (d, 1H, J=8.8 Hz), 8.15 (s, 1H), 8.25 (s, 1H), 8.46 (s, 1H). $^{13}$C NMR (100 MHz, CDCl$_3$, a mixture of rotamers): 14.0, 14.2, 28.4, 28.5, 28.8, 30.8, 35.6, 50.5, 51.4, 51.9, 52.1, 53.2, 56.9, 61.6, 61.8, 104.9, 105.1, 105.4, 105.6, 112.0, 112.3, 114.6, 116.0, 122.1, 122.3, 122.4, 1, 125.3, 126.1, 127.2, 131.8, 131.9, 136.1, 136.2, 160.8, 160.9, 161.2, 163.2, 164.0, 167.7, 168.0.

Ethyl 3-(2-(tert-butylamino)-2-oxo-1-(N-(2,3,4,6-tetrafluorobenzyl)formamido)ethyl)-6-chloro-1H-indole-2-carboxylate (6R)

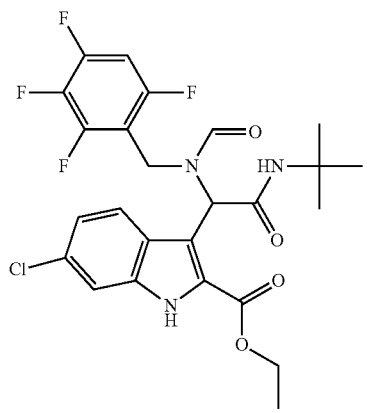 [SMILES: CCOC(=O)c1[nH]c2cc(Cl)ccc2c1C(C(=O)NC(C)(C)C)N(C=O)Cc1c(F)cc(F)c(F)c1F]

The final compound was obtained as a yellowish solid (60 mg, yield: 55%). HRMS: $C_{25}H_{24}ClF_4N_3O_4Na$, 564.1289 (calcd.), 564.1314 (found). $^1$H NMR (600 MHz, CDCl$_3$, a mixture of rotamers): 1.25 (s, 9H), 1.33 (s, 6H), 1.35-1.40 (m, 6H), 4.32-4.37 (m, 4H), 4.59 (m, 2H), 4.69 (ABd, 1H, J=14.4 Hz), 5.04 (ABd, 1H, J=15.0 Hz), 5.53 (s, 1H), 5.62 (s, 1H), 6.04 (s, 1H), 6.43 (m, 1H), 6.57 (s, 1H), 6.66 (m, 1H), 7.10-7.12 (m, 2H), 7.38 (m, 2H), 7.68 (d, 1H, J=8.4 Hz), 7.77 (d, 1H, J=8.4 Hz), 8.25 (s, 1H), 8.46 (s, 1H), 9.82 (s, 1H), 10.04 (s, 1H). $^{13}$C NMR (150 MHz, CDCl$_3$, a mixture of rotamers): 14.2, 14.3, 28.4, 28.6, 30.8, 35.3, 39.1, 45.6, 52.0, 52.1, 53.2, 56.8, 61.7, 61.9, 100.3, 100.5, 111.8, 112.2, 112.8, 115.0, 122.3, 122.4, 122.7, 122.8, 124.6, 125.4, 125.9, 127.0, 132.0, 132.1, 135.9, 136.0, 160.7, 163.9, 167.6, 167.9.

Ethyl 3-(2-(tert-butylamino)-2-oxo-1-(N-(2,3,4,5-tetrafluorobenzyl)formamido)ethyl)-6-chloro-1H-indole-2-carboxylate (6S)

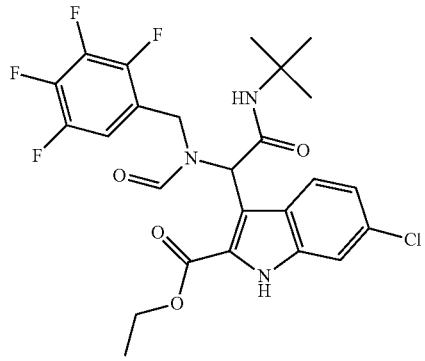 [SMILES: CCOC(=O)c1[nH]c2cc(Cl)ccc2c1C(C(=O)NC(C)(C)C)N(C=O)Cc1cc(F)c(F)c(F)c1F]

The final compound was obtained as a yellowish solid (44 mg, yield: 41%). HRMS: $C_{25}H_{24}ClF_4N_3O_4Na$, 564.1289 (calcd.), 564.1298 (found). $^1$H NMR (600 MHz, CDCl$_3$, a mixture of rotamers): 1.22 (s, 9H), 1.31 (s, 7H), 1.38-1.41 (m, 6H), 4.34-4.39 (m, 4H), 4.48-4.51 (m, 2H), 4.62 (ABd, 1H, J=16.2 Hz), 4.83 (ABd, 1H, J=15.0 Hz), 5.50 (s, 1H), 5.57 (s, 1H), 6.14 (s, 1H), 6.56 (m, 2H), 6.73 (s, 1H), 6.95-6.98 (m, 2H), 7.01-7.05 (m, 3H), 7.15-7.17 (m, 5H), 7.30-7.32 (m, 2H), 7.62 (d, 1H, J=9.0 Hz), 7.88 (d, 1H, J=8.4 Hz), 8.05 (s, 1H), 8.29 (m, 1H), 8.45 (s, 1H), 8.53 (s, 1H). $^{13}$C NMR (150 MHz, CDCl$_3$, a mixture of rotamers): 14.4, 28.4, 28.6, 28.9, 30.9, 46.7, 50.1, 51.9, 52.6, 57.6, 61.6, 61.7, 111.8, 112.2, 113.5, 115.6, 122.3, 122.5, 122.9, 124.9, 125.7, 125.8, 126.3, 127.1, 127.3, 127.8, 127.9, 128.4, 128.8, 131.7, 131.9, 135.9, 136.0, 137.4, 137.5, 160.6, 160.7, 161.4, 163.0, 163.6, 164.7, 168.1, 168.2.

Ethyl 3-(2-(tert-butylamino)-2-oxo-1-(N-(perfluorobenzyl)formamido)ethyl)-6-chloro-1H-indole-2-carboxylate (6T)

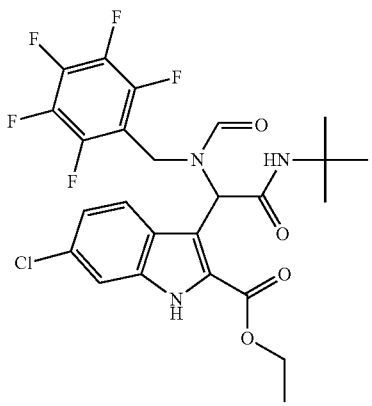 [SMILES: CCOC(=O)c1[nH]c2cc(Cl)ccc2c1C(C(=O)NC(C)(C)C)N(C=O)Cc1c(F)c(F)c(F)c(F)c1F]

The final compound was obtained as a yellowish solid (68 mg, yield: 61%). HPLC/MS: t$_R$=11.76 min; m/z=559.7 [M+H]$^+$ HRMS: C$_{25}$H$_{23}$ClF$_5$N$_3$O$_4$Na, 582.1195 (calcd.), 582.1151 (found). $^1$H NMR (600 MHz, CDCl$_3$, a mixture of rotamers): 1.28 (s, 9H), 1.33 (s, 5H), 1.38-1.43 (m, 5H), 4.36-4.43 (m, 3H), 4.65 (m, 1H), 4.76 (ABd, 1H, J=15.0 Hz), 5.03 (ABd, 1H, J=15.0 Hz), 5.44 (s, 1H), 5.51 (s, 1H), 6.05 (s, 1H), 6.57 (s, 1H), 7.14 (m, 1H), 7.38 (m, 1H), 7.69 (d, 1H, J=9.0 Hz), 7.78 (d, 1H, J=8.4 Hz), 8.25 (s, 1H), 8.47 (s, 1H). $^{13}$C NMR (150 MHz, CDCl$_3$, a mixture of rotamers): 14.2, 14.3, 28.5, 28.6, 35.2, 39.1, 50.8, 52.1, 52.2, 53.0, 56.8, 61.8, 62.1, 111.8, 112.1, 112.8, 115.0, 122.3, 122.7, 123.0, 124.6, 125.3, 125.9, 127.0, 132.3, 132.4, 135.8, 135.9, 160.6, 160.7, 160.9, 163.7, 167.5, 167.7.

General Procedure for Hydrolysis of the C-2 Ester of Fluorinated Formula I Compounds The ester compound was treated with LiOH in EtOH/water (1:1), and stirring under RT for 2 days. Then the reaction mixture was acidified with 1M. HCl (pH~6). The mixture was extracted with dichloromethane (10 mL×3). The combined organic layer was dried over sodium sulfate, and filtered. After evaporation of the solvent, compound 7 was obtained without further purification.

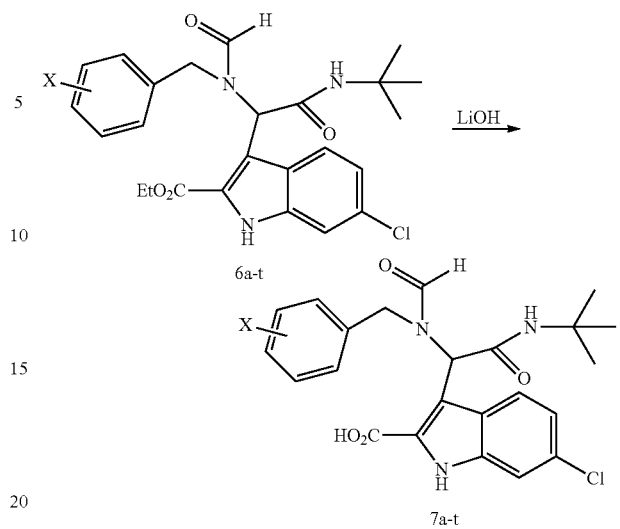

3-(2-(tert-butylamino)-1-(N-(4-fluorobenzyl)formamido)-2-oxoethyl)-6-chloro-1H-indole-2-carboxylic acid (7B)

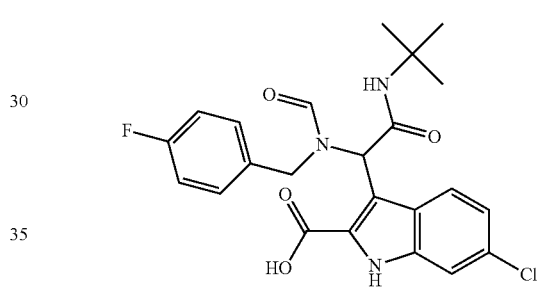

The final compound was obtained as a white solid (30 mg, 62%). HPLC/MS: t$_R$=11.45 min; m/z=459.8 [M+H]$^+$ HRMS: C$_{23}$H$_{23}$ClFN$_3$O$_4$Na, 482.1259 (calcd.), 482.1286 (found). $^1$H NMR (400 MHz, MeOD, a mixture of rotamers): 1.24 (s, 9H), 1.31 (s, 5H), 4.27-4.32 (m, 2H), 4.68 (ABd, 1H, J=16.0 Hz), 5.12 (ABd, 1H, J=15.2 Hz), 6.25 (s, 1H), 6.48-6.51 (m, 1H), 6.62-6.67 (m, 1H), 6.74-6.79 (m, 3H), 6.86-6.89 (m, 2H), 7.10-7.14 (m, 2H), 7.39-7.42 (m, 2H), 7.56 (s, 1H), 7.80 (d, 1H, J=8.8 Hz), 7.84 (d, 1H, J=8.8 Hz), 8.36 (s, 1H), 8.46 (s, 1H). $^{13}$C NMR (100 MHz, MeOD, a mixture of rotamers): 27.4, 27.5, 46.1, 49.4, 51.1, 51.2, 52.7, 56.8, 56.9, 111.8, 111.9, 113.7, 113.9, 114.0, 114.1, 120.9, 121.1, 121.8, 122.0, 124.7, 125.5, 127.0, 127.1, 129.0, 129.1, 130.3, 130.4, 132.9, 133.6, 136.3, 160.6, 163.0, 164.6, 165.2, 169.6, 169.8.

3-(2-(tert-butylamino)-1-(N-(3-fluorobenzyl)formamido)-2-oxoethyl)-6-chloro-1H-indole-2-carboxylic acid (7C)

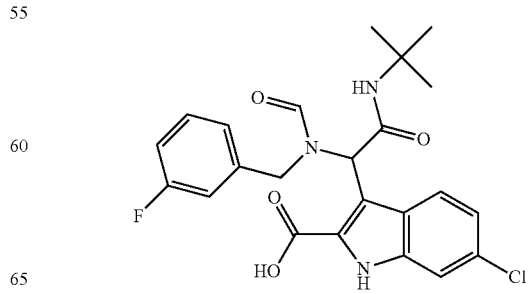

The final compound was obtained as a yellowish solid (65 mg, 91%). HPLC/MS: $t_R$=11.30 min; m/z=459.9 [M+H]$^+$ HRMS: $C_{23}H_{23}ClFN_3O_4Na$, 482.1259 (calcd.), 482.1257 (found). $^1$H NMR (600 MHz, MeOD, a mixture of rotamers): 1.13 (s, 9H), 1.19 (s, 5H), 4.17-4.19 (m, 2H), 4.60 (ABd, 1H, J=16.8 Hz), 5.03 (ABd, 1H, J=15.6 Hz), 6.17 (m, 2H), 6.46-6.50 (m, 2H), 6.58 (m, 1H), 6.65-6.68 (m, 2H), 6.79 (m, 1H), 6.88-6.90 (m, 1H), 6.98-7.01 (m, 2H), 7.26-7.29 (m, 2H), 7.41 (s, 1H), 7.47 (s, 1H), 7.68 (m, 1H), 7.73 (m, 1H), 8.28 (s, 1H), 8.34 (s, 1H). $^{13}$C NMR (150 MHz, MeOD, a mixture of rotamers): 28.9, 29.0, 47.8, 49.5, 51.0, 52.7, 54.1, 58.4, 113.2, 113.3, 113.5, 113.8, 114.4, 114.5, 114.6, 115.0, 115.2, 115.3, 122.4, 122.6, 123.1, 123.3, 124.1, 126.1, 127.0, 129.6, 130.4, 131.7, 131.8, 137.7, 141.2, 142.0, 163.0, 164.6, 166.1, 166.8, 171.1, 171.3.

3-(2-(tert-butylamino)-1-(N-(2-fluorobenzyl)formamido)-2-oxoethyl)-6-chloro-1H-indole-2-carboxylic acid (7D)

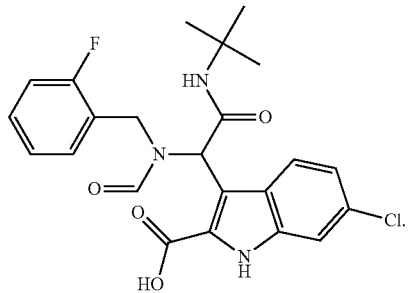 [SMILES: CC(C)(C)NC(=O)C(c1c(C(=O)O)[nH]c2cc(Cl)ccc12)N(C=O)Cc1ccccc1F]

The final compound was obtained as a yellowish solid (55 mg, 78%). HPLC/MS: $t_R$=11.27 min; m/z=459.8 [M+H] HRMS: $C_{23}H_{23}ClFN_3O_4Na$, 482.1259 (calcd.), 482.1237 (found). $^1$H NMR (600 MHz, MeOD, a mixture of rotamers): 1.10 (s, 9H), 1.18 (s, 5H), 4.39 (ABd, 1H, J=16.2 Hz), 4.52 (ABd, 1H, J=15.6 Hz), 4.61 (ABd, 1H, J=16.8 Hz), 4.92 (ABd, 1H, J=15.6 Hz), 6.16 (s, 1H), 6.35 (m, 1H), 6.56-6.62 (m, 2H), 6.68 (m, 1H), 6.79 (m, 1H), 6.90-6.99 (m, 4H), 7.26 (m, 2H), 7.35 (s, 1H), 7.49 (s, 1H), 7.64 (m, 1H), 7.68 (m, 1H), 8.24 (s, 1H), 8.34 (s, 1H). $^{13}$C NMR (150 MHz, MeOD, a mixture of rotamers): 28.8, 28.9, 41.9, 42.0, 45.8, 45.9, 52.7, 54.3, 58.5, 113.1, 113.2, 115.5, 115.6, 115.8, 122.3, 122.5, 123.2, 123.5, 124.4, 124.5, 124.7, 124.8, 124.9, 126.0, 126.9, 129.1, 129.4, 129.8, 129.9, 130.9, 131.8, 131.9, 137.7, 161.0, 162.6, 163.6, 163.9, 166.6, 166.7, 170.8, 171.2.

3-(2-(tert-butylamino)-1-(N-(3,4-difluorobenzyl)formamido)-2-oxoethyl)-6-chloro-1H-indole-2-carboxylic acid (7E)

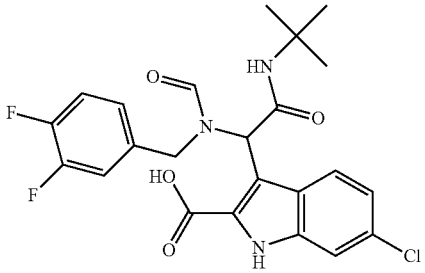 [SMILES: CC(C)(C)NC(=O)C(c1c(C(=O)O)[nH]c2cc(Cl)ccc12)N(C=O)Cc1ccc(F)c(F)c1]

The final compound was obtained as a yellowish solid (62 mg, 91%). HPLC/MS: $t_R$=10.85 min; m/z=477.9 [M+H]$^+$ HRMS: $C_{22}H_{22}N_3O_4F_2ClNa$, 500.1165 (calcd.), 500.1166 (found). $^1$H NMR (400 MHz, MeOD, a mixture of rotamers): 1.20 (s, 9H), 1.26 (s, 3H), 4.32-4.40 (m, 2H), 4.59 (ABd, 1H, J=16.4 Hz), 5.01 (ABd, 1H, J=15.2 Hz), 6.39-6.44 (m, 1H), 6.58 (s, 1H), 6.76-6.78 (m, 2H), 6.85-6.97 (m, 2H), 7.00-7.02 (m, 2H), 7.09 (s, 1H), 7.32-7.37 (m, 2H), 7.69 (d, 1H, J=8.8 Hz), 7.73 (d, 1H, J=8.8 Hz), 8.34 (s, 1H), 8.37 (s, 1H). $^{13}$C NMR (100 MHz, MeOD, a mixture of rotamers): 27.4, 27.5, 46.3, 49.0, 50.9, 53.1, 57.1, 108.2, 109.8, 111.4, 111.5, 116.0, 116.2, 116.3, 116.5, 120.1, 120.3; 121.2, 121.5, 123.8, 123.9, 125.0, 128.7, 128.8, 134.4, 134.5, 135.3, 147.9, 148.3, 148.4, 150.3, 150.4, 150.8, 164.9, 165.4, 167.6, 170.0, 170.4.

3-(2-(tert-butylamino)-1-(N-(2,4-difluorobenzyl)formamido)-2-oxoethyl)-6-chloro-1H-indole-2-carboxylic acid (7F)

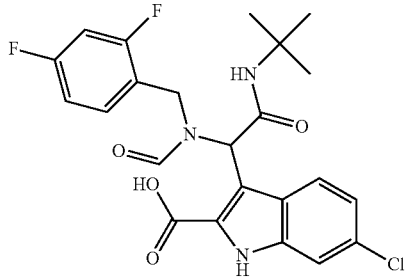 [SMILES: CC(C)(C)NC(=O)C(c1c(C(=O)O)[nH]c2cc(Cl)ccc12)N(C=O)Cc1ccc(F)cc1F]

The final compound was obtained as a yellowish solid (50 mg, 78%). HPLC/MS: $t_R$=11.64 min; m/z=477.5 [M+H] HRMS: $C_{23}H_{22}ClF_2N_3O_4Na$, 500.1165 (calcd.), 500.1190 (found). $^1$H NMR (400 MHz, MeOD, a mixture of rotamers): 1.21 (s, 9H), 1.27 (s, 5H), 4.44 (ABd, 1H, J=16.4 Hz), 4.57 (ABd, 1H, J=15.2 Hz), 4.66 (ABd, 1H, J=16.4 Hz), 4.95 (ABd, 1H, J=15.6 Hz), 6.26 (s, 1H), 6.43-6.52 (m, 2H), 6.60-6.70 (m, 3H), 7.02-7.09 (m, 3H), 7.37 (m, 2H), 7.73 (d, 1H, J=8.8 Hz), 7.79 (d, 1H, J=8.8 Hz), 8.31 (s, 1H), 8.42 (s, 1H). $^{13}$C NMR (100 MHz, MeOD, a mixture of rotamers): 27.4, 27.5, 40.0, 44.0, 51.1, 51.2, 52.9, 57.0, 102.2, 102.5, 102.7, 110.0, 110.1, 110.4, 111.7, 111.8, 113.7, 119.7, 119.8, 120.9, 121.1, 121.7, 122.0, 124.6, 125.4, 129.1, 130.4, 130.6, 130.7, 136.2, 136.3, 159.1, 159.2, 163.2, 163.3, 165.2, 169.4, 169.7.

3-(2-(tert-butylamino)-1-(N-(2,3-difluorobenzyl)formamido)-2-oxoethyl)-6-chloro-1H-indole-2-carboxylic acid (7G)

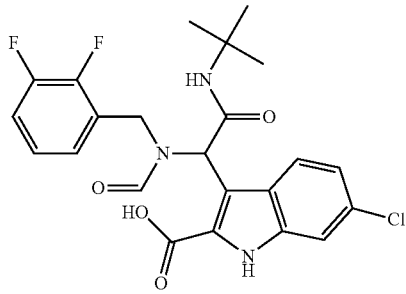 [SMILES: CC(C)(C)NC(=O)C(c1c(C(=O)O)[nH]c2cc(Cl)ccc12)N(C=O)Cc1cccc(F)c1F]

The final compound was obtained as a white solid (32 mg, 55%). HPLC/MS: $t_R$=12.13 min; m/z=477.4 [M+H]$^+$ HRMS: $C_{23}H_{23}ClF_2N_3O_4$, 478.1345 (calcd.), 478.1375 (found). $^1$H NMR (400 MHz, MeOD, a mixture of rotamers): 1.25 (s, 9H), 1.31 (s, 5H), 4.54 (ABd, 1H, J=16.8 Hz), 4.65 (ABd, 1H, J=15.6 Hz), 4.76 (ABd, 1H, J=16.8 Hz), 5.06 (ABd, 1H, J=15.6 Hz), 6.25-6.29 (m, 2H), 6.69-6.74 (m, 2H), 6.84-6.91 (m, 2H), 6.94-7.01 (m, 1H), 7.07-7.11 (m, 2H), 7.40 (m, 2H), 7.77 (d, 1H, J=8.8 Hz), 7.82 (d, 1H, J=8.8 Hz), 8.36 (s, 1H), 8.48 (s, 1H). $^{13}$C NMR (100 MHz, MeOD, a mixture of rotamers): 27.4, 27.5, 40.1, 44.1, 51.1, 51.3, 52.8, 57.0, 111.7, 111.8, 112.3, 114.0, 115.2, 115.4, 121.0, 121.2, 121.7, 121.9, 122.8, 123.0, 123.3, 123.4, 124.5, 125.4, 126.3, 126.4, 127.3, 127.4, 130.4, 130.5, 136.2, 136.3, 165.0, 165.2, 169.3, 169.6.

3-(2-(tert-butylamino)-1-(N-(2,5-difluorobenzyl)formamido)-2-oxoethyl)-6-chloro-1H-indole-2-carboxylic acid (7H)

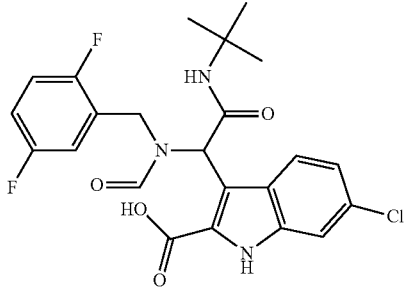 [SMILES: CC(C)(C)NC(=O)C(c1c(C(=O)O)[nH]c2cc(Cl)ccc12)N(C=O)Cc1cc(F)ccc1F]

The final compound was obtained as a yellowish solid (30 mg, 74%). HPLC/MS: $t_R$=11.73 min; m/z=477.8 [M+H]$^+$ HRMS: $C_{23}H_{23}ClF_2N_3O_4$, 478.1345 (calcd.), 478.1321 (found). $^1$H NMR (400 MHz, MeOD, a mixture of rotamers): 1.24 (s, 9H), 1.29 (s, 3H), 4.60-4.65 (m, 2H), 4.98 (ABd, 1H, J=16.0 Hz), 6.42-6.46 (m, 1H), 6.68 (s, 1H), 6.71 (m, 1H), 6.80-6.90 (m, 3H), 6.97-7.01 (m, 2H), 7.06 (s, 1H), 7.34-7.37 (m, 2H), 7.69 (d, 1H, J=8.8 Hz), 7.73 (d, 1H, J=8.4 Hz), 8.37 (s, 1H), 8.40 (s, 1H). $^{13}$C NMR (100 MHz, MeOD, a mixture of rotamers): 25.9, 26.0, 39.4, 49.4, 55.9, 108.0, 109.9, 112.65, 112.74, 113.0, 113.7, 113.96, 114.02, 114.3, 118.7, 119.6, 123.4, 127.2, 133.7, 163.9, 165.9, 168.5.

3-(2-(tert-butylamino)-1-(N-(3,5-difluorobenzyl)formamido)-2-oxoethyl)-6-chloro-1H-indole-2-carboxylic acid (7I)

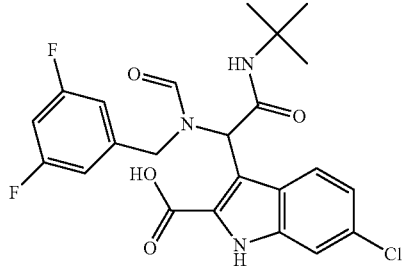 [SMILES: CC(C)(C)NC(=O)C(c1c(C(=O)O)[nH]c2cc(Cl)ccc12)N(C=O)Cc1cc(F)cc(F)c1]

The final compound was obtained as a yellowish solid (60 mg, 93%). HPLC/MS: $t_R$=11.93 min; m/z=477.5 [M+H]$^+$ HRMS: $C_{23}H_{23}ClF_2N_3O_4$, 478.1345 (calcd.), 478.1353 (found). $^1$H NMR (600 MHz, MeOD, a mixture of rotamers): 1.28 (s, 9H), 1.31 (s, 4H), 4.27 (ABd, 1H, J=15.6 Hz), 4.33 (ABd, 1H, J=16.8 Hz), 4.71 (ABd, 1H, J=16.8 Hz), 5.14 (ABd, 1H, J=15.6 Hz), 6.06 (m, 1H), 6.33 (s, 1H), 6.35 (m, 2H), 6.53-6.61 (m, 2H), 6.80 (s, 1H), 7.13-7.16 (m, 2H), 7.41 (m, 1H), 7.42 (m, 1H), 7.58 (s, 1H), 7.65 (s, 1H), 7.80 (d, 1H, J=9.0 Hz), 7.84 (d, 1H, J=8.4 Hz), 8.42 (s, 1H), 8.46 (s, 1H). $^{13}$C NMR (150 MHz, MeOD, a mixture of rotamers): 27.4, 27.5, 46.1, 48.1, 49.4, 51.3, 52.6, 56.9, 101.1, 101.3, 101.4, 101.5, 108.0, 108.1, 109.4, 109.5, 109.6, 111.8, 111.9, 112.3, 113.7, 121.1, 121.2, 121.6, 121.7, 124.7, 125.5, 128.3, 128.8, 130.4, 136.2, 141.6, 141.7, 161.5, 161.6, 162.2, 162.6, 163.2, 163.3, 164.7, 165.4, 169.7.

3-(2-(tert-butylamino)-1-(N-(2,6-difluorobenzyl)formamido)-2-oxoethyl)-6-chloro-1H-indole-2-carboxylic acid (7J)

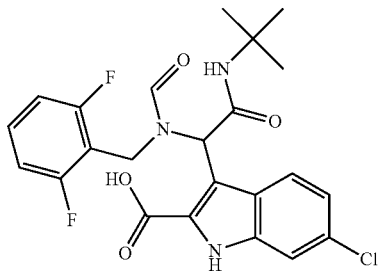 [SMILES: CC(C)(C)NC(=O)C(c1c(C(=O)O)[nH]c2cc(Cl)ccc12)N(C=O)Cc1c(F)cccc1F]

The final compound was obtained as a yellowish solid (30 mg, 64%). HPLC/MS: $t_R$=10.88 min; m/z=477.4 [M+H] HRMS: $C_{23}H_{22}ClF_2N_3O_4Na$, 500.1165 (calcd.), 500.1121 (found). $^1$H NMR (600 MHz, MeOD, a mixture of rotamers): 1.17 (s, 9H), 1.30 (s, 5H), 4.61 (ABd, 1H, J=16.2 Hz), 4.70 (ABd, 1H, J=15.6 Hz), 4.86-5.01 (m, 2H), 6.14 (s, 1H), 6.57 (m, 2H), 6.87-6.90 (m, 2H), 7.02-7.07 (m, 2H), 7.29-7.32 (m, 1H), 7.40-7.46 (m, 2H), 7.74-7.76 (m, 2H), 8.11 (s, 1H), 8.50 (s, 1H). $^{13}$C NMR (150 MHz, MeOD, a mixture of rotamers): 27.4, 27.5, 34.6, 39.3, 48.5, 51.0, 51.1, 51.2, 53.6, 56.6, 110.5, 110.6, 110.7, 110.8, 110.9, 111.0, 111.5, 111.7, 111.8, 120.7, 121.1, 121.8, 122.1, 124.8, 125.7, 129.1, 129.8, 129.9, 130.3, 130.4, 136.2, 136.4, 160.3, 160.4, 161.2, 162.0, 162.8, 162.9, 164.5, 165.4, 169.0, 169.6.

3-(2-(tert-butylamino)-2-oxo-1-(N-(2,3,4-trifluorobenzyl)formamido)ethyl)-6-chloro-1H-indole-2-carboxylic acid (7K)

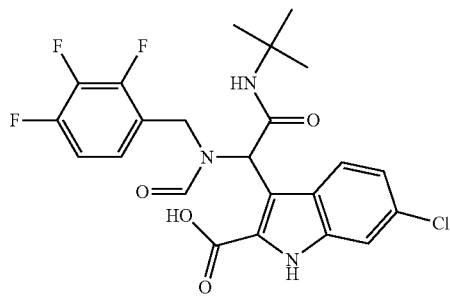 [SMILES: CC(C)(C)NC(=O)C(c1c(C(=O)O)[nH]c2cc(Cl)ccc12)N(C=O)Cc1ccc(F)c(F)c1F]

The final compound was obtained as a white solid (29 mg, 79%). HPLC/MS: $t_R$=12.39 min; m/z=495.6 [M+H]HRMS:

$C_{23}H_{21}ClF_3N_3O_4Na$, 518.1070 (calcd.), 518.1038 (found). $^1$H NMR (600 MHz, MeOD, a mixture of rotamers): 1.26 (s, 9H), 1.31 (s, 5H), 4.49 (ABd, 1H, J=16.2 Hz), 4.61 (ABd, 1H, J=15.0 Hz), 4.73 (ABd, 1H, J=16.8 Hz), 5.01 (ABd, 1H, J=15.6 Hz), 6.29 (s, 1H), 6.72 (s, 1H), 6.86-6.88 (m, 2H), 7.08-7.12 (m, 2H), 7.42 (m, 2H), 7.58 (s, 1H), 7.71 (s, 1H), 7.76 (d, 1H, J=8.4 Hz), 7.82 (d, 1H, J=9.0 Hz), 8.33 (s, 1H), 8.48 (s, 1H). $^{13}$C NMR (150 MHz, MeOD, a mixture of rotamers): 27.4, 27.5, 39.8, 43.9, 51.3, 52.0, 52.8, 57.0, 110.7, 110.8, 111.1, 111.2, 111.7, 111.8, 112.1, 113.6, 121.0, 121.2, 121.6, 121.8, 121.9, 123.6, 124.5, 125.4, 130.5, 136.1, 136.2, 165.0, 165.2, 169.4, 169.7.

3-(2-(tert-butylamino)-2-oxo-1-(N-(2,4,5-trifluorobenzyl)formamido)ethyl)-6-chloro-1H-indole-2-carboxylic acid (7L)

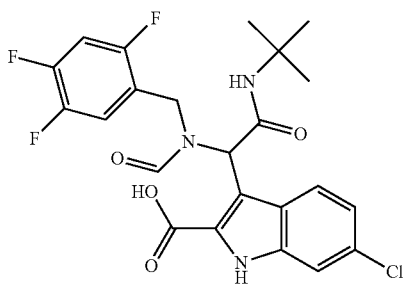 [SMILES: CC(C)(C)NC(=O)C(c1c(C(=O)O)[nH]c2cc(Cl)ccc12)N(C=O)Cc1cc(F)c(F)cc1F]

The final compound was obtained as a yellowish solid (36 mg, 93%). HPLC/MS: $t_R$=12.16 min; m/z=495.7 [M+H]$^+$ HRMS: $C_{23}H_{21}ClF_3N_3O_4Na$, 518.1070 (calcd.), 518.1069 (found). $^1$H NMR (400 MHz, MeOD, a mixture of rotamers): 1.27 (s, 9H), 1.31 (s, 5H), 4.48 (ABd, 1H, J=16.8 Hz), 4.57 (ABd, 1H, J=16.0 Hz), 4.68 (ABd, 1H, J=16.8 Hz), 4.97 (m, 1H), 6.30 (s, 1H), 6.40 (m, 1H), 6.69-6.74 (m, 1H), 6.79-6.96 (m, 2H), 7.07-7.12 (m, 2H), 7.41 (m, 2H), 7.77 (m, 1H), 7.82 (m, 1H), 8.38 (s, 1H), 8.45 (s, 1H). $^{13}$C NMR (100 MHz, MeOD, a mixture of rotamers): 27.4, 27.5, 39.7, 43.7, 51.2, 52.7, 57.0, 104.1, 104.3, 104.4, 104.6, 111.7, 111.8, 112.3, 113.8, 116.8, 117.0, 121.1, 121.2, 121.7, 121.9, 124.5, 125.3, 127.9, 128.5, 130.6, 136.2, 136.3, 162.1, 162.5, 165.0, 165.4, 169.4, 169.6.

3-(2-(tert-butylamino)-2-oxo-1-(N-(3,4,5-trifluorobenzyl)formamido)ethyl)-6-chloro-1H-indole-2-carboxylic acid (7M)

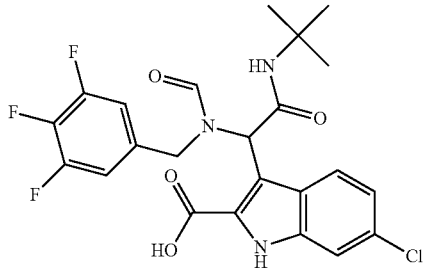 [SMILES: CC(C)(C)NC(=O)C(c1c(C(=O)O)[nH]c2cc(Cl)ccc12)N(C=O)Cc1cc(F)c(F)c(F)c1]

The final compound was obtained as a yellowish solid (65 mg, 95%). HPLC/MS: $t_R$=111.59 min; m/z=495.7 [M+H]$^+$ HRMS: $C_{23}H_{22}ClF_3N_3O_4$, 496.1251 (calcd.), 496.1249 (found). $^1$H NMR (600 MHz, MeOD, a mixture of rotamers): 1.17 (s, 9H), 1.19 (s, 4H), 4.10 (ABd, 1H, J=15.6 Hz), 4.16 (ABd, 1H, J=16.2 Hz), 4.56 (ABd, 1H, J=16.8 Hz), 4.97 (ABd, 1H, J=15.6 Hz), 6.07 (m, 1H), 6.19 (m, 1H), 6.32-6.35 (m, 2H), 6.65 (s, 1H), 7.02-7.04 (m, 2H), 7.30-7.32 (m, 2H), 7.50 (s, 1H), 7.55 (s, 1H), 7.67 (m, 1H), 7.69 (m, 1H), 8.28 (s, 1H), 8.33 (s, 1H). $^{13}$C NMR (150 MHz, MeOD, a mixture of rotamers): 28.85, 28.94, 47.1, 49.5, 50.5, 52.8, 53.4, 54.0, 58.3, 110.8, 110.9, 112.2, 112.3, 112.4, 113.2, 113.3, 113.8, 115.2, 122.6, 122.7, 123.0, 123.2, 126.1, 126.8, 131.9, 132.0, 135.9, 137.6, 137.7, 138.6, 140.2, 150.7, 152.3, 166.1, 166.8, 171.1.

3-(2-(tert-butylamino)-2-oxo-1-(N-(2,3,6-trifluorobenzyl)formamido)ethyl)-6-chloro-H-indole-2-carboxylic acid (7N)

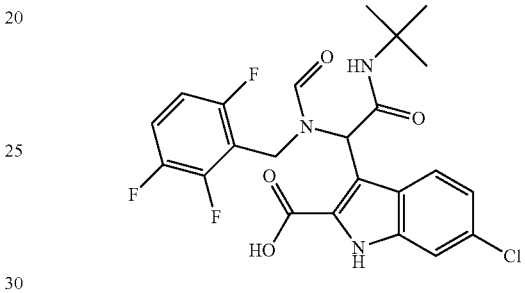

The final compound was obtained as a yellowish solid (15 mg, 79%). HPLC/MS: $t_R$=11.19 min; m/z=495.9 [M+H]$^+$ HRMS: $C_{23}H_{21}ClF_3N_3O_4Na$, 518.1070 (calcd.), 518.1078 (found). $^1$H NMR (600 MHz, MeOD, a mixture of rotamers): 1.20 (s, 9H), 1.31 (s, 7H), 4.63 (ABd, 1H, J=15.6 Hz), 4.76 (ABd, 1H, J=16.2 Hz), 4.93-5.02 (m, 2H), 6.15 (s, 1H), 6.57 (s, 1H), 6.86 (m, 1H), 6.96 (m, 1H), 7.04-7.08 (m, 2H), 7.17-7.20 (m, 2H), 7.41-7.45 (m, 2H), 7.74-7.80 (m, 2H), 8.12 (s, 1H), 8.52 (s, 1H). $^{13}$C NMR (150 MHz, MeOD, a mixture of rotamers): 27.4, 27.5, 34.8, 39.5, 51.2, 53.4, 56.7, 110.5, 111.5, 111.8, 113.4, 116.5, 120.8, 121.1, 121.7, 122.0, 124.7, 125.6, 130.4, 136.2, 136.4, 164.4, 165.3, 169.0, 169.6.

3-(2-(tert-butylamino)-2-oxo-1-(N-(2,4,6-trifluorobenzyl)formamido)ethyl)-6-chloro-1H-indole-2-carboxylic acid (7O)

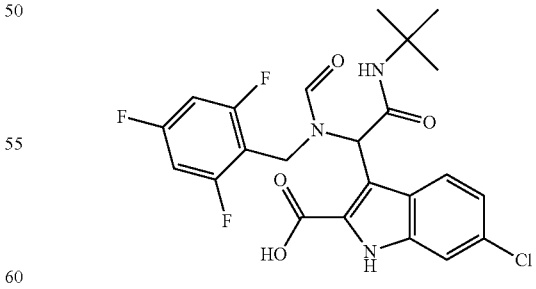

The final compound was obtained as a yellowish solid (42 mg, 74%). HPLC/MS: $t_R$=11.57 min; m/z=495.4 [M+H]$^+$ HRMS: $C_{23}H_{22}ClF_3N_3O_4$, 496.1251 (calcd.), 496.1260 (found). $^1$H NMR (400 MHz, MeOD, a mixture of rotamers): 1.20 (s, 9H), 1.30 (s, 5H), 4.55 (ABd, 1H, J=16.0 Hz), 4.68 (ABd, 1H, J=16.0 Hz), 4.83-4.93 (m, 2H), 6.09 (s, 1H), 6.44

(m, 1H), 6.55 (s, 1H), 6.75-6.79 (m, 2H), 7.03-7.08 (m, 2H), 7.42-7.47 (m, 2H), 7.74-7.78 (m, 2H), 8.08 (s, 1H), 8.49 (s, 1H). $^{13}$C NMR (100 MHz, MeOD, a mixture of rotamers): 27.4, 27.5, 34.2, 39.0, 51.0, 51.1, 53.5, 56.5, 99.4, 99.7, 99.9, 111.5, 111.8, 111.9, 113.4, 120.8, 121.1, 121.8, 122.1, 124.8, 125.6, 130.4, 130.5, 136.2, 136.5, 164.4, 168.9, 169.5.

3-(2-(tert-butylamino)-2-oxo-1-(N-(2,3,5-trifluorobenzyl)formamido)ethyl)-6-chloro-1H-indole-2-carboxylic acid (7P)

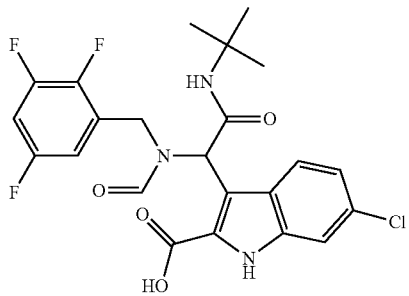 [SMILES: CC(C)(C)NC(=O)C(c1c(C(=O)O)[nH]c2cc(Cl)ccc12)N(C=O)Cc1cc(F)cc(F)c1F]

The final compound was obtained as a white solids (28 mg, 60%). HPLC/MS: $t_R$=11.96 min; m/z=495.4 [M+H]$^+$ HRMS: $C_{23}H_{21}ClF_3N_3O_4Na$, 518.1070 (calcd.), 518.0989 (found). $^1$H NMR (600 MHz, MeOD, a mixture of rotamers): 1.28 (s, 9H), 1.32 (s, 5H), 4.56 (ABd, 1H, J=15.6 Hz), 4.63 (ABd, 1H, J=16.2 Hz), 4.75 (ABd, 1H, J=16.8 Hz), 5.03 (ABd, 1H, J=15.6 Hz), 6.11 (m, 1H), 6.34 (s, 1H), 6.58 (m, 1H), 6.75-6.86 (m, 2H), 7.09 (m, 1H), 7.41 (s, 1H), 7.71 (s, 1H), 7.77 (d, 1H, J=9.0 Hz), 7.82 (d, 1H, J=9.0 Hz), 8.40 (s, 1H), 8.47 (s, 1H). $^{13}$C NMR (150 MHz, MeOD, a mixture of rotamers): 27.4, 27.5, 40.0, 43.9, 51.3, 52.7, 57.0, 103.1, 103.3, 103.5, 110.2, 110.4, 111.7, 111.8, 112.1, 113.6, 121.1, 121.2, 121.5, 121.8, 124.5, 125.3, 127.6, 127.7, 130.5, 136.1, 136.2, 165.0, 165.4, 169.5, 169.6.

3-(2-(tert-butylamino)-2-oxo-1-(N-(2,3,5,6-tetrafluorobenzyl)formamido)ethyl)-6-chloro-1H-indole-2-carboxylic acid (7Q)

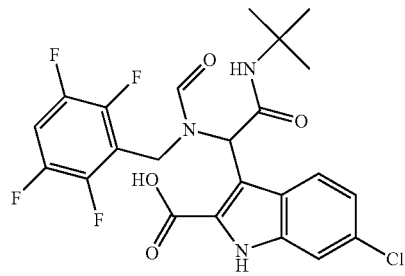 [SMILES: CC(C)(C)NC(=O)C(c1c(C(=O)O)[nH]c2cc(Cl)ccc12)N(C=O)Cc1c(F)c(F)cc(F)c1F]

The final compound was obtained as a white solid (22 mg, 93%). HPLC/MS: $t_R$=11.44 min; m/z=513.8 [M+H]$^+$ HRMS: $C_{23}H_{20}ClF_4N_3O_4Na$, 536.85898 (calcd.), 537.3983 (found). $^1$H NMR (400 MHz, MeOD, a mixture of rotamers): 1.20 (s, 9H), 1.28 (s, 5H), 4.65 (ABd, 1H, J=16.4 Hz), 4.78 (ABd, 1H, J=16.0 Hz), 4.92-5.02 (m, 2H), 6.15 (s, 1H), 6.55 (s, 1H), 7.01-7.06 (m, 2H), 7.20-7.29 (m, 2H), 7.39-7.43 (m, 2H), 7.51 (s, 1H), 7.70-7.73 (m, 2H), 7.79 (s, 1H), 8.11 (s, 1H), 8.50 (s, 1H). $^{13}$C NMR (100 MHz, MeOD, a mixture of rotamers): 27.4, 27.5, 34.8, 39.6, 51.1, 53.2, 56.9, 104.6, 105.1, 105.3, 105.6, 111.5, 111.7, 111.8, 113.1, 115.7, 121.0, 121.2, 121.6, 121.9, 124.7, 125.5, 130.4, 130.5, 136.1, 136.3, 164.5, 165.3, 168.9, 169.4.

3-(2-(tert-butylamino)-2-oxo-1-(N-(2,3,4,6-tetrafluorobenzyl)formamido)ethyl)-6-chloro-1H-indole-2-carboxylic acid (7R)

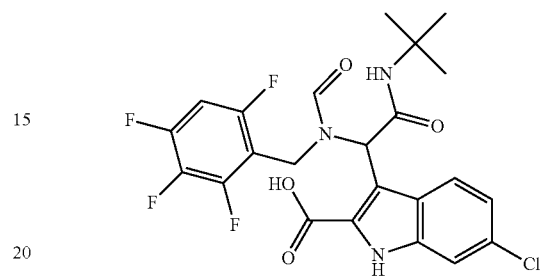

The final compound was obtained as a white solid (38 mg, 73%). HPLC/MS: $t_R$=11.93 min; m/z=513.6 [M+H]$^+$ HRMS: $C_{23}H_{20}ClF_4N_3O_4K$, 552.0716 (calcd.), 552.0752 (found). $^1$H NMR (400 MHz, MeOD, a mixture of rotamers): 1.22 (s, 9H), 1.30 (s, 5H), 4.58 (ABd, 1H, J=16.0 Hz), 4.73 (ABd, 1H, J=16.0 Hz), 4.91 (m, 2H), 6.08 (s, 1H), 6.55 (s, 1H), 6.61-6.68 (m, 1H), 6.93-7.00 (m, 1H), 7.04-7.09 (m, 2H), 7.43-7.47 (m, 2H), 7.74-7.77 (m, 2H), 7.82 (s, 1H), 8.09 (s, 1H), 8.51 (s, 1H). $^{13}$C NMR (100 MHz, MeOD, a mixture of rotamers): 27.4, 27.5, 31.3, 34.3, 39.2, 51.1, 51.2, 53.3, 56.5, 111.6, 111.8, 120.0, 113.5, 120.9, 121.2, 121.7, 122.0, 124.7, 125.5, 127.7, 130.55, 130.61, 136.2, 136.4, 164.4, 165.2, 168.86, 168.94, 169.4.

3-(2-(tert-butylamino)-2-oxo-1-(N-(2,3,4,5-tetrafluorobenzyl)formamido)ethyl)-6-chloro-1H-indole-2-carboxylic acid (7S)

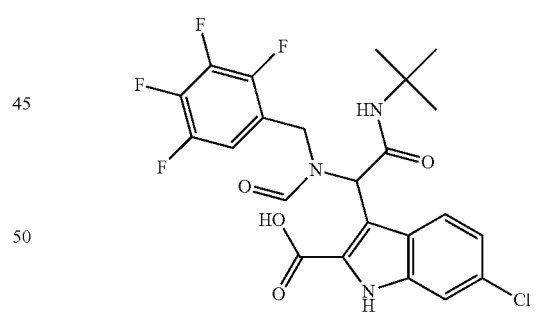

The final compound was obtained as a white solid (27 mg, 84%). HPLC/MS: $t_R$=11.36 min; m/z=441.8 [M+H]$^+$ HRMS: $C_{23}H_{20}ClF_4N_3O_4Na$, 536.85898 (calcd.), 537.3737 (found). $^1$H NMR (600 MHz, MeOD, a mixture of rotamers): 1.22 (s, 9H), 1.31 (s, 6H), 4.30-4.35 (m, 2H), 4.71 (ABd, 1H, J=16.2 Hz), 5.14 (ABd, 1H, J=15.0 Hz), 6.27 (s, 1H), 6.52 (m, 1H), 6.80 (s, 1H), 6.92-6.95 (m, 3H), 7.05-7.13 (m, 5H), 7.37-7.47 (m, 4H), 7.80 (d, 1H, J=9.0 Hz), 7.85 (d, 1H, J=9.0 Hz), 8.39 (s, 1H), 8.45 (s, 1H). $^{13}$C NMR (150 MHz, MeOD, a mixture of rotamers): 27.4, 27.5, 47.0, 51.1, 51.2, 52.0, 52.8, 56.9, 111.7, 111.8, 112.5, 114.0, 120.8, 121.0, 121.8, 122.0, 124.8, 125.3, 125.6, 126.5, 127.3, 130.2, 136.3, 136.8, 137.5, 162.6, 164.7, 165.3, 169.6, 169.9.

3-(2-(tert-butylamino)-2-oxo-1-(N-(perfluorobenzyl)formamido)ethyl)-6-chloro-1H-indole-2-carboxylic acid (7T)

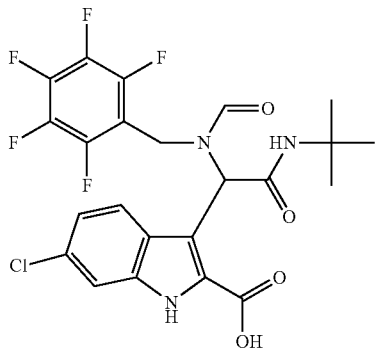 [SMILES: CC(C)(C)NC(=O)C(c1c(C(=O)O)[nH]c2cc(Cl)ccc12)N(C=O)Cc1c(F)c(F)c(F)c(F)c1F]

The final compound was obtained as a white solid (55 mg, 92%). HPLC/MS: $t_R$=12.18 min; m/z=531.7 [M+H]HRMS: $C_{23}H_{19}ClF_5N_3O_4K$, 570.0621 (calcd.), 570.0630 (found). $^1$H NMR (400 MHz, MeOD, a mixture of rotamers): 1.25 (s, 9H), 1.31 (s, 6H), 4.63 (ABd, 1H, J=16.0 Hz), 4.79 (ABd, 1H, J=16.0 Hz), 4.90-5.01 (m, 2H), 6.10 (s, 1H), 6.55 (s, 1H), 7.06-7.11 (m, 2H), 7.43-7.47 (m, 2H), 7.73-7.76 (m, 2H), 8.11 (s, 1H), 8.52 (s, 1H). $^{13}$C NMR (100 MHz, MeOD, a mixture of rotamers): 27.3, 27.5, 34.1, 39.3, 51.1, 51.2, 53.2, 56.5, 111.5, 111.8, 113.1, 121.0, 121.2, 121.6, 121.9, 124.7, 125.5, 130.5, 130.6, 136.1, 136.3, 164.4, 168.9.

(C) Synthesis of Formula II Compounds

Compounds according to Formula II were synthesized using the Ugi reaction. Briefly, 1 mmol aldehyde, isocyanide, and amino acid are added together in 10 mL methanol. The reaction mixture is allowed to sit overnight at room temperature. The methanol is evaporated under reduced pressure. The residue is dissolved in ethyl acetate, and washed 2 times each with saturated sodium bicarbonate and saturated sodium chloride and dried over sodium sulfate. The ethyl acetate is evaporated under reduced pressure, and the residue is purified via chromatography to afford the final product. NMR analysis was performed on a Bruker 600 MHz NMR. LC-MS analysis was performed on an SHIMADZU instrument, using an analytical C18 column (Dionex Acclaim 120 Å, 2.1×50 mm, 3.0 μm, 0.2 mL/min).

Ethyl 3-(2-(benzylamino)-1-(((S)-1-methoxy-3-methyl-1-oxobutan-2-yl)amino)-2-oxoethyl)-6-chloro-1H-indole-2-carboxylate (KK228)

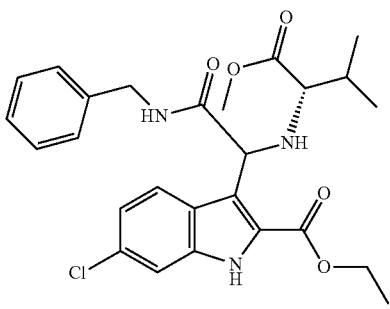 [SMILES: CCOC(=O)c1[nH]c2cc(Cl)ccc2c1C(N[C@H](C(=O)OC)C(C)C)C(=O)NCc1ccccc1]

The final product has Molecular Wt: 499.9 g/mol and was obtained in an overall yield of 24%. HPLC-MS r_t:12.35, m/z [M+H]$^+$:500.2, [M−H]$^+$:498.1.

$^1$H NMR (600 MHz, CDCl3) δ 9.091 (1H, s), 7.756-7.742 (1H, m), 7.291-7.236 (3H, m), 7.205-7.194 (3H, d), 7.050-7.036 (1H, d), 5.275 (1H, s), 4.527-4.417 (2H, m), 4.329-4.293 (2H, q), 3.655 (1H, s), 2.907-2.897 (1H, d), 1.911-1.877 (1H, m), 1.360-1.336 (3H, t) 1.276-1.244 (1H, m), 0.835-0.823 (3H, d), 0.742-0.730 (3H, d).

Ethyl 3-(2-(benzylamino)-1-(((R)-1-methoxy-4-methyl-1-oxopentan-2-yl)amino)-2-oxoethyl)-6-chloro-1H-indole-2-carboxylate (KK229)

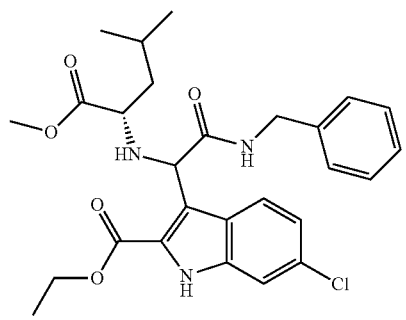 [SMILES: CCOC(=O)c1[nH]c2cc(Cl)ccc2c1C(N[C@@H](CC(C)C)C(=O)OC)C(=O)NCc1ccccc1]

The final product has a Molecular Wt=513.20 g/mol and was obtained in an overall yield of 20%. HPLC-MS r_t:12.48, m/z [M+H]$^+$:513.9, [M−H]$^+$:512.0

$^1$H NMR (600 MHz, CDCl3) δ 9.306 (1H, s), 7.637-7.622 (1H, d), 7.563 (1H, s), 7.376-7.305 (2H, m), 7.276-7.260 (2H, m), 7.130-7.128 (1H, d), 7.024-7.007 (1H, m), 5.281 (1H, s), 4.581-4.454 (2H, m), 4.361-4.254 (2H, m), 3.640 (1H, s), 3220-3.191 (1H, m), 1.629-1.374 (3H, m), 1.352-1.382 (3H, t), 0.762-0.751 (3H, d), 0.480-0.496 (3H, d).

$^{13}$C NMR (600 MHz, CDCl3) δ 175.51, 171.74, 161.37, 138.36, 136.14, 131.68, 128.81, 128.63, 128.11, 127.85, 127.69, 127.38, 125.14, 122.50, 121.63, 120.41, 118.74, 111.92, 61.34, 57.68, 56.38, 51.76, 43.49, 42.16, 24.61, 22.93, 21.25, 14.21.

2-((2-(benzylamino)-1-(6-chloro-2-(ethoxycarbonyl)-1H-indol-3-yl)-2-oxoethyl)amino)-4-methylpentanoic acid (KK272)

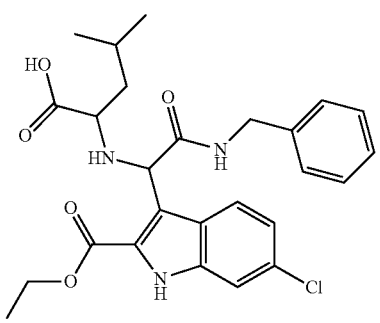 [SMILES: CCOC(=O)c1[nH]c2cc(Cl)ccc2c1C(NC(CC(C)C)C(=O)O)C(=O)NCc1ccccc1]

The final product has a Molecular Wt of 499.99 g/mol and was obtained in an overall yield of 30%. HPLC-MS r_t:17.04, m/z [M−H]:500.4, [M−H]$^+$:498.5.

¹H NMR (600 MHz, CDCl3) δ 9.6 (1H, s), 7.81 (1H, s), 7.57 (1H, d), 7.38-7.29 (6H, m), 7.28 (1H, s), 7.07 (1H, s), 7.04-7.01 (1H, d), 5.28 (1H, s), 476-4.62 (1H, m), 4.54-4.49 (1H, m), 3.78 (1H, s), 3.75 (3H, s), 3.66 (3H, s), 3.63 (1H, s) 3.25-2.23 (1H, s), 0.77-0.76 (3H, d), 0.50-0.49 (3H, d).

¹³C NMR (600 MHz, CDCl3) δ 175.48, 174.49, 172.57, 172.04, 161.67, 161.54, 138.60, 138.34, 136.28, 136.14, 131.87, 131.56, 124.97, 124.87, 122.16, 122.02, 121.67, 120.15, 112.18, 60.11, 58.08, 57.76, 57.40, 56.36, 54.58, 52.58, 52.11, 51.87, 51.50, 51.72, 43.51, 43.12, 43.03, 42.81, 42.09, 24.92, 24.71, 23.41, 22.91, 22.68, 22.55, 22.17, 21.26, 20.74.

Additionally, certain Formula II compounds were synthesized as follows. Briefly, 1 mmol aldehyde, isocyanide, amino acid, and amine are added together in 10 mL trifluoroethanol. The reaction mixture is allowed to sit overnight at room temperature. The trifluoroethanol is evaporated under reduced pressure. The residue is dissolved in ethyl acetate, and washed two (2) times each with saturated sodium bicarbonate and saturated sodium chloride and dried over sodium sulfate. The ethyl acetate is evaporated under reduced pressure, and the residue is purified via chromatography to afford the final product.

Ethyl 3-(2-(benzylamino)-1-(((S)-4-methyl-1-((2-morpholinoethyl)amino)-1-oxopentan-2-yl)amino)-2-oxoethyl)-6-chloro-1H-indole-2-carboxylate (KK242)

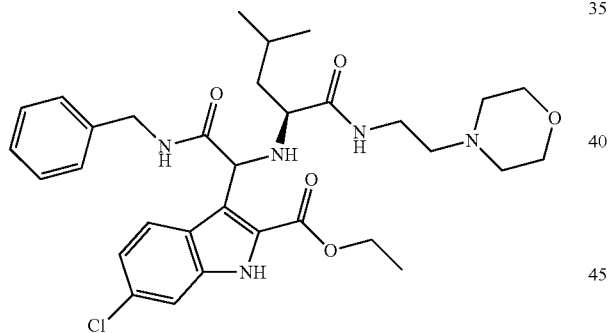

The final product has a Molecular Wt of 611.29 g/mol and was obtained in an overall yield of 35%. HPLC-MS r_t:14.01, m/z [M−H]⁺:612.0, [M−H]⁺:610.0.

¹H NMR (600 MHz, CDCl3) δ 10.31 (1H, s), 8.94 (1H, s), 7.72-7.71 (1H, d), 7.52 (1H, s), 7.28 (1H, s), 7.21 (1H, s), 7.19-7.18 (1H, d), 7.03-7.01 (2H, m), 6.88 (1H, s), 6.14 (1H, s) 4.44-4.32 (3H, m), 4.29-4.25 (1H, m), 4.10-4.07 (1H, t), 3.94-3.85 (2H, m), 3.78-3.70 (3H, m), 3.63 (1H, s), 3.38-3.33 (2H, t), 3.08 (1H, m), 2.96-2.95 (1H, m), 2.86-2.85 (2H, m), 1.88-1.86 (1H, m), 1.76-1.74 (1H, m), 1.62-1.60 (1H, m), 1.40-1.37 (3H, t), 0.91-0.90 (3H, d), 0.82-0.81 (3H, d).

¹³C NMR (600 MHz, CDCl3) δ 166.59, 161.70, 136.54, 136.15, 132.97, 128.69, 127.79, 127.06, 126.71, 123.50, 120.60, 112.95, 110.32, 69.45, 63.49, 62.87, 58.94, 57.39, 55.69, 53.06, 52.43, 44.15, 39.60, 33.88, 24.58, 21.91, 21.73, 13.80.

Ethyl 3-(2-(benzylamino)-1-(((R)-1-((cyclopropylmethyl)amino)-4-methyl-1-oxopentan-2-yl)amino)-2-oxoethyl)-6-chloro-1H-indole-2-carboxylate (KK257)

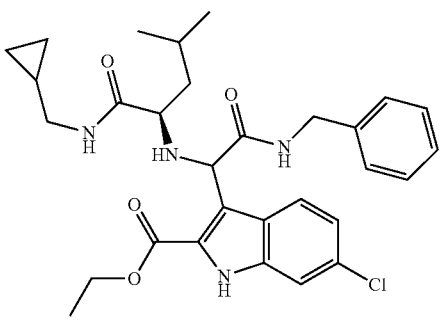 [SMILES: CCOC(=O)c1[nH]c2cc(Cl)ccc2c1C(N[C@H](CC(C)C)C(=O)NCC1CC1)C(=O)NCc1ccccc1]

The final product has a Molecular Wt of 568.25 g/mol and was obtained in an overall yield of 20%. HPLC-MS r_t:16.06, m/z [M−H]⁺:569.4, [M−H]⁺:567.6.

¹H NMR (600 MHz, CDCl3) δ 11.23 (1H, s), 7.62 (1H, s), 7.45-7.44 (1H, d), 7.28 (1H, s), 7.25-7.24 (1H, m), 7.21-7.19 (1H, m), 7.11-7.10 (2H, m), 6.90-6.88 (1H, t), 5.93 (1H, s), 4.48-4.45 (1H, m) 4.32-4.27 (2H, m), 4.23-4.21 (1H, m), 3.49-3.43 (3H, m), 3.07-3.01 (2H, m), 2.76-2.74 (1H, m) 1.93-1.88 (1H, m), 1.49-1.45 (1H, m), 0.95-0.94 (3H, d), 0.81-0.80 (3H, d).

¹³C NMR (600 MHz, CDCl3) δ 166.19, 165.84, 162.44, 160.45, 160.19, 136.51, 136.26, 133.45, 128.81, 128.66, 127.93, 127.84, 127.31, 124.77, 124.03, 119.29, 113.70, 107.80, 66.16, 65.49, 63.35, 55.48, 54, 88, 45.35, 44.44, 42.81, 39.32, 24.20, 22.92, 21.31, 13.69.

Ethyl 3-(2-(benzylamino)-1-(((S)-1-((2-hydroxyethyl)amino)-4-methyl-1-oxopentan-2-yl)amino)-2-oxoethyl)-6-chloro-1H-indole-2-carboxylate (KK259)

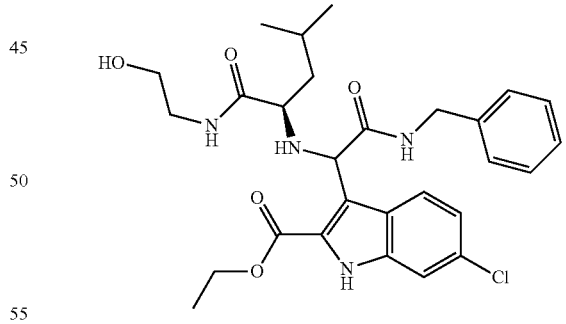

The final product has a Molecular Wt of 542.23 g/mol and was obtained in an overall yield of 15%. HPLC-MS r.t:15.19, m/z [M−H]⁺:543.1, [M−H]⁺:541.2.

¹H NMR (600 MHz, CDCl3) δ 10.57 (1H, s), 8.07 (1H, t), 7.57 (1H, s), 7.49-7.48 (1H, d), 7.27-7.23 (3H, m), 7.08-7.06 (2H, m), 6.22-6.20 (1H, m), 5.68 (1H, s), 4.52-4.49 (1H, m), 4.44-4.36 (4H, m), 4.31-4.27 (1H, m), 4.20-4.16 (1H, q), 4.11-4.09 (1H, t), 3.70-3.66 (1H, m), 3.50-3.46 (1H, m), 1.83-1.71 (2H, m), 1.83-1.71 (2H, m), 1.61-1.56 (1H, m), 1.42-1.39 (3H, t), 1.31-1.27 (1H, t), 0.88-0.87 (3H, d), 0.78-0.77 (3H, d).

$^{13}$C NMR (600 MHz, CDCl3) δ 168.67, 165.87, 162.75, 160.21, 159.94, 136.42, 135.82, 134.16, 128.85, 128.22, 127.55, 125.83, 125.01, 124.39, 118.94, 115.80, 113.56, 108.56, 65.68, 63.74, 58.10, 55.33, 44.55, 39.84, 38.57, 24.47, 21.96, 21.54, 14.02, 13.69.

3-(2-(benzylamino)-1-((1-((2-hydroxyethyl)amino)-4-methyl-1-oxopentan-2-yl)amino)-2-oxoethyl)-6-chloro-1H-indole-2-carboxylic acid (KK278)

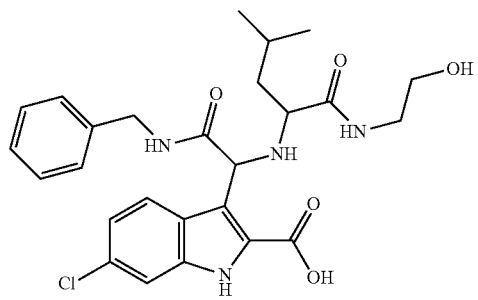 [SMILES: CC(C)CC(NC(C(=O)NCc1ccccc1)c1c(C(=O)O)[nH]c2cc(Cl)ccc12)C(=O)NCCO]

The final product has a Molecular Wt of 514.20 g/mol and was obtained in an overall yield of 92%. HPLC-MS rt:15.81, m/z [M−H]$^+$:515.4, [M−H]$^+$:513.3.

Ethyl 3-(2-(benzylamino)-1-(((S)-4-methyl-1-((3-morpholinopropyl)amino)-1-oxopentan-2-yl)amino)-2-oxoethyl)-6-chloro-1H-indole-2-carboxylate (KK261)

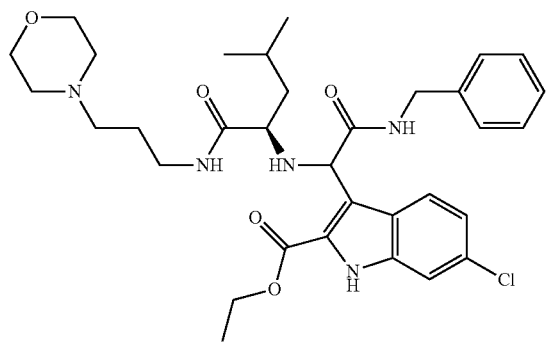 [SMILES: CCOC(=O)c1[nH]c2cc(Cl)ccc2c1C(N[C@H](CC(C)C)C(=O)NCCCN1CCOCC1)C(=O)NCc1ccccc1]

The final product has a Molecular Wt of 625.30 g/mol and was obtained in an overall yield of 25%. HPLC-MS r_t:14.99, m/z [M−H]$^+$:626.3, [M−H]$^+$:624.7

$^1$H NMR (600 MHz, CDCl3) δ 9.85 (1H, s), 8.13-8.12 (1H, m), 7.56-7.54 (3H, m), 7.28-7.27 (1H, m), 7.24 (1H, s), 7.22 (1H, s), 7.21 (1H, s), 7.05 (2H, m), 6.73-6.71 (1H, t), 5.87 (1H, s) 4.48-4.45 (1H, m), 4.27-4.24 (1H, m), 4.12-4.06 (3H, m), 4.03-4.00 (2H, m), 3.89-3.82 (4H, m), 3.59-3.56 (1H, m), 3.52-350 (1H, d), 3.46-3.42 (1H, d), 3.32-3.23 (4H, m), 3.15-3.13 (1H, m), 1.94-1.92 (2H, t), 1.87-1.86 (2H, m), 1.69-1.67 (1H, m), 1.58 (2H, s), 1.41-1.36 (3H, m), 0.89-0.88 (3H, d), 0.74-0.73 (3H, d)

$^{13}$C NMR (600 MHz, CDCl3) δ 166.13, 162.21, 160.88, 160.61, 160.34, 160.07, 136.19, 136.07, 133.74, 128.9, 128.78, 128.71 128.01, 127.53, 127.45, 126.19, 124.11, 119.64, 117.82, 115.92, 114.02, 113.19, 112.13, 109.12, 63.82, 63.76, 63.70, 63.45, 58.53, 55.57, 54.94, 52.53, 52.20, 44.47, 39.86, 36.73, 27.56, 24.47, 22.84, 22.10, 21.03, 13.69.

3-(2-(benzylamino)-1-((4-methyl-1-((3-morpholinopropyl)amino)-1-oxopentan-2-yl)amino)-2-oxoethyl)-6-chloro-1H-indole-2-carboxylic acid (KK2791)

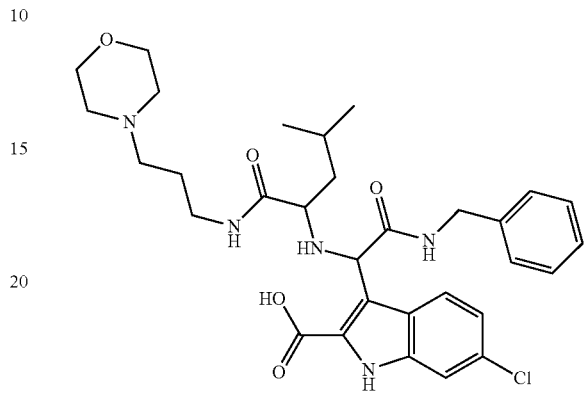

The final product has a Molecular Wt of 597.27 g/mol and was obtained in an overall yield of 91%. HPLC-MS rt:15.44, m/z [M−H]$^+$:598.2, [M−H]$^+$:596.6.

(D) Synthesis of Formula II Compounds Having Hydroxamic Acid (N(H)(OH)—C(O)—) Functionality To 1 equivalent of ester add 10 equivalents of H$_2$NOH.HCl, 10 equivalents of NaOH, and 3 equivalents of Et$_3$N After standing overnight the desired product precipitated out.

3-(2-(benzylamino)-1-((1-(hydroxyamino)-4-methyl-1-oxopentan-2-yl)amino)-2-oxoethyl)-6-chloro-N-hydroxy-1H-indole-2-carboxamide (KK271)

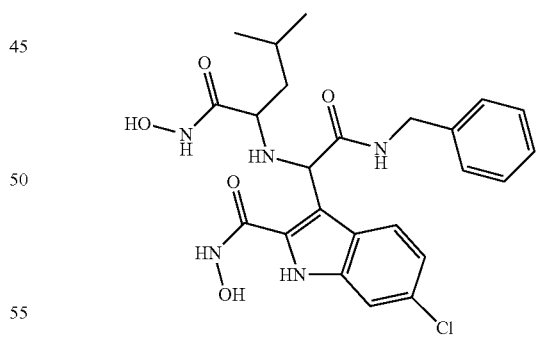

The final product has a Molecular Wt of 501.18 g/mol and was obtained in an overall yield of 95%. HPLC-MS r_t:17.29, m/z [M−H]$^+$:502.3, [M−H]$^+$:500.34.

$^1$H NMR (600 MHz, MeOD) δ 7.81-7.73 (2H, m), 7.51 (1H, s), 7.46-7.45 (2H, s), 7.34-7.31 (2H, s), 7.01-6.98 (2H, m), 5.32 (1H, s), 4.46-4.43 (1H, d) 4.37-4.35 (3H, m), 4.33-4.28 (2H, m), 4.13-4.09 (2H, m), 3.69-3.68 (1H, d), 3.09-3.07 (1H, t), 2.02 (2H, s), 0.98-0.96 (4H, m), 0.93-0.90 (2H, m), 0.85-0.84 (3H, d), 0.67-0.66 (2H, d), 0.57-0.56 (1H, d), 0.54-0.53 (3H, d).

$^{13}$C NMR (600 MHz, MeOD) δ 167.53, 167.44, 140.21, 138.49, 138.45, 138.37, 128.02, 136.14, 135.56, 133.29, 133.16, 129.91, 129.03, 128.95, 128.79, 128.73, 128.55, 128.21, 128.01, 127.96, 127.38, 127.06, 126.82, 126.76, 126.68, 126.55, 126.51, 126.04, 121.96, 121.56, 120.99, 120.69, 119.84, 119.69, 111.60, 111.27, 60.14, 58.62, 57.58, 56.69, 56.19, 55.90, 55.72, 54.72, 54.49, 52.00, 51.04, 42.96, 42.90, 42.73, 42.59, 42.52, 42.48, 42.07, 41.90, 41.10, 24.39, 24.29, 24.16, 22.05, 21.97, 21.76, 21.64, 20.90, 20.68, 20.61, 20.57, 19.47, 13.07, 7.77, 7.01, 6.49.

3-(2-(benzylamino)-1-(4-methyl-1-(2-morpholinoethylamino)-1-oxopentan-2-ylamino)-2-oxoethyl)-6-chloro-1H-indole-2-carboxylic acid (KK273)

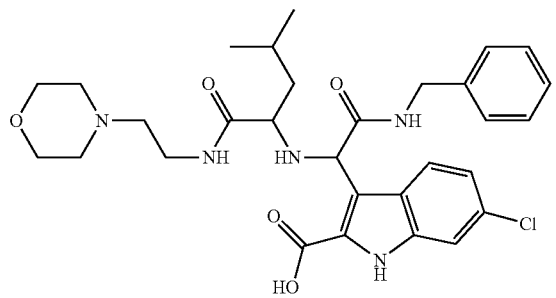 [SMILES: CC(C)CC(NC(C(=O)NCc1ccccc1)c1c(C(=O)O)[nH]c2cc(Cl)ccc12)C(=O)NCCN1CCOCC1]

The final product has a Molecular Wt of 583.26 g/mol and was obtained in an overall yield of 91%. HPLC-MS r_t:15.81, m/z [M–H]$^+$:584.6, [M–H]$^+$:582.6

Resolution Of Enantiomers Using Supercritical Fluid Chromatography (SFC)

Inventive compounds according to Formulae I or II that contain a chiral center can be resolved using chiral supercritical fluid column chromatography (SFC). For instance, the two enantiomers of compound 8l were obtained in 20 milligram (mg) amounts using SFC. Experiments were performed using the analytical SFC-MS Resolution System (Waters 2998 Photodiode Array Detector, Waters 3100 Mass Detector), and the preparative TharSFC System (Waters 2998 Photodiode Array Detector). Both analytical and preparative SFC columns were operating at 40° C. in Analytical-2-Prep Column Oven. Carbon dioxide supplied by BDS 500 Gas Delivery System was used as the primary mobile phase for SFC.

The enantiomers of 8l were separated by preparative SFC. Enantiomer 1 had a retention time of 1.55 minutes ($t_R$=1.55 min), while the second enantiomer eluted at 2.07 minutes ($t_R$=2.07 min). Preparative SFC was performed using Regis-Cell (#784106, OD), column that has 5 µM particles, and an internal diameter (i.d), of 250 mm×21.1 mm. The flow rate was 100 ml/minute and an isocratic elution was performed using 20% ethanol. The injection volume was maintained at 500l. The concentration of stock solution was 100 mg/mL. Representative chromatographic traces for the separation of enantiomers of compound 8l using (A) analytical and (B) preparative SFC is shown in FIG. 3.

The enantiomers of 91 were obtained after hydrolysis of the corresponding enantiomers of 81 (Method D). The optical rotations and binding affinities with Mdm2 (FP assay) for each enantiomer of 81 and 91 are shown in Table 7. Optical rotations were measured using Perkin Elmer 241 Polarimeter at 20° C. in a 10 cm cell in methanol.

TABLE 7

| | enantiomer 1 | enantiomer 2 |
|---|---|---|
| 81 | [α]$_D$ = +144.0° (c = 0.4)<br>$K_i$ = 2 µM (Mdm2) | [α]$_D$ = –140.6° (c = 0.3)<br>Ki = 5 µM (Mdm2) |
| 91 | [α]$_D$ = +50.6° (c = 1.1)<br>Ki = 0.3 µM (Mdm2) | [α]$_D$ = –51.1° (c = 0.3)<br>Ki = 0.7 µM (Mdm2) |

The binding constants ($K_i$ values), of representative Formula II compounds was determined using fluorescence polarization or NMR spectroscopy and are illustrated in Table 8.

TABLE 8

| Name | Molecular Weight (g/mol) | $K_i$ (µM) |
|---|---|---|
| KK228 | 499.99 | <<1 |
| KK229 | 513.20 | 1.7* |
| KK242 | 611.29 | 10 |
| KK257 | 568.25 | 8 |
| KK259 | 542.23 | 9 |
| KK261 | 625.30 | 11 |
| KK271 | 501.18 | 0.9 |
| KK272 | 499.99 | 1.4 |
| KK273 | 583.26 | 0.4* |
| KK276 | 540.21 | 2 |
| KK277 | 524.22 | 10 |
| KK278 | 514.20 | 9 |
| KK279 | 597.27 | 7 |

*Measured by NMR (AIDA), all other measured by FP

Pharmaceutical Compositions and Dosage

The invention further comprehends a pharmaceutical composition that comprises, with a pharmaceutically acceptable carrier, a Formula I or Formula II compound, its stereoisomers, tautomers, an ester, or a pharmaceutically acceptable salt, thereof. The inventive pharmaceutical composition, which can be in a single-unit dosage form, may contain one or more additional therapeutic agents, such as a Mdm2-p53 complex antagonist.

Any conventional carrier material can be utilized in this regard. The carrier material can be an organic or inorganic inert carrier material, for example one that is suitable for oral administration. Suitable carriers include water, gelatin, gum arabic, lactose, starch, magnesium stearate, talc, vegetable oils, polyalkylene-glycols, petroleum jelly and the like. Furthermore, the pharmaceutical preparations may also contain other pharmaceutically active agents. Additional additives such as flavoring agents, preservatives, stabilizers, emulsifying agents, buffers and the like may be added in accordance with accepted practices of pharmaceutical compounding.

Pharmaceutical preparations of the invention can be made up in any conventional form including a solid form for oral administration such as tablets, capsules, pills, powders, granules, and the like. The pharmaceutical preparations may be sterilized and/or may contain adjuvants such as preservatives, stabilizers, wetting agents, emulsifiers, salts for varying the osmotic pressure and/or buffers.

The compounds of the invention can also be administered to a patient in accordance with the invention by topical (including transdermal, buccal or sublingual), or parenteral (including intraperitoneal, subcutaneous, intravenous, intradermal or intramuscular injection) routes. In one embodiment, the compounds are administered orally. An oral dosage form comprises tablets, capsules of hard or soft gelatin methylcellulose or of another suitable material easily dissolved in the digestive tract. The oral dosages contemplated in accordance with the present invention will vary in accordance with the needs of the individual patient as determined by the prescribing physician.

For parenteral application, particularly suitable are solutions, preferably oily or aqueous solutions as well as suspensions, emulsions, or implants, including suppositories. Therapeutic compounds will be formulated in sterile form in multiple or single dose formats such as being dispersed in a fluid carrier such as sterile physiological saline or 5% saline dextrose solutions commonly used with injectables.

The actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests. The dosage for treatment typically depends on the route of administration, the age, and weight of the patient.

What is claimed is:

1. A compound according to Formula I,

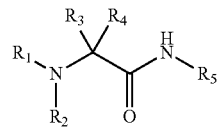

wherein $R_1$ and $R_2$ are each independently selected from the group consisting of hydrogen, straight or branched chain ($C_1$-$C_6$)alkyl, ($C_3$-$C_{14}$)aryl, formyl, acetyl, benzyl, ($C_3$-$C_{14}$)aryl($C_1$-$C_6$)alkylene-, —C(O)—($C_1$-$C_6$)alkyl, ($C_3$-$C_{14}$)heteroaryl-($C_1$-$C_6$)alkylene-, and ($C_3$-$C_{14}$)heterocycloalkyl-($C_1$-$C_6$)alkylene-;

$R_3$ is a

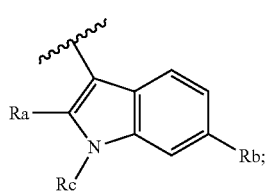

$R_a$ is selected from the group consisting of hydrogen, —C(O)R', and —C(O)OR';

$R_b$ is Cl, Br, or F;

$R_c$ is H or —C(O)OR$^d$, wherein R$^d$ is hydrogen or straight or branched chain ($C_1$-$C_6$)alkyl;

$R_4$ is hydrogen;

$R_5$ is selected from the group consisting of straight or branched chain ($C_1$-$C_6$)alkyl, ($C_3$-$C_{14}$)aryl, benzyl, ($C_3$-$C_{14}$)aryl($C_1$-$C_6$)alkylene-, ($C_3$-$C_{14}$)cycloalkyl, and ($C_3$-$C_{14}$)heteroaryl-($C_1$-$C_6$)alkylene-;

wherein any alkyl, benzyl, aryl, ($C_3$-$C_{14}$)aryl($C_1$-$C_6$)alkylene-, heteroaryl, cycloalkyl, ($C_3$-$C_{14}$)heteroaryl-($C_1$-$C_6$)alkylene-, or heterocycloalkyl is optionally substituted with one or more members selected from the group consisting of —OH, —Cl, —F, —Br, —I, -oxy($C_3$-$C_{14}$)aryl, ($C_1$-$C_6$)alkyl, ($C_3$-$C_{14}$)aryl, ($C_3$-$C_{14}$)heteroaryl, ($C_3$-$C_{14}$)aryl($C_1$-$C_6$)alkylene-, ($C_3$-$C_{14}$)heterocycloalkyl-($C_1$-$C_6$)alkylene-, —C(O)R', —C(O)OR', and oxo;

R' is selected from the group consisting of hydrogen, straight or branched chain ($C_1$-$C_6$)alkyl, —NH—(OH), —NH—($C_1$-$C_6$)alkylene-($C_3$-$C_{14}$)heteroaryl, —($C_3$-$C_{14}$)heterocycloalkylene-N(R")(R'''), —NH—($C_1$-$C_6$)alkylene-OR$^e$, —NH—($C_1$-$C_6$)alkylene-N(R")(R''') and —($C_1$-$C_6$)alkylene-OH;

R" and R''' are each independently selected from the group consisting of hydrogen, straight or branched chain ($C_1$-$C_6$)alkyl, and —($C_1$-$C_6$)alkylene-OH, —($C_1$-$C_6$)alkylene-N(R$^f$)(R$^g$), or R" and R''' together with the nitrogen atom to which they are bonded form a an aryl ring, a saturated or unsaturated ($C_3$-$C_{14}$) cyclic structure that optionally has 1-3 heteroatoms selected from —N, —S, or —O; and R$^e$, R$^f$, and R$^g$, are each independently hydrogen or straight or branched chain ($C_1$-$C_6$)alkyl, or a pharmaceutically acceptable salt, ester, stereoisomer, or tautomer thereof.

2. The compound according to claim 1, wherein R$^b$ is chlorine, R$^a$ is hydrogen, —C(O)R', or —C(O)OR', and R$^c$ is hydrogen.

3. The compound according to claim 2, wherein R$^a$ is —C(O)OR'.

4. The compound according to claim 3, wherein R' is hydrogen or ethyl.

5. The compound according to claim 2, wherein R$^a$ is —C(O)R'.

6. The compound according to claim 5, wherein R' is —NH—($C_1$-$C_6$)alkylene-($C_3$-$C_{14}$)heteroaryl.

7. The compound according to claim 6, wherein R' is

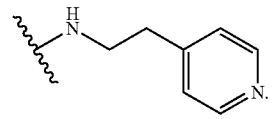 [SMILES: *NCCc1ccncc1]

8. The compound according to claim 5, wherein R' is —($C_3$-$C_{14}$)heterocycloalkylene-N(R")(R''').

9. The compound according to claim 8, wherein R' is

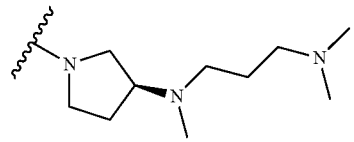

10. The compound according to claim 1, wherein $R_1$ and $R_2$ are each independently selected from the group consisting of straight or branched chain ($C_1$-$C_6$)alkyl, ($C_3$-$C_{14}$)aryl, formyl, acetyl, benzyl, ($C_3$-$C_{14}$)aryl($C_1$-$C_6$)alkylene-, —C(O)—($C_1$-$C_6$)alkyl, ($C_3$-$C_{14}$)heteroaryl-($C_1$-$C_6$)alkylene-, and ($C_3$-$C_{14}$)heterocycloalkyl-($C_1$-$C_6$)alkylene-.

11. The compound according to claim 1, wherein $R_5$ is benzyl.

12. A compound according to a structure selected from the following table:

| 111 | 112 |
|---|---|
| 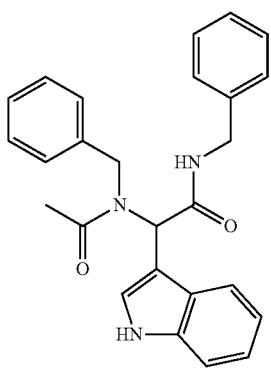 [SMILES: CC(=O)N(Cc1ccccc1)C(C(=O)NCc1ccccc1)c1c[nH]c2ccccc12] | -continued<br/>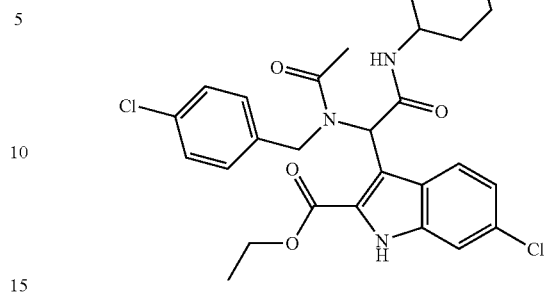 |
| 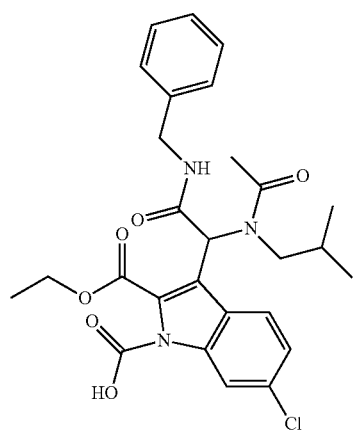 [SMILES: CCOC(=O)c1c(C(C(=O)NCc2ccccc2)N(CC(C)C)C(C)=O)c2ccc(Cl)cc2n1C(=O)O] | 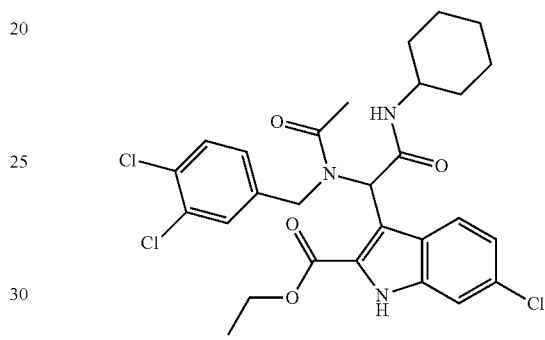 |
| 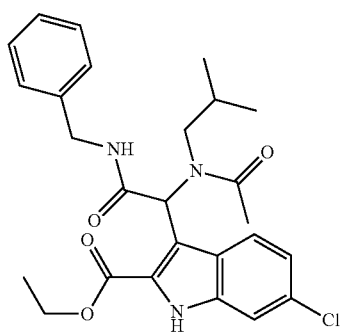 [SMILES: CCOC(=O)c1[nH]c2cc(Cl)ccc2c1C(C(=O)NCc1ccccc1)N(CC(C)C)C(C)=O] | 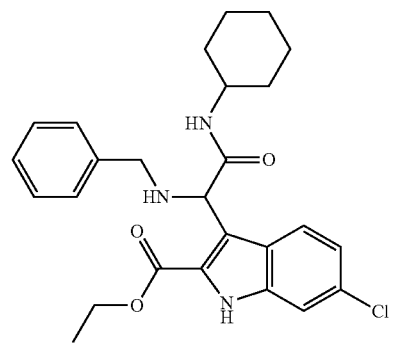 |
| 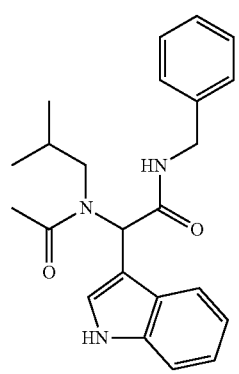 [SMILES: CC(=O)N(CC(C)C)C(C(=O)NCc1ccccc1)c1c[nH]c2ccccc12] | 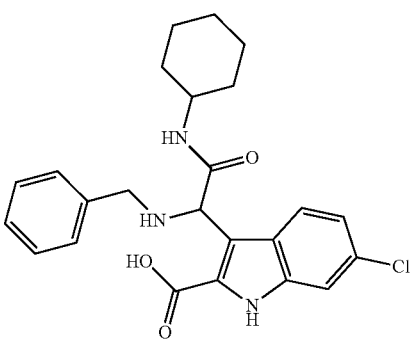 [SMILES: O=C(O)c1[nH]c2cc(Cl)ccc2c1C(NCc1ccccc1)C(=O)NC1CCCCC1] |

113
-continued
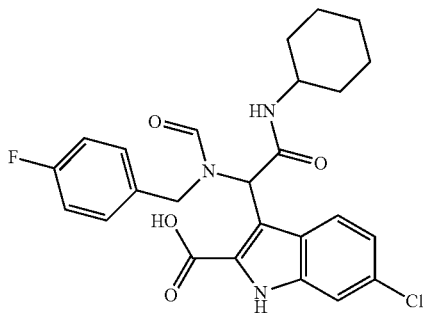 [SMILES: O=CN(Cc1ccc(F)cc1)C(C(=O)NC1CCCCC1)c1c(C(=O)O)[nH]c2cc(Cl)ccc12]
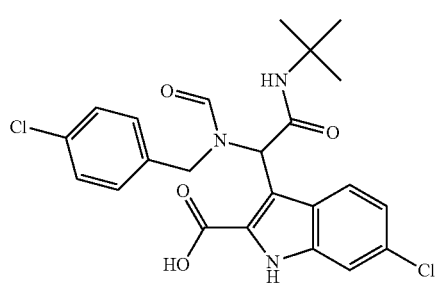 [SMILES: CC(C)(C)NC(=O)C(c1c(C(=O)O)[nH]c2cc(Cl)ccc12)N(C=O)Cc1ccc(Cl)cc1]
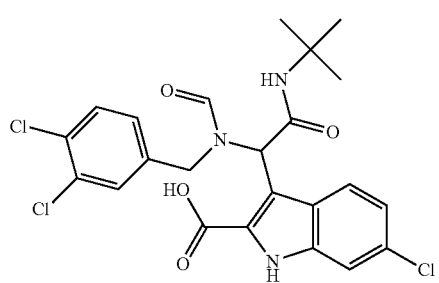 [SMILES: CC(C)(C)NC(=O)C(c1c(C(=O)O)[nH]c2cc(Cl)ccc12)N(C=O)Cc1ccc(Cl)c(Cl)c1]
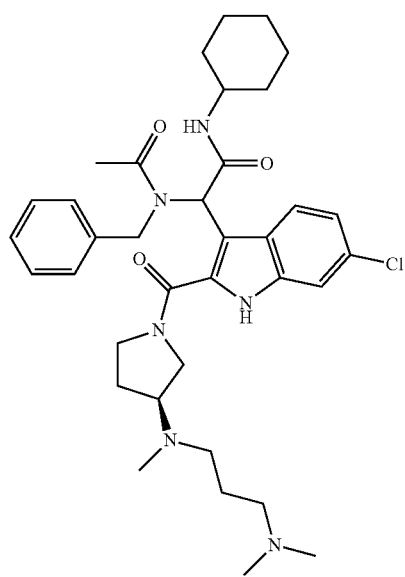 [SMILES: CC(=O)N(Cc1ccccc1)C(C(=O)NC1CCCCC1)c1c(C(=O)N2CC[C@H](N(C)CCCN(C)C)C2)[nH]c2cc(Cl)ccc12]
114
-continued
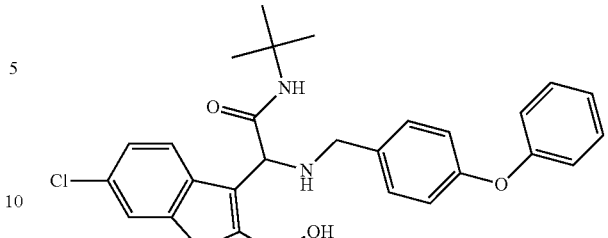
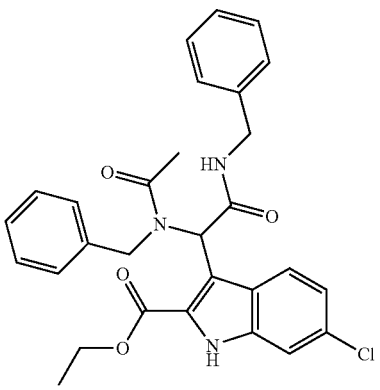 [SMILES: CCOC(=O)c1[nH]c2cc(Cl)ccc2c1C(C(=O)NCc1ccccc1)N(Cc1ccccc1)C(C)=O]
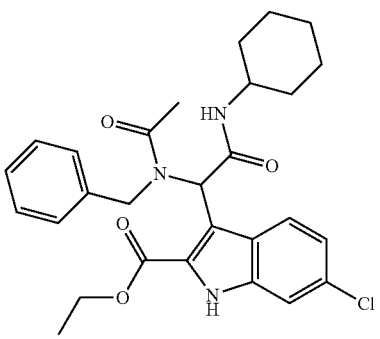 [SMILES: CCOC(=O)c1[nH]c2cc(Cl)ccc2c1C(C(=O)NC1CCCCC1)N(Cc1ccccc1)C(C)=O]
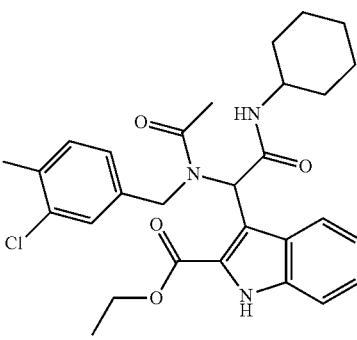

| 115 -continued | 116 -continued |
|---|---|
| 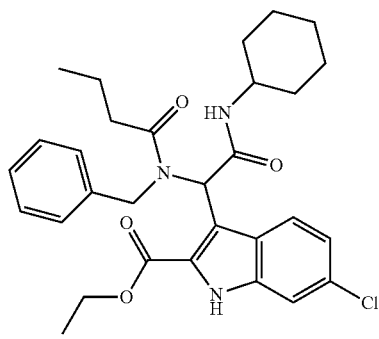 [SMILES: CCCC(=O)N(Cc1ccccc1)C(C(=O)NC1CCCCC1)c1c(C(=O)OCC)[nH]c2cc(Cl)ccc12] | 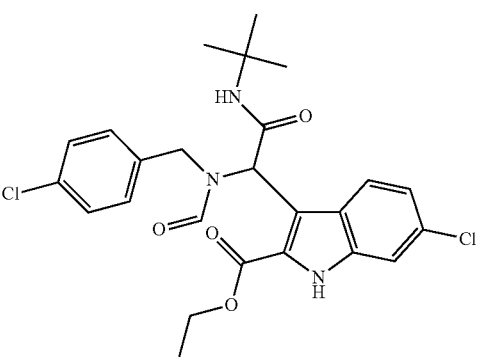 |
| 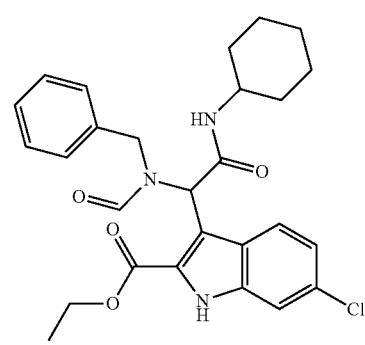 [SMILES: CCOC(=O)c1[nH]c2cc(Cl)ccc2c1C(C(=O)NC1CCCCC1)N(C=O)Cc1ccccc1] | 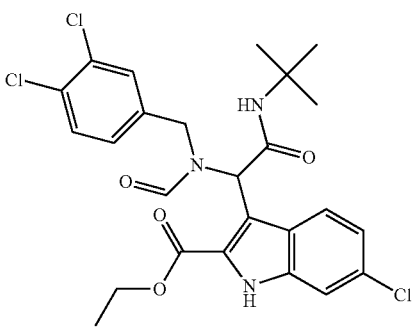 |
| 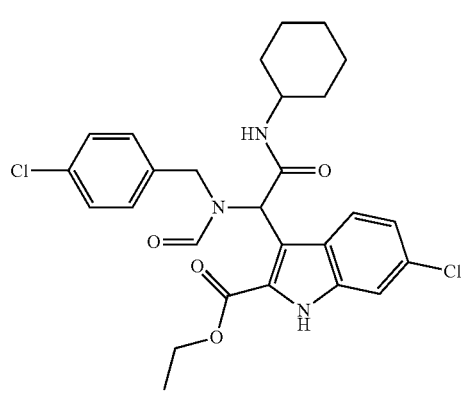 [SMILES: CCOC(=O)c1[nH]c2cc(Cl)ccc2c1C(C(=O)NC1CCCCC1)N(C=O)Cc1ccc(Cl)cc1] | 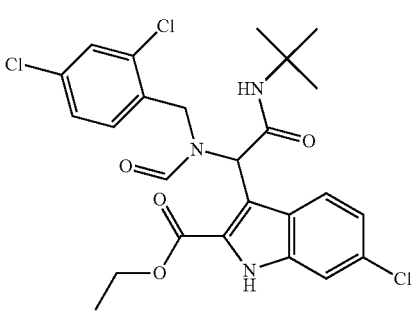 |
| 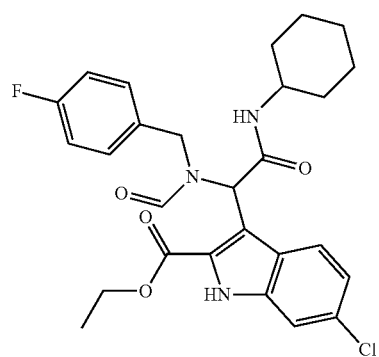 [SMILES: CCOC(=O)c1[nH]c2cc(Cl)ccc2c1C(C(=O)NC1CCCCC1)N(C=O)Cc1ccc(F)cc1] | 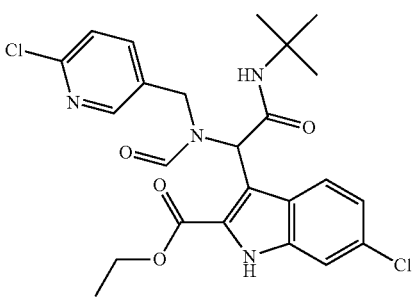 [SMILES: CCOC(=O)c1[nH]c2cc(Cl)ccc2c1C(C(=O)NC(C)(C)C)N(C=O)Cc1ccc(Cl)nc1] |

117
-continued
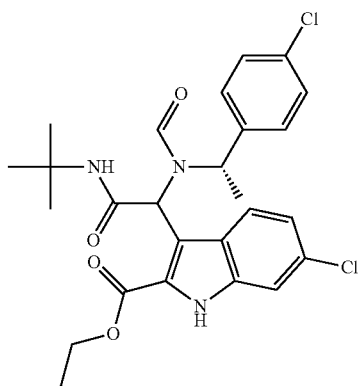 [SMILES: CCOC(=O)c1[nH]c2cc(Cl)ccc2c1C(C(=O)NC(C)(C)C)N(C=O)[C@@H](C)c1ccc(Cl)cc1]
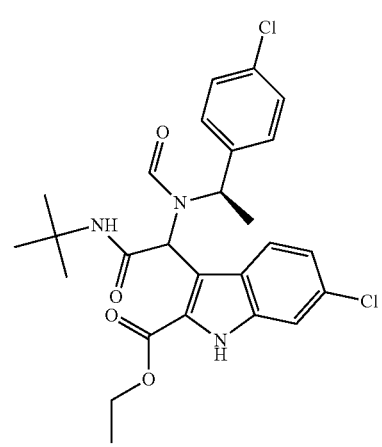 [SMILES: CCOC(=O)c1[nH]c2cc(Cl)ccc2c1C(C(=O)NC(C)(C)C)N(C=O)[C@H](C)c1ccc(Cl)cc1]
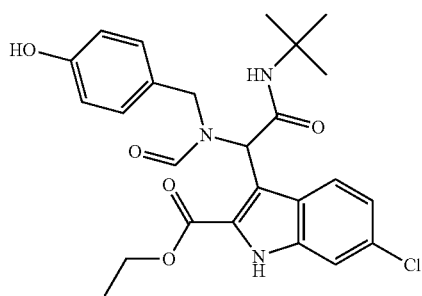 [SMILES: CCOC(=O)c1[nH]c2cc(Cl)ccc2c1C(C(=O)NC(C)(C)C)N(C=O)Cc1ccc(O)cc1]
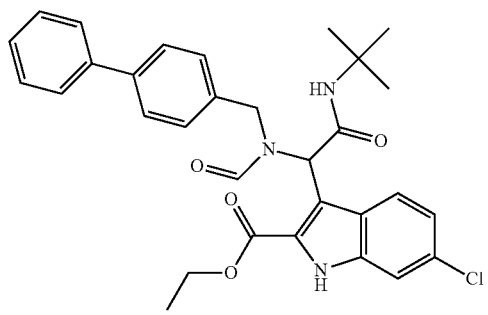 [SMILES: CCOC(=O)c1[nH]c2cc(Cl)ccc2c1C(C(=O)NC(C)(C)C)N(C=O)Cc1ccc(-c2ccccc2)cc1]
118
-continued
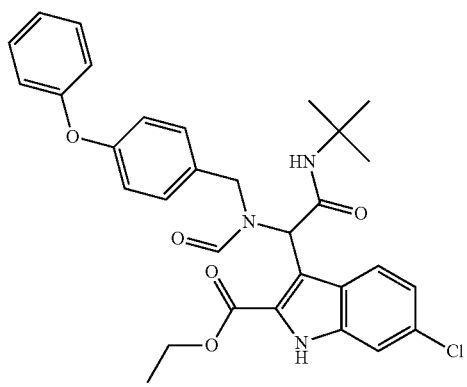 [SMILES: CCOC(=O)c1[nH]c2cc(Cl)ccc2c1C(C(=O)NC(C)(C)C)N(C=O)Cc1ccc(Oc2ccccc2)cc1]
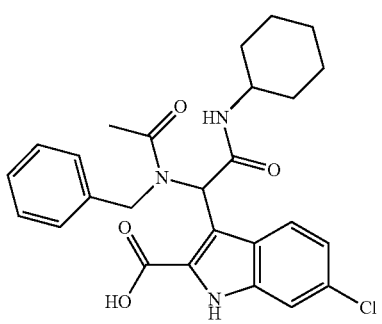 [SMILES: CC(=O)N(Cc1ccccc1)C(C(=O)NC1CCCCC1)c1c(C(=O)O)[nH]c2cc(Cl)ccc12]
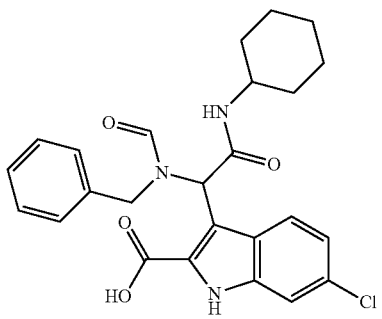 [SMILES: O=CN(Cc1ccccc1)C(C(=O)NC1CCCCC1)c1c(C(=O)O)[nH]c2cc(Cl)ccc12]
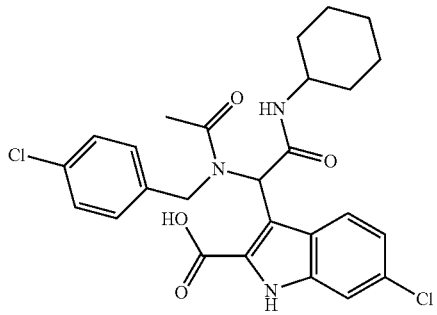 [SMILES: CC(=O)N(Cc1ccc(Cl)cc1)C(C(=O)NC1CCCCC1)c1c(C(=O)O)[nH]c2cc(Cl)ccc12]

| 119 -continued | 120 -continued |
|---|---|
| 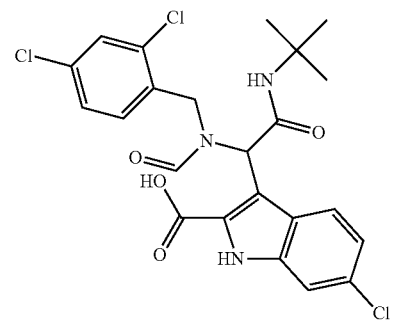 [SMILES: CC(C)(C)NC(=O)C(c1c(C(=O)O)[nH]c2cc(Cl)ccc12)N(C=O)Cc1ccc(Cl)cc1Cl] | 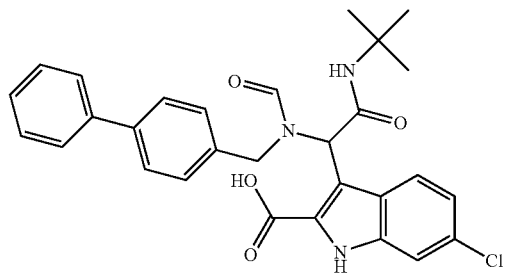 |
| 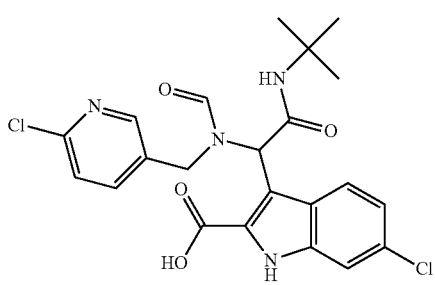 [SMILES: CC(C)(C)NC(=O)C(c1c(C(=O)O)[nH]c2cc(Cl)ccc12)N(C=O)Cc1ccc(Cl)nc1] | 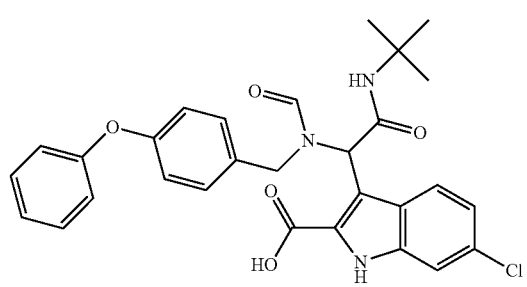 |
| 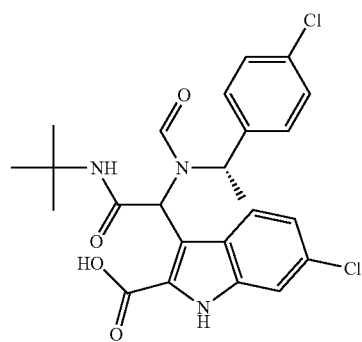 [SMILES: C[C@@H](c1ccc(Cl)cc1)N(C=O)C(C(=O)NC(C)(C)C)c1c(C(=O)O)[nH]c2cc(Cl)ccc12] | 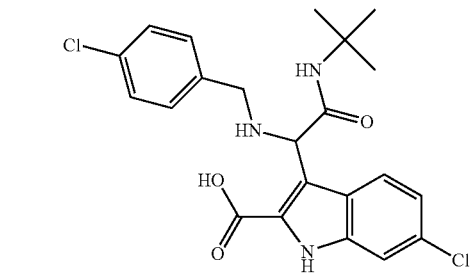 |
| 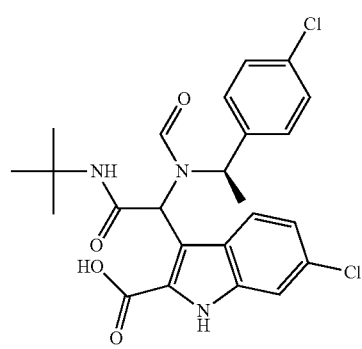 [SMILES: C[C@H](c1ccc(Cl)cc1)N(C=O)C(C(=O)NC(C)(C)C)c1c(C(=O)O)[nH]c2cc(Cl)ccc12] | 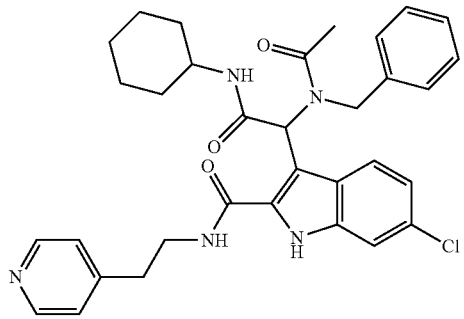 |
| 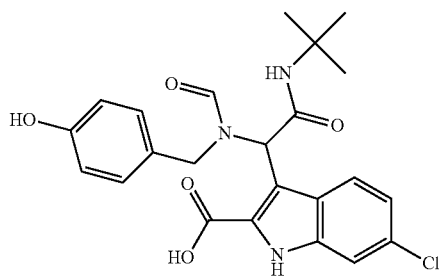 [SMILES: CC(C)(C)NC(=O)C(c1c(C(=O)O)[nH]c2cc(Cl)ccc12)N(C=O)Cc1ccc(O)cc1] | 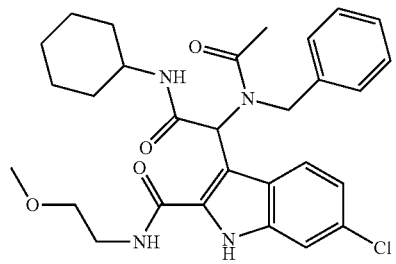 [SMILES: COCCNC(=O)c1[nH]c2cc(Cl)ccc2c1C(C(=O)NC1CCCCC1)N(Cc1ccccc1)C(C)=O] |

-continued

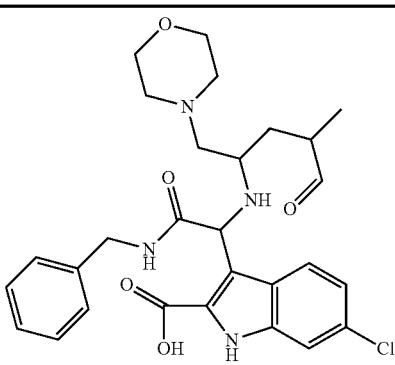

13. A compound according to Formula II,

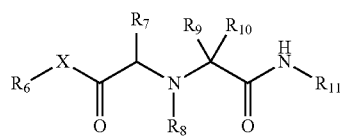

wherein
X is —(O)—, or —NH—;
$R_6$ is selected from the group consisting of hydrogen, straight or branched chain $(C_1-C_6)$alkyl, and —NH—(OH);
$R_7$ is hydrogen or straight or branched chain —$(C_1-C_6)$ alkyl;
$R_8$ and $R_{10}$ are hydrogen;
$R_9$ is a

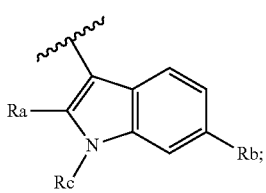

$R_a$ is selected from the group consisting of hydrogen, —C(O)R', and —C(O)OR';
$R_b$ is hydrogen, Cl, Br, or F;
$R_c$ is H or —C(O)OR$^d$;
$R^d$ is hydrogen or straight or branched chain $(C_1-C_6)$alkyl;
$R_{11}$ is selected from the group consisting of straight or branched chain $(C_1-C_6)$alkyl, $(C_3-C_{14})$aryl, benzyl, $(C_3-C_{14})$aryl$(C_1-C_6)$alkylene-, $(C_3-C_{14})$cycloalkyl, and $(C_3-C_{14})$heteroaryl-$(C_1-C_6)$alkylene-;
wherein any alkyl, benzyl, aryl, $(C_3-C_{14})$aryl$(C_1-C_6)$alkylene-, heteroaryl, cycloalkyl, or heterocycloalkyl is optionally substituted with one or more members selected from the group consisting of —OH, —Cl, —F, —Br, —I, -oxy$(C_3-C_{14})$aryl, $(C_1-C_6)$alkyl, $(C_3-C_{14})$aryl, $(C_3-C_{14})$hetero aryl, $(C_3-C_{14})$aryl$(C_1-C_6)$alkylene-, $(C_3-C_{14})$heterocycloalkyl-$(C_1-C_6)$alkylene-, —C(O)R', —C(O)OR', and oxo;

R' is selected from the group consisting of hydrogen, straight or branched chain $(C_1-C_6)$alkyl, —NH—(OH), —NH—$(C_1-C_6)$alkylene-$(C_3-C_{14})$heteroaryl, and —$(C_1-C_6)$alkylene-OH;
or a pharmaceutically acceptable salt, ester, stereoisomer, or tautomer thereof.

14. The compound according to claim 13, wherein $R_{11}$ is benzyl and X is —(O) and $R_6$ is hydrogen.

15. The compound according to claim 13, wherein $R_6$ is —$(C_1-C_6)$alkyl.

16. The compound according to claim 15, wherein $R_6$ is methyl.

17. The compound according to claim 13, wherein $R_{11}$ is benzyl and X is —NH— and $R_6$ is —$(C_1-C_6)$alkyl.

18. The compound according to claim 17, wherein $R_6$ is selected from the group consisting of

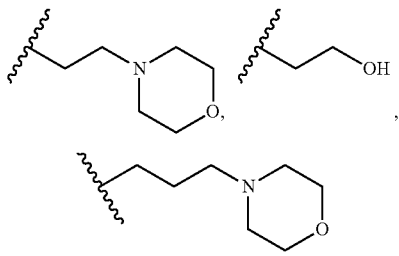

and NH(OH).

19. The compound according to claim 13, wherein $R_7$ is isobutyl.

20. A compound according to a structure selected from the following table:

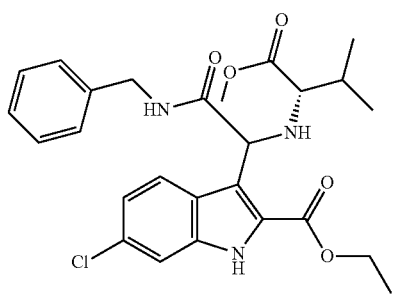 [SMILES: CCOC(=O)c1[nH]c2cc(Cl)ccc2c1C(N[C@H](C(=O)OC)C(C)C)C(=O)NCc1ccccc1]

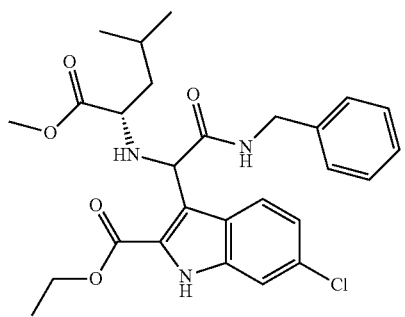 [SMILES: CCOC(=O)c1[nH]c2cc(Cl)ccc2c1C(N[C@@H](CC(C)C)C(=O)OC)C(=O)NCc1ccccc1]

| 123 -continued | 124 -continued |
|---|---|
| 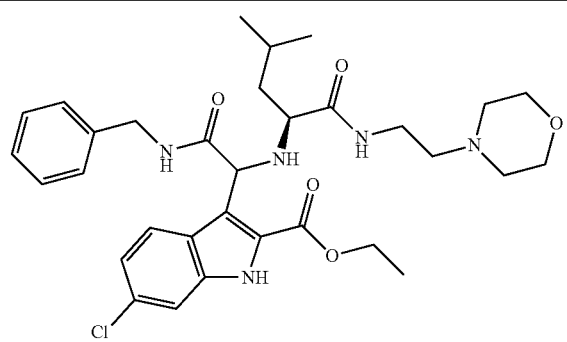 | 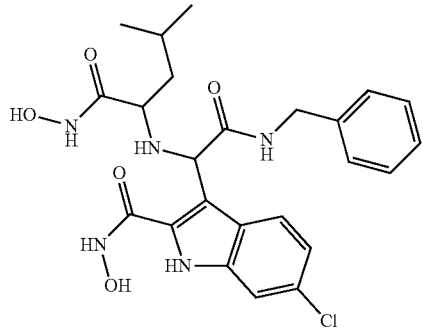 |
| 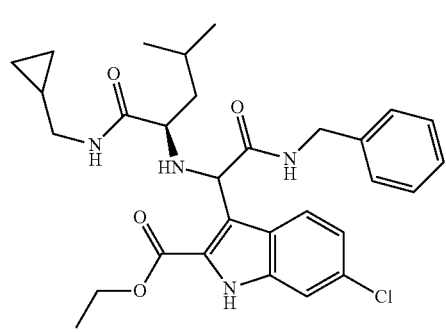 [SMILES: CCOC(=O)c1[nH]c2cc(Cl)ccc2c1C(N[C@H](CC(C)C)C(=O)NCC1CC1)C(=O)NCc1ccccc1] | 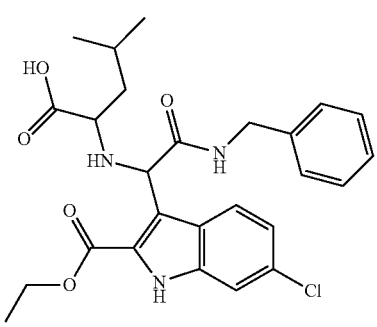 |
| 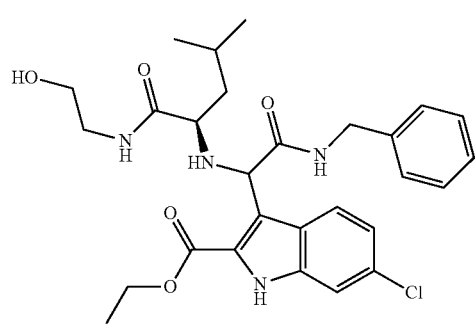 [SMILES: CCOC(=O)c1[nH]c2cc(Cl)ccc2c1C(N[C@H](CC(C)C)C(=O)NCCO)C(=O)NCc1ccccc1] | 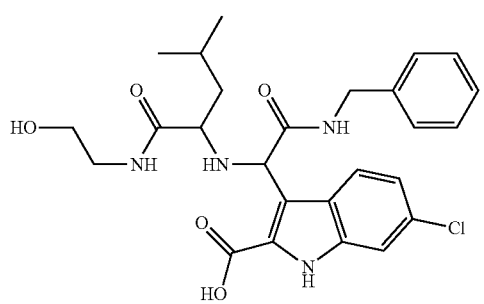 |
| 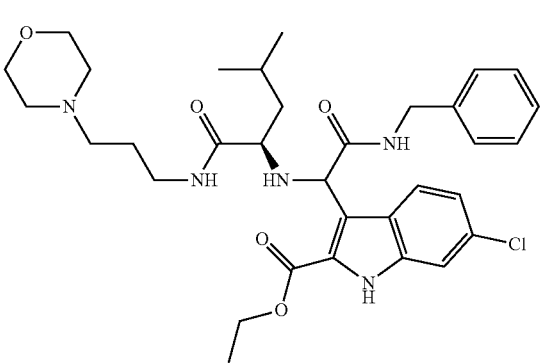 [SMILES: CCOC(=O)c1[nH]c2cc(Cl)ccc2c1C(N[C@H](CC(C)C)C(=O)NCCCN1CCOCC1)C(=O)NCc1ccccc1] | 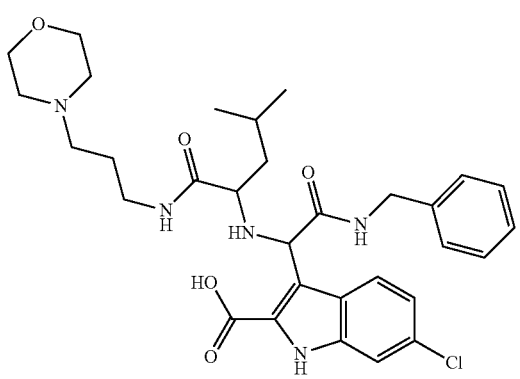 [SMILES: CC(C)CC(NC(C(=O)NCc1ccccc1)c1c(C(=O)O)[nH]c2cc(Cl)ccc12)C(=O)NCCCN1CCOCC1] |

-continued
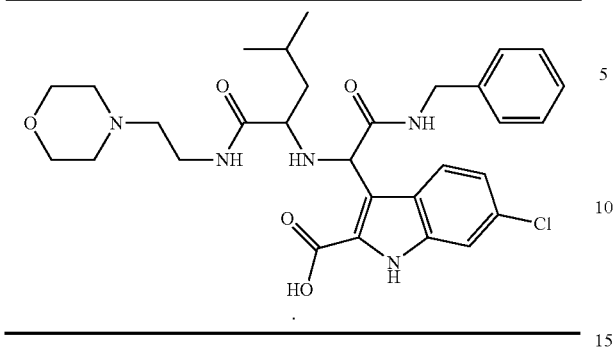
* * * * *